US012662546B2

(12) United States Patent
Walter et al.

(10) Patent No.: US 12,662,546 B2
(45) Date of Patent: Jun. 23, 2026

(54) HUMAN ANTI-CD33 ANTIBODIES AND USES THEREOF

(71) Applicant: Fred Hutchinson Cancer Center, Seattle, WA (US)

(72) Inventors: Roland B. Walter, Seattle, WA (US); George S. Laszlo, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 836 days.

(21) Appl. No.: 17/907,655

(22) PCT Filed: Mar. 31, 2021

(86) PCT No.: PCT/US2021/025220

§ 371 (c)(1),
(2) Date: Sep. 28, 2022

(87) PCT Pub. No.: WO2021/202770

PCT Pub. Date: Oct. 7, 2021

(65) Prior Publication Data

US 2023/0144405 A1 May 11, 2023

Related U.S. Application Data

(60) Provisional application No. 63/003,203, filed on Mar. 31, 2020.

(51) Int. Cl.
*C07K 16/28* (2006.01)
*A61P 37/02* (2006.01)
*A61K 47/68* (2017.01)

(52) U.S. Cl.
CPC .......... *C07K 16/2896* (2013.01); *A61P 37/02* (2018.01); *C07K 16/2809* (2013.01); *A61K 47/68* (2017.08); *A61K 47/6849* (2017.08); *C07K 2317/31* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 2005/0152903 | A1 | 7/2005 | Newman et al. |
| 2007/0117185 | A1 | 5/2007 | Kopetzki |
| 2010/0150927 | A1 | 6/2010 | Kimura et al. |
| 2011/0059095 | A1 | 3/2011 | MacDonald et al. |
| 2012/0251554 | A1 | 10/2012 | Bachmann et al. |
| 2016/0002333 | A1 | 1/2016 | Ellwanger et al. |
| 2016/0317657 | A1 | 11/2016 | Walter |
| 2019/0038248 | A1 | 2/2019 | Martelon |
| 2019/0194319 | A1 | 6/2019 | Bernstein et al. |
| 2019/0382481 | A1 | 12/2019 | Diem et al. |
| 2023/0190810 | A1 | 6/2023 | Walter |

FOREIGN PATENT DOCUMENTS

| | | | | |
|---|---|---|---|---|
| CN | 103145849 A | 6/2013 | | |
| CN | 104936617 A | 9/2015 | | |
| CN | 108064245 A | 5/2018 | | |
| JP | 2015520758 A | 7/2015 | | |
| JP | 2017505604 A | 2/2017 | | |
| JP | 2018518176 A | 7/2018 | | |
| JP | 2019532017 A | 11/2019 | | |
| JP | 2020509050 A | 3/2020 | | |
| WO | WO2010072740 A2 | 7/2010 | | |
| WO | WO2018211245 A1 | 11/2018 | | |
| WO | WO2018218207 A1 | 11/2018 | | |
| WO | WO-2019215500 A1 | * 11/2019 | ............. | C12N 15/86 |
| WO | WO2019224711 A2 | 11/2019 | | |

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Rudikoff et al., Proc. Natl. Acad. Sci. USA vol. 79 p. 1979 (Year: 1982).*
Wu et al., J Mol Biol 294: 151-162 (Year: 1999).*
Strop et al., Chemistry and Biology 20: 161-167 (Year: 2013).*
Nejadmoghaddam et al., Avicenna Journal of Medical Biotechnology 2(1): 3-23 (Year: 2019).*
Search Report and Written Opinion for European Application No. 21781573.7, Dated Jun. 11, 2024, 12 pages.
Bluemel, et al., "Epitope distance to the target cell membrane and antigen size determine the potency of T cell-mediated lysis by BiTE antibodies specific for a large melanoma surface antigen," Cancer Immunol Immunother, vol. 58, No. 8, 2010, pp. 1197-11209.
Clearly, et al., "Antibody Distance from the Cell Membrane Regulates Antibody Effector Mechanisms," J. Immunol., vol. 198, No. 10, 2017, pp. 3999-4011.
Cowan, et al., "Antibody-based therapy of acute myeloid leukemia with gemtuzumab ozogamicin," Front Biosci., vol. 18, No. 4, 2013, pp. 1311-1334.
Duan and Paulson, "Siglecs as Immune Cell Checkpoints in Disease," Annu. Rev. Immunol., vol. 38, 2020, pp. 365-395.
Godwin, "The Bruton's tyrosine kinase inhibitor ibrutinib abrogates bispecific antibody-mediated T-cell cytotoxicity," British Journal of Haematology, vol. 189, 2020, 5 pages.
Godwin, et al., "Gemtuzumab ozogamicin in acute myeloid leukemia," Leukemia, vol. 31, No. 9, 2017, pp. 1855-1868.
Godwin, et al., "Targeting the membrane-proximal C2-set domain of CD33 for improved CD33-directed immunotherapy," Leukemia, vol. 35, No. 9, 2021, pp. 2496-2507.

(Continued)

*Primary Examiner* — Phuong Huynh
(74) *Attorney, Agent, or Firm* — C. Rachal Winger; Chrystal Quisenberry; Lee & Hayes PC

(57) ABSTRACT

A suite of novel human anti-CD33 antibodies is described. The provided antibodies are pan-binders, binding the C2-set Ig-like domain in the presence or absence of the V-set Ig-like domain of CD33 or are V-set binders, binding the V-set Ig-like domain of CD33. The antibodies provide novel therapeutic and diagnostic tools against CD33-related disorders, such as acute myeloid leukemia (AML).

13 Claims, 30 Drawing Sheets

Specification includes a Sequence Listing.

(56) References Cited

OTHER PUBLICATIONS

Grossbard, et al., "Monoclonal antibody-based therapies of leukemia and lymphoma," Blood., vol. 80, No. 4, 1992, pp. 863-878.
Harrington, "The Broad Anti-AML Activity of the CD33/CD3 BiTE Antibody Construct, AMG 330, Is Impacted by Disease Stage and Risk," PLOS One, 2015, 13 pages.
Haso, et al., "Anti-CD22-chimeric antigen receptors targeting B-cell precursor acute lymphoblastic leukemia," Blood, vol. 121, No. 7, 2013, pp. 1165-1174.
Humbert, et al., "Engineering resistance to CD33-targeted immunotherapy in normal hematopoiesis by CRISPR/Cas9-deletion of CD33 exon 2," Leukimia, vol. 33, No. 3, 2019, pp. 762-808.
Laszlo, et al., "The past and future of CD33 as therapeutic target in acute myeloid leukemia," Blood Rev., vol. 28, No. 4, 2014, pp. 143-153.
Lin, Thomas S., "Ofatumumab: a novel monoclonal anti-CD20 antibody," Pharmgenomics Pers. Med., vol. 3, 2010, pp. 51-59.
Walter, et al., "Acute myeloid leukemia stem cells and CD33-targeted immunotherapy," Blood, vol. 119, No. 26, 2012, pp. 6198-6208.
Walter, Roland B., "Expanding use of CD33-directed immunotherapy," Expert Opin. Biol. Ther., vol. 20, No. 9, 2020, pp. 955-958.
Walter, Roland B., "Investigational CD33-targeted therapeutics for acute myeloid leukemia," Expert Opin. Investig Drugs., vol. 27, No. 4, 2018, pp. 339-348.
Partial European Search Report Dated Mar. 18, 2024 for European Application No. 21781573.7, 14 pages.
Invitation to Pay Additional Fees Dated Jun. 29, 2021 for International Application No. PCT/US2021/025220, 3 pages.
Nair-Gupta, et al., "A novel C2 domain binding CD33xCD3 bispecific antibody with potent T-cell redirection activity against acute myeloid leukemia," Blood Adv., vol. 4, No. 5, 2020, pp. 906-919.
Search Report and Written Opinion Dated Oct. 12, 2021 for International Application No. PCT/US2021/025166, 14 pages.
Search Report and Written Opinion Dated Oct. 5, 2021 for International Application No. PCT/US2021/025220, 14 pages.
Perez-Oliva, et al., "Epitope mapping, expression and post-translational modifications of two isoforms of CD33 (CD33M and CD33m) on lymphoid and myeloid human cells", Glycobiology, vol. 21, No. 6, Jan. 28, 2011, pp. 757-770.
Zuo, et al., "Preliminary Study on Antigen Recognition Epitopes of Anti-human CD33 Monoclonal Antibodies (HIM3-4, WM53, M195)" Chinese Journal of Immunology, vol. 23, Issue 1, Jan. 20, 2007, pp. 16-20.

* cited by examiner

FIG. 7A

| Carterra binding data for purified monoclonal anti-CD33 antibodies (Trianni mice) | | | | | | | |
|---|---|---|---|---|---|---|---|
| Clone | $CD33^{FL}$ kD (nM), 4 μg/mL | $CD33^{FL}$ kD (nM), 1 μg/mL | Hybridoma supernatant ($CD33^{FL}$) | $CD33^{\Delta E2}$ kD (nM), 4 μg/mL | $CD33^{\Delta E2}$ kD (nM), 1 μg/mL | Hybridoma supernatant ($CD33^{\Delta E2}$) | mAb type |
| 1H10 | 42 | 13 | 112 | 13 | 0.154 | 31 | Pan |
| 2D3 | 27 | 18 | N.D. | --- | --- | N.D. | V-set |
| 1H8 | 40 | 24 | --- | --- | --- | --- | V-set |
| 1A9 | 130 | 36 | 67 | 23 | 1.3 | 19 | Pan |
| 1B9 | --- | --- | 77 | --- | --- | 44 | Pan |
| 1E6 | 78 | 67 | 69 | 49 | 25 | 37 | Pan |
| 1D2 | --- | --- | 116 | --- | --- | 115 | Pan |
| 2E3 | 2300 | --- | 3000 | --- | --- | --- | V-set |

CD33$^{FL}$

1H10

$k_a = 1.40 \times 10^5\ M^{-1}s^{-1}$
$k_d = 5.20 \times 10^{-4}\ s^{-1}$
$K_D = 3.71$ nM 57.2 ± 0.8 RUs captured 1H10

2D3

$k_a = 1.28 \times 10^5\ M^{-1}s^{-1}$
$k_d = 6.27 \times 10^{-4}\ s^{-1}$
$K_D = 4.89$ nM 39.7 ± 0.5 RUs captured 2D3

CD33<sup>ΔE2</sup>

1H10

$k_a = 3.87 \times 10^5 \text{ M}^{-1}\text{s}^{-1}$
$k_d = 5.27 \times 10^{-5} \text{ s}^{-1}$
$K_D = 136 \text{ pM}$ 95 ± 1 RUs
captured 1H10

20 nM (triplicate)

2D3 Did not bind

FIG. 14

Human full-length (FL) CD33 with a mouse Fc domain, used as an immunogen for human FL CD33:
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGGGSGCKPCICTVPEVSSVFIFPPKPKDVLTITLTPKVTCVVVDISKDDPEVQFSWFVDDVEVH
TAQTQPREEQFNSTFRSVSELPIMHQDWLNGKEFKCRVNSAAFPAPIEKTISKTKGRPKAPQV
YTIPPPKEQMAKDKVSLTCMITDFFPEDITVEWQWNGQPAENYKNTQPIMNTNGSYFVYSKLN
VQKSNWEAGNTFTCSVLHEGLHNHHTEKSLSHSPGK (SEQ ID NO: 2)

Human ΔE2 version of CD33 (CD33ΔE2) with a mouse Fc domain, used as immunogen for human CD33ΔE2:
MPLLLLLPLLWADLTHRPKILIPGTLEPGHSKNLTCSVSWACEQGTPPIFSWLSAAPTSLGPRTT
HSSVLIITPRPQDHGTNLTCQVKFAGAGVTTERTIQLNVTYVPQNPTTGIFPGDGSGKQETRAG
GGSGCKPCICTVPEVSSVFIFPPKPKDVLTITLTPKVTCVVVDISKDDPEVQFSWFVDDVEVHTA
QTQPREEQFNSTFRSVSELPIMHQDWLNGKEFKCRVNSAAFPAPIEKTISKTKGRPKAPQVYTI
PPPKEQMAKDKVSLTCMITDFFPEDITVEWQWNGQPAENYKNTQPIMNTNGSYFVYSKLNVQ
KS NWEAGNTFTCSVLHEGLHNHHTEKSLSHSPGK (SEQ ID NO: 3)

Extracellular domain of mouse CD33 where the C2-set Ig-like domain from mouse is replaced with the C2-set Ig-like domain from human CD33, combined with a Fc region from human IgG1, used as immunogen to generate antibodies against human C2-set domain of CD33:
MLWPLPLFLLCAGSLAQDLEFQLVAPESVTVEEGLCVHVPCSVFYPSIKLTLGPVTGSWLRKGV
SLHEDSPVATSDPRQLVQKATQGRFQLLGDPQKHDCSLFIRDAQKNDTGMYFFRVVREPFVR
YSYKKSQLSLHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGSEPKSSDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK (SEQ ID NO: 4)

Extracellular domain of mouse CD33 (codon optimized) where the C2-set Ig-like domain from mouse is replaced with the C2-set Ig-like domain from human CD33, combined with a Fc region from human IgG1, used as immunogen to generate antibodies against human C2-set domain of CD33:
ATGCTGTGGCCTCTGCCTCTGTTTCTGCTGTGCGCTGGAAGTCTGGCTCAGGATCTGGAAT
TTCAGCTGGTGGCTCCCGAATCAGTCACCGTGGAGGAGGGCCTGTGCGTGCACGTGCCTT
GTAGCGTGTTCTACCCAAGCATCAAGCTGACCCTGGGCCCTGTGACAGGCTCCTGGCTGA
GGAAGGGCGTGTCCCTGCACGAGGACTCTCCAGTGGCCACCAGCGATCCTAGGCAGCTG
GTGCAGAAGGCCACACAGGGCAGATTCCAGCTGCTGGGCGACCCTCAGAAGCACGATTG
CAGCCTGTTTATCCGCGACGCCCAGAAGAACGATACCGGCATGTATTTCTTTCGGGTGGT
GAGAGAGCCATTCGTGAGGTACTCCTATAAGAAGTCTCAGCTGAGCCTGCACGTGACCGA
CCTGACACACCGCCCAAAGATCCTGATCCCAGGCACCCTGGAGCCTGGACACTCTAAGAA
CCTGACATGCTCCGTGTCTTGGGCATGTGAGCAGGGAACCCCACCTATCTTTTCCTGGCT
GTCTGCCGCACCAACAAGCCTGGGACCAAGGACCACACACAGCTCCGTGCTGATCATCAC
CCCTAGACCACAGGATCACGGCACCAATCTGACATGCCAGGTGAAGTTCGCAGGAGCAGG
AGTGACCACAGAGAGGACCATCCAGCTGAACGTGACATACGTGCCTCAGAATCCAACCAC

FIG. 14 cont'd

AGGCATCTTTCCAGGCGACGGCTCCGGCAAGCAGGAGACACGGGCCGGATCCGAGCCCA
AGTCTAGCGATAAGACCCACACATGCCCACCATGTCCAGCACCTGAGCTGCTGGGAGGAC
CAAGCGTGTTCCTGTTTCCTCCAAAGCCCAAGGACACACTGATGATCTCTCGGACCCCCGA
GGTGACATGCGTGGTGGTGGACGTGAGCCACGAGGACCCCGAGGTGAAGTTTAACTGGT
ACGTGGATGGCGTGGAGGTGCACAATGCCAAGACCAAGCCCAGGGAGGAGCAGTACAAC
TCCACCTATCGCGTGGTGTCTGTGCTGACAGTGCTGCACCAGGACTGGCTGAACGGCAAG
GAGTATAAGTGCAAGGTGTCCAATAAGGCCCTGCCAGCCCCCATCGAGAAGACCATCTCT
AAGGCAAAGGGACAGCCCAGGGAGCCTCAGGTGTACACACTGCCCCCTAGCCGCGACGA
GCTGACCAAGAACCAGGTGTCCCTGACATGTCTGGTGAAGGGCTTCTATCCTTCTGATATC
GCCGTGGAGTGGGAGAGCAATGGCCAGCCAGAGAACAATTACAAGACCACACCACCCGT
GCTGGACAGCGATGGCTCCTTCTTTCTGTATAGCAAGCTGACCGTGGATAAGTCCAGGTG
GCAGCAGGGCAACGTGTTCAGCTGTTCCGTGATGCACGAAGCACTGCACAACCACTACAC
TCAGAAATCACTGTCACTGTCCCCAGGAAAGTAA (SEQ ID NO: 5)

Extracellular domain of mouse CD33 where the C2-set Ig-like domain from mouse has been replaced with the C2-set Ig-like domain from human CD33 combined with the transmembrane domain and a truncated intracellular domain both derived from human CD33, used as immunogen to generate antibodies against human C2-set domain of CD33:
MLWPLPLFLLCAGSLAQDLEFQLVAPESVTVEEGLCVHVPCSVFYPSIKLTLGPVTGSWLRKGV
SLHEDSPVATSDPRQLVQKATQGRFQLLGDPQKHDCSLFIRDAQKNDTGMYFFRVVREPFVR
YSYKKSQLSLHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGVVHGAIGGAGVTALLALCLCLIFFIVKT (SEQ ID NO: 6)

Extracellular domain of mouse CD33 where the C2-set Ig-like domain from mouse has been replaced with the C2-set Ig-like domain from human CD33 combined with the transmembrane domain and a truncated intracellular domain both derived from human CD33, used as immunogen to generate antibodies against human C2-set domain of CD33:
ATGCTGTGGCCTCTGCCTCTGTTTCTGCTGTGCGCTGGAAGTCTGGCTCAGGATCTGGAAT
TTCAGCTGGTGGCTCCCGAATCAGTCACCGTGGAGGAGGGCCTGTGCGTGCACGTGCCTT
GTAGCGTGTTCTACCCAAGCATCAAGCTGACCCTGGGCCCTGTGACAGGCTCCTGGCTGA
GGAAGGGCGTGTCCCTGCACGAGGACTCTCCAGTGGCCACCAGCGATCCTAGGCAGCTG
GTGCAGAAGGCCACACAGGGCAGATTCCAGCTGCTGGGCGACCCTCAGAAGCACGATTG
CAGCCTGTTTATCCGCGACGCCCAGAAGAACGATACCGGCATGTATTTCTTTCGGGTGGT
GAGAGAGCCATTCGTGAGGTACTCCTATAAGAAGTCTCAGCTGAGCCTGCACGTGACCGA
CCTGACACACCGCCCAAAGATCCTGATCCCAGGCACCCTGGAGCCTGGACACTCTAAGAA
CCTGACATGCTCCGTGTCTTGGGCATGTGAGCAGGGAACCCCACCTATCTTTTCCTGGCT
GTCTGCCGCACCAACAAGCCTGGGACCAAGGACCACACACAGCTCCGTGCTGATCATCAC
CCCTAGACCACAGGATCACGGCACCAATCTGACATGCCAGGTGAAGTTCGCAGGAGCAGG
AGTGACCACAGAGAGGACCATCCAGCTGAACGTGACATACGTGCCTCAGAATCCAACCAC
AGGCATCTTTCCAGGCGACGGCTCCGGCAAGCAGGAGACACGGGCCGGAGTGGTTCATG
GGGCCATTGGAGGAGCTGGTGTTACAGCCCTGCTCGCTCTTTGTCTCTGCCTCATCTTCTT
CATAGTGAAGACCTGA (SEQ ID NO: 7)

Full length human CD33, immunogen for human CD33:
MPLLLLLPLLWAGALAMDPNFWLQVQESVTVQEGLCVLVPCTFFHPIPYYDKNSPVHGYWFRE

FIG. 14 cont'd

GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGLVHGAIGGAGVTALLALCLCLIFFIVKTHRRKAARTAVGSNDTHPTTGSASPKHQKNSKLHG
PTETSSCSGAAPTVEMDEELHYASLNFHGMNPSKDTSTEYSEVRTQ (SEQ ID NO: 8)

Full length human CD33:
ATGCCGCTGCTGCTACTGCTGCCCCTGCTGTGGGCAGGGGCCCTGGCTATGGATCCAAAT
TTCTGGCTGCAAGTGCAGGAGTCAGTGACGGTACAGGAGGGTTTGTGCGTCCTCGTGCCC
TGCACTTTCTTCCATCCCATACCCTACTACGACAAGAACTCCCCAGTTCATGGTTACTGGTT
CCGGGAAGGAGCCATTATATCCAGGGACTCTCCAGTGGCCACAAACAAGCTAGATCAAGA
AGTACAGGAGGAGACTCAGGGCAGATTCCGCCTCCTTGGGGATCCCAGTAGGAACAACTG
CTCCCTGAGCATCGTAGACGCCAGGAGGAGGGATAATGGTTCATACTTCTTTCGGATGGA
GAGAGGAAGTACCAAATACAGTTACAAATCTCCCCAGCTCTCTGTGCATGTGACAGACTTG
ACCCACAGGCCCAAAATCCTCATCCCTGGCACTCTAGAACCCGGCCACTCCAAAAACCTTA
CCTGCTCTGTGTCCTGGGCCTGTGAGCAGGGAACACCCCCGATCTTCTCCTGGTTGTCAG
CTGCCCCCACCTCCCTGGGCCCCAGGACTACTCACTCCTCGGTGCTCATAATCACCCCAC
GGCCCCAGGACCACGGCACCAACCTGACCTGTCAGGTGAAGTTCGCTGGAGCTGGTGTG
ACTACGGAGAGAACCATCCAGCTCAACGTCACCTATGTTCCACAGAACCCAACAACTGGTA
TCTTTCCAGGAGATGGCTCAGGGAAACAAGAGACCAGAGCAGGACTGGTTCATGGGGCCA
TTGGAGGAGCTGGTGTTACAGCCCTGCTCGCTCTTTGTCTCTGCCTCATCTTCTTCATAGT
GAAGACCCACAGGAGGAAAGCAGCCAGGACAGCAGTGGGCAGCAATGACACCCACCCTA
CCACAGGGTCAGCCTCCCCGAAACACCAGAAGAACTCCAAGTTACATGGCCCCACTGAAA
CCTCAAGCTGTTCAGGTGCCGCCCCTACTGTGGAGATGGATGAGGAGCTGCATTATGCTT
CCCTCAACTTTCATGGGATGAATCCTTCCAAGGACACCTCCACCGAATACTCAGAGGTCAG
GACCCAGTGA (SEQ ID NO: 9)

Human ΔE2 version of CD33, immunogen for human ΔE2:
MPLLLLLPLLWADLTHRPKILIPGTLEPGHSKNLTCSVSWACEQGTPPIFSWLSAAPTSLGPRTT
HSSVLIITPRPQDHGTNLTCQVKFAGAGVTTERTIQLNVTYVPQNPTTGIFPGDGSGKQETRAG
LVHGAIGGAGVTALLALCLCLIFFIVKTHRRKAARTAVGSNDTHPTTGSASPKHQKNSKLHGPTE
TSSCSGAAPTVEMDEELHYASLNFHGMNPSKDTSTEYSEVRTQ (SEQ ID NO: 10)

Human ΔE2 version of CD33:
ATGCCGCTGCTGCTACTGCTGCCCCTGCTGTGGGCAGACTTGACCCACAGGCCCAAAATC
CTCATCCCTGGCACTCTAGAACCCGGCCACTCCAAAAACCTTACCTGCTCTGTGTCCTGGG
CCTGTGAGCAGGGAACACCCCCGATCTTCTCCTGGTTGTCAGCTGCCCCCACCTCCCTGG
GCCCCAGGACTACTCACTCCTCGGTGCTCATAATCACCCCACGGCCCCAGGACCACGGCA
CCAACCTGACCTGTCAGGTGAAGTTCGCTGGAGCTGGTGTGACTACGGAGAGAACCATCC
AGCTCAACGTCACCTATGTTCCACAGAACCCAACAACTGGTATCTTTCCAGGAGATGGCTC
AGGGAAACAAGAGACCAGAGCAGGACTGGTTCATGGGGCCATTGGAGGAGCTGGTGTTA
CAGCCCTGCTCGCTCTTTGTCTCTGCCTCATCTTCTTCATAGTGAAGACCCACAGGAGGAA
AGCAGCCAGGACAGCAGTGGGCAGCAATGACACCCACCCTACCACAGGGTCAGCCTCCC
CGAAACACCAGAAGAACTCCAAGTTACATGGCCCCACTGAAACCTCAAGCTGTTCAGGTGC
CGCCCCTACTGTGGAGATGGATGAGGAGCTGCATTATGCTTCCCTCAACTTTCATGGGATG
AATCCTTCCAAGGACACCTCCACCGAATACTCAGAGGTCAGGACCCAGTGA (SEQ ID NO:
11)

FIG. 14 cont'd

**CD33:CD22 4D protein (*CD33 signal peptide is in bold and italicized*; 6-histidine tag is underlined; *3 x glycine linker is italicized, bold, and underlined****;* CD33 extracellular domain is in normal font; the portion of CD22 extracellular domain that contains CD22 domains defined as Ig-like C2-type 3, Ig-like C2-type 4, Ig-like C2-type 5, Ig-like C2-type 6 is in bold; CD33 transmembrane domain is double underlined; and *CD33 intracellular domain is italicized*):

*MPLLLLLPLLWAGALAM*HHHHHH*GGG*DPNFWLQVQESVTVQEGLCVLVPCTFFHPIPYYDK
NSPVHGYWFREGAIISRDSPVATNKLDQEVQEETQGRFRLLGDPSRNNCSLSIVDARRRDNGS
YFFRMERGSTKYSYKSPQLSVHVTDLTHRPKILIPGTLEPGHSKNLTCSVSWACEQGTPPIFSW
LSAAPTSLGPRTTHSSVLIITPRPQDHGTNLTCQVKFAGAGVTTERTIQLNVTYVPQNPTTGIFP
GDGSGKQETRAGVVH**PEPSTVQILHSPAVEGSQVEFLCMSLANPLPTNYTWYHNGKEMQGR
TEEKVHIPKILPWHAGTYSCVAENILGTGQRGPGAELDVQYPPKKVTTVIQNPMPIREGDTVTL
SCNYNSSNPSVTRYEWKPHGAWEEPSLGVLKIQNVGWDNTTIACAACNSWCSWASPVALN
VQYAPRDVRVRKIKPLSEIHSGNSVSLQCDFSSSHPKEVQFFWEKNGRLLGKESQLNFDSISP
EDAGSYSCWVNNSIGQTASKAWTLEVLYAPRRLRVSMSPGDQVMEGKSATLTCESDANPPV
SHYTWFDWNNQSLPYHSQKLRLEPVKVQHSGAYWCQGTNSVGKGRSPLSTLTVYYSPET**G
AIGGAGVTALLALCLCLIFFIV*KTHRRKAARTAVGRNDTHPTTGSASPKHQKKSKLHGPTETSSC
SGAAPTVEMDEELHYASLNFHGMNPSKDTSTEYSEVRTQ* (SEQ ID NO: 1)

**CD33:CD22 4D nucleotides (*CD33 signal peptide is in bold and italicized*; 6-histidine tag is underlined; *3 x glycine linker is italicized, bold, and underlined****;* CD33 extracellular domain is in normal font; the portion of CD22 extracellular domain that contains CD22 domains defined as Ig-like C2-type 3, Ig-like C2-type 4, Ig-like C2-type 5, Ig-like C2-type 6 is in bold; CD33 transmembrane domain is double underlined; and *CD33 intracellular domain is italicized)*:

*ATGCCTCTGCTGCTACTGCTACCTCTGCTGTGGGCTGGAGCCCTGGCTATG*CATCATCAC
CACCATCAC*GGCGGCGGC*GATCCAAATTTCTGGCTGCAAGTGCAGGAGTCAGTGACGGTA
CAGGAGGGTTTGTGCGTCCTCGTGCCCTGCACTTTCTTCCATCCCATACCCTACTACGACA
AGAACTCCCCAGTTCATGGTTACTGGTTCCGGGAAGGAGCCATTATATCCAGGGACTCTCC
AGTGGCCACAAACAAGCTAGATCAAGAAGTACAGGAGGAGACTCAGGGCAGATTCCGCCT
CCTTGGGGATCCCAGTAGGAACAACTGCTCCCTGAGCATCGTAGACGCCAGGAGGAGGG
ATAATGGTTCATACTTCTTTCGGATGGAGAGAGGAAGTACCAAATACAGTTACAAATCTCCC
CAGCTCTCTGTGCATGTGACAGACTTGACCCACAGGCCCAAAATCCTCATCCCTGGCACTC
TAGAACCCGGCCACTCCAAAAACCTGACCTGCTCTGTGTCCTGGGCCTGTGAGCAGGGAA
CACCCCCGATCTTCTCCTGGTTGTCAGCTGCCCCCACCTCCCTGGGCCCCAGGACTACTC
ACTCCTCGGTGCTCATAATCACCCCACGGCCCCAGGACCACGGCACCAACCTGACCTGTC
AGGTGAAGTTCGCTGGAGCTGGTGTGACTACGGAGAGAACCATCCAGCTGAACGTCACCT
ATGTTCCACAGAACCCAACAACTGGTATCTTTCCAGGAGATGGCTCAGGGAAACAAGAGAC
CAGAGCAGGAGTGGTTCAT**CCGGAACCTTCCACGGTTCAGATCCTCCACTCACCGGCTGT
GGAGGGAAGTCAAGTCGAGTTTCTTTGCATGTCACTGGCCAATCCTCTTCCAACAAATTA
CACGTGGTACCACAATGGGAAAGAAATGCAGGGAAGGACAGAGGAGAAAGTCCACATC
CCAAAGATCCTCCCTTGGCACGCTGGGACTTATTCCTGTGTGGCAGAAAACATTCTTGGT
ACTGGACAGAGGGGCCCTGGAGCTGAGCTGGATGTCCAGTATCCTCCCAAGAAGGTGA
CCACAGTGATTCAAAACCCCATGCCGATTCGAGAAGGAGACACAGTGACCCTTTCCTGT
AACTACAATTCCAGTAACCCCAGTGTTACCCGGTATGAATGGAAACCCCATGGCGCCTG
GGAGGAGCCATCGCTTGGGGTGCTGAAGATCCAAAACGTTGGCTGGGACAACACAACC
ATCGCCTGCGCAGCTTGTAATAGTTGGTGCTCGTGGGCCTCCCCTGTCGCCCTGAATGTC
CAGTATGCCCCCCGAGACGTGAGGGTCCGGAAAATCAAGCCCCTTTCCGAGATTCACTC**

FIG. 14 cont'd

**TGGAAACTCGGTCAGCCTCCAATGTGACTTCTCAAGCAGCCACCCCAAAGAAGTCCAGT
TCTTCTGGGAGAAAAATGGCAGGCTTCTGGGGAAAGAAAGCCAGCTGAATTTTGACTCC
ATCTCCCCAGAAGATGCTGGGAGTTACAGCTGCTGGGTGAACAACTCCATAGGACAGAC
AGCGTCCAAGGCCTGGACACTTGAAGTGCTGTATGCACCCAGGAGGCTGCGTGTGTCCA
TGAGCCCAGGGGACCAAGTGATGGAGGGGAAGAGTGCAACCCTGACCTGTGAGAGCGA
CGCCAACCCTCCCGTCTCCCACTACACCTGGTTTGACTGGAATAACCAAAGCCTCCCCTA
CCACAGCCAGAAGCTGAGATTGGAGCCGGTGAAGGTCCAGCACTCGGGTGCCTACTGG
TGCCAGGGGACCAACAGTGTGGGCAAGGGCCGTTCGCCTCTCAGCACCCTCACCGTCTA
CTATAGCCCGGAGACC**GGGGCCATTGGAGGAGCTGGTGTTACAGCCCTGCTCGCTCTTT
GTCTCTGCCTCATCTTCTTCATAGTG*AAGACCCACAGGAGGAAAGCAGCCAGGACAGCAG
TGGGCAGGAATGACACCCACCCTACCACAGGGTCAGCCTCCCCGAAACACCAGAAGAAGT
CCAAGTTACATGGCCCCACTGAAACCTCAAGCTGTTCAGGTGCCGCCCCTACTGTGGAGA
TGGATGAGGAGCTGCATTATGCTTCCCTCAACTTTCATGGGATGAATCCTTCCAAGGACAC
CTCCACCGAATACTCAGAGGTCAGGACCCAG* (SEQ ID NO: 135)

**CD33:CD22 2D protein *(CD33 signal peptide is in bold and italicized*; 6-histidine tag is underlined; *3 x glycine linker is italicized, bold, and underlined****;* CD33 extracellular domain is in normal font; the portion of CD22 extracellular domain that contains CD22 domains defined as Ig-like C2-type 5, Ig-like C2-type 6is in bold; CD33 transmembrane domain is double underlined; and *CD33 intracellular domain is italicized*):
*MPLLLLLPLLWAGALAM*HHHHHH*GGG*DPNFWLQVQESVTVQEGLCVLVPCTFFHPIPYYDK
NSPVHGYWFREGAIISRDSPVATNKLDQEVQEETQGRFRLLGDPSRNNCSLSIVDARRRDNGS
YFFRMERGSTKYSYKSPQLSVHVTDLTHRPKILIPGTLEPGHSKNLTCSVSWACEQGTPPIFSW
LSAAPTSLGPRTTHSSVLIITPRPQDHGTNLTCQVKFAGAGVTTERTIQLNVTYVPQNPTTGIFP
GDGSGKQETRAGVVH**PRDVRVRKIKPLSEIHSGNSVSLQCDFSSSHPKEVQFFWEKNGRLLG
KESQLNFDSISPEDAGSYSCWVNNSIGQTASKAWTLEVLYAPRRLRVSMSPGDQVMEGKSA
TLTCESDANPPVSHYTWFDWNNQSLPYHSQKLRLEPVKVQHSGAYWCQGTNSVGKGRSPL
STLTVYYSPET**GAIGGAGVTALLALCLCLIFFIV*KTHRRKAARTAVGRNDTHPTTGSASPKHQKK
SKLHGPTETSSCSGAAPTVEMDEELHYASLNFHGMNPSKDTSTEYSEVRTQ* (SEQ ID NO: 136)

**CD33:CD22 2D nucleotides *(CD33 signal peptide is in bold and italicized*; 6-histidine tag is underlined; *3 x glycine linker is italicized, bold, and underlined****;* CD33 extracellular domain is in normal font; the portion of CD22 extracellular domain that contains CD22 domains defined as Ig-like C2-type 5, Ig-like C2-type 6is in bold; CD33 transmembrane domain is double underlined; and *CD33 intracellular domain is italicized*):
*ATGCCTCTGCTGCTACTGCTACCTCTGCTGTGGGCTGGAGCCCTGGCTATG*CATCATCAC
CACCATCAC*GGCGGCGGC*GATCCAAATTTCTGGCTGCAAGTGCAGGAGTCAGTGACGGTA
CAGGAGGGTTTGTGCGTCCTCGTGCCCTGCACTTTCTTCCATCCCATACCCTACTACGACA
AGAACTCCCCAGTTCATGGTTACTGGTTCCGGGAAGGAGCCATTATATCCAGGGACTCTCC
AGTGGCCACAAACAAGCTAGATCAAGAAGTACAGGAGGAGACTCAGGGCAGATTCCGCCT
CCTTGGGGATCCCAGTAGGAACAACTGCTCCCTGAGCATCGTAGACGCCAGGAGGAGGG
ATAATGGTTCATACTTCTTTCGGATGGAGAGAGGAAGTACCAAATACAGTTACAAATCTCCC
CAGCTCTCTGTGCATGTGACAGACTTGACCCACAGGCCCAAAATCCTCATCCCTGGCACTC
TAGAACCCGGCCACTCCAAAAACCTGACCTGCTCTGTGTCCTGGGCCTGTGAGCAGGGAA
CACCCCCGATCTTCTCCTGGTTGTCAGCTGCCCCCACCTCCCTGGGCCCCAGGACTACTC
ACTCCTCGGTGCTCATAATCACCCCACGGCCCCAGGACCACGGCACCAACCTGACCTGTC
AGGTGAAGTTCGCTGGAGCTGGTGTGACTACGGAGAGAACCATCCAGCTGAACGTCACCT

FIG. 14 cont'd

ATGTTCCACAGAACCCAACAACTGGTATCTTTCCAGGAGATGGCTCAGGGAAACAAGAGAC
CAGAGCAGGAGTGGTTCAT**CCCCGAGACGTGAGGGTCCGGAAAATCAAGCCCCTTTCCG
AGATTCACTCTGGAAACTCGGTCAGCCTCCAATGTGACTTCTCAAGCAGCCACCCCAAA
GAAGTCCAGTTCTTCTGGGAGAAAAATGGCAGGCTTCTGGGGAAAGAAAGCCAGCTGAA
TTTTGACTCCATCTCCCCAGAAGATGCTGGGAGTTACAGCTGCTGGGTGAACAACTCCAT
AGGACAGACAGCGTCCAAGGCCTGGACACTTGAAGTGCTGTATGCACCCAGGAGGCTG
CGTGTGTCCATGAGCCCAGGGGACCAAGTGATGGAGGGGAAGAGTGCAACCCTGACCT
GTGAGAGCGACGCCAACCCTCCCGTCTCCCACTACACCTGGTTTGACTGGAATAACCAA
AGCCTCCCCTACCACAGCCAGAAGCTGAGATTGGAGCCGGTGAAGGTCCAGCACTCGG
GTGCCTACTGGTGCCAGGGGACCAACAGTGTGGGCAAGGGCCGTTCGCCTCTCAGCAC
CCTCACCGTCTACTATAGCCCGGAGACC**GGGGCCATTGGAGGAGCTGGTGTTACAGCCC
TGCTCGCTCTTTGTCTCTGCCTCATCTTCTTCATAGTG*AAGACCCACAGGAGGAAAGCAGC
CAGGACAGCAGTGGGCAGGAATGACACCCACCCTACCACAGGGTCAGCCTCCCCGAAAC
ACCAGAAGAAGTCCAAGTTACATGGCCCCACTGAAACCTCAAGCTGTTCAGGTGCCGCCC
CTACTGTGGAGATGGATGAGGAGCTGCATTATGCTTCCCTCAACTTTCATGGGATGAATCC
TTCCAAGGACACCTCCACCGAATACTCAGAGGTCAGGACCCAG* (SEQ ID NO: 137)

**CD33 V-set construct (exon 3 and 4 deleted) protein (*CD33 signal peptide is in bold and italicized*; 6-histidine tag is underlined; *3 x glycine linker is italicized, bold, and underlined***; CD33 extracellular domain lacking CD33 amino acids 140-232 is in normal font; CD33 transmembrane domain is double underlined; and *CD33 intracellular domain is italicized*):
*MPLLLLLPLLWAGALAM*HHHHHH*GGG*DPNFWLQVQESVTVQEGLCVLVPCTFFHPIPYYDK
NSPVHGYWFREGAIISRDSPVATNKLDQEVQEETQGRFRLLGDPSRNNCSLSIVDARRRDNGS
YFFRMERGSTKYSYKSPQLSVHVTYVPQNPTTGIFPGDGSGKQETRAGVVHGAIGGAGVTALL
ALCLCLIFFIV*KTHRRKAARTAVGRNDTHPTTGSASPKHQKKSKLHGPTETSSCSGAAPTVEMD
EELHYASLNFHGMNPSKDTSTEYSEVRTQ* (SEQ ID NO: 138)

**CD33 V-set construct (exon 3 and 4 deleted) nucleotides (*CD33 signal peptide is in bold and italicized*; 6-histidine tag is underlined; *3 x glycine linker is italicized, bold, and underlined***; CD33 extracellular domain lacking CD33 amino acids 140-232 is in normal font; CD33 transmembrane domain is double underlined; and *CD33 intracellular domain is italicized*):
*ATGCCTCTGCTGCTACTGCTACCTCTGCTGTGGGCTGGAGCCCTGGCTATG*CATCATCAC
CACCATCAC*GGCGGCGGC*GATCCAAATTTCTGGCTGCAAGTGCAGGAGTCAGTGACGGTA
CAGGAGGGTTTGTGCGTCCTCGTGCCCTGCACTTTCTTCCATCCCATACCCTACTACGACA
AGAACTCCCCAGTTCATGGTTACTGGTTCCGGGAAGGAGCCATTATATCCAGGGACTCTCC
AGTGGCCACAAACAAGCTAGATCAAGAAGTACAGGAGGAGACTCAGGGCAGATTCCGCCT
CCTTGGGGATCCCAGTAGGAACAACTGCTCCCTGAGCATCGTAGACGCCAGGAGGAGGG
ATAATGGTTCATACTTCTTTCGGATGGAGAGAGGAAGTACCAAATACAGTTACAAATCTCCC
CAGCTCTCTGTGCATGTGACATATGTTCCACAGAACCCAACAACTGGTATCTTTCCAGGAG
ATGGCTCAGGGAAACAAGAGACCAGAGCAGGAGTGGTTCATGGGGCCATTGGAGGAGCT
GGTGTTACAGCCCTGCTCGCTCTTTGTCTCTGCCTCATCTTCTTCATAGTG*AAGACCCACA
GGAGGAAAGCAGCCAGGACAGCAGTGGGCAGGAATGACACCCACCCTACCACAGGGTCA
GCCTCCCCGAAACACCAGAAGAAGTCCAAGTTACATGGCCCCACTGAAACCTCAAGCTGTT
CAGGTGCCGCCCCTACTGTGGAGATGGATGAGGAGCTGCATTATGCTTCCCTCAACTTTCA
TGGGATGAATCCTTCCAAGGACACCTCCACCGAATACTCAGAGGTCAGGACCCAG*(SEQ ID
NO: 139)

CD33 signal peptide: MPLLLLLPLLWAGALAM (SEQ ID NO: 140)

FIG. 14 cont'd

CD33 signal peptide coding sequence:
ATGCCTCTGCTGCTACTGCTACCTCTGCTGTGGGCTGGAGCCCTGGCTATG (SEQ ID NO: 141)

6-histidine tag: HHHHHH (SEQ ID NO: 142)

6-histidine tag coding sequence: CATCATCACCACCATCAC (SEQ ID NO: 143)

3 x glycine linker: GGG

3 x glycine linker coding sequence: GGCGGCGGC

CD33 extracellular domain:
DPNFWLQVQESVTVQEGLCVLVPCTFFHPIPYYDKNSPVHGYWFREGAIISRDSPVATNKLDQ
EVQEETQGRFRLLGDPSRNNCSLSIVDARRRDNGSYFFRMERGSTKYSYKSPQLSVHVTDLT
HRPKILIPGTLEPGHSKNLTCSVSWACEQGTPPIFSWLSAAPTSLGPRTTHSSVLIITPRPQDHG
TNLTCQVKFAGAGVTTERTIQLNVTYVPQNPTTGIFPGDGSGKQETRAGVVH (SEQ ID NO: 145)

CD33 extracellular domain coding sequence:
GATCCAAATTTCTGGCTGCAAGTGCAGGAGTCAGTGACGGTACAGGAGGGTTTGTGCGTC
CTCGTGCCCTGCACTTTCTTCCATCCCATACCCTACTACGACAAGAACTCCCCAGTTCATG
GTTACTGGTTCCGGGAAGGAGCCATTATATCCAGGGACTCTCCAGTGGCCACAAACAAGC
TAGATCAAGAAGTACAGGAGGAGACTCAGGGCAGATTCCGCCTCCTTGGGGATCCCAGTA
GGAACAACTGCTCCCTGAGCATCGTAGACGCCAGGAGGAGGGATAATGGTTCATACTTCT
TTCGGATGGAGAGAGGAAGTACCAAATACAGTTACAAATCTCCCCAGCTCTCTGTGCATGT
GACAGACTTGACCCACAGGCCCAAAATCCTCATCCCTGGCACTCTAGAACCCGGCCACTC
CAAAAACCTGACCTGCTCTGTGTCCTGGGCCTGTGAGCAGGGAACACCCCCGATCTTCTC
CTGGTTGTCAGCTGCCCCCACCTCCCTGGGCCCCAGGACTACTCACTCCTCGGTGCTCAT
AATCACCCCACGGCCCCAGGACCACGGCACCAACCTGACCTGTCAGGTGAAGTTCGCTGG
AGCTGGTGTGACTACGGAGAGAACCATCCAGCTGAACGTCACCTATGTTCCACAGAACCC
AACAACTGGTATCTTTCCAGGAGATGGCTCAGGGAAACAAGAGACCAGAGCAGGAGTGGT
TCAT (SEQ ID NO: 146)

CD33 extracellular domain lacking CD33 amino acids 140-232:
DPNFWLQVQESVTVQEGLCVLVPCTFFHPIPYYDKNSPVHGYWFREGAIISRDSPVATNKLDQ
EVQEETQGRFRLLGDPSRNNCSLSIVDARRRDNGSYFFRMERGSTKYSYKSPQLSVHVTYVP
QNPTTGIFPGDGSGKQETRAGVVH (SEQ ID NO: 147)

CD33 extracellular domain lacking CD33 amino acids 140-232 coding sequence:
GATCCAAATTTCTGGCTGCAAGTGCAGGAGTCAGTGACGGTACAGGAGGGTTTGTGCGTC
CTCGTGCCCTGCACTTTCTTCCATCCCATACCCTACTACGACAAGAACTCCCCAGTTCATG
GTTACTGGTTCCGGGAAGGAGCCATTATATCCAGGGACTCTCCAGTGGCCACAAACAAGC
TAGATCAAGAAGTACAGGAGGAGACTCAGGGCAGATTCCGCCTCCTTGGGGATCCCAGTA
GGAACAACTGCTCCCTGAGCATCGTAGACGCCAGGAGGAGGGATAATGGTTCATACTTCT
TTCGGATGGAGAGAGGAAGTACCAAATACAGTTACAAATCTCCCCAGCTCTCTGTGCATGT

FIG. 14 cont'd

GACATATGTTCCACAGAACCCAACAACTGGTATCTTTCCAGGAGATGGCTCAGGGAAACAA
GAGACCAGAGCAGGAGTGGTTCAT (SEQ ID NO: 148)

CD33 transmembrane domain: GAIGGAGVTALLALCLCLIFFIV (SEQ ID NO: 149)

CD33 transmembrane domain coding sequence:
GGGGCCATTGGAGGAGCTGGTGTTACAGCCCTGCTCGCTCTTTGTCTCTGCCTCATCTTCT
TCATAGTG (SEQ ID NO: 150)

CD33 intracellular domain:
KTHRRKAARTAVGRNDTHPTTGSASPKHQKKSKLHGPTETSSCSGAAPTVEMDEELHYASLN
FHGMNPSKDTSTEYSEVRTQ (SEQ ID NO: 151)

CD33 intracellular domain coding sequence:
AAGACCCACAGGAGGAAAGCAGCCAGGACAGCAGTGGGCAGGAATGACACCCACCCTAC
CACAGGGTCAGCCTCCCCGAAACACCAGAAGAAGTCCAAGTTACATGGCCCCACTGAAAC
CTCAAGCTGTTCAGGTGCCGCCCCTACTGTGGAGATGGATGAGGAGCTGCATTATGCTTC
CCTCAACTTTCATGGGATGAATCCTTCCAAGGACACCTCCACCGAATACTCAGAGGTCAGG
ACCCAG (SEQ ID NO: 152)

Portion of CD22 extracellular domain that contains CD22 domains defined as Ig-like C2-type 3, Ig-like C2-type 4, Ig-like C2-type 5, Ig-like C2-type 6:
PEPSTVQILHSPAVEGSQVEFLCMSLANPLPTNYTWYHNGKEMQGRTEEKVHIPKILPWHAGT
YSCVAENILGTGQRGPGAELDVQYPPKKVTTVIQNPMPIREGDTVTLSCNYNSSNPSVTRYEW
KPHGAWEEPSLGVLKIQNVGWDNTTIACAACNSWCSWASPVALNVQYAPRDVRVRKIKPLSEI
HSGNSVSLQCDFSSSHPKEVQFFWEKNGRLLGKESQLNFDSISPEDAGSYSCWVNNSIGQTA
SKAWTLEVLYAPRRLRVSMSPGDQVMEGKSATLTCESDANPPVSHYTWFDWNNQSLPYHSQ
KLRLEPVKVQHSGAYWCQGTNSVGKGRSPLSTLTVYYSPET (SEQ ID NO: 153)

Portion of CD22 extracellular domain that contains CD22 domains defined as Ig-like C2-type 3, Ig-like C2-type 4, Ig-like C2-type 5, Ig-like C2-type 6 coding sequence:
CCGGAACCTTCCACGGTTCAGATCCTCCACTCACCGGCTGTGGAGGGAAGTCAAGTCGAG
TTTCTTTGCATGTCACTGGCCAATCCTCTTCCAACAAATTACACGTGGTACCACAATGGGAA
AGAAATGCAGGGAAGGACAGAGGAGAAAGTCCACATCCCAAAGATCCTCCCTTGGCACGC
TGGGACTTATTCCTGTGTGGCAGAAAACATTCTTGGTACTGGACAGAGGGGCCCTGGAGC
TGAGCTGGATGTCCAGTATCCTCCCAAGAAGGTGACCACAGTGATTCAAAACCCCATGCC
GATTCGAGAAGGAGACACAGTGACCCTTTCCTGTAACTACAATTCCAGTAACCCCAGTGTT
ACCCGGTATGAATGGAAACCCCATGGCGCCTGGGAGGAGCCATCGCTTGGGGTGCTGAA
GATCCAAAACGTTGGCTGGGACAACACAACCATCGCCTGCGCAGCTTGTAATAGTTGGTG
CTCGTGGGCCTCCCCTGTCGCCCTGAATGTCCAGTATGCCCCCCGAGACGTGAGGGTCC
GGAAAATCAAGCCCCTTTCCGAGATTCACTCTGGAAACTCGGTCAGCCTCCAATGTGACTT
CTCAAGCAGCCACCCCAAAGAAGTCCAGTTCTTCTGGGAGAAAAATGGCAGGCTTCTGGG
GAAAGAAAGCCAGCTGAATTTTGACTCCATCTCCCCAGAAGATGCTGGGAGTTACAGCTGC
TGGGTGAACAACTCCATAGGACAGACAGCGTCCAAGGCCTGGACACTTGAAGTGCTGTAT
GCACCCAGGAGGCTGCGTGTGTCCATGAGCCCAGGGGACCAAGTGATGGAGGGGAAGAG
TGCAACCCTGACCTGTGAGAGCGACGCCAACCCTCCCGTCTCCCACTACACCTGGTTTGA
CTGGAATAACCAAAGCCTCCCCTACCACAGCCAGAAGCTGAGATTGGAGCCGGTGAAGGT

FIG. 14 cont'd

CCAGCACTCGGGTGCCTACTGGTGCCAGGGGACCAACAGTGTGGGCAAGGGCCGTTCGC
CTCTCAGCACCCTCACCGTCTACTATAGCCCGGAGACC (SEQ ID NO: 154)

Portion of CD22 extracellular domain that contains CD22 domains defined as Ig-like C2-type 5, Ig-like C2-type 6:
PRDVRVRKIKPLSEIHSGNSVSLQCDFSSSHPKEVQFFWEKNGRLLGKESQLNFDSISPEDAG
SYSCWVNNSIGQTASKAWTLEVLYAPRRLRVSMSPGDQVMEGKSATLTCESDANPPVSHYT
WFDWNNQSLPYHSQKLRLEPVKVQHSGAYWCQGTNSVGKGRSPLSTLTVYYSPET (SEQ ID NO: 155)

Portion of CD22 extracellular domain that contains CD22 domains defined as Ig-like C2-type 5, Ig-like C2-type 6 coding sequence:
CCCCGAGACGTGAGGGTCCGGAAAATCAAGCCCCTTTCCGAGATTCACTCTGGAAACTCG
GTCAGCCTCCAATGTGACTTCTCAAGCAGCCACCCCAAAGAAGTCCAGTTCTTCTGGGAGA
AAAATGGCAGGCTTCTGGGGAAAGAAAGCCAGCTGAATTTTGACTCCATCTCCCCAGAAGA
TGCTGGGAGTTACAGCTGCTGGGTGAACAACTCCATAGGACAGACAGCGTCCAAGGCCTG
GACACTTGAAGTGCTGTATGCACCCAGGAGGCTGCGTGTGTCCATGAGCCCAGGGGACCA
AGTGATGGAGGGGAAGAGTGCAACCCTGACCTGTGAGAGCGACGCCAACCCTCCCGTCT
CCCACTACACCTGGTTTGACTGGAATAACCAAAGCCTCCCCTACCACAGCCAGAAGCTGA
GATTGGAGCCGGTGAAGGTCCAGCACTCGGGTGCCTACTGGTGCCAGGGGACCAACAGT
GTGGGCAAGGGCCGTTCGCCTCTCAGCACCCTCACCGTCTACTATAGCCCGGAGACC
(SEQ ID NO: 156)

1E6/CD3 bispecific molecule was generated as single chain antibody construct including 1E6 scFv in VH-VL orientation and binding domains specific for human CD3 using published sequences available in United States patent application publication US 16/317,657

**1E6/CD3 bispecific molecule (*IgK signal peptide is bold and italicized;*** 1E6 HcFv is underlined; *$G_4Sx3$ linker is italicized;* 1E6 LcFv is in normal font; *$G_4S$ linker is bold, italic and underlined;* CD3 HcFv is double underlined; CD3 LcFv is in bold; and *6-histidine tag is italic and underlined*):
*METDTLLLWVLLLWVPGSTG*QVQLVESGGGVVQPGRSLRLSCAASGFTFSSYDIHWVRQAP
GKGLEWVAVIWYDGSHNYYSDSVKGRFTISRDNSKNTLYLQMNSLRAEDTAVYYCARDYSGS
YYDYWGQGTLVTVSS*GGGGSGGGGSGGGGS*AIQMTQSPSSLSASVGDRVTITCRASQGIRN
DLGWYQQKPGKAPKLLIYAASNLQSGVPSRFSGSGSGTDFTLTISSLQPEDFATYYCLQDYSY
PRTFGQGTKVEIK*GGGGS*EVQLVESGGGLVQPGGSLKLSCAASGFTFNKYAMNWVRQAPGK
GLEWVARIRSKYNNYATYYADSVKDRFTISRDDSKNTAYLQMNNLKTEDTAVYYCVRHGNFGN
SYISYWAYWGQGTLVTVSS*GGGGSGGGGSGGGGS*QTVVTQEPSLTVSPGGTVTLTCGSSTG
AVTSGNYPNWVQQKPGQAPRGLIGGTKFLAPGTPARFSGSLLGGKAALTLSGVQPEDEAEY
YCVLWYSNRWVFGGGTKLTVL*HHHHHH* (SEQ ID NO: 157)

IgK signal peptide: METDTLLLWVLLLWVPGSTG (SEQ ID NO: 158)

**1H10 scFv VH-VL orientation (*IgK signal peptide is bold and italicized***; VH is underlined; *$G_4Sx3$ linker is italicized*; VL is normal font):
*METDTLLLWVLLLWVPGSTG*QVQLVQSGAEVKKPGASVKVSCKGSGYIFTSYDMHWVRQAP
GQGLEWMGIIDPSGGSTSYAQKFQGRVTMTRDTSMSTVYMELSSLRSEDTAVYYCTRDYSWS

FIG. 14 cont'd

YFDYWGQGTLVTVSS*GGGGSGGGGSGGGGS*AIQMTQSPSSLSASVGDRVTITCRASQGIRIYLGWYQQKPGKAPKLLIYATSSLQSGVPSRFSGSGSGTDFTLTISSLQPEDFATYYCLQDYNYPWTFGQGTKVEIK (SEQ ID NO: 230)

**1H10 scFv VL-VH orientation (*IgK signal peptide is bold and italicized*; VL is normal font; *$G_4Sx3$ linker is italicized*; VH is underlined):**
*METDTLLLWVLLLWVPGSTG*AIQMTQSPSSLSASVGDRVTITCRASQGIRIYLGWYQQKPGKAPKLLIYATSSLQSGVPSRFSGSGSGTDFTLTISSLQPEDFATYYCLQDYNYPWTFGQGTKVEIK*GGGGSGGGGSGGGGS*QVQLVQSGAEVKKPGASVKVSCKGSGYIFTSYDMHWVRQAPGQGLEWMGIIDPSGGSTSYAQKFQGRVTMTRDTSMSTVYMELSSLRSEDTAVYYCTRDYSWSYFDYWGQGTLVTVSS (SEQ ID NO: 231)

**1A9 scFv VH-VL orientation (*IgK signal peptide is bold and italicized*; VH is underlined; *$G_4Sx3$ linker is italicized*; VL is normal font):**
*METDTLLLWVLLLWVPGSTG*EVQLVESGGGLVQPGGSLRLSCAASGFTFSIYDMHWVRQATGKGLEWVSAIGTAGDTYYAGSVKGRFTISRENAKNSLYLQMNSLRAGDTAVYYCAREYSGYYFDYWGQGTLVTVSS*GGGGSGGGGSGGGGS*AIQMTQSPSSLSASVGDRVTITCRASQDIRNDLGWYQQKPGKAPKILIYGASSLQSGVPSRFSGSGSGTDFTFTISSLQPEDFATYYCLQEYNYPCTFGQGTKLEIK (SEQ ID NO: 232)

**1A9 scFv VL-VH orientation (*IgK signal peptide is bold and italicized*; VL is normal font; *$G_4Sx3$ linker is italicized*; VH is underlined):**
*METDTLLLWVLLLWVPGSTG*AIQMTQSPSSLSASVGDRVTITCRASQDIRNDLGWYQQKPGKAPKILIYGASSLQSGVPSRFSGSGSGTDFTFTISSLQPEDFATYYCLQEYNYPCTFGQGTKLEIK*GGGGSGGGGSGGGGS*EVQLVESGGGLVQPGGSLRLSCAASGFTFSIYDMHWVRQATGKGLEWVSAIGTAGDTYYAGSVKGRFTISRENAKNSLYLQMNSLRAGDTAVYYCAREYSGYYFDYWGQGTLVTVSS (SEQ ID NO: 233)

**1E6 scFv VH-VL orientation (*IgK signal peptide is bold and italicized*; VH is underlined; *$G_4Sx3$ linker is italicized*; VL is normal font):**
*METDTLLLWVLLLWVPGSTG*QVQLVESGGGVVQPGRSLRLSCAASGFTFSSYDIHWVRQAPGKGLEWVAVIWYDGSHNYYSDSVKGRFTISRDNSKNTLYLQMNSLRAEDTAVYYCARDYSGSYYDYWGQGTLVTVSS*GGGGSGGGGSGGGGS*AIQMTQSPSSLSASVGDRVTITCRASQGIRNDLGWYQQKPGKAPKLLIYAASNLQSGVPSRFSGSGSGTDFTLTISSLQPEDFATYYCLQDYSYPRTFGQGTKVEIK (SEQ ID NO: 234)

**1E6 scFv VL-VH orientation (*IgK signal peptide is bold and italicized*; VL is normal font; *$G_4Sx3$ linker is italicized*; VH is underlined):**
*METDTLLLWVLLLWVPGSTG*AIQMTQSPSSLSASVGDRVTITCRASQGIRNDLGWYQQKPGKAPKLLIYAASNLQSGVPSRFSGSGSGTDFTLTISSLQPEDFATYYCLQDYSYPRTFGQGTKVEIK*GGGGSGGGGSGGGGS*QVQLVESGGGVVQPGRSLRLSCAASGFTFSSYDIHWVRQAPGKGLEWVAVIWYDGSHNYYSDSVKGRFTISRDNSKNTLYLQMNSLRAEDTAVYYCARDYSGSYYDYWGQGTLVTVSS (SEQ ID NO: 235)

FIG. 14 cont'd

**2D3 scFv VH-VL orientation (*IgK signal peptide is bold and italicized*; VH is underlined; *$G_4Sx3$ linker is italicized*; VL is normal font):**
*METDTLLLWVLLLWVPGSTG*EVQLLESGGGLVQPGGSLSLSCAASGFTFSIYAMSWVRQAPG
KGLEWVSAISDSGGTTYYADSVKGRFTISRDNSKNMLYLEMNSLRAEDTAIYYCAKRTRYFNG
MDVWGQGTTVTVSS*GGGGSGGGGSGGGGS*EIVMTQSPATLSLSPGERATLSCRASQSGSS
SFLSWYQQKPGQAPRLLIYGASTRATGIPARFSGSGSGTDFTLTISSLQPEDFAVYYCQQDYNL
PFTFGPGTKVDIK (SEQ ID NO: 236)

**2D3 scFv VL-VH orientation (*IgK signal peptide is bold and italicized*; VL is normal font; *$G_4Sx3$ linker is italicized*; VH is underlined):**
*METDTLLLWVLLLWVPGSTG*EIVMTQSPATLSLSPGERATLSCRASQSGSSSFLSWYQQKPG
QAPRLLIYGASTRATGIPARFSGSGSGTDFTLTISSLQPEDFAVYYCQQDYNLPFTFGPGTKVDI
K*GGGGSGGGGSGGGGS*EVQLLESGGGLVQPGGSLSLSCAASGFTFSIYAMSWVRQAPGKG
LEWVSAISDSGGTTYYADSVKGRFTISRDNSKNMLYLEMNSLRAEDTAIYYCAKRTRYFNGMD
VWGQGTTVTVSS (SEQ ID NO: 237)

1H10 scFv VH-VL orientation, bispecific antibody CD33/CD3 engager:
METDTLLLWVLLLWVPGSTGQVQLVQSGAEVKKPGASVKVSCKGSGYIFTSYDMHWVRQAP
GQGLEWMGIIDPSGGSTSYAQKFQGRVTMTRDTSMSTVYMELSSLRSEDTAVYYCTRDYSWS
YFDYWGQGTLVTVSSGGGGSGGGGSGGGGSAIQMTQSPSSLSASVGDRVTITCRASQGIRIY
LGWYQQKPGKAPKLLIYATSSLQSGVPSRFSGSGSGTDFTLTISSLQPEDFATYYCLQDYNYP
WTFGQGTKVEIKGGGGSEVQLVESGGGLVQPGGSLKLSCAASGFTFNKYAMNWVRQAPGKG
LEWVARIRSKYNNYATYYADSVKDRFTISRDDSKNTAYLQMNNLKTEDTAVYYCVRHGNFGNS
YISYWAYWGQGTLVTVSSGGGGSGGGGSGGGGSQTVVTQEPSLTVSPGGTVTLTCGSSTGA
VTSGNYPNWVQQKPGQAPRGLIGGTKFLAPGTPARFSGSLLGGKAALTLSGVQPEDEAEYYC
VLWYSNRWVFGGGTKLTVLHHHHHH (SEQ ID NO: 238)

1H10 scFv VL-VH orientation, bispecific antibody CD33/CD3:
METDTLLLWVLLLWVPGSTGAIQMTQSPSSLSASVGDRVTITCRASQGIRIYLGWYQQKPGKA
PKLLIYATSSLQSGVPSRFSGSGSGTDFTLTISSLQPEDFATYYCLQDYNYPWTFGQGTKVEIK
GGGGSGGGGSGGGGSQVQLVQSGAEVKKPGASVKVSCKGSGYIFTSYDMHWVRQAPGQGL
EWMGIIDPSGGSTSYAQKFQGRVTMTRDTSMSTVYMELSSLRSEDTAVYYCTRDYSWSYFDY
WGQGTLVTVSSGGGGSEVQLVESGGGLVQPGGSLKLSCAASGFTFNKYAMNWVRQAPGKG
LEWVARIRSKYNNYATYYADSVKDRFTISRDDSKNTAYLQMNNLKTEDTAVYYCVRHGNFGNS
YISYWAYWGQGTLVTVSSGGGGSGGGGSGGGGSQTVVTQEPSLTVSPGGTVTLTCGSSTGA
VTSGNYPNWVQQKPGQAPRGLIGGTKFLAPGTPARFSGSLLGGKAALTLSGVQPEDEAEYYC
VLWYSNRWVFGGGTKLTVLHHHHHH (SEQ ID NO: 239)

1A9 scFv VH-VL orientation, bispecific antibody CD33/CD3 engager:
METDTLLLWVLLLWVPGSTGEVQLVESGGGLVQPGGSLRLSCAASGFTFSIYDMHWVRQATG
KGLEWVSAIGTAGDTYYAGSVKGRFTISRENAKNSLYLQMNSLRAGDTAVYYCAREYSGYYFD
YWGQGTLVTVSSGGGGSGGGGSGGGGSAIQMTQSPSSLSASVGDRVTITCRASQDIRNDLG
WYQQKPGKAPKILIYGASSLQSGVPSRFSGSGSGTDFTFTISSLQPEDFATYYCLQEYNYPCTF
GQGTKLEIKGGGGSEVQLVESGGGLVQPGGSLKLSCAASGFTFNKYAMNWVRQAPGKGLEW
VARIRSKYNNYATYYADSVKDRFTISRDDSKNTAYLQMNNLKTEDTAVYYCVRHGNFGNSYISY
WAYWGQGTLVTVSSGGGGSGGGGSGGGGSQTVVTQEPSLTVSPGGTVTLTCGSSTGAVTS
GNYPNWVQQKPGQAPRGLIGGTKFLAPGTPARFSGSLLGGKAALTLSGVQPEDEAEYYCVLW
YSNRWVFGGGTKLTVLHHHHHH (SEQ ID NO: 240)

FIG. 14 cont'd

1A9 scFv VL-VH orientation, bispecific antibody CD33/CD3 engager:
METDTLLLWVLLLWVPGSTGAIQMTQSPSSLSASVGDRVTITCRASQDIRNDLGWYQQKPGKA
PKILIYGASSLQSGVPSRFSGSGSGTDFTFTISSLQPEDFATYYCLQEYNYPCTFGQGTKLEIKG
GGGSGGGGSGGGGSEVQLVESGGGLVQPGGSLRLSCAASGFTFSIYDMHWVRQATGKGLE
WVSAIGTAGDTYYAGSVKGRFTISRENAKNSLYLQMNSLRAGDTAVYYCAREYSGYYFDYWG
QGTLVTVSSGGGGSEVQLVESGGGLVQPGGSLKLSCAASGFTFNKYAMNWVRQAPGKGLE
WVARIRSKYNNYATYYADSVKDRFTISRDDSKNTAYLQMNNLKTEDTAVYYCVRHGNFGNSYI
SYWAYWGQGTLVTVSSGGGGSGGGGSGGGGSQTVVTQEPSLTVSPGGTVTLTCGSSTGAV
TSGNYPNWVQQKPGQAPRGLIGGTKFLAPGTPARFSGSLLGGKAALTLSGVQPEDEAEYYCV
LWYSNRWVFGGGTKLTVLHHHHHH (SEQ ID NO: 241)

1E6 scFv VH-VL orientation, bispecific antibody CD33/CD3 engager:
METDTLLLWVLLLWVPGSTGQVQLVESGGGVVQPGRSLRLSCAASGFTFSSYDIHWVRQAPG
KGLEWVAVIWYDGSHNYYSDSVKGRFTISRDNSKNTLYLQMNSLRAEDTAVYYCARDYSGSY
YDYWGQGTLVTVSSGGGGSGGGGSGGGGSAIQMTQSPSSLSASVGDRVTITCRASQGIRND
LGWYQQKPGKAPKLLIYAASNLQSGVPSRFSGSGSGTDFTLTISSLQPEDFATYYCLQDYSYP
RTFGQGTKVEIKGGGGSEVQLVESGGGLVQPGGSLKLSCAASGFTFNKYAMNWVRQAPGKG
LEWVARIRSKYNNYATYYADSVKDRFTISRDDSKNTAYLQMNNLKTEDTAVYYCVRHGNFGNS
YISYWAYWGQGTLVTVSSGGGGSGGGGSGGGGSQTVVTQEPSLTVSPGGTVTLTCGSSTGA
VTSGNYPNWVQQKPGQAPRGLIGGTKFLAPGTPARFSGSLLGGKAALTLSGVQPEDEAEYYC
VLWYSNRWVFGGGTKLTVLHHHHHH (SEQ ID NO: 242)

1E6 scFv VL-VH orientation, bispecific antibody CD33/CD3 engager:
METDTLLLWVLLLWVPGSTGAIQMTQSPSSLSASVGDRVTITCRASQGIRNDLGWYQQKPGKA
PKLLIYAASNLQSGVPSRFSGSGSGTDFTLTISSLQPEDFATYYCLQDYSYPRTFGQGTKVEIK
GGGGSGGGGSGGGGSQVQLVESGGGVVQPGRSLRLSCAASGFTFSSYDIHWVRQAPGKGL
EWVAVIWYDGSHNYYSDSVKGRFTISRDNSKNTLYLQMNSLRAEDTAVYYCARDYSGSYYDY
WGQGTLVTVSSGGGGSEVQLVESGGGLVQPGGSLKLSCAASGFTFNKYAMNWVRQAPGKG
LEWVARIRSKYNNYATYYADSVKDRFTISRDDSKNTAYLQMNNLKTEDTAVYYCVRHGNFGNS
YISYWAYWGQGTLVTVSSGGGGSGGGGSGGGGSQTVVTQEPSLTVSPGGTVTLTCGSSTGA
VTSGNYPNWVQQKPGQAPRGLIGGTKFLAPGTPARFSGSLLGGKAALTLSGVQPEDEAEYYC
VLWYSNRWVFGGGTKLTVLHHHHHH (SEQ ID NO: 243)

2D3 scFv VH-VL orientation, bispecific antibody CD33/CD3 engager:
METDTLLLWVLLLWVPGSTGEVQLLESGGGLVQPGGSLSLSCAASGFTFSIYAMSWVRQAPG
KGLEWVSAISDSGGTTYYADSVKGRFTISRDNSKNMLYLEMNSLRAEDTAIYYCAKRTRYFNG
MDVWGQGTTVTVSSGGGGSGGGGSGGGGSEIVMTQSPATLSLSPGERATLSCRASQSGSS
SFLSWYQQKPGQAPRLLIYGASTRATGIPARFSGSGSGTDFTLTISSLQPEDFAVYYCQQDYNL
PFTFGPGTKVDIKGGGGSEVQLVESGGGLVQPGGSLKLSCAASGFTFNKYAMNWVRQAPGK
GLEWVARIRSKYNNYATYYADSVKDRFTISRDDSKNTAYLQMNNLKTEDTAVYYCVRHGNFGN
SYISYWAYWGQGTLVTVSSGGGGSGGGGSGGGGSQTVVTQEPSLTVSPGGTVTLTCGSSTG
AVTSGNYPNWVQQKPGQAPRGLIGGTKFLAPGTPARFSGSLLGGKAALTLSGVQPEDEAEYY
CVLWYSNRWVFGGGTKLTVLHHHHHH (SEQ ID NO: 244)

2D3 scFv VL-VH orientation, bispecific antibody CD33/CD3 engager:
METDTLLLWVLLLWVPGSTGEIVMTQSPATLSLSPGERATLSCRASQSGSSSFLSWYQQKPG
QAPRLLIYGASTRATGIPARFSGSGSGTDFTLTISSLQPEDFAVYYCQQDYNLPFTFGPGTKVDI
KGGGGSGGGGSGGGGSEVQLLESGGGLVQPGGSLSLSCAASGFTFSIYAMSWVRQAPGKG

FIG. 14 cont'd

LEWVSAISDSGGTTYYADSVKGRFTISRDNSKNMLYLEMNSLRAEDTAIYYCAKRTRYFNGMD
VWGQGTTVTVSSGGGGSEVQLVESGGGLVQPGGSLKLSCAASGFTFNKYAMNWVRQAPGK
GLEWVARIRSKYNNYATYYADSVKDRFTISRDDSKNTAYLQMNNLKTEDTAVYYCVRHGNFGN
SYISYWAYWGQGTLVTVSSGGGGSGGGGSGGGGSQTVVTQEPSLTVSPGGTVTLTCGSSTG
AVTSGNYPNWVQQKPGQAPRGLIGGTKFLAPGTPARFSGSLLGGKAALTLSGVQPEDEAEYY
CVLWYSNRWVFGGGTKLTVLHHHHHH (SEQ ID NO: 245)

human CD33 full length DNA coding (used for cell based immunogen; CD33 signal peptide coding sequence in bold):
ATGCCGCTGCTGCTACTGCTGCCCCTGCTGTGGGCAGGGGCCCTGGCTATGGATCCAAA
TTTCTGGCTGCAAGTGCAGGAGTCAGTGACGGTACAGGAGGGTTTGTGCGTCCTCGTGCC
CTGCACTTTCTTCCATCCCATACCCTACTACGACAAGAACTCCCCAGTTCATGGTTACTGGT
TCCGGGAAGGAGCCATTATATCCAGGGACTCTCCAGTGGCCACAAACAAGCTAGATCAAG
AAGTACAGGAGGAGACTCAGGGCAGATTCCGCCTCCTTGGGGATCCCAGTAGGAACAACT
GCTCCCTGAGCATCGTAGACGCCAGGAGGAGGGATAATGGTTCATACTTCTTTCGGATGG
AGAGAGGAAGTACCAAATACAGTTACAAATCTCCCCAGCTCTCTGTGCATGTGACAGACTT
GACCCACAGGCCCAAAATCCTCATCCCTGGCACTCTAGAACCCGGCCACTCCAAAAACCT
GACCTGCTCTGTGTCCTGGGCCTGTGAGCAGGGAACACCCCCGATCTTCTCCTGGTTGTC
AGCTGCCCCCACCTCCCTGGGCCCCAGGACTACTCACTCCTCGGTGCTCATAATCACCCC
ACGGCCCCAGGACCACGGCACCAACCTGACCTGTCAGGTGAAGTTCGCTGGAGCTGGTG
TGACTACGGAGAGAACCATCCAGCTCAACGTCACCTATGTTCCACAGAACCCAACAACTGG
TATCTTTCCAGGAGATGGCTCAGGGAAACAAGAGACCAGAGCAGGAGTGGTTCATGGGGC
CATTGGAGGAGCTGGTGTTACAGCCCTGCTCGCTCTTTGTCTCTGCCTCATCTTCTTCATA
GTGAAGACCCACAGGAGGAAAGCAGCCAGGACAGCAGTGGGCAGGAATGACACCCACCC
TACCACAGGGTCAGCCTCCCCGAAACACCAGAAGAAGTCCAAGTTACATGGCCCCACTGA
AACCTCAAGCTGTTCAGGTGCCGCCCCTACTGTGGAGATGGATGAGGAGCTGCATTATGC
TTCCCTCAACTTTCATGGGATGAATCCTTCCAAGGACACCTCCACCGAATACTCAGAGGTC
AGGACCCAG (SEQ ID NO: 246)

human CD33 full length protein (used for cell based immunogen):
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGVVHGAIGGAGVTALLALCLCLIFFIVKTHRRKAARTAVGRNDTHPTTGSASPKHQKKSKLHG
PTETSSCSGAAPTVEMDEELHYASLNFHGMNPSKDTSTEYSEVRTQ* (SEQ ID NO: 247)

1H10, 1A9, 1E6, and/or 1B9 light chain signal peptide: MDMRVPAQLLGLLLLWLPGARC (SEQ ID NO: 248)

1D2 light chain signal peptide: MRVPAQLLGLLLLWLPGARC (SEQ ID NO: 249)

1H8 light chain signal peptide: MDMRLPAQLLGLLMLWVPASRG (SEQ ID NO: 250)

2D3 light chain signal peptide: MEPWKPQHSFFFLLLWLPDSTG (SEQ ID NO: 251)

1H10 heavy chain signal peptide: MDWTWRVFCLLAVAPGVHS (SEQ ID NO: 252)

FIG. 14 cont'd

1A9 heavy chain signal peptide: MELGLSWVFLVAILEGVQC (SEQ ID NO: 253)

1E6 and/or 2E3 heavy chain signal peptide: MEFGLSWVFLVALLRGVQC (SEQ ID NO: 254)

1D2 heavy chain signal peptide: MESGLSWVFLVALLRGVQC (SEQ ID NO: 255)

1B9 heavy chain signal peptide: MEFGLSWVFLIALLRGVQC (SEQ ID NO: 256)

1H8 heavy chain signal peptide: MLLLVTSLLLCELPHPAFLLIP (SEQ ID NO: 257)

2D3 heavy chain signal peptide: MEFGLSWLFLVAILKGVQC (SEQ ID NO: 258)

V-set directed CD33/CD3 BsAb (RC1) (*Igk leader sequence italicized*; CD33 scFv in bold; *linker is italicized and underlined*; CD3 scFv is in normal text; and His tag is underlined):
*METDTLLLWVLLLWVPGSTG*QVQLVQSGAEVKKPGESVKVSCKASGYTFTNYGMNWVKQAPGQGLEWMGWINTYTGEPTYADKFQGRVTMTTDTSTSTAYMEIRNLGGDDTAVYYCARWSWSDGYYVYFDYWGQGTSVTVSSGGGGSGGGGSGGGGSDIVMTQSPDSLTVSLGERTTINCKSSQSVLDSSTNKNSLAWYQQKPGQPPKLLLSWASTRESGIPDRFSGSGSGTDFTLTIDSPQPEDSATYYCQQSAHFPITFGQGTRLEIK*SGGGGS*EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLHHHHHH (SEQ ID NO: 259)

V-set directed CD33/CD3 BsAb (RC1) without leader sequence or His tag (CD33 scFv in bold; *linker is italicized and underlined*; CD3 scFv is in normal text):
QVQLVQSGAEVKKPGESVKVSCKASGYTFTNYGMNWVKQAPGQGLEWMGWINTYTGEPTYADKFQGRVTMTTDTSTSTAYMEIRNLGGDDTAVYYCARWSWSDGYYVYFDYWGQGTSVTVSSGGGGSGGGGSGGGGSDIVMTQSPDSLTVSLGERTTINCKSSQSVLDSSTNKNSLAWYQQKPGQPPKLLLSWASTRESGIPDRFSGSGSGTDFTLTIDSPQPEDSATYYCQQSAHFPITFGQGTRLEIK*SGGGGS*EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL (SEQ ID NO: 260)
S

SEQUENCE LISTING

```
<160> NUMBER OF SEQ ID NOS: 260

<210> SEQ ID NO 1
<211> LENGTH: 726
<212> TYPE: PRT
<213> ORGANISM: Artificial Sequence
<220> FEATURE:
<223> OTHER INFORMATION: CD33:CD22 4D protein

<400> SEQUENCE: 1

Met Pro Leu Leu Leu Leu Leu Pro Leu Leu Trp Ala Gly Ala Leu Ala
1               5                   10                  15

Met His His His His His His Gly Gly Gly Asp Pro Asn Phe Trp Leu
            20                  25                  30

Gln Val Gln Glu Ser Val Thr Val Gln Glu Gly Leu Cys Val Leu Val
        35                  40                  45

Pro Cys Thr Phe Phe His Pro Ile Pro Tyr Tyr Asp Lys Asn Ser Pro
    50                  55                  60

Val His Gly Tyr Trp Phe Arg Glu Gly Ala Ile Ile Ser Arg Asp Ser
65                  70                  75                  80

Pro Val Ala Thr Asn Lys Leu Asp Gln Glu Val Gln Glu Glu Thr Gln
                85                  90                  95

Gly Arg Phe Arg Leu Leu Gly Asp Pro Ser Arg Asn Asn Cys Ser Leu
            100                 105                 110

Ser Ile Val Asp Ala Arg Arg Arg Asp Asn Gly Ser Tyr Phe Phe Arg
        115                 120                 125

Met Glu Arg Gly Ser Thr Lys Tyr Ser Tyr Lys Ser Pro Gln Leu Ser
    130                 135                 140

Val His Val Thr Asp Leu Thr His Arg Pro Lys Ile Leu Ile Pro Gly
145                 150                 155                 160
```

-continued

```
Thr Leu Glu Pro Gly His Ser Lys Asn Leu Thr Cys Ser Val Ser Trp
                165                 170                 175

Ala Cys Glu Gln Gly Thr Pro Pro Ile Phe Ser Trp Leu Ser Ala Ala
            180                 185                 190

Pro Thr Ser Leu Gly Pro Arg Thr Thr His Ser Ser Val Leu Ile Ile
        195                 200                 205

Thr Pro Arg Pro Gln Asp His Gly Thr Asn Leu Thr Cys Gln Val Lys
    210                 215                 220

Phe Ala Gly Ala Gly Val Thr Thr Glu Arg Thr Ile Gln Leu Asn Val
225                 230                 235                 240

Thr Tyr Val Pro Gln Asn Pro Thr Thr Gly Ile Phe Pro Gly Asp Gly
                245                 250                 255

Ser Gly Lys Gln Glu Thr Arg Ala Gly Val Val His Pro Glu Pro Ser
            260                 265                 270

Thr Val Gln Ile Leu His Ser Pro Ala Val Glu Gly Ser Gln Val Glu
        275                 280                 285

Phe Leu Cys Met Ser Leu Ala Asn Pro Leu Pro Thr Asn Tyr Thr Trp
    290                 295                 300

Tyr His Asn Gly Lys Glu Met Gln Gly Arg Thr Glu Glu Lys Val His
305                 310                 315                 320

Ile Pro Lys Ile Leu Pro Trp His Ala Gly Thr Tyr Ser Cys Val Ala
                325                 330                 335

Glu Asn Ile Leu Gly Thr Gly Gln Arg Gly Pro Gly Ala Glu Leu Asp
            340                 345                 350

Val Gln Tyr Pro Pro Lys Lys Val Thr Thr Val Ile Gln Asn Pro Met
        355                 360                 365

Pro Ile Arg Glu Gly Asp Thr Val Thr Leu Ser Cys Asn Tyr Asn Ser
    370                 375                 380

Ser Asn Pro Ser Val Thr Arg Tyr Glu Trp Lys Pro His Gly Ala Trp
385                 390                 395                 400

Glu Glu Pro Ser Leu Gly Val Leu Lys Ile Gln Asn Val Gly Trp Asp
                405                 410                 415

Asn Thr Thr Ile Ala Cys Ala Ala Cys Asn Ser Trp Cys Ser Trp Ala
            420                 425                 430

Ser Pro Val Ala Leu Asn Val Gln Tyr Ala Pro Arg Asp Val Arg Val
        435                 440                 445

Arg Lys Ile Lys Pro Leu Ser Glu Ile His Ser Gly Asn Ser Val Ser
    450                 455                 460

Leu Gln Cys Asp Phe Ser Ser Ser His Pro Lys Glu Val Gln Phe Phe
465                 470                 475                 480

Trp Glu Lys Asn Gly Arg Leu Leu Gly Lys Glu Ser Gln Leu Asn Phe
                485                 490                 495

Asp Ser Ile Ser Pro Glu Asp Ala Gly Ser Tyr Ser Cys Trp Val Asn
            500                 505                 510

Asn Ser Ile Gly Gln Thr Ala Ser Lys Ala Trp Thr Leu Glu Val Leu
        515                 520                 525

Tyr Ala Pro Arg Arg Leu Arg Val Ser Met Ser Pro Gly Asp Gln Val
    530                 535                 540

Met Glu Gly Lys Ser Ala Thr Leu Thr Cys Glu Ser Asp Ala Asn Pro
545                 550                 555                 560

Pro Val Ser His Tyr Thr Trp Phe Asp Trp Asn Asn Gln Ser Leu Pro
                565                 570                 575

Tyr His Ser Gln Lys Leu Arg Leu Glu Pro Val Lys Val Gln His Ser
```

```
            580                 585                 590

Gly Ala Tyr Trp Cys Gln Gly Thr Asn Ser Val Gly Lys Gly Arg Ser
        595                 600                 605

Pro Leu Ser Thr Leu Thr Val Tyr Tyr Ser Pro Glu Thr Gly Ala Ile
    610                 615                 620

Gly Gly Ala Gly Val Thr Ala Leu Leu Ala Leu Cys Leu Cys Leu Ile
625                 630                 635                 640

Phe Phe Ile Val Lys Thr His Arg Arg Lys Ala Ala Arg Thr Ala Val
                645                 650                 655

Gly Arg Asn Asp Thr His Pro Thr Thr Gly Ser Ala Ser Pro Lys His
            660                 665                 670

Gln Lys Lys Ser Lys Leu His Gly Pro Thr Glu Thr Ser Ser Cys Ser
        675                 680                 685

Gly Ala Ala Pro Thr Val Glu Met Asp Glu Glu Leu His Tyr Ala Ser
    690                 695                 700

Leu Asn Phe His Gly Met Asn Pro Ser Lys Asp Thr Ser Thr Glu Tyr
705                 710                 715                 720

Ser Glu Val Arg Thr Gln
                725


<210> SEQ ID NO 2
<211> LENGTH: 481
<212> TYPE: PRT
<213> ORGANISM: Artificial Sequence
<220> FEATURE:
<223> OTHER INFORMATION: Human full-length (FL)CD33 with a mouse Fc
      domain, used as an immunogen for human FL CD33

<400> SEQUENCE: 2

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205
```

```
Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Gly Gly Ser Gly Cys Lys Pro Cys Ile Cys Thr Val Pro Glu Val Ser
            260                 265                 270

Ser Val Phe Ile Phe Pro Pro Lys Pro Lys Asp Val Leu Thr Ile Thr
        275                 280                 285

Leu Thr Pro Lys Val Thr Cys Val Val Val Asp Ile Ser Lys Asp Asp
    290                 295                 300

Pro Glu Val Gln Phe Ser Trp Phe Val Asp Asp Val Glu Val His Thr
305                 310                 315                 320

Ala Gln Thr Gln Pro Arg Glu Glu Gln Phe Asn Ser Thr Phe Arg Ser
                325                 330                 335

Val Ser Glu Leu Pro Ile Met His Gln Asp Trp Leu Asn Gly Lys Glu
            340                 345                 350

Phe Lys Cys Arg Val Asn Ser Ala Ala Phe Pro Ala Pro Ile Glu Lys
        355                 360                 365

Thr Ile Ser Lys Thr Lys Gly Arg Pro Lys Ala Pro Gln Val Tyr Thr
    370                 375                 380

Ile Pro Pro Pro Lys Glu Gln Met Ala Lys Asp Lys Val Ser Leu Thr
385                 390                 395                 400

Cys Met Ile Thr Asp Phe Phe Pro Glu Asp Ile Thr Val Glu Trp Gln
                405                 410                 415

Trp Asn Gly Gln Pro Ala Glu Asn Tyr Lys Asn Thr Gln Pro Ile Met
            420                 425                 430

Asn Thr Asn Gly Ser Tyr Phe Val Tyr Ser Lys Leu Asn Val Gln Lys
        435                 440                 445

Ser Asn Trp Glu Ala Gly Asn Thr Phe Thr Cys Ser Val Leu His Glu
    450                 455                 460

Gly Leu His Asn His His Thr Glu Lys Ser Leu Ser His Ser Pro Gly
465                 470                 475                 480

Lys
```

```
<210> SEQ ID NO 3
<211> LENGTH: 354
<212> TYPE: PRT
<213> ORGANISM: Artificial Sequence
<220> FEATURE:
<223> OTHER INFORMATION: Human delta E2 version of CD33 (CD33 delta E2)
      with a mouse Fc domain, used as immunogen for human CD33 delta E2

<400> SEQUENCE: 3

Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80
```

-continued

```
Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Gly Gly Ser Gly Cys Lys Pro Cys Ile Cys Thr Val Pro Glu Val
    130                 135                 140

Ser Ser Val Phe Ile Phe Pro Pro Lys Pro Lys Asp Val Leu Thr Ile
145                 150                 155                 160

Thr Leu Thr Pro Lys Val Thr Cys Val Val Val Asp Ile Ser Lys Asp
                165                 170                 175

Asp Pro Glu Val Gln Phe Ser Trp Phe Val Asp Asp Val Glu Val His
            180                 185                 190

Thr Ala Gln Thr Gln Pro Arg Glu Glu Gln Phe Asn Ser Thr Phe Arg
        195                 200                 205

Ser Val Ser Glu Leu Pro Ile Met His Gln Asp Trp Leu Asn Gly Lys
    210                 215                 220

Glu Phe Lys Cys Arg Val Asn Ser Ala Ala Phe Pro Ala Pro Ile Glu
225                 230                 235                 240

Lys Thr Ile Ser Lys Thr Lys Gly Arg Pro Lys Ala Pro Gln Val Tyr
                245                 250                 255

Thr Ile Pro Pro Pro Lys Glu Gln Met Ala Lys Asp Lys Val Ser Leu
            260                 265                 270

Thr Cys Met Ile Thr Asp Phe Phe Pro Glu Asp Ile Thr Val Glu Trp
        275                 280                 285

Gln Trp Asn Gly Gln Pro Ala Glu Asn Tyr Lys Asn Thr Gln Pro Ile
    290                 295                 300

Met Asn Thr Asn Gly Ser Tyr Phe Val Tyr Ser Lys Leu Asn Val Gln
305                 310                 315                 320

Lys Ser Asn Trp Glu Ala Gly Asn Thr Phe Thr Cys Ser Val Leu His
                325                 330                 335

Glu Gly Leu His Asn His His Thr Glu Lys Ser Leu Ser His Ser Pro
            340                 345                 350

Gly Lys


<210> SEQ ID NO 4
<211> LENGTH: 489
<212> TYPE: PRT
<213> ORGANISM: Artificial Sequence
<220> FEATURE:
<223> OTHER INFORMATION: Extracellular domain of mouse CD33 where the
      C2-set Ig-like domain from mouse is replaced with the C2-set
      Ig-like domain from human CD33, combined with a Fc region from
      human lgG1, used as immunogen to generate antibodies against human
      C2-set domain of

<400> SEQUENCE: 4

Met Leu Trp Pro Leu Pro Leu Phe Leu Leu Cys Ala Gly Ser Leu Ala
1               5                   10                  15

Gln Asp Leu Glu Phe Gln Leu Val Ala Pro Glu Ser Val Thr Val Glu
            20                  25                  30

Glu Gly Leu Cys Val His Val Pro Cys Ser Val Phe Tyr Pro Ser Ile
        35                  40                  45

Lys Leu Thr Leu Gly Pro Val Thr Gly Ser Trp Leu Arg Lys Gly Val
    50                  55                  60
```

-continued

```
Ser Leu His Glu Asp Ser Pro Val Ala Thr Ser Asp Pro Arg Gln Leu
65                  70                  75                  80

Val Gln Lys Ala Thr Gln Gly Arg Phe Gln Leu Leu Gly Asp Pro Gln
                85                  90                  95

Lys His Asp Cys Ser Leu Phe Ile Arg Asp Ala Gln Lys Asn Asp Thr
            100                 105                 110

Gly Met Tyr Phe Phe Arg Val Val Arg Glu Pro Phe Val Arg Tyr Ser
        115                 120                 125

Tyr Lys Lys Ser Gln Leu Ser Leu His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Ser Glu Pro Lys Ser Ser Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
```

485

<210> SEQ ID NO 5
<211> LENGTH: 1470
<212> TYPE: DNA
<213> ORGANISM: Artificial Sequence
<220> FEATURE:
<223> OTHER INFORMATION: Extracellular domain of mouse CD33 (codon optimized) where the C2-set Ig-like domain from mouse is replaced with the C2-set Ig-like domain from human CD33, combined with a Fc region from human lgG1

<400> SEQUENCE: 5

```
atgctgtggc ctctgcctct gtttctgctg tgcgctggaa gtctggctca ggatctggaa     60

tttcagctgg tggctcccga atcagtcacc gtggaggagg gcctgtgcgt gcacgtgcct    120

tgtagcgtgt tctacccaag catcaagctg accctgggcc ctgtgacagg ctcctggctg    180

aggaagggcg tgtccctgca cgaggactct ccagtggcca ccagcgatcc taggcagctg    240

gtgcagaagg ccacacaggg cagattccag ctgctgggcg accctcagaa gcacgattgc    300

agcctgttta tccgcgacgc ccagaagaac gataccggca tgtatttctt tcgggtggtg    360

agagagccat tcgtgaggta ctcctataag aagtctcagc tgagcctgca cgtgaccgac    420

ctgacacacc gcccaaagat cctgatccca ggcaccctgg agcctggaca ctctaagaac    480

ctgacatgct ccgtgtcttg ggcatgtgag cagggaaccc cacctatctt ttcctggctg    540

tctgccgcac caacaagcct gggaccaagg accacacaca gctccgtgct gatcatcacc    600

cctagaccac aggatcacgg caccaatctg acatgccagg tgaagttcgc aggagcagga    660

gtgaccacag agaggaccat ccagctgaac gtgacatacg tgcctcagaa tccaaccaca    720

ggcatctttc caggcgacgg ctccggcaag caggagacac gggccggatc cgagcccaag    780

tctagcgata agacccacac atgcccacca tgtccagcac ctgagctgct gggaggacca    840

agcgtgttcc tgtttcctcc aaagcccaag gacacactga tgatctctcg gacccccgag    900

gtgacatgcg tggtggtgga cgtgagccac gaggaccccg aggtgaagtt taactggtac    960

gtggatggcg tggaggtgca caatgccaag accaagccca gggaggagca gtacaactcc   1020

acctatcgcg tggtgtctgt gctgacagtg ctgcaccagg actggctgaa cggcaaggag   1080

tataagtgca aggtgtccaa taaggccctg ccagccccca tcgagaagac catctctaag   1140

gcaaagggac agcccaggga gcctcaggtg tacacactgc cccctagccg cgacgagctg   1200

accaagaacc aggtgtccct gacatgtctg gtgaagggct tctatccttc tgatatcgcc   1260

gtggagtggg agagcaatgg ccagccagag aacaattaca agaccacacc acccgtgctg   1320

gacagcgatg gctccttctt tctgtatagc aagctgaccg tggataagtc caggtggcag   1380

cagggcaacg tgttcagctg ttccgtgatg cacgaagcac tgcacaacca ctacactcag   1440

aaatcactgt cactgtcccc aggaaagtaa                                    1470
```

<210> SEQ ID NO 6
<211> LENGTH: 284
<212> TYPE: PRT
<213> ORGANISM: Artificial Sequence
<220> FEATURE:
<223> OTHER INFORMATION: ECD of mouse CD33; C2-set Ig-like domain of human CD33 combined with the transmembrane domain and a truncated intracellular domain both derived from human CD33

<400> SEQUENCE: 6

```
Met Leu Trp Pro Leu Pro Leu Phe Leu Leu Cys Ala Gly Ser Leu Ala
1               5                   10                  15
```

```
Gln Asp Leu Glu Phe Gln Leu Val Ala Pro Glu Ser Val Thr Val Glu
            20                  25                  30

Glu Gly Leu Cys Val His Val Pro Cys Ser Val Phe Tyr Pro Ser Ile
        35                  40                  45

Lys Leu Thr Leu Gly Pro Val Thr Gly Ser Trp Leu Arg Lys Gly Val
    50                  55                  60

Ser Leu His Glu Asp Ser Pro Val Ala Thr Ser Asp Pro Arg Gln Leu
65                  70                  75                  80

Val Gln Lys Ala Thr Gln Gly Arg Phe Gln Leu Leu Gly Asp Pro Gln
                85                  90                  95

Lys His Asp Cys Ser Leu Phe Ile Arg Asp Ala Gln Lys Asn Asp Thr
            100                 105                 110

Gly Met Tyr Phe Phe Arg Val Val Arg Glu Pro Phe Val Arg Tyr Ser
        115                 120                 125

Tyr Lys Lys Ser Gln Leu Ser Leu His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr
        275                 280
```

```
<210> SEQ ID NO 7
<211> LENGTH: 855
<212> TYPE: DNA
<213> ORGANISM: Artificial Sequence
<220> FEATURE:
<223> OTHER INFORMATION: Extracellular domain of mouse CD33 where the
      C2-set Ig-like domain from mouse has been replaced with the C2-set
      Ig-like domain from human CD33 combined with the transmembrane
      domain and a truncated intracellular domain both derived from
      human CD33

<400> SEQUENCE: 7

atgctgtggc ctctgcctct gtttctgctg tgcgctggaa gtctggctca ggatctggaa      60

tttcagctgg tggctcccga atcagtcacc gtggaggagg gcctgtgcgt gcacgtgcct     120

tgtagcgtgt tctacccaag catcaagctg accctgggcc ctgtgacagg ctcctggctg     180

aggaagggcg tgtccctgca cgaggactct ccagtggcca ccagcgatcc taggcagctg     240

gtgcagaagg ccacacaggg cagattccag ctgctgggcg accctcagaa gcacgattgc     300

agcctgttta tccgcgacgc ccagaagaac gataccggca tgtatttctt tcgggtggtg     360

agagagccat tcgtgaggta ctcctataag aagtctcagc tgagcctgca cgtgaccgac     420
```

```
ctgacacacc gcccaaagat cctgatccca ggcaccctgg agcctggaca ctctaagaac    480

ctgacatgct ccgtgtcttg ggcatgtgag cagggaaccc cacctatctt ttcctggctg    540

tctgccgcac caacaagcct gggaccaagg accacacaca gctccgtgct gatcatcacc    600

cctagaccac aggatcacgg caccaatctg acatgccagg tgaagttcgc aggagcagga    660

gtgaccacag agaggaccat ccagctgaac gtgacatacg tgcctcagaa tccaaccaca    720

ggcatctttc caggcgacgg ctccggcaag caggagacac gggccggagt ggttcatggg    780

gccattggag gagctggtgt tacagccctg ctcgctcttt gtctctgcct catcttcttc    840

atagtgaaga cctga                                                     855
```

```
<210> SEQ ID NO 8
<211> LENGTH: 364
<212> TYPE: PRT
<213> ORGANISM: Homo sapiens

<400> SEQUENCE: 8

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Leu Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285
```

-continued

```
Ala Ala Arg Thr Ala Val Gly Ser Asn Asp Thr His Pro Thr Thr Gly
    290                 295                 300

Ser Ala Ser Pro Lys His Gln Lys Asn Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360


<210> SEQ ID NO 9
<211> LENGTH: 1095
<212> TYPE: DNA
<213> ORGANISM: Homo sapiens

<400> SEQUENCE: 9

atgccgctgc tgctactgct gcccctgctg tgggcagggg ccctggctat ggatccaaat      60

ttctggctgc aagtgcagga gtcagtgacg gtacaggagg gtttgtgcgt cctcgtgccc     120

tgcactttct tccatcccat accctactac gacaagaact ccccagttca tggttactgg     180

ttccgggaag gagccattat atccagggac tctccagtgg ccacaaacaa gctagatcaa     240

gaagtacagg aggagactca gggcagattc cgcctccttg gggatcccag taggaacaac     300

tgctccctga gcatcgtaga cgccaggagg agggataatg gttcatactt ctttcggatg     360

gagagaggaa gtaccaaata cagttacaaa tctccccagc tctctgtgca tgtgacagac     420

ttgacccaca ggcccaaaat cctcatccct ggcactctag aacccggcca ctccaaaaac     480

cttacctgct ctgtgtcctg ggcctgtgag cagggaacac cccgatctt ctcctggttg      540

tcagctgccc ccacctccct gggccccagg actactcact cctcggtgct cataatcacc     600

ccacggcccc aggaccacgg caccaacctg acctgtcagg tgaagttcgc tggagctggt     660

gtgactacgg agagaaccat ccagctcaac gtcacctatg ttccacagaa cccaacaact     720

ggtatctttc caggagatgg ctcagggaaa caagagacca gagcaggact ggttcatggg     780

gccattggag gagctggtgt tacagccctg ctcgctcttt gtctctgcct catcttcttc     840

atagtgaaga cccacaggag gaaagcagcc aggacagcag tgggcagcaa tgacacccac     900

cctaccacag ggtcagcctc cccgaaacac cagaagaact ccaagttaca tggccccact     960

gaaacctcaa gctgttcagg tgccgcccct actgtggaga tggatgagga gctgcattat    1020

gcttccctca actttcatgg gatgaatcct tccaaggaca cctccaccga atactcagag    1080

gtcaggaccc agtga                                                     1095


<210> SEQ ID NO 10
<211> LENGTH: 237
<212> TYPE: PRT
<213> ORGANISM: Homo sapiens

<400> SEQUENCE: 10

Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
```

-continued

```
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Leu Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Ser Asn Asp Thr His Pro Thr Thr
                165                 170                 175

Gly Ser Ala Ser Pro Lys His Gln Lys Asn Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235
```

<210> SEQ ID NO 11
<211> LENGTH: 714
<212> TYPE: DNA
<213> ORGANISM: Homo sapiens

<400> SEQUENCE: 11

```
atgccgctgc tgctactgct gcccctgctg tgggcagact tgacccacag gcccaaaatc     60

ctcatccctg gcactctaga acccggccac tccaaaaacc ttacctgctc tgtgtcctgg    120

gcctgtgagc agggaacacc cccgatcttc tcctggttgt cagctgcccc cacctccctg    180

ggccccagga ctactcactc ctcggtgctc ataatcaccc cacggcccca ggaccacggc    240

accaacctga cctgtcaggt gaagttcgct ggagctggtg tgactacgga gagaaccatc    300

cagctcaacg tcacctatgt tccacagaac ccaacaactg gtatctttcc aggagatggc    360

tcagggaaac aagagaccag agcaggactg gttcatgggg ccattggagg agctggtgtt    420

acagccctgc tcgctctttg tctctgcctc atcttcttca tagtgaagac ccacaggagg    480

aaagcagcca ggacagcagt gggcagcaat gacacccacc ctaccacagg gtcagcctcc    540

ccgaaacacc agaagaactc caagttacat ggccccactg aaacctcaag ctgttcaggt    600

gccgccccta ctgtggagat ggatgaggag ctgcattatg cttccctcaa ctttcatggg    660

atgaatcctt ccaaggacac ctccaccgaa tactcagagg tcaggaccca gtga          714
```

<210> SEQ ID NO 12
<211> LENGTH: 11
<212> TYPE: PRT
<213> ORGANISM: Artificial Sequence
<220> FEATURE:
<223> OTHER INFORMATION: CDRL1 of 1H10

<400> SEQUENCE: 12

```
Arg Ala Ser Gln Gly Ile Arg Ile Tyr Leu Gly
1               5                   10
```

<210> SEQ ID NO 13
<211> LENGTH: 8
<212> TYPE: PRT
<213> ORGANISM: Artificial Sequence
<220> FEATURE:
<223> OTHER INFORMATION: CDRL2 of 1H10 and/or 1D2

<400> SEQUENCE: 13

Tyr Ala Thr Ser Ser Leu Gln Ser
1 5

<210> SEQ ID NO 14
<211> LENGTH: 9
<212> TYPE: PRT
<213> ORGANISM: Artificial Sequence
<220> FEATURE:
<223> OTHER INFORMATION: CDRL3 of 1H10

<400> SEQUENCE: 14

Leu Gln Asp Tyr Asn Tyr Pro Trp Thr
1 5

<210> SEQ ID NO 15
<211> LENGTH: 13
<212> TYPE: PRT
<213> ORGANISM: Artificial Sequence
<220> FEATURE:
<223> OTHER INFORMATION: CDRH1 of 1H10

<400> SEQUENCE: 15

Lys Gly Ser Gly Tyr Ile Phe Thr Ser Tyr Asp Met His
1 5 10

<210> SEQ ID NO 16
<211> LENGTH: 10
<212> TYPE: PRT
<213> ORGANISM: Artificial Sequence
<220> FEATURE:
<223> OTHER INFORMATION: CDRH2 of 1H10

<400> SEQUENCE: 16

Ile Ile Asp Pro Ser Gly Gly Ser Thr Ser
1 5 10

<210> SEQ ID NO 17
<211> LENGTH: 11
<212> TYPE: PRT
<213> ORGANISM: Artificial Sequence
<220> FEATURE:
<223> OTHER INFORMATION: CDRH3 of 1H10

<400> SEQUENCE: 17

Thr Arg Asp Tyr Ser Trp Ser Tyr Phe Asp Tyr
1 5 10

<210> SEQ ID NO 18
<211> LENGTH: 11
<212> TYPE: PRT
<213> ORGANISM: Artificial Sequence
<220> FEATURE:
<223> OTHER INFORMATION: CDRL1 of 1A9 and/or 1B9

<400> SEQUENCE: 18

Arg Ala Ser Gln Asp Ile Arg Asn Asp Leu Gly
1 5 10

-continued

<210> SEQ ID NO 19
<211> LENGTH: 8
<212> TYPE: PRT
<213> ORGANISM: Artificial Sequence
<220> FEATURE:
<223> OTHER INFORMATION: CDRL2 of 1A9

<400> SEQUENCE: 19

Tyr Gly Ala Ser Ser Leu Gln Ser
1               5

<210> SEQ ID NO 20
<211> LENGTH: 9
<212> TYPE: PRT
<213> ORGANISM: Artificial Sequence
<220> FEATURE:
<223> OTHER INFORMATION: CDRL3 of 1A9

<400> SEQUENCE: 20

Leu Gln Glu Tyr Asn Tyr Pro Cys Thr
1               5

<210> SEQ ID NO 21
<211> LENGTH: 13
<212> TYPE: PRT
<213> ORGANISM: Artificial Sequence
<220> FEATURE:
<223> OTHER INFORMATION: CDRH1 of 1A9

<400> SEQUENCE: 21

Ala Ala Ser Gly Phe Thr Phe Ser Ile Tyr Asp Met His
1               5                   10

<210> SEQ ID NO 22
<211> LENGTH: 9
<212> TYPE: PRT
<213> ORGANISM: Artificial Sequence
<220> FEATURE:
<223> OTHER INFORMATION: CDRH2 of 1A9

<400> SEQUENCE: 22

Ala Ile Gly Thr Ala Gly Asp Thr Tyr
1               5

<210> SEQ ID NO 23
<211> LENGTH: 11
<212> TYPE: PRT
<213> ORGANISM: Artificial Sequence
<220> FEATURE:
<223> OTHER INFORMATION: CDRH3 of 1A9

<400> SEQUENCE: 23

Ala Arg Glu Tyr Ser Gly Tyr Tyr Phe Asp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: CDRL1 of 1E6 and/or 1D2

<400> SEQUENCE: 24

Arg Ala Ser Gln Gly Ile Arg Asn Asp Leu Gly
1               5                   10

```
<210> SEQ ID NO 25
<211> LENGTH: 8
<212> TYPE: PRT
<213> ORGANISM: Artificial Sequence
<220> FEATURE:
<223> OTHER INFORMATION: CDRL2 of 1E6

<400> SEQUENCE: 25

Tyr Ala Ala Ser Asn Leu Gln Ser
1               5


<210> SEQ ID NO 26
<211> LENGTH: 9
<212> TYPE: PRT
<213> ORGANISM: Artificial Sequence
<220> FEATURE:
<223> OTHER INFORMATION: CDRL3 of 1E6, 1D2, and/or 1B9

<400> SEQUENCE: 26

Leu Gln Asp Tyr Ser Tyr Pro Arg Thr
1               5


<210> SEQ ID NO 27
<211> LENGTH: 13
<212> TYPE: PRT
<213> ORGANISM: Artificial Sequence
<220> FEATURE:
<223> OTHER INFORMATION: CDRH1 of 1E6 and/or 1D2

<400> SEQUENCE: 27

Ala Ala Ser Gly Phe Thr Phe Ser Ser Tyr Asp Ile His
1               5                   10


<210> SEQ ID NO 28
<211> LENGTH: 10
<212> TYPE: PRT
<213> ORGANISM: Artificial Sequence
<220> FEATURE:
<223> OTHER INFORMATION: CDRH2 of 1E6 and/or 1D2

<400> SEQUENCE: 28

Val Ile Trp Tyr Asp Gly Ser His Asn Tyr
1               5                   10


<210> SEQ ID NO 29
<211> LENGTH: 11
<212> TYPE: PRT
<213> ORGANISM: Artificial Sequence
<220> FEATURE:
<223> OTHER INFORMATION: CDRH3 of 1E6 and/or 1D2

<400> SEQUENCE: 29

Ala Arg Asp Tyr Ser Gly Ser Tyr Tyr Asp Tyr
1               5                   10


<210> SEQ ID NO 30
<211> LENGTH: 10
<212> TYPE: PRT
<213> ORGANISM: Artificial Sequence
<220> FEATURE:
<223> OTHER INFORMATION: CDRH2 of 1D2

<400> SEQUENCE: 30

Val Ile Trp Tyr Asp Gly Ser Gln Lys Tyr
1               5                   10


<210> SEQ ID NO 31
```

-continued

<211> LENGTH: 8
<212> TYPE: PRT
<213> ORGANISM: Artificial Sequence
<220> FEATURE:
<223> OTHER INFORMATION: CDRL2 of 1B9

<400> SEQUENCE: 31

Tyr Ala Ala Ser Ser Leu Gln Ser
1 5

<210> SEQ ID NO 32
<211> LENGTH: 13
<212> TYPE: PRT
<213> ORGANISM: Artificial Sequence
<220> FEATURE:
<223> OTHER INFORMATION: CDRH1 of 1B9

<400> SEQUENCE: 32

Ala Ala Ser Gly Phe Ile Phe Ser Ser Tyr Asp Ile His
1 5 10

<210> SEQ ID NO 33
<211> LENGTH: 11
<212> TYPE: PRT
<213> ORGANISM: Artificial Sequence
<220> FEATURE:
<223> OTHER INFORMATION: CDRH3 of 1B9

<400> SEQUENCE: 33

Ala Arg Asp Tyr Ser Gly Ser Tyr Phe Asp Tyr
1 5 10

<210> SEQ ID NO 34
<211> LENGTH: 11
<212> TYPE: PRT
<213> ORGANISM: Artificial Sequence
<220> FEATURE:
<223> OTHER INFORMATION: CDRL1 of 1H8

<400> SEQUENCE: 34

Arg Ala Ser Gln Asn Ile Gly Gly Asn Leu His
1 5 10

<210> SEQ ID NO 35
<211> LENGTH: 7
<212> TYPE: PRT
<213> ORGANISM: Artificial Sequence
<220> FEATURE:
<223> OTHER INFORMATION: CDRL2 of 1H8

<400> SEQUENCE: 35

Tyr Ala Thr Gln Pro Phe Ser
1 5

<210> SEQ ID NO 36
<211> LENGTH: 9
<212> TYPE: PRT
<213> ORGANISM: Artificial Sequence
<220> FEATURE:
<223> OTHER INFORMATION: CDRL3 of 1H8

<400> SEQUENCE: 36

His Gln Ser Ser Ser Leu Pro Leu Thr
1 5

<210> SEQ ID NO 37
<211> LENGTH: 5

<212> TYPE: PRT
<213> ORGANISM: Artificial Sequence
<220> FEATURE:
<223> OTHER INFORMATION: CDRH1 of 1H8 and/or 2E3

<400> SEQUENCE: 37

Ser Tyr Gly Met His
1 5

<210> SEQ ID NO 38
<211> LENGTH: 16
<212> TYPE: PRT
<213> ORGANISM: Artificial Sequence
<220> FEATURE:
<223> OTHER INFORMATION: CDRH2 of 1H8

<400> SEQUENCE: 38

Ile Trp Tyr Asp Gly Ser Asn Glu Tyr Tyr Ala Asp Ser Val Lys Gly
1 5 10 15

<210> SEQ ID NO 39
<211> LENGTH: 8
<212> TYPE: PRT
<213> ORGANISM: Artificial Sequence
<220> FEATURE:
<223> OTHER INFORMATION: CDRH3 of 1H8

<400> SEQUENCE: 39

Asp Leu Asp Tyr Asp Ser Ser Gly
1 5

<210> SEQ ID NO 40
<211> LENGTH: 9
<212> TYPE: PRT
<213> ORGANISM: Artificial Sequence
<220> FEATURE:
<223> OTHER INFORMATION: CDRL1 of 2D3

<400> SEQUENCE: 40

Gln Ser Gly Ser Ser Ser Phe Leu Ser
1 5

<210> SEQ ID NO 41
<211> LENGTH: 7
<212> TYPE: PRT
<213> ORGANISM: Artificial Sequence
<220> FEATURE:
<223> OTHER INFORMATION: CDRL2 of 2D3

<400> SEQUENCE: 41

Gly Ala Ser Thr Arg Ala Thr
1 5

<210> SEQ ID NO 42
<211> LENGTH: 9
<212> TYPE: PRT
<213> ORGANISM: Artificial Sequence
<220> FEATURE:
<223> OTHER INFORMATION: CDRL3 of 2D3

<400> SEQUENCE: 42

Gln Gln Asp Tyr Asn Leu Pro Phe Thr
1 5

<210> SEQ ID NO 43
<211> LENGTH: 5
<212> TYPE: PRT

<213> ORGANISM: Artificial Sequence
<220> FEATURE:
<223> OTHER INFORMATION: CDRH1 of 2D3

<400> SEQUENCE: 43

Ile Tyr Ala Met Ser
1 5

<210> SEQ ID NO 44
<211> LENGTH: 16
<212> TYPE: PRT
<213> ORGANISM: Artificial Sequence
<220> FEATURE:
<223> OTHER INFORMATION: CDRH2 of 2D3

<400> SEQUENCE: 44

Ile Ser Asp Ser Gly Gly Thr Thr Tyr Tyr Ala Asp Ser Val Lys Gly
1 5 10 15

<210> SEQ ID NO 45
<211> LENGTH: 7
<212> TYPE: PRT
<213> ORGANISM: Artificial Sequence
<220> FEATURE:
<223> OTHER INFORMATION: CDRH3 of 2D3

<400> SEQUENCE: 45

Arg Thr Arg Tyr Phe Asn Gly
1 5

<210> SEQ ID NO 46
<211> LENGTH: 9
<212> TYPE: PRT
<213> ORGANISM: Artificial Sequence
<220> FEATURE:
<223> OTHER INFORMATION: CDRL1 of 2E3

<400> SEQUENCE: 46

Gln Ser Val Ser Ser Ser Tyr Leu Ala
1 5

<210> SEQ ID NO 47
<211> LENGTH: 7
<212> TYPE: PRT
<213> ORGANISM: Artificial Sequence
<220> FEATURE:
<223> OTHER INFORMATION: CDRL2 of 2E3

<400> SEQUENCE: 47

Gly Thr Ser Ser Arg Ala Thr
1 5

<210> SEQ ID NO 48
<211> LENGTH: 8
<212> TYPE: PRT
<213> ORGANISM: Artificial Sequence
<220> FEATURE:
<223> OTHER INFORMATION: CDRL3 of 2E3

<400> SEQUENCE: 48

Gln Gln Tyr Gly Ser Ser Pro Thr
1 5

<210> SEQ ID NO 49
<211> LENGTH: 16
<212> TYPE: PRT
<213> ORGANISM: Artificial Sequence

```
<220> FEATURE:
<223> OTHER INFORMATION: CDRH2 of 2E3

<400> SEQUENCE: 49

Ile Trp Tyr Gly Gly Ser Asn Lys Tyr Tyr Ala Asp Ser Val Lys Gly
1               5                   10                  15


<210> SEQ ID NO 50
<211> LENGTH: 11
<212> TYPE: PRT
<213> ORGANISM: Artificial Sequence
<220> FEATURE:
<223> OTHER INFORMATION: CDRH3 of 2E3

<400> SEQUENCE: 50

Asp Gly Thr Gly Glu Asn Tyr Tyr Tyr Tyr Val
1               5                   10


<210> SEQ ID NO 51
<211> LENGTH: 107
<212> TYPE: PRT
<213> ORGANISM: Artificial Sequence
<220> FEATURE:
<223> OTHER INFORMATION: 1H10 variable light chain

<400> SEQUENCE: 51

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ile Tyr
            20                  25                  30

Leu Gly Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105


<210> SEQ ID NO 52
<211> LENGTH: 118
<212> TYPE: PRT
<213> ORGANISM: Artificial Sequence
<220> FEATURE:
<223> OTHER INFORMATION: 1H10 variable heavy chain

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Ile Phe Thr Ser Tyr
            20                  25                  30

Asp Met His Trp Val Arg Gln Ala Pro Gly Gln Gly Leu Glu Trp Met
        35                  40                  45

Gly Ile Ile Asp Pro Ser Gly Gly Ser Thr Ser Tyr Ala Gln Lys Phe
    50                  55                  60

Gln Gly Arg Val Thr Met Thr Arg Asp Thr Ser Met Ser Thr Val Tyr
65                  70                  75                  80

Met Glu Leu Ser Ser Leu Arg Ser Glu Asp Thr Ala Val Tyr Tyr Cys
                85                  90                  95
```

```
Thr Arg Asp Tyr Ser Trp Ser Tyr Phe Asp Tyr Trp Gly Gln Gly Thr
            100                 105                 110

Leu Val Thr Val Ser Ser
        115


<210> SEQ ID NO 53
<211> LENGTH: 107
<212> TYPE: PRT
<213> ORGANISM: Artificial Sequence
<220> FEATURE:
<223> OTHER INFORMATION: 1A9 variable light chain

<400> SEQUENCE: 53

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Ile Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Glu Tyr Asn Tyr Pro Cys
                85                  90                  95

Thr Phe Gly Gln Gly Thr Lys Leu Glu Ile Lys
            100                 105


<210> SEQ ID NO 54
<211> LENGTH: 117
<212> TYPE: PRT
<213> ORGANISM: Artificial Sequence
<220> FEATURE:
<223> OTHER INFORMATION: 1A9 variable heavy chain

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Ala Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Tyr Ser Gly Tyr Tyr Phe Asp Tyr Trp Gly Gln Gly Thr Leu
            100                 105                 110

Val Thr Val Ser Ser
        115


<210> SEQ ID NO 55
<211> LENGTH: 107
<212> TYPE: PRT
<213> ORGANISM: Artificial Sequence
<220> FEATURE:
<223> OTHER INFORMATION: 1E6 variable light chain
```

<400> SEQUENCE: 55

Ala Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Tyr Ser Tyr Pro Arg
85 90 95

Thr Phe Gly Gln Gly Thr Lys Val Glu Ile Lys
100 105

<210> SEQ ID NO 56
<211> LENGTH: 118
<212> TYPE: PRT
<213> ORGANISM: Artificial Sequence
<220> FEATURE:
<223> OTHER INFORMATION: 1E6 variable heavy chain

<400> SEQUENCE: 56

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Asp Ile His Trp Val Arg Gln Ala Pro Gly Lys Gly Leu Glu Trp Val
35 40 45

Ala Val Ile Trp Tyr Asp Gly Ser His Asn Tyr Tyr Ser Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Tyr Ser Gly Ser Tyr Tyr Asp Tyr Trp Gly Gln Gly Thr
100 105 110

Leu Val Thr Val Ser Ser
115

<210> SEQ ID NO 57
<211> LENGTH: 107
<212> TYPE: PRT
<213> ORGANISM: Artificial Sequence
<220> FEATURE:
<223> OTHER INFORMATION: 1D2 variable light chain

<400> SEQUENCE: 57

Ala Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Glu Leu Leu Ile
35 40 45

Tyr Ala Thr Ser Ser Leu Gln Ser Gly Val Pro Ser Arg Phe Ser Gly
50 55 60

```
Ser Gly Ser Gly Thr Asp Phe Thr Leu Ile Ile Ser Ser Leu Gln Pro
65                  70                  75                  80

Glu Asp Phe Ala Thr Tyr Tyr Cys Leu Gln Asp Tyr Ser Tyr Pro Arg
                85                  90                  95

Thr Phe Gly Gln Gly Thr Lys Val Glu Ile Lys
            100                 105


<210> SEQ ID NO 58
<211> LENGTH: 118
<212> TYPE: PRT
<213> ORGANISM: Artificial Sequence
<220> FEATURE:
<223> OTHER INFORMATION: 1D2 variable heavy chain

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Val Ile Trp Tyr Asp Gly Ser Gln Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Gly Ser Tyr Tyr Asp Tyr Trp Gly Gln Gly Thr
            100                 105                 110

Leu Val Thr Val Ser Ser
        115


<210> SEQ ID NO 59
<211> LENGTH: 107
<212> TYPE: PRT
<213> ORGANISM: Artificial Sequence
<220> FEATURE:
<223> OTHER INFORMATION: 1B9 variable light chain

<400> SEQUENCE: 59

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Leu Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Ser Tyr Pro Arg
                85                  90                  95

Thr Phe Gly Gln Gly Thr Thr Val Glu Ile Lys
            100                 105


<210> SEQ ID NO 60
<211> LENGTH: 118
<212> TYPE: PRT
```

<213> ORGANISM: Artificial Sequence
<220> FEATURE:
<223> OTHER INFORMATION: 1B9 variable heavy chain

<400> SEQUENCE: 60

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Asp Ile His Trp Val Arg Gln Ala Pro Gly Lys Gly Leu Glu Trp Val
        35                  40                  45

Ala Val Ile Trp Tyr Asp Gly Ser His Asn Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Gly Ser Tyr Phe Asp Tyr Trp Gly Gln Gly Thr
            100                 105                 110

Leu Val Thr Val Ser Ser
        115
```

<210> SEQ ID NO 61
<211> LENGTH: 107
<212> TYPE: PRT
<213> ORGANISM: Artificial Sequence
<220> FEATURE:
<223> OTHER INFORMATION: 1H8 variable light chain

<400> SEQUENCE: 61

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asn Ile Gly Gly Asn
            20                  25                  30

Leu His Trp Tyr Gln Gln Lys Pro Asp Gln Ser Pro Lys Leu Leu Ile
        35                  40                  45

Arg Tyr Ala Thr Gln Pro Phe Ser Gly Val Pro Ser Arg Phe Gly Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Leu
                85                  90                  95

Thr Phe Gly Gly Gly Thr Lys Val Glu Ile Lys
            100                 105
```

<210> SEQ ID NO 62
<211> LENGTH: 120
<212> TYPE: PRT
<213> ORGANISM: Artificial Sequence
<220> FEATURE:
<223> OTHER INFORMATION: 1H8 variable heavy chain

<400> SEQUENCE: 62

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45
```

```
Ala Val Ile Trp Tyr Asp Gly Ser Asn Glu Tyr Tyr Ala Asp Ser Val
    50                  55                  60

Lys Gly Arg Phe Thr Val Ser Arg Asp Asn Ser Lys His Thr Leu Tyr
65                  70                  75                  80

Leu Gln Met Asn Arg Leu Arg Ala Glu Asp Thr Ala Val Tyr Tyr Cys
                85                  90                  95

Ala Arg Asp Leu Asp Tyr Asp Ser Ser Gly Gly Asp Tyr Trp Gly Gln
            100                 105                 110

Gly Ile Leu Val Leu Val Ser Ser
        115                 120


<210> SEQ ID NO 63
<211> LENGTH: 108
<212> TYPE: PRT
<213> ORGANISM: Artificial Sequence
<220> FEATURE:
<223> OTHER INFORMATION: 2D3 variable light chain

<400> SEQUENCE: 63

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Gly Ser Ser Ser
            20                  25                  30

Phe Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Phe Thr Phe Gly Pro Gly Thr Lys Val Asp Ile Lys
            100                 105


<210> SEQ ID NO 64
<211> LENGTH: 119
<212> TYPE: PRT
<213> ORGANISM: Artificial Sequence
<220> FEATURE:
<223> OTHER INFORMATION: 2D3 variable heavy chain

<400> SEQUENCE: 64

Glu Val Gln Leu Leu Glu Ser Gly Gly Gly Leu Val Gln Pro Gly Gly
1               5                   10                  15

Ser Leu Ser Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Ala Ile Ser Asp Ser Gly Gly Thr Thr Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Glu Met Asn Ser Leu Arg Ala Glu Asp Thr Ala Ile Tyr Tyr Cys
                85                  90                  95

Ala Lys Arg Thr Arg Tyr Phe Asn Gly Met Asp Val Trp Gly Gln Gly
            100                 105                 110

Thr Thr Val Thr Val Ser Ser
```

115

<210> SEQ ID NO 65
<211> LENGTH: 107
<212> TYPE: PRT
<213> ORGANISM: Artificial Sequence
<220> FEATURE:
<223> OTHER INFORMATION: 2E3 variable light chain

<400> SEQUENCE: 65

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys
            100                 105
```

<210> SEQ ID NO 66
<211> LENGTH: 122
<212> TYPE: PRT
<213> ORGANISM: Artificial Sequence
<220> FEATURE:
<223> OTHER INFORMATION: 2E3 variable heavy chain

<400> SEQUENCE: 66

```
Gln Val Cys Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Gly Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Gly Glu Asn Tyr Tyr Tyr Tyr Val Met Asp Val
            100                 105                 110

Trp Gly Gln Gly Thr Thr Val Thr Val Ser
        115                 120
```

<210> SEQ ID NO 67
<211> LENGTH: 10
<212> TYPE: PRT
<213> ORGANISM: Artificial Sequence
<220> FEATURE:
<223> OTHER INFORMATION: CDRL1 of OKT3

<400> SEQUENCE: 67

```
Ser Ala Ser Ser Ser Val Ser Tyr Met Asn
1               5                   10
```

-continued

<210> SEQ ID NO 68
<211> LENGTH: 11
<212> TYPE: PRT
<213> ORGANISM: Artificial Sequence
<220> FEATURE:
<223> OTHER INFORMATION: CDRL2 of OKT3

<400> SEQUENCE: 68

Arg Trp Ile Tyr Asp Thr Ser Lys Leu Ala Ser
1 5 10

<210> SEQ ID NO 69
<211> LENGTH: 9
<212> TYPE: PRT
<213> ORGANISM: Artificial Sequence
<220> FEATURE:
<223> OTHER INFORMATION: CDRL3 of OKT3

<400> SEQUENCE: 69

Gln Gln Trp Ser Ser Asn Pro Phe Thr
1 5

<210> SEQ ID NO 70
<211> LENGTH: 13
<212> TYPE: PRT
<213> ORGANISM: Artificial Sequence
<220> FEATURE:
<223> OTHER INFORMATION: CDRH1 of OKT3

<400> SEQUENCE: 70

Lys Ala Ser Gly Tyr Thr Phe Thr Arg Tyr Thr Met His
1 5 10

<210> SEQ ID NO 71
<211> LENGTH: 16
<212> TYPE: PRT
<213> ORGANISM: Artificial Sequence
<220> FEATURE:
<223> OTHER INFORMATION: CDRH2 of OKT3

<400> SEQUENCE: 71

Ile Asn Pro Ser Arg Gly Tyr Thr Asn Tyr Asn Gln Lys Phe Lys Asp
1 5 10 15

<210> SEQ ID NO 72
<211> LENGTH: 10
<212> TYPE: PRT
<213> ORGANISM: Artificial Sequence
<220> FEATURE:
<223> OTHER INFORMATION: CDRH3 of OKT3

<400> SEQUENCE: 72

Tyr Tyr Asp Asp His Tyr Cys Leu Asp Tyr
1 5 10

<210> SEQ ID NO 73
<211> LENGTH: 242
<212> TYPE: PRT
<213> ORGANISM: Artificial Sequence
<220> FEATURE:
<223> OTHER INFORMATION: OKT3 scFv

<400> SEQUENCE: 73

Gln Val Gln Leu Gln Gln Ser Gly Ala Glu Leu Ala Arg Pro Gly Ala
1 5 10 15

-continued

```
Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ser Gly Gly Gly Gly Ser Gly Gly Gly
        115                 120                 125

Gly Ser Gly Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met Asn Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Ala His Phe Arg Gly Ser Gly Ser Gly Thr Ser Tyr Ser Leu Thr
        195                 200                 205

Ile Ser Gly Met Glu Ala Glu Asp Ala Ala Thr Tyr Tyr Cys Gln Gln
    210                 215                 220

Trp Ser Ser Asn Pro Phe Thr Phe Gly Ser Gly Thr Lys Leu Glu Ile
225                 230                 235                 240

Asn Arg


<210> SEQ ID NO 74
<211> LENGTH: 11
<212> TYPE: PRT
<213> ORGANISM: Artificial Sequence
<220> FEATURE:
<223> OTHER INFORMATION: CDRL1 of 20G6-F3

<400> SEQUENCE: 74

Gln Ser Leu Val His Asn Asn Gly Asn Thr Tyr
1               5                   10


<210> SEQ ID NO 75
<211> LENGTH: 9
<212> TYPE: PRT
<213> ORGANISM: Artificial Sequence
<220> FEATURE:
<223> OTHER INFORMATION: CDRL3 of 20G6-F3, 4B4-D7, and/or  4E7-C9

<400> SEQUENCE: 75

Gly Gln Gly Thr Gln Tyr Pro Phe Thr
1               5


<210> SEQ ID NO 76
<211> LENGTH: 8
<212> TYPE: PRT
<213> ORGANISM: Artificial Sequence
<220> FEATURE:
<223> OTHER INFORMATION: CDRH1 of 20G6-F3

<400> SEQUENCE: 76
```

Gly Phe Thr Phe Thr Lys Ala Trp
1 5

<210> SEQ ID NO 77
<211> LENGTH: 10
<212> TYPE: PRT
<213> ORGANISM: Artificial Sequence
<220> FEATURE:
<223> OTHER INFORMATION: CDRH2 of 20G6-F3

<400> SEQUENCE: 77

Ile Lys Asp Lys Ser Asn Ser Tyr Ala Thr
1 5 10

<210> SEQ ID NO 78
<211> LENGTH: 12
<212> TYPE: PRT
<213> ORGANISM: Artificial Sequence
<220> FEATURE:
<223> OTHER INFORMATION: CDRH3 of 20G6-F3

<400> SEQUENCE: 78

Arg Gly Val Tyr Tyr Ala Leu Ser Pro Phe Asp Tyr
1 5 10

<210> SEQ ID NO 79
<211> LENGTH: 11
<212> TYPE: PRT
<213> ORGANISM: Artificial Sequence
<220> FEATURE:
<223> OTHER INFORMATION: CDRL1 of 4B4-D7

<400> SEQUENCE: 79

Gln Ser Leu Val His Asp Asn Gly Asn Thr Tyr
1 5 10

<210> SEQ ID NO 80
<211> LENGTH: 8
<212> TYPE: PRT
<213> ORGANISM: Artificial Sequence
<220> FEATURE:
<223> OTHER INFORMATION: CDRH1 of 4B4-D7 and/or 4E7-C9

<400> SEQUENCE: 80

Gly Phe Thr Phe Ser Asn Ala Trp
1 5

<210> SEQ ID NO 81
<211> LENGTH: 10
<212> TYPE: PRT
<213> ORGANISM: Artificial Sequence
<220> FEATURE:
<223> OTHER INFORMATION: CDRH2 of 4B4-D7

<400> SEQUENCE: 81

Ile Lys Ala Arg Ser Asn Asn Tyr Ala Thr
1 5 10

<210> SEQ ID NO 82
<211> LENGTH: 12
<212> TYPE: PRT
<213> ORGANISM: Artificial Sequence
<220> FEATURE:
<223> OTHER INFORMATION: CDRH3 of 4B4-D7

<400> SEQUENCE: 82

Arg Gly Thr Tyr Tyr Ala Ser Lys Pro Phe Asp Tyr
1 5 10

<210> SEQ ID NO 83
<211> LENGTH: 11
<212> TYPE: PRT
<213> ORGANISM: Artificial Sequence
<220> FEATURE:
<223> OTHER INFORMATION: CDRL1 of 4E7-C9

<400> SEQUENCE: 83

Gln Ser Leu Glu His Asn Asn Gly Asn Thr Tyr
1 5 10

<210> SEQ ID NO 84
<211> LENGTH: 10
<212> TYPE: PRT
<213> ORGANISM: Artificial Sequence
<220> FEATURE:
<223> OTHER INFORMATION: CDRH2 of 4E7-C9

<400> SEQUENCE: 84

Ile Lys Asp Lys Ser Asn Asn Tyr Ala Thr
1 5 10

<210> SEQ ID NO 85
<211> LENGTH: 13
<212> TYPE: PRT
<213> ORGANISM: Artificial Sequence
<220> FEATURE:
<223> OTHER INFORMATION: CDRH3 of 4E7-C9

<400> SEQUENCE: 85

Arg Tyr Val His Tyr Gly Ile Gly Tyr Ala Met Asp Ala
1 5 10

<210> SEQ ID NO 86
<211> LENGTH: 11
<212> TYPE: PRT
<213> ORGANISM: Artificial Sequence
<220> FEATURE:
<223> OTHER INFORMATION: CDRL1 of 18F5-H10

<400> SEQUENCE: 86

Gln Ser Leu Val His Thr Asn Gly Asn Thr Tyr
1 5 10

<210> SEQ ID NO 87
<211> LENGTH: 9
<212> TYPE: PRT
<213> ORGANISM: Artificial Sequence
<220> FEATURE:
<223> OTHER INFORMATION: CDRL3 of 18F5-H10

<400> SEQUENCE: 87

Gly Gln Gly Thr His Tyr Pro Phe Thr
1 5

<210> SEQ ID NO 88
<211> LENGTH: 8
<212> TYPE: PRT
<213> ORGANISM: Artificial Sequence
<220> FEATURE:
<223> OTHER INFORMATION: CDRH1 of 18F5-H10

<400> SEQUENCE: 88

Gly Phe Thr Phe Thr Asn Ala Trp

```
1               5


<210> SEQ ID NO 89
<211> LENGTH: 9
<212> TYPE: PRT
<213> ORGANISM: Artificial Sequence
<220> FEATURE:
<223> OTHER INFORMATION: CDRH2 of 18F5-H10

<400> SEQUENCE: 89

Lys Asp Lys Ser Asn Asn Tyr Ala Thr
1               5


<210> SEQ ID NO 90
<211> LENGTH: 13
<212> TYPE: PRT
<213> ORGANISM: Artificial Sequence
<220> FEATURE:
<223> OTHER INFORMATION: CDRH3 of 18F5-H10

<400> SEQUENCE: 90

Arg Tyr Val His Tyr Arg Phe Ala Tyr Ala Leu Asp Ala
1               5                   10


<210> SEQ ID NO 91
<211> LENGTH: 120
<212> TYPE: PRT
<213> ORGANISM: Artificial Sequence
<220> FEATURE:
<223> OTHER INFORMATION: TGN1412 variable heavy chain

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120


<210> SEQ ID NO 92
<211> LENGTH: 107
<212> TYPE: PRT
<213> ORGANISM: Artificial Sequence
<220> FEATURE:
<223> OTHER INFORMATION: TGN1412 variable light chain

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
```

```
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105


<210> SEQ ID NO 93
<211> LENGTH: 11
<212> TYPE: PRT
<213> ORGANISM: Artificial Sequence
<220> FEATURE:
<223> OTHER INFORMATION: anti-CD28 CDRL1

<400> SEQUENCE: 93

His Ala Ser Gln Asn Ile Tyr Val Trp Leu Asn
1               5                   10


<210> SEQ ID NO 94
<211> LENGTH: 7
<212> TYPE: PRT
<213> ORGANISM: Artificial Sequence
<220> FEATURE:
<223> OTHER INFORMATION: anti-CD28 CDRL2

<400> SEQUENCE: 94

Lys Ala Ser Asn Leu His Thr
1               5


<210> SEQ ID NO 95
<211> LENGTH: 9
<212> TYPE: PRT
<213> ORGANISM: Artificial Sequence
<220> FEATURE:
<223> OTHER INFORMATION: anti-CD28 CDRL3

<400> SEQUENCE: 95

Gln Gln Gly Gln Thr Tyr Pro Tyr Thr
1               5


<210> SEQ ID NO 96
<211> LENGTH: 10
<212> TYPE: PRT
<213> ORGANISM: Artificial Sequence
<220> FEATURE:
<223> OTHER INFORMATION: anti-CD28 CDRH1

<400> SEQUENCE: 96

Gly Tyr Thr Phe Thr Ser Tyr Tyr Ile His
1               5                   10


<210> SEQ ID NO 97
<211> LENGTH: 14
<212> TYPE: PRT
<213> ORGANISM: Artificial Sequence
<220> FEATURE:
<223> OTHER INFORMATION: anti-CD28 CDRH2

<400> SEQUENCE: 97

Cys Ile Tyr Pro Gly Asn Val Asn Thr Asn Tyr Asn Glu Lys
1               5                   10
```

-continued

<210> SEQ ID NO 98
<211> LENGTH: 11
<212> TYPE: PRT
<213> ORGANISM: Artificial Sequence
<220> FEATURE:
<223> OTHER INFORMATION: anti-CD28 CDRH3

<400> SEQUENCE: 98

Ser His Tyr Gly Leu Asp Trp Asn Phe Asp Val
1 5 10

<210> SEQ ID NO 99
<211> LENGTH: 5
<212> TYPE: PRT
<213> ORGANISM: Artificial Sequence
<220> FEATURE:
<223> OTHER INFORMATION: anti-CD28 CDRH1

<400> SEQUENCE: 99

Ser Tyr Tyr Ile His
1 5

<210> SEQ ID NO 100
<211> LENGTH: 17
<212> TYPE: PRT
<213> ORGANISM: Artificial Sequence
<220> FEATURE:
<223> OTHER INFORMATION: anti-CD28 CDRH2

<400> SEQUENCE: 100

Cys Ile Tyr Pro Gly Asn Val Asn Thr Asn Tyr Asn Glu Lys Phe Lys
1 5 10 15

Asp

<210> SEQ ID NO 101
<211> LENGTH: 7
<212> TYPE: PRT
<213> ORGANISM: Artificial Sequence
<220> FEATURE:
<223> OTHER INFORMATION: anti-4-1BB CDRL1

<400> SEQUENCE: 101

Arg Ala Ser Gln Ser Val Ser
1 5

<210> SEQ ID NO 102
<211> LENGTH: 6
<212> TYPE: PRT
<213> ORGANISM: Artificial Sequence
<220> FEATURE:
<223> OTHER INFORMATION: anti-4-1BB CDRL2

<400> SEQUENCE: 102

Ala Ser Asn Arg Ala Thr
1 5

<210> SEQ ID NO 103
<211> LENGTH: 10
<212> TYPE: PRT
<213> ORGANISM: Artificial Sequence
<220> FEATURE:
<223> OTHER INFORMATION: anti-4-1BB CDRL3

<400> SEQUENCE: 103

Gln Arg Ser Asn Trp Pro Pro Ala Leu Thr
1 5 10

<210> SEQ ID NO 104
<211> LENGTH: 4
<212> TYPE: PRT
<213> ORGANISM: Artificial Sequence
<220> FEATURE:
<223> OTHER INFORMATION: anti-4-1BB CDRH1

<400> SEQUENCE: 104

Tyr Tyr Trp Ser
1

<210> SEQ ID NO 105
<211> LENGTH: 12
<212> TYPE: PRT
<213> ORGANISM: Artificial Sequence
<220> FEATURE:
<223> OTHER INFORMATION: anti-4-1BB CDRH3

<400> SEQUENCE: 105

Tyr Gly Pro Gly Asn Tyr Asp Trp Tyr Phe Asp Leu
1 5 10

<210> SEQ ID NO 106
<211> LENGTH: 11
<212> TYPE: PRT
<213> ORGANISM: Artificial Sequence
<220> FEATURE:
<223> OTHER INFORMATION: anti-4-1BB CDRL1

<400> SEQUENCE: 106

Ser Gly Asp Asn Ile Gly Asp Gln Tyr Ala His
1 5 10

<210> SEQ ID NO 107
<211> LENGTH: 7
<212> TYPE: PRT
<213> ORGANISM: Artificial Sequence
<220> FEATURE:
<223> OTHER INFORMATION: anti-4-1BB CDRL2

<400> SEQUENCE: 107

Gln Asp Lys Asn Arg Pro Ser
1 5

<210> SEQ ID NO 108
<211> LENGTH: 11
<212> TYPE: PRT
<213> ORGANISM: Artificial Sequence
<220> FEATURE:
<223> OTHER INFORMATION: anti-4-1BB CDRL3

<400> SEQUENCE: 108

Ala Thr Tyr Thr Gly Phe Gly Ser Leu Ala Val
1 5 10

<210> SEQ ID NO 109
<211> LENGTH: 10
<212> TYPE: PRT
<213> ORGANISM: Artificial Sequence
<220> FEATURE:
<223> OTHER INFORMATION: anti-4-1BB CDRH1

<400> SEQUENCE: 109

Gly Tyr Ser Phe Ser Thr Tyr Trp Ile Ser
1 5 10

-continued

<210> SEQ ID NO 110
<211> LENGTH: 14
<212> TYPE: PRT
<213> ORGANISM: Artificial Sequence
<220> FEATURE:
<223> OTHER INFORMATION: anti-4-1BB CDRH2

<400> SEQUENCE: 110

Lys Ile Tyr Pro Gly Asp Ser Tyr Thr Asn Tyr Ser Pro Ser
1 5 10

<210> SEQ ID NO 111
<211> LENGTH: 7
<212> TYPE: PRT
<213> ORGANISM: Artificial Sequence
<220> FEATURE:
<223> OTHER INFORMATION: anti-4-1BB CDRH3

<400> SEQUENCE: 111

Gly Tyr Gly Ile Phe Asp Tyr
1 5

<210> SEQ ID NO 112
<211> LENGTH: 11
<212> TYPE: PRT
<213> ORGANISM: Artificial Sequence
<220> FEATURE:
<223> OTHER INFORMATION: CDRL1 of OKT8

<400> SEQUENCE: 112

Arg Thr Ser Arg Ser Ile Ser Gln Tyr Leu Ala
1 5 10

<210> SEQ ID NO 113
<211> LENGTH: 7
<212> TYPE: PRT
<213> ORGANISM: Artificial Sequence
<220> FEATURE:
<223> OTHER INFORMATION: CDRL2 of OKT8

<400> SEQUENCE: 113

Ser Gly Ser Thr Leu Gln Ser
1 5

<210> SEQ ID NO 114
<211> LENGTH: 9
<212> TYPE: PRT
<213> ORGANISM: Artificial Sequence
<220> FEATURE:
<223> OTHER INFORMATION: CDRL3 of OKT8

<400> SEQUENCE: 114

Gln Gln His Asn Glu Asn Pro Leu Thr
1 5

<210> SEQ ID NO 115
<211> LENGTH: 6
<212> TYPE: PRT
<213> ORGANISM: Artificial Sequence
<220> FEATURE:
<223> OTHER INFORMATION: CDRH1 of OKT8

<400> SEQUENCE: 115

Gly Phe Asn Ile Lys Asp
1 5

<210> SEQ ID NO 116
<211> LENGTH: 9
<212> TYPE: PRT
<213> ORGANISM: Artificial Sequence
<220> FEATURE:
<223> OTHER INFORMATION: CDRLH2 of OKT8

<400> SEQUENCE: 116

```
Arg Ile Asp Pro Ala Asn Asp Asn Thr
1               5
```

<210> SEQ ID NO 117
<211> LENGTH: 9
<212> TYPE: PRT
<213> ORGANISM: Artificial Sequence
<220> FEATURE:
<223> OTHER INFORMATION: CDRH3 of OKT8

<400> SEQUENCE: 117

```
Gly Tyr Gly Tyr Tyr Val Phe Asp His
1               5
```

<210> SEQ ID NO 118
<211> LENGTH: 109
<212> TYPE: PRT
<213> ORGANISM: Artificial Sequence
<220> FEATURE:
<223> OTHER INFORMATION: Variable light chain of KIR2DL1 and KIR2DL2/3

<400> SEQUENCE: 118

```
Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
            100                 105
```

<210> SEQ ID NO 119
<211> LENGTH: 123
<212> TYPE: PRT
<213> ORGANISM: Artificial Sequence
<220> FEATURE:
<223> OTHER INFORMATION: Variable heavy chain of KIR2DL1 and KIR2DL2/3

<400> SEQUENCE: 119

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
```

-continued

```
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120


<210> SEQ ID NO 120
<211> LENGTH: 20
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(20)
<223> OTHER INFORMATION: Any of residues 1 to 20 can be present or
      absent
<220> FEATURE:
<221> NAME/KEY: MISC_FEATURE
<222> LOCATION: (1)..(20)
<223> OTHER INFORMATION: Entire sequence can be repeated n times wherein
      n is an integer of 1, 2, 3, 4, 5, 6, 7, 8, 9 or 10).

<400> SEQUENCE: 120

Gly Gly Gly Gly Gly Gly Gly Gly Gly Gly Ser Ser Ser Ser Ser Ser
1               5                   10                  15

Ser Ser Ser Ser
            20


<210> SEQ ID NO 121
<211> LENGTH: 5
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(5)
<223> OTHER INFORMATION: (GlyGlyGlyGlySer) can be repeated n times,
      wherein n is an integer of 1, 2, 3, 4, 5, 6, 7, 8, 9 or 10.

<400> SEQUENCE: 121

Gly Gly Gly Gly Ser
1               5


<210> SEQ ID NO 122
<211> LENGTH: 9
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: (GlyGlyGlySer) can be repeated n times, wherein
      n is an integer of 1, 2, 3, 4, 5, 6, 7, 8, 9 or 10.
<220> FEATURE:
<221> NAME/KEY: MISC_FEATURE
<222> LOCATION: (5)..(9)
<223> OTHER INFORMATION: (GlyGlyGlyGlySer) can be repeated n times,
      wherein n is an integer of 1, 2, 3, 4, 5, 6, 7, 8, 9 or 10.

<400> SEQUENCE: 122

Gly Gly Gly Ser Gly Gly Gly Gly Ser
1               5
```

-continued

<210> SEQ ID NO 123
<211> LENGTH: 7
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: (GlyGlyGlySer) can be repeated n times, wherein n is an integer of 1, 2, 3, 4, 5, 6, 7, 8, 9 or 10.
<220> FEATURE:
<221> NAME/KEY: MISC_FEATURE
<222> LOCATION: (5)..(7)
<223> OTHER INFORMATION: (GlyGlySer) can be repeated n times, wherein n is an integer of 1, 2, 3, 4, 5, 6, 7, 8, 9 or 10.

<400> SEQUENCE: 123

Gly Gly Gly Ser Gly Gly Ser
1 5

<210> SEQ ID NO 124
<211> LENGTH: 9
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: (GlyGlyGlySer) can be repeated n times, wherein n is an integer of 1, 2, 3, 4, 5, 6, 7, 8, 9 or 10.

<400> SEQUENCE: 124

Gly Gly Gly Ser Gly Gly Gly Gly Ser
1 5

<210> SEQ ID NO 125
<211> LENGTH: 20
<212> TYPE: PRT
<213> ORGANISM: Artificial Sequence
<220> FEATURE:
<223> OTHER INFORMATION: GlySer linker

<400> SEQUENCE: 125

Gly Gly Gly Gly Ser Gly Gly Gly Gly Ser Gly Gly Gly Gly Ser Gly
1 5 10 15

Gly Gly Gly Ser
20

<210> SEQ ID NO 126
<211> LENGTH: 15
<212> TYPE: PRT
<213> ORGANISM: Artificial Sequence
<220> FEATURE:
<223> OTHER INFORMATION: GlySer linker

<400> SEQUENCE: 126

Gly Gly Gly Gly Ser Gly Gly Gly Gly Ser Gly Gly Gly Gly Ser
1 5 10 15

<210> SEQ ID NO 127
<211> LENGTH: 10
<212> TYPE: PRT
<213> ORGANISM: Artificial Sequence
<220> FEATURE:
<223> OTHER INFORMATION: GlySer linker

<400> SEQUENCE: 127

Gly Gly Gly Gly Ser Gly Gly Gly Gly Ser
1 5 10

<210> SEQ ID NO 128
<211> LENGTH: 5
<212> TYPE: PRT
<213> ORGANISM: Artificial Sequence
<220> FEATURE:
<223> OTHER INFORMATION: GlySer linker

<400> SEQUENCE: 128

Gly Gly Gly Gly Ser
1 5

<210> SEQ ID NO 129
<211> LENGTH: 8
<212> TYPE: PRT
<213> ORGANISM: Artificial Sequence
<220> FEATURE:
<223> OTHER INFORMATION: GlySer linker

<400> SEQUENCE: 129

Gly Gly Gly Ser Gly Gly Gly Ser
1 5

<210> SEQ ID NO 130
<211> LENGTH: 4
<212> TYPE: PRT
<213> ORGANISM: Artificial Sequence
<220> FEATURE:
<223> OTHER INFORMATION: GlySer linker

<400> SEQUENCE: 130

Gly Gly Gly Ser
1

<210> SEQ ID NO 131
<211> LENGTH: 6
<212> TYPE: PRT
<213> ORGANISM: Artificial Sequence
<220> FEATURE:
<223> OTHER INFORMATION: GlySer linker

<400> SEQUENCE: 131

Gly Gly Ser Gly Gly Ser
1 5

<210> SEQ ID NO 132
<211> LENGTH: 11
<212> TYPE: PRT
<213> ORGANISM: Artificial Sequence
<220> FEATURE:
<223> OTHER INFORMATION: GlySer linker

<400> SEQUENCE: 132

Gly Gly Ser Gly Gly Gly Ser Gly Gly Ser Gly
1 5 10

<210> SEQ ID NO 133
<211> LENGTH: 10
<212> TYPE: PRT
<213> ORGANISM: Artificial Sequence
<220> FEATURE:
<223> OTHER INFORMATION: GlySer linker

<400> SEQUENCE: 133

Gly Gly Ser Gly Gly Gly Ser Gly Ser Gly

-continued 1 5 10

<210> SEQ ID NO 134
<211> LENGTH: 8
<212> TYPE: PRT
<213> ORGANISM: Artificial Sequence
<220> FEATURE:
<223> OTHER INFORMATION: GlySer linker

<400> SEQUENCE: 134

Gly Gly Ser Gly Gly Gly Ser Gly
1 5

<210> SEQ ID NO 135
<211> LENGTH: 2178
<212> TYPE: DNA
<213> ORGANISM: Artificial Sequence
<220> FEATURE:
<223> OTHER INFORMATION: CD33:CD22 4D nucleotides

<400> SEQUENCE: 135
atgcctctgc tgctactgct acctctgctg tgggctggag ccctggctat gcatcatcac 60
caccatcacg gcggcggcga tccaaatttc tggctgcaag tgcaggagtc agtgacggta 120
caggagggtt tgtgcgtcct cgtgccctgc actttcttcc atcccatacc ctactacgac 180
aagaactccc cagttcatgg ttactggttc cgggaaggag ccattatatc cagggactct 240
ccagtggcca caaacaagct agatcaagaa gtacaggagg agactcaggg cagattccgc 300
ctccttgggg atcccagtag gaacaactgc tccctgagca tcgtagacgc caggaggagg 360
gataatggtt catacttctt tcggatggag agaggaagta ccaaatacag ttacaaatct 420
ccccagctct ctgtgcatgt gacagacttg acccacaggc ccaaaatcct catccctggc 480
actctagaac ccggccactc caaaaacctg acctgctctg tgtcctgggc ctgtgagcag 540
ggaacacccc cgatcttctc ctggttgtca gctgccccca cctccctggg ccccaggact 600
actcactcct cggtgctcat aatcacccca cggccccagg accacggcac caacctgacc 660
tgtcaggtga agttcgctgg agctggtgtg actacggaga gaaccatcca gctgaacgtc 720
acctatgttc cacagaaccc aacaactggt atctttccag gagatggctc agggaaacaa 780
gagaccagag caggagtggt tcatccggaa ccttccacgg ttcagatcct ccactcaccg 840
gctgtggagg gaagtcaagt cgagtttctt tgcatgtcac tggccaatcc tcttccaaca 900
aattacacgt ggtaccacaa tgggaaagaa atgcagggaa ggacagagga gaaagtccac 960
atcccaaaga tcctcccttg gcacgctggg acttattcct gtgtggcaga aaacattctt 1020
ggtactggac agaggggccc tggagctgag ctggatgtcc agtatcctcc caagaaggtg 1080
accacagtga ttcaaaaccc catgccgatt cgagaaggag acacagtgac cctttcctgt 1140
aactacaatt ccagtaaccc cagtgttacc cggtatgaat ggaaacccca tggcgcctgg 1200
gaggagccat cgcttggggt gctgaagatc caaaacgttg gctgggacaa cacaaccatc 1260
gcctgcgcag cttgtaatag ttggtgctcg tgggcctccc ctgtcgccct gaatgtccag 1320
tatgcccccc gagacgtgag ggtccggaaa atcaagcccc tttccgagat tcactctgga 1380
aactcggtca gcctccaatg tgacttctca agcagccacc ccaaagaagt ccagttcttc 1440
tgggagaaaa atggcaggct tctggggaaa gaaagccagc tgaattttga ctccatctcc 1500
ccagaagatg ctgggagtta cagctgctgg gtgaacaact ccataggaca gacagcgtcc 1560
aaggcctgga cacttgaagt gctgtatgca cccaggaggc tgcgtgtgtc catgagccca 1620

-continued

```
ggggaccaag tgatggaggg gaagagtgca accctgacct gtgagagcga cgccaaccct   1680

cccgtctccc actacacctg gtttgactgg aataaccaaa gcctccccta ccacagccag   1740

aagctgagat tggagccggt gaaggtccag cactcgggtg cctactggtg ccaggggacc   1800

aacagtgtgg gcaagggccg ttcgcctctc agcaccctca ccgtctacta tagcccggag   1860

accggggcca ttggaggagc tggtgttaca gccctgctcg ctctttgtct ctgcctcatc   1920

ttcttcatag tgaagaccca caggaggaaa gcagccagga cagcagtggg caggaatgac   1980

acccacccta ccacagggtc agcctccccg aaacaccaga agaagtccaa gttacatggc   2040

cccactgaaa cctcaagctg ttcaggtgcc gcccctactg tggagatgga tgaggagctg   2100

cattatgctt ccctcaactt tcatgggatg aatccttcca aggacacctc caccgaatac   2160

tcagaggtca ggacccag                                                 2178
```

```
<210> SEQ ID NO 136
<211> LENGTH: 552
<212> TYPE: PRT
<213> ORGANISM: Artificial Sequence
<220> FEATURE:
<223> OTHER INFORMATION: CD33:CD22 2D protein

<400> SEQUENCE: 136

Met Pro Leu Leu Leu Leu Leu Pro Leu Leu Trp Ala Gly Ala Leu Ala
1               5                   10                  15

Met His His His His His His Gly Gly Gly Asp Pro Asn Phe Trp Leu
            20                  25                  30

Gln Val Gln Glu Ser Val Thr Val Gln Glu Gly Leu Cys Val Leu Val
        35                  40                  45

Pro Cys Thr Phe Phe His Pro Ile Pro Tyr Tyr Asp Lys Asn Ser Pro
    50                  55                  60

Val His Gly Tyr Trp Phe Arg Glu Gly Ala Ile Ile Ser Arg Asp Ser
65                  70                  75                  80

Pro Val Ala Thr Asn Lys Leu Asp Gln Glu Val Gln Glu Glu Thr Gln
                85                  90                  95

Gly Arg Phe Arg Leu Leu Gly Asp Pro Ser Arg Asn Asn Cys Ser Leu
            100                 105                 110

Ser Ile Val Asp Ala Arg Arg Arg Asp Asn Gly Ser Tyr Phe Phe Arg
        115                 120                 125

Met Glu Arg Gly Ser Thr Lys Tyr Ser Tyr Lys Ser Pro Gln Leu Ser
    130                 135                 140

Val His Val Thr Asp Leu Thr His Arg Pro Lys Ile Leu Ile Pro Gly
145                 150                 155                 160

Thr Leu Glu Pro Gly His Ser Lys Asn Leu Thr Cys Ser Val Ser Trp
                165                 170                 175

Ala Cys Glu Gln Gly Thr Pro Pro Ile Phe Ser Trp Leu Ser Ala Ala
            180                 185                 190

Pro Thr Ser Leu Gly Pro Arg Thr Thr His Ser Ser Val Leu Ile Ile
        195                 200                 205

Thr Pro Arg Pro Gln Asp His Gly Thr Asn Leu Thr Cys Gln Val Lys
    210                 215                 220

Phe Ala Gly Ala Gly Val Thr Thr Glu Arg Thr Ile Gln Leu Asn Val
225                 230                 235                 240

Thr Tyr Val Pro Gln Asn Pro Thr Thr Gly Ile Phe Pro Gly Asp Gly
                245                 250                 255

Ser Gly Lys Gln Glu Thr Arg Ala Gly Val Val His Pro Arg Asp Val
```

```
            260                 265                 270

Arg Val Arg Lys Ile Lys Pro Leu Ser Glu Ile His Ser Gly Asn Ser
        275                 280                 285

Val Ser Leu Gln Cys Asp Phe Ser Ser Ser His Pro Lys Glu Val Gln
    290                 295                 300

Phe Phe Trp Glu Lys Asn Gly Arg Leu Leu Gly Lys Glu Ser Gln Leu
305                 310                 315                 320

Asn Phe Asp Ser Ile Ser Pro Glu Asp Ala Gly Ser Tyr Ser Cys Trp
                325                 330                 335

Val Asn Asn Ser Ile Gly Gln Thr Ala Ser Lys Ala Trp Thr Leu Glu
            340                 345                 350

Val Leu Tyr Ala Pro Arg Arg Leu Arg Val Ser Met Ser Pro Gly Asp
        355                 360                 365

Gln Val Met Glu Gly Lys Ser Ala Thr Leu Thr Cys Glu Ser Asp Ala
    370                 375                 380

Asn Pro Pro Val Ser His Tyr Thr Trp Phe Asp Trp Asn Asn Gln Ser
385                 390                 395                 400

Leu Pro Tyr His Ser Gln Lys Leu Arg Leu Glu Pro Val Lys Val Gln
                405                 410                 415

His Ser Gly Ala Tyr Trp Cys Gln Gly Thr Asn Ser Val Gly Lys Gly
            420                 425                 430

Arg Ser Pro Leu Ser Thr Leu Thr Val Tyr Tyr Ser Pro Glu Thr Gly
        435                 440                 445

Ala Ile Gly Gly Ala Gly Val Thr Ala Leu Leu Ala Leu Cys Leu Cys
    450                 455                 460

Leu Ile Phe Phe Ile Val Lys Thr His Arg Arg Lys Ala Ala Arg Thr
465                 470                 475                 480

Ala Val Gly Arg Asn Asp Thr His Pro Thr Thr Gly Ser Ala Ser Pro
                485                 490                 495

Lys His Gln Lys Lys Ser Lys Leu His Gly Pro Thr Glu Thr Ser Ser
            500                 505                 510

Cys Ser Gly Ala Ala Pro Thr Val Glu Met Asp Glu Glu Leu His Tyr
        515                 520                 525

Ala Ser Leu Asn Phe His Gly Met Asn Pro Ser Lys Asp Thr Ser Thr
    530                 535                 540

Glu Tyr Ser Glu Val Arg Thr Gln
545                 550


<210> SEQ ID NO 137
<211> LENGTH: 1656
<212> TYPE: DNA
<213> ORGANISM: Artificial Sequence
<220> FEATURE:
<223> OTHER INFORMATION: CD33:CD22 2D nucleotides

<400> SEQUENCE: 137

atgcctctgc tgctactgct acctctgctg tgggctggag ccctggctat gcatcatcac     60

caccatcacg gcggcggcga tccaaatttc tggctgcaag tgcaggagtc agtgacggta    120

caggagggtt tgtgcgtcct cgtgccctgc actttcttcc atcccatacc ctactacgac    180

aagaactccc cagttcatgg ttactggttc cgggaaggag ccattatatc cagggactct    240

ccagtggcca caaacaagct agatcaagaa gtacaggagg agactcaggg cagattccgc    300

ctccttgggg atcccagtag gaacaactgc tccctgagca tcgtagacgc caggaggagg    360

gataatggtt catacttctt tcggatggag agaggaagta ccaaatacag ttacaaatct    420
```

```
ccccagctct ctgtgcatgt gacagacttg acccacaggc ccaaaatcct catccctggc    480

actctagaac ccggccactc caaaaacctg acctgctctg tgtcctgggc ctgtgagcag    540

ggaacacccc cgatcttctc ctggttgtca gctgccccca cctccctggg ccccaggact    600

actcactcct cggtgctcat aatcacccca cggccccagg accacggcac caacctgacc    660

tgtcaggtga agttcgctgg agctggtgtg actacggaga gaaccatcca gctgaacgtc    720

acctatgttc cacagaaccc aacaactggt atctttccag gagatggctc agggaaacaa    780

gagaccagag caggagtggt tcatccccga gacgtgaggg tccggaaaat caagcccctt    840

tccgagattc actctggaaa ctcggtcagc ctccaatgtg acttctcaag cagccacccc    900

aaagaagtcc agttcttctg ggagaaaaat ggcaggcttc tggggaaaga aagccagctg    960

aattttgact ccatctcccc agaagatgct gggagttaca gctgctgggt gaacaactcc   1020

ataggacaga cagcgtccaa ggcctggaca cttgaagtgc tgtatgcacc caggaggctg   1080

cgtgtgtcca tgagcccagg ggaccaagtg atggagggga agagtgcaac cctgacctgt   1140

gagagcgacg ccaaccctcc cgtctcccac tacacctggt ttgactggaa taaccaaagc   1200

ctcccctacc acagccagaa gctgagattg gagccggtga aggtccagca ctcgggtgcc   1260

tactggtgcc aggggaccaa cagtgtgggc aagggccgtt cgcctctcag caccctcacc   1320

gtctactata gcccggagac cggggccatt ggaggagctg gtgttacagc cctgctcgct   1380

ctttgtctct gcctcatctt cttcatagtg aagacccaca ggaggaaagc agccaggaca   1440

gcagtgggca ggaatgacac ccaccctacc acagggtcag cctccccgaa acaccagaag   1500

aagtccaagt tacatggccc cactgaaacc tcaagctgtt caggtgccgc ccctactgtg   1560

gagatggatg aggagctgca ttatgcttcc ctcaactttc atgggatgaa tccttccaag   1620

gacacctcca ccgaatactc agaggtcagg acccag                             1656
```

<210> SEQ ID NO 138
<211> LENGTH: 280
<212> TYPE: PRT
<213> ORGANISM: Artificial Sequence
<220> FEATURE:
<223> OTHER INFORMATION: CD33 V-set construct (exon 3 and 4 deleted) protein

<400> SEQUENCE: 138

```
Met Pro Leu Leu Leu Leu Leu Pro Leu Leu Trp Ala Gly Ala Leu Ala
1               5                   10                  15

Met His His His His His His Gly Gly Gly Asp Pro Asn Phe Trp Leu
            20                  25                  30

Gln Val Gln Glu Ser Val Thr Val Gln Glu Gly Leu Cys Val Leu Val
        35                  40                  45

Pro Cys Thr Phe Phe His Pro Ile Pro Tyr Tyr Asp Lys Asn Ser Pro
    50                  55                  60

Val His Gly Tyr Trp Phe Arg Glu Gly Ala Ile Ile Ser Arg Asp Ser
65                  70                  75                  80

Pro Val Ala Thr Asn Lys Leu Asp Gln Glu Val Gln Glu Glu Thr Gln
                85                  90                  95

Gly Arg Phe Arg Leu Leu Gly Asp Pro Ser Arg Asn Asn Cys Ser Leu
            100                 105                 110

Ser Ile Val Asp Ala Arg Arg Arg Asp Asn Gly Ser Tyr Phe Phe Arg
        115                 120                 125

Met Glu Arg Gly Ser Thr Lys Tyr Ser Tyr Lys Ser Pro Gln Leu Ser
```

```
    130                 135                 140

Val His Val Thr Tyr Val Pro Gln Asn Pro Thr Thr Gly Ile Phe Pro
145                 150                 155                 160

Gly Asp Gly Ser Gly Lys Gln Glu Thr Arg Ala Gly Val Val His Gly
                165                 170                 175

Ala Ile Gly Gly Ala Gly Val Thr Ala Leu Leu Ala Leu Cys Leu Cys
            180                 185                 190

Leu Ile Phe Phe Ile Val Lys Thr His Arg Arg Lys Ala Ala Arg Thr
        195                 200                 205

Ala Val Gly Arg Asn Asp Thr His Pro Thr Thr Gly Ser Ala Ser Pro
    210                 215                 220

Lys His Gln Lys Lys Ser Lys Leu His Gly Pro Thr Glu Thr Ser Ser
225                 230                 235                 240

Cys Ser Gly Ala Ala Pro Thr Val Glu Met Asp Glu Glu Leu His Tyr
                245                 250                 255

Ala Ser Leu Asn Phe His Gly Met Asn Pro Ser Lys Asp Thr Ser Thr
            260                 265                 270

Glu Tyr Ser Glu Val Arg Thr Gln
        275                 280
```

<210> SEQ ID NO 139
<211> LENGTH: 840
<212> TYPE: DNA
<213> ORGANISM: Artificial Sequence
<220> FEATURE:
<223> OTHER INFORMATION: CD33 V-set construct (exon 3 and 4 deleted) nucleotides

<400> SEQUENCE: 139

```
atgcctctgc tgctactgct acctctgctg tgggctggag ccctggctat gcatcatcac      60

caccatcacg gcggcggcga tccaaatttc tggctgcaag tgcaggagtc agtgacggta     120

caggagggtt tgtgcgtcct cgtgccctgc actttcttcc atcccatacc ctactacgac     180

aagaactccc cagttcatgg ttactggttc cgggaaggag ccattatatc cagggactct     240

ccagtggcca caaacaagct agatcaagaa gtacaggagg agactcaggg cagattccgc     300

ctccttgggg atcccagtag gaacaactgc tccctgagca tcgtagacgc caggaggagg     360

gataatggtt catacttctt tcggatggag agaggaagta ccaaatacag ttacaaatct     420

ccccagctct ctgtgcatgt gacatatgtt ccacagaacc caacaactgg tatctttcca     480

ggagatggct cagggaaaca agagaccaga gcaggagtgg ttcatggggc cattggagga     540

gctggtgtta cagccctgct cgctctttgt ctctgcctca tcttcttcat agtgaagacc     600

cacaggagga aagcagccag gacagcagtg ggcaggaatg acacccaccc taccacaggg     660

tcagcctccc cgaaacacca gaagaagtcc aagttacatg gccccactga aacctcaagc     720

tgttcaggtg ccgcccctac tgtggagatg gatgaggagc tgcattatgc ttccctcaac     780

tttcatggga tgaatccttc caaggacacc tccaccgaat actcagaggt caggacccag     840
```

<210> SEQ ID NO 140
<211> LENGTH: 17
<212> TYPE: PRT
<213> ORGANISM: Artificial Sequence
<220> FEATURE:
<223> OTHER INFORMATION: CD33 signal peptide

<400> SEQUENCE: 140

```
Met Pro Leu Leu Leu Leu Leu Pro Leu Leu Trp Ala Gly Ala Leu Ala
```

-continued

```
1               5                   10                  15

Met


<210> SEQ ID NO 141
<211> LENGTH: 51
<212> TYPE: DNA
<213> ORGANISM: Artificial Sequence
<220> FEATURE:
<223> OTHER INFORMATION: CD33 signal peptide coding sequence

<400> SEQUENCE: 141

atgcctctgc tgctactgct acctctgctg tgggctggag ccctggctat g              51


<210> SEQ ID NO 142
<211> LENGTH: 6
<212> TYPE: PRT
<213> ORGANISM: Artificial Sequence
<220> FEATURE:
<223> OTHER INFORMATION: His tag

<400> SEQUENCE: 142

His His His His His His
1               5


<210> SEQ ID NO 143
<211> LENGTH: 18
<212> TYPE: DNA
<213> ORGANISM: Artificial Sequence
<220> FEATURE:
<223> OTHER INFORMATION: His tag coding sequence

<400> SEQUENCE: 143

catcatcacc accatcac                                                   18


<210> SEQ ID NO 144

<400> SEQUENCE: 144

000


<210> SEQ ID NO 145
<211> LENGTH: 242
<212> TYPE: PRT
<213> ORGANISM: Artificial Sequence
<220> FEATURE:
<223> OTHER INFORMATION: CD33 extracellular domain

<400> SEQUENCE: 145

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110
```

-continued

```
Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His


<210> SEQ ID NO 146
<211> LENGTH: 726
<212> TYPE: DNA
<213> ORGANISM: Artificial Sequence
<220> FEATURE:
<223> OTHER INFORMATION: CD33 extracellular domain coding sequence

<400> SEQUENCE: 146

gatccaaatt tctggctgca agtgcaggag tcagtgacgg tacaggaggg tttgtgcgtc      60

ctcgtgccct gcactttctt ccatcccata ccctactacg acaagaactc cccagttcat     120

ggttactggt tccgggaagg agccattata tccagggact ctccagtggc cacaaacaag     180

ctagatcaag aagtacagga ggagactcag ggcagattcc gcctccttgg ggatcccagt     240

aggaacaact gctccctgag catcgtagac gccaggagga gggataatgg ttcatacttc     300

tttcggatgg agagaggaag taccaaatac agttacaaat ctccccagct ctctgtgcat     360

gtgacagact tgacccacag gcccaaaatc ctcatccctg gcactctaga acccggccac     420

tccaaaaacc tgacctgctc tgtgtcctgg gcctgtgagc agggaacacc cccgatcttc     480

tcctggttgt cagctgcccc cacctccctg ggccccagga ctactcactc ctcggtgctc     540

ataatcaccc cacggcccca ggaccacggc accaacctga cctgtcaggt gaagttcgct     600

ggagctggtg tgactacgga gagaaccatc cagctgaacg tcacctatgt tccacagaac     660

ccaacaactg gtatctttcc aggagatggc tcagggaaac aagagaccag agcaggagtg     720

gttcat                                                                 726


<210> SEQ ID NO 147
<211> LENGTH: 149
<212> TYPE: PRT
<213> ORGANISM: Artificial Sequence
<220> FEATURE:
<223> OTHER INFORMATION: CD33 extracellular domain lacking CD33 amino
      acids 140-232

<400> SEQUENCE: 147

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30
```

-continued

```
Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Tyr Val Pro Gln Asn Pro
        115                 120                 125

Thr Thr Gly Ile Phe Pro Gly Asp Gly Ser Gly Lys Gln Glu Thr Arg
    130                 135                 140

Ala Gly Val Val His
145
```

<210> SEQ ID NO 148
<211> LENGTH: 447
<212> TYPE: DNA
<213> ORGANISM: Artificial Sequence
<220> FEATURE:
<223> OTHER INFORMATION: CD33 extracellular domain lacking CD33 amino acids 140-232 coding sequence

<400> SEQUENCE: 148

```
gatccaaatt tctggctgca agtgcaggag tcagtgacgg tacaggaggg tttgtgcgtc     60

ctcgtgccct gcactttctt ccatcccata ccctactacg acaagaactc cccagttcat    120

ggttactggt tccgggaagg agccattata tccagggact ctccagtggc cacaaacaag    180

ctagatcaag aagtacagga ggagactcag ggcagattcc gcctccttgg ggatcccagt    240

aggaacaact gctccctgag catcgtagac gccaggagga gggataatgg ttcatacttc    300

tttcggatgg agagaggaag taccaaatac agttacaaat ctccccagct ctctgtgcat    360

gtgacatatg ttccacagaa cccaacaact ggtatctttc caggagatgg ctcagggaaa    420

caagagacca gagcaggagt ggttcat                                        447
```

<210> SEQ ID NO 149
<211> LENGTH: 23
<212> TYPE: PRT
<213> ORGANISM: Artificial Sequence
<220> FEATURE:
<223> OTHER INFORMATION: CD33 transmembrane domain

<400> SEQUENCE: 149

```
Gly Ala Ile Gly Gly Ala Gly Val Thr Ala Leu Leu Ala Leu Cys Leu
1               5                   10                  15

Cys Leu Ile Phe Phe Ile Val
            20
```

<210> SEQ ID NO 150
<211> LENGTH: 69
<212> TYPE: DNA
<213> ORGANISM: Artificial Sequence
<220> FEATURE:
<223> OTHER INFORMATION: CD33 transmembrane domain coding sequence

<400> SEQUENCE: 150

```
ggggccattg gaggagctgg tgttacagcc ctgctcgctc tttgtctctg cctcatcttc     60
```

-continued

```
ttcatagtg                                                              69


<210> SEQ ID NO 151
<211> LENGTH: 82
<212> TYPE: PRT
<213> ORGANISM: Artificial Sequence
<220> FEATURE:
<223> OTHER INFORMATION: CD33 intracellular domain

<400> SEQUENCE: 151

Lys Thr His Arg Arg Lys Ala Ala Arg Thr Ala Val Gly Arg Asn Asp
1               5                   10                  15

Thr His Pro Thr Thr Gly Ser Ala Ser Pro Lys His Gln Lys Lys Ser
            20                  25                  30

Lys Leu His Gly Pro Thr Glu Thr Ser Ser Cys Ser Gly Ala Ala Pro
        35                  40                  45

Thr Val Glu Met Asp Glu Glu Leu His Tyr Ala Ser Leu Asn Phe His
    50                  55                  60

Gly Met Asn Pro Ser Lys Asp Thr Ser Thr Glu Tyr Ser Glu Val Arg
65                  70                  75                  80

Thr Gln


<210> SEQ ID NO 152
<211> LENGTH: 246
<212> TYPE: DNA
<213> ORGANISM: Artificial Sequence
<220> FEATURE:
<223> OTHER INFORMATION: CD33 intracellular domain coding sequence

<400> SEQUENCE: 152

aagacccaca ggaggaaagc agccaggaca gcagtgggca ggaatgacac ccaccctacc      60

acagggtcag cctccccgaa acaccagaag aagtccaagt tacatggccc cactgaaacc     120

tcaagctgtt caggtgccgc ccctactgtg gagatggatg aggagctgca ttatgcttcc     180

ctcaactttc atgggatgaa tccttccaag gacacctcca ccgaatactc agaggtcagg     240

acccag                                                                246


<210> SEQ ID NO 153
<211> LENGTH: 353
<212> TYPE: PRT
<213> ORGANISM: Artificial Sequence
<220> FEATURE:
<223> OTHER INFORMATION: Portion of CD22 extracellular domain that
      contains CD22 domains defined as Ig-like C2-type 3, Ig-like
      C2-type 4, Ig-like C2-type 5, Ig-like C2-type 6

<400> SEQUENCE: 153

Pro Glu Pro Ser Thr Val Gln Ile Leu His Ser Pro Ala Val Glu Gly
1               5                   10                  15

Ser Gln Val Glu Phe Leu Cys Met Ser Leu Ala Asn Pro Leu Pro Thr
            20                  25                  30

Asn Tyr Thr Trp Tyr His Asn Gly Lys Glu Met Gln Gly Arg Thr Glu
        35                  40                  45

Glu Lys Val His Ile Pro Lys Ile Leu Pro Trp His Ala Gly Thr Tyr
    50                  55                  60

Ser Cys Val Ala Glu Asn Ile Leu Gly Thr Gly Gln Arg Gly Pro Gly
65                  70                  75                  80

Ala Glu Leu Asp Val Gln Tyr Pro Pro Lys Lys Val Thr Thr Val Ile
                85                  90                  95
```

```
Gln Asn Pro Met Pro Ile Arg Glu Gly Asp Thr Val Thr Leu Ser Cys
            100                 105                 110

Asn Tyr Asn Ser Ser Asn Pro Ser Val Thr Arg Tyr Glu Trp Lys Pro
        115                 120                 125

His Gly Ala Trp Glu Glu Pro Ser Leu Gly Val Leu Lys Ile Gln Asn
    130                 135                 140

Val Gly Trp Asp Asn Thr Thr Ile Ala Cys Ala Ala Cys Asn Ser Trp
145                 150                 155                 160

Cys Ser Trp Ala Ser Pro Val Ala Leu Asn Val Gln Tyr Ala Pro Arg
                165                 170                 175

Asp Val Arg Val Arg Lys Ile Lys Pro Leu Ser Glu Ile His Ser Gly
            180                 185                 190

Asn Ser Val Ser Leu Gln Cys Asp Phe Ser Ser Ser His Pro Lys Glu
        195                 200                 205

Val Gln Phe Phe Trp Glu Lys Asn Gly Arg Leu Leu Gly Lys Glu Ser
    210                 215                 220

Gln Leu Asn Phe Asp Ser Ile Ser Pro Glu Asp Ala Gly Ser Tyr Ser
225                 230                 235                 240

Cys Trp Val Asn Asn Ser Ile Gly Gln Thr Ala Ser Lys Ala Trp Thr
                245                 250                 255

Leu Glu Val Leu Tyr Ala Pro Arg Arg Leu Arg Val Ser Met Ser Pro
            260                 265                 270

Gly Asp Gln Val Met Glu Gly Lys Ser Ala Thr Leu Thr Cys Glu Ser
        275                 280                 285

Asp Ala Asn Pro Pro Val Ser His Tyr Thr Trp Phe Asp Trp Asn Asn
    290                 295                 300

Gln Ser Leu Pro Tyr His Ser Gln Lys Leu Arg Leu Glu Pro Val Lys
305                 310                 315                 320

Val Gln His Ser Gly Ala Tyr Trp Cys Gln Gly Thr Asn Ser Val Gly
                325                 330                 335

Lys Gly Arg Ser Pro Leu Ser Thr Leu Thr Val Tyr Tyr Ser Pro Glu
            340                 345                 350

Thr
```

<210> SEQ ID NO 154
<211> LENGTH: 1059
<212> TYPE: DNA
<213> ORGANISM: Artificial Sequence
<220> FEATURE:
<223> OTHER INFORMATION: Portion of CD22 extracellular domain that contains CD22 domains defined as Ig-like C2-type 3, Ig-like C2-type 4, Ig-like C2-type 5, Ig-like C2-type 6 coding sequence

<400> SEQUENCE: 154

```
ccggaacctt ccacggttca gatcctccac tcaccggctg tggagggaag tcaagtcgag     60

tttctttgca tgtcactggc caatcctctt ccaacaaatt acacgtggta ccacaatggg    120

aaagaaatgc agggaaggac agaggagaaa gtccacatcc caaagatcct ccccttggcac    180

gctgggactt attcctgtgt ggcagaaaac attcttggta ctggacagag ggccctgga    240

gctgagctgg atgtccagta tcctcccaag aaggtgacca cagtgattca aaaccccatg    300

ccgattcgag aaggagacac agtgaccctt tcctgtaact acaattccag taaccccagt    360

gttacccggt atgaatggaa accccatggc gcctgggagg agccatcgct tggggtgctg    420

aagatccaaa acgttggctg ggacaacaca accatcgcct gcgcagcttg taatagttgg    480

tgctcgtggg cctcccctgt cgccctgaat gtccagtatg ccccccgaga cgtgagggtc    540
```

```
cggaaaatca agcccctttc cgagattcac tctggaaact cggtcagcct ccaatgtgac    600

ttctcaagca gccaccccaa agaagtccag ttcttctggg agaaaaatgg caggcttctg    660

gggaaagaaa gccagctgaa ttttgactcc atctccccag aagatgctgg gagttacagc    720

tgctgggtga acaactccat aggacagaca gcgtccaagg cctggacact tgaagtgctg    780

tatgcaccca ggaggctgcg tgtgtccatg agcccagggg accaagtgat ggaggggaag    840

agtgcaaccc tgacctgtga gagcgacgcc aaccctcccg tctcccacta cacctggttt    900

gactggaata accaaagcct cccctaccac agccagaagc tgagattgga gccggtgaag    960

gtccagcact cgggtgccta ctggtgccag gggaccaaca gtgtgggcaa gggccgttcg   1020

cctctcagca ccctcaccgt ctactatagc ccggagacc                          1059
```

<210> SEQ ID NO 155
<211> LENGTH: 179
<212> TYPE: PRT
<213> ORGANISM: Artificial Sequence
<220> FEATURE:
<223> OTHER INFORMATION: Portion of CD22 extracellular domain that contains CD22 domains defined as Ig-like C2-type 5, Ig-like C2-type 6

<400> SEQUENCE: 155

```
Pro Arg Asp Val Arg Val Arg Lys Ile Lys Pro Leu Ser Glu Ile His
1               5                   10                  15

Ser Gly Asn Ser Val Ser Leu Gln Cys Asp Phe Ser Ser Ser His Pro
            20                  25                  30

Lys Glu Val Gln Phe Phe Trp Glu Lys Asn Gly Arg Leu Leu Gly Lys
        35                  40                  45

Glu Ser Gln Leu Asn Phe Asp Ser Ile Ser Pro Glu Asp Ala Gly Ser
    50                  55                  60

Tyr Ser Cys Trp Val Asn Asn Ser Ile Gly Gln Thr Ala Ser Lys Ala
65                  70                  75                  80

Trp Thr Leu Glu Val Leu Tyr Ala Pro Arg Arg Leu Arg Val Ser Met
                85                  90                  95

Ser Pro Gly Asp Gln Val Met Glu Gly Lys Ser Ala Thr Leu Thr Cys
            100                 105                 110

Glu Ser Asp Ala Asn Pro Pro Val Ser His Tyr Thr Trp Phe Asp Trp
        115                 120                 125

Asn Asn Gln Ser Leu Pro Tyr His Ser Gln Lys Leu Arg Leu Glu Pro
    130                 135                 140

Val Lys Val Gln His Ser Gly Ala Tyr Trp Cys Gln Gly Thr Asn Ser
145                 150                 155                 160

Val Gly Lys Gly Arg Ser Pro Leu Ser Thr Leu Thr Val Tyr Tyr Ser
                165                 170                 175

Pro Glu Thr
```

<210> SEQ ID NO 156
<211> LENGTH: 537
<212> TYPE: DNA
<213> ORGANISM: Artificial Sequence
<220> FEATURE:
<223> OTHER INFORMATION: Portion of CD22 extracellular domain that contains CD22 domains defined as Ig-like C2-type 5, Ig-like C2-type 6 coding sequence

<400> SEQUENCE: 156

```
ccccgagacg tgagggtccg gaaaatcaag ccccttttccg agattcactc tggaaactcg     60
```

```
gtcagcctcc aatgtgactt ctcaagcagc caccccaaag aagtccagtt cttctgggag    120

aaaaatggca ggcttctggg gaaagaaagc cagctgaatt ttgactccat ctccccagaa    180

gatgctggga gttacagctg ctgggtgaac aactccatag gacagacagc gtccaaggcc    240

tggacacttg aagtgctgta tgcacccagg aggctgcgtg tgtccatgag cccaggggac    300

caagtgatgg aggggaagag tgcaaccctg acctgtgaga gcgacgccaa ccctcccgtc    360

tcccactaca cctggtttga ctggaataac caaagcctcc cctaccacag ccagaagctg    420

agattggagc cggtgaaggt ccagcactcg ggtgcctact ggtgccaggg gaccaacagt    480

gtgggcaagg gccgttcgcc tctcagcacc ctcaccgtct actatagccc ggagacc       537
```

<210> SEQ ID NO 157
<211> LENGTH: 520
<212> TYPE: PRT
<213> ORGANISM: Artificial Sequence
<220> FEATURE:
<223> OTHER INFORMATION: 1E6/CD3 bispecific molecule

<400> SEQUENCE: 157

```
Met Glu Thr Asp Thr Leu Leu Leu Trp Val Leu Leu Leu Trp Val Pro
1               5                   10                  15

Gly Ser Thr Gly Gln Val Gln Leu Val Glu Ser Gly Gly Gly Val Val
            20                  25                  30

Gln Pro Gly Arg Ser Leu Arg Leu Ser Cys Ala Ala Ser Gly Phe Thr
        35                  40                  45

Phe Ser Ser Tyr Asp Ile His Trp Val Arg Gln Ala Pro Gly Lys Gly
    50                  55                  60

Leu Glu Trp Val Ala Val Ile Trp Tyr Asp Gly Ser His Asn Tyr Tyr
65                  70                  75                  80

Ser Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Tyr Ser Gly Ser Tyr Tyr Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Ala Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Gly Ile Arg Asn Asp Leu Gly Trp Tyr Gln Gln Lys
            180                 185                 190

Pro Gly Lys Ala Pro Lys Leu Leu Ile Tyr Ala Ala Ser Asn Leu Gln
        195                 200                 205

Ser Gly Val Pro Ser Arg Phe Ser Gly Ser Gly Ser Gly Thr Asp Phe
    210                 215                 220

Thr Leu Thr Ile Ser Ser Leu Gln Pro Glu Asp Phe Ala Thr Tyr Tyr
225                 230                 235                 240

Cys Leu Gln Asp Tyr Ser Tyr Pro Arg Thr Phe Gly Gln Gly Thr Lys
                245                 250                 255

Val Glu Ile Lys Gly Gly Gly Gly Ser Glu Val Gln Leu Val Glu Ser
            260                 265                 270

Gly Gly Gly Leu Val Gln Pro Gly Gly Ser Leu Lys Leu Ser Cys Ala
```

```
        275                 280                 285

Ala Ser Gly Phe Thr Phe Asn Lys Tyr Ala Met Asn Trp Val Arg Gln
    290                 295                 300

Ala Pro Gly Lys Gly Leu Glu Trp Val Ala Arg Ile Arg Ser Lys Tyr
305                 310                 315                 320

Asn Asn Tyr Ala Thr Tyr Tyr Ala Asp Ser Val Lys Asp Arg Phe Thr
                325                 330                 335

Ile Ser Arg Asp Asp Ser Lys Asn Thr Ala Tyr Leu Gln Met Asn Asn
            340                 345                 350

Leu Lys Thr Glu Asp Thr Ala Val Tyr Tyr Cys Val Arg His Gly Asn
        355                 360                 365

Phe Gly Asn Ser Tyr Ile Ser Tyr Trp Ala Tyr Trp Gly Gln Gly Thr
    370                 375                 380

Leu Val Thr Val Ser Ser Gly Gly Gly Gly Ser Gly Gly Gly Gly Ser
385                 390                 395                 400

Gly Gly Gly Gly Ser Gln Thr Val Val Thr Gln Glu Pro Ser Leu Thr
                405                 410                 415

Val Ser Pro Gly Gly Thr Val Thr Leu Thr Cys Gly Ser Ser Thr Gly
            420                 425                 430

Ala Val Thr Ser Gly Asn Tyr Pro Asn Trp Val Gln Gln Lys Pro Gly
        435                 440                 445

Gln Ala Pro Arg Gly Leu Ile Gly Gly Thr Lys Phe Leu Ala Pro Gly
    450                 455                 460

Thr Pro Ala Arg Phe Ser Gly Ser Leu Leu Gly Gly Lys Ala Ala Leu
465                 470                 475                 480

Thr Leu Ser Gly Val Gln Pro Glu Asp Glu Ala Glu Tyr Tyr Cys Val
                485                 490                 495

Leu Trp Tyr Ser Asn Arg Trp Val Phe Gly Gly Gly Thr Lys Leu Thr
            500                 505                 510

Val Leu His His His His His His
        515                 520


<210> SEQ ID NO 158
<211> LENGTH: 20
<212> TYPE: PRT
<213> ORGANISM: Artificial Sequence
<220> FEATURE:
<223> OTHER INFORMATION: IgK signal peptide

<400> SEQUENCE: 158

Met Glu Thr Asp Thr Leu Leu Leu Trp Val Leu Leu Leu Trp Val Pro
1               5                   10                  15

Gly Ser Thr Gly
            20


<210> SEQ ID NO 159

<400> SEQUENCE: 159

000


<210> SEQ ID NO 160

<400> SEQUENCE: 160

000


<210> SEQ ID NO 161
```

<211> LENGTH: 125
<212> TYPE: PRT
<213> ORGANISM: Artificial Sequence
<220> FEATURE:
<223> OTHER INFORMATION: variable heavy chain of anti-CD3

<400> SEQUENCE: 161

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Ile Ser Tyr Trp
100 105 110

Ala Tyr Trp Gly Gln Gly Thr Leu Val Thr Val Ser Ser
115 120 125

<210> SEQ ID NO 162
<211> LENGTH: 109
<212> TYPE: PRT
<213> ORGANISM: Artificial Sequence
<220> FEATURE:
<223> OTHER INFORMATION: variable light chain of anti-CD3

<400> SEQUENCE: 162

Gln Thr Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Asn Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Val Leu Trp Tyr Ser Asn
85 90 95

Arg Trp Val Phe Gly Gly Gly Thr Lys Leu Thr Val Leu
100 105

<210> SEQ ID NO 163
<211> LENGTH: 8
<212> TYPE: PRT
<213> ORGANISM: Artificial Sequence
<220> FEATURE:
<223> OTHER INFORMATION: CDRL2 of 1H8

<400> SEQUENCE: 163

Arg Tyr Ala Thr Gln Pro Phe Ser
1 5

<210> SEQ ID NO 164
<211> LENGTH: 13

<212> TYPE: PRT
<213> ORGANISM: Artificial Sequence
<220> FEATURE:
<223> OTHER INFORMATION: CDRH1 of 1H8

<400> SEQUENCE: 164

Ala Ala Ser Gly Phe Thr Phe Gly Ser Tyr Gly Met His
1 5 10

<210> SEQ ID NO 165
<211> LENGTH: 10
<212> TYPE: PRT
<213> ORGANISM: Artificial Sequence
<220> FEATURE:
<223> OTHER INFORMATION: CDRH2 of 1H8

<400> SEQUENCE: 165

Val Ile Trp Tyr Asp Gly Ser Asn Glu Tyr
1 5 10

<210> SEQ ID NO 166
<211> LENGTH: 13
<212> TYPE: PRT
<213> ORGANISM: Artificial Sequence
<220> FEATURE:
<223> OTHER INFORMATION: CDRH3 of 1H8

<400> SEQUENCE: 166

Ala Arg Asp Leu Asp Tyr Asp Ser Ser Gly Gly Asp Tyr
1 5 10

<210> SEQ ID NO 167
<211> LENGTH: 12
<212> TYPE: PRT
<213> ORGANISM: Artificial Sequence
<220> FEATURE:
<223> OTHER INFORMATION: CDRL1 of 2D3

<400> SEQUENCE: 167

Arg Ala Ser Gln Ser Gly Ser Ser Ser Phe Leu Ser
1 5 10

<210> SEQ ID NO 168
<211> LENGTH: 8
<212> TYPE: PRT
<213> ORGANISM: Artificial Sequence
<220> FEATURE:
<223> OTHER INFORMATION: CDRL2 of 2D3

<400> SEQUENCE: 168

Tyr Gly Ala Ser Thr Arg Ala Thr
1 5

<210> SEQ ID NO 169
<211> LENGTH: 13
<212> TYPE: PRT
<213> ORGANISM: Artificial Sequence
<220> FEATURE:
<223> OTHER INFORMATION: CDRH1 of 2D3

<400> SEQUENCE: 169

Ala Ala Ser Gly Phe Thr Phe Ser Ile Tyr Ala Met Ser
1 5 10

<210> SEQ ID NO 170
<211> LENGTH: 10
<212> TYPE: PRT

<213> ORGANISM: Artificial Sequence
<220> FEATURE:
<223> OTHER INFORMATION: CDRH2 of 2D3

<400> SEQUENCE: 170

Ala Ile Ser Asp Ser Gly Gly Thr Thr Tyr
1 5 10

<210> SEQ ID NO 171
<211> LENGTH: 12
<212> TYPE: PRT
<213> ORGANISM: Artificial Sequence
<220> FEATURE:
<223> OTHER INFORMATION: CDRH3 of 2D3

<400> SEQUENCE: 171

Ala Lys Arg Thr Arg Tyr Phe Asn Gly Met Asp Val
1 5 10

<210> SEQ ID NO 172
<211> LENGTH: 12
<212> TYPE: PRT
<213> ORGANISM: Artificial Sequence
<220> FEATURE:
<223> OTHER INFORMATION: CDRL1 of 2E3

<400> SEQUENCE: 172

Arg Ala Ser Gln Ser Val Ser Ser Ser Tyr Leu Ala
1 5 10

<210> SEQ ID NO 173
<211> LENGTH: 8
<212> TYPE: PRT
<213> ORGANISM: Artificial Sequence
<220> FEATURE:
<223> OTHER INFORMATION: CDRL2 of 2E3

<400> SEQUENCE: 173

Tyr Gly Thr Ser Ser Arg Ala Thr
1 5

<210> SEQ ID NO 174
<211> LENGTH: 13
<212> TYPE: PRT
<213> ORGANISM: Artificial Sequence
<220> FEATURE:
<223> OTHER INFORMATION: CDRH1 of 2E3

<400> SEQUENCE: 174

Ala Ala Ser Gly Phe Thr Phe Ser Ser Tyr Gly Met His
1 5 10

<210> SEQ ID NO 175
<211> LENGTH: 10
<212> TYPE: PRT
<213> ORGANISM: Artificial Sequence
<220> FEATURE:
<223> OTHER INFORMATION: CDRH2 of 2E3

<400> SEQUENCE: 175

Val Ile Trp Tyr Gly Gly Ser Asn Lys Tyr
1 5 10

<210> SEQ ID NO 176
<211> LENGTH: 16
<212> TYPE: PRT
<213> ORGANISM: Artificial Sequence -continued
<220> FEATURE:
<223> OTHER INFORMATION: CDRH3 of 2E3

<400> SEQUENCE: 176

Ala Arg Asp Gly Thr Gly Glu Asn Tyr Tyr Tyr Tyr Val Met Asp Val
1 5 10 15

<210> SEQ ID NO 177
<211> LENGTH: 6
<212> TYPE: PRT
<213> ORGANISM: Artificial Sequence
<220> FEATURE:
<223> OTHER INFORMATION: CDRL1 of 1H10

<400> SEQUENCE: 177

Gln Gly Ile Arg Ile Tyr
1 5

<210> SEQ ID NO 178
<211> LENGTH: 8
<212> TYPE: PRT
<213> ORGANISM: Artificial Sequence
<220> FEATURE:
<223> OTHER INFORMATION: CDRH1 of 1H10

<400> SEQUENCE: 178

Gly Tyr Ile Phe Thr Ser Tyr Asp
1 5

<210> SEQ ID NO 179
<211> LENGTH: 8
<212> TYPE: PRT
<213> ORGANISM: Artificial Sequence
<220> FEATURE:
<223> OTHER INFORMATION: CDRH2 of 1H10

<400> SEQUENCE: 179

Ile Asp Pro Ser Gly Gly Ser Thr
1 5

<210> SEQ ID NO 180
<211> LENGTH: 6
<212> TYPE: PRT
<213> ORGANISM: Artificial Sequence
<220> FEATURE:
<223> OTHER INFORMATION: CDRL1 of 1A9 and/or 1B9

<400> SEQUENCE: 180

Gln Asp Ile Arg Asn Asp
1 5

<210> SEQ ID NO 181
<211> LENGTH: 8
<212> TYPE: PRT
<213> ORGANISM: Artificial Sequence
<220> FEATURE:
<223> OTHER INFORMATION: CDRH1 of 1A9

<400> SEQUENCE: 181

Gly Phe Thr Phe Ser Ile Tyr Asp
1 5

<210> SEQ ID NO 182
<211> LENGTH: 7
<212> TYPE: PRT
<213> ORGANISM: Artificial Sequence
<220> FEATURE:

<223> OTHER INFORMATION: CDRH2 of 1A9

<400> SEQUENCE: 182

Ile Gly Thr Ala Gly Asp Thr
1 5

<210> SEQ ID NO 183
<211> LENGTH: 6
<212> TYPE: PRT
<213> ORGANISM: Artificial Sequence
<220> FEATURE:
<223> OTHER INFORMATION: CDRL1 of 1E6 and/or 1D2

<400> SEQUENCE: 183

Gln Gly Ile Arg Asn Asp
1 5

<210> SEQ ID NO 184
<211> LENGTH: 8
<212> TYPE: PRT
<213> ORGANISM: Artificial Sequence
<220> FEATURE:
<223> OTHER INFORMATION: CDRH1 of 1E6 and/or 1D2

<400> SEQUENCE: 184

Gly Phe Thr Phe Ser Ser Tyr Asp
1 5

<210> SEQ ID NO 185
<211> LENGTH: 8
<212> TYPE: PRT
<213> ORGANISM: Artificial Sequence
<220> FEATURE:
<223> OTHER INFORMATION: CDRH2 of 1E6 and/or 1B9

<400> SEQUENCE: 185

Ile Trp Tyr Asp Gly Ser His Asn
1 5

<210> SEQ ID NO 186
<211> LENGTH: 8
<212> TYPE: PRT
<213> ORGANISM: Artificial Sequence
<220> FEATURE:
<223> OTHER INFORMATION: CDRH2 of 1D2

<400> SEQUENCE: 186

Ile Trp Tyr Asp Gly Ser Gln Lys
1 5

<210> SEQ ID NO 187
<211> LENGTH: 8
<212> TYPE: PRT
<213> ORGANISM: Artificial Sequence
<220> FEATURE:
<223> OTHER INFORMATION: CDRH1 of 1B9

<400> SEQUENCE: 187

Gly Phe Ile Phe Ser Ser Tyr Asp
1 5

<210> SEQ ID NO 188
<211> LENGTH: 6
<212> TYPE: PRT
<213> ORGANISM: Artificial Sequence
<220> FEATURE:
<223> OTHER INFORMATION: CDRL1 of 1H8

<400> SEQUENCE: 188

Gln Asn Ile Gly Gly Asn
1               5

<210> SEQ ID NO 189
<211> LENGTH: 8
<212> TYPE: PRT
<213> ORGANISM: Artificial Sequence
<220> FEATURE:
<223> OTHER INFORMATION: CDRH1 of 1H8

<400> SEQUENCE: 189

Gly Phe Thr Phe Gly Ser Tyr Gly
1               5

<210> SEQ ID NO 190
<211> LENGTH: 8
<212> TYPE: PRT
<213> ORGANISM: Artificial Sequence
<220> FEATURE:
<223> OTHER INFORMATION: CDRH2 of 1H8

<400> SEQUENCE: 190

Ile Trp Tyr Asp Gly Ser Asn Glu
1               5

<210> SEQ ID NO 191
<211> LENGTH: 7
<212> TYPE: PRT
<213> ORGANISM: Artificial Sequence
<220> FEATURE:
<223> OTHER INFORMATION: CDRL1 of 2D3

<400> SEQUENCE: 191

Gln Ser Gly Ser Ser Ser Phe
1               5

<210> SEQ ID NO 192
<211> LENGTH: 8
<212> TYPE: PRT
<213> ORGANISM: Artificial Sequence
<220> FEATURE:
<223> OTHER INFORMATION: CDRH1 of 2D3

<400> SEQUENCE: 192

Gly Phe Thr Phe Ser Ile Tyr Ala
1               5

<210> SEQ ID NO 193
<211> LENGTH: 8
<212> TYPE: PRT
<213> ORGANISM: Artificial Sequence
<220> FEATURE:
<223> OTHER INFORMATION: CDRH2 of 2D3

<400> SEQUENCE: 193

Ile Ser Asp Ser Gly Gly Thr Thr
1               5

<210> SEQ ID NO 194
<211> LENGTH: 7
<212> TYPE: PRT
<213> ORGANISM: Artificial Sequence
<220> FEATURE:
<223> OTHER INFORMATION: CDRL1 of 2E3

<400> SEQUENCE: 194

Gln Ser Val Ser Ser Ser Tyr
1 5

<210> SEQ ID NO 195
<211> LENGTH: 8
<212> TYPE: PRT
<213> ORGANISM: Artificial Sequence
<220> FEATURE:
<223> OTHER INFORMATION: CDRH1 of 2E3

<400> SEQUENCE: 195

Gly Phe Thr Phe Ser Ser Tyr Gly
1 5

<210> SEQ ID NO 196
<211> LENGTH: 8
<212> TYPE: PRT
<213> ORGANISM: Artificial Sequence
<220> FEATURE:
<223> OTHER INFORMATION: CDRH2 of 2E3

<400> SEQUENCE: 196

Ile Trp Tyr Gly Gly Ser Asn Lys
1 5

<210> SEQ ID NO 197
<211> LENGTH: 5
<212> TYPE: PRT
<213> ORGANISM: Artificial Sequence
<220> FEATURE:
<223> OTHER INFORMATION: CDRH1 of 1H10

<400> SEQUENCE: 197

Ser Tyr Asp Met His
1 5

<210> SEQ ID NO 198
<211> LENGTH: 17
<212> TYPE: PRT
<213> ORGANISM: Artificial Sequence
<220> FEATURE:
<223> OTHER INFORMATION: CDRH2 of 1H10

<400> SEQUENCE: 198

Ile Ile Asp Pro Ser Gly Gly Ser Thr Ser Tyr Ala Gln Lys Phe Gln
1 5 10 15

Gly

<210> SEQ ID NO 199
<211> LENGTH: 9
<212> TYPE: PRT
<213> ORGANISM: Artificial Sequence
<220> FEATURE:
<223> OTHER INFORMATION: CDRH3 of 1H10

<400> SEQUENCE: 199

Asp Tyr Ser Trp Ser Tyr Phe Asp Tyr
1 5

<210> SEQ ID NO 200
<211> LENGTH: 7
<212> TYPE: PRT
<213> ORGANISM: Artificial Sequence
<220> FEATURE:
<223> OTHER INFORMATION: CDRL2 of 1A9

<400> SEQUENCE: 200

Gly Ala Ser Ser Leu Gln Ser
1 5

<210> SEQ ID NO 201
<211> LENGTH: 5
<212> TYPE: PRT
<213> ORGANISM: Artificial Sequence
<220> FEATURE:
<223> OTHER INFORMATION: CDRH1 of 1A9

<400> SEQUENCE: 201

Ile Tyr Asp Met His
1 5

<210> SEQ ID NO 202
<211> LENGTH: 16
<212> TYPE: PRT
<213> ORGANISM: Artificial Sequence
<220> FEATURE:
<223> OTHER INFORMATION: CDRH2 of 1A9

<400> SEQUENCE: 202

Ala Ile Gly Thr Ala Gly Asp Thr Tyr Tyr Ala Gly Ser Val Lys Gly
1 5 10 15

<210> SEQ ID NO 203
<211> LENGTH: 9
<212> TYPE: PRT
<213> ORGANISM: Artificial Sequence
<220> FEATURE:
<223> OTHER INFORMATION: CDRH3 of 1A9

<400> SEQUENCE: 203

Glu Tyr Ser Gly Tyr Tyr Phe Asp Tyr
1 5

<210> SEQ ID NO 204
<211> LENGTH: 7
<212> TYPE: PRT
<213> ORGANISM: Artificial Sequence
<220> FEATURE:
<223> OTHER INFORMATION: CDRL2 of 1E6

<400> SEQUENCE: 204

Ala Ala Ser Asn Leu Gln Ser
1 5

<210> SEQ ID NO 205
<211> LENGTH: 5
<212> TYPE: PRT
<213> ORGANISM: Artificial Sequence
<220> FEATURE:
<223> OTHER INFORMATION: CDRH1 of 1E6, 1D2, and/or 1B9

<400> SEQUENCE: 205

Ser Tyr Asp Ile His
1 5

<210> SEQ ID NO 206
<211> LENGTH: 17
<212> TYPE: PRT
<213> ORGANISM: Artificial Sequence
<220> FEATURE:
<223> OTHER INFORMATION: CDRH2 of 1E6 and/or 1B9

-continued

<400> SEQUENCE: 206

Val Ile Trp Tyr Asp Gly Ser His Asn Tyr Tyr Ser Asp Ser Val Lys
1 5 10 15

Gly

<210> SEQ ID NO 207
<211> LENGTH: 9
<212> TYPE: PRT
<213> ORGANISM: Artificial Sequence
<220> FEATURE:
<223> OTHER INFORMATION: CDRH3 of 1E6 and/or 1D2

<400> SEQUENCE: 207

Asp Tyr Ser Gly Ser Tyr Tyr Asp Tyr
1 5

<210> SEQ ID NO 208
<211> LENGTH: 7
<212> TYPE: PRT
<213> ORGANISM: Artificial Sequence
<220> FEATURE:
<223> OTHER INFORMATION: CDRL2 of 1H10 and/or 1D2

<400> SEQUENCE: 208

Ala Thr Ser Ser Leu Gln Ser
1 5

<210> SEQ ID NO 209
<211> LENGTH: 17
<212> TYPE: PRT
<213> ORGANISM: Artificial Sequence
<220> FEATURE:
<223> OTHER INFORMATION: CDRH2 of 1D2

<400> SEQUENCE: 209

Val Ile Trp Tyr Asp Gly Ser Gln Lys Tyr Tyr Ala Asp Ser Val Lys
1 5 10 15

Gly

<210> SEQ ID NO 210
<211> LENGTH: 7
<212> TYPE: PRT
<213> ORGANISM: Artificial Sequence
<220> FEATURE:
<223> OTHER INFORMATION: CDRL2 of 1B9

<400> SEQUENCE: 210

Ala Ala Ser Ser Leu Gln Ser
1 5

<210> SEQ ID NO 211
<211> LENGTH: 9
<212> TYPE: PRT
<213> ORGANISM: Artificial Sequence
<220> FEATURE:
<223> OTHER INFORMATION: CDRH3 of 1B9

<400> SEQUENCE: 211

Asp Tyr Ser Gly Ser Tyr Phe Asp Tyr
1 5

<210> SEQ ID NO 212
<211> LENGTH: 17
<212> TYPE: PRT
<213> ORGANISM: Artificial Sequence
<220> FEATURE:
<223> OTHER INFORMATION: CDRH2 of 1H8

<400> SEQUENCE: 212

Val Ile Trp Tyr Asp Gly Ser Asn Glu Tyr Tyr Ala Asp Ser Val Lys
1 5 10 15

Gly

<210> SEQ ID NO 213
<211> LENGTH: 11
<212> TYPE: PRT
<213> ORGANISM: Artificial Sequence
<220> FEATURE:
<223> OTHER INFORMATION: CDRH3 of 1H8

<400> SEQUENCE: 213

Asp Leu Asp Tyr Asp Ser Ser Gly Gly Asp Tyr
1 5 10

<210> SEQ ID NO 214
<211> LENGTH: 17
<212> TYPE: PRT
<213> ORGANISM: Artificial Sequence
<220> FEATURE:
<223> OTHER INFORMATION: CDRH2 of 2D3

<400> SEQUENCE: 214

Ala Ile Ser Asp Ser Gly Gly Thr Thr Tyr Tyr Ala Asp Ser Val Lys
1 5 10 15

Gly

<210> SEQ ID NO 215
<211> LENGTH: 10
<212> TYPE: PRT
<213> ORGANISM: Artificial Sequence
<220> FEATURE:
<223> OTHER INFORMATION: CDRH3 of 2D3

<400> SEQUENCE: 215

Arg Thr Arg Tyr Phe Asn Gly Met Asp Val
1 5 10

<210> SEQ ID NO 216
<211> LENGTH: 17
<212> TYPE: PRT
<213> ORGANISM: Artificial Sequence
<220> FEATURE:
<223> OTHER INFORMATION: CDRH2 of 2E3

<400> SEQUENCE: 216

Val Ile Trp Tyr Gly Gly Ser Asn Lys Tyr Tyr Ala Asp Ser Val Lys
1 5 10 15

Gly

<210> SEQ ID NO 217
<211> LENGTH: 14
<212> TYPE: PRT
<213> ORGANISM: Artificial Sequence
<220> FEATURE:
<223> OTHER INFORMATION: CDRH3 of 2E3

<400> SEQUENCE: 217

Asp Gly Thr Gly Glu Asn Tyr Tyr Tyr Tyr Val Met Asp Val
1 5 10

-continued

<210> SEQ ID NO 218
<211> LENGTH: 7
<212> TYPE: PRT
<213> ORGANISM: Artificial Sequence
<220> FEATURE:
<223> OTHER INFORMATION: CDRH1 of 1H10

<400> SEQUENCE: 218

Gly Tyr Ile Phe Thr Ser Tyr
1 5

<210> SEQ ID NO 219
<211> LENGTH: 6
<212> TYPE: PRT
<213> ORGANISM: Artificial Sequence
<220> FEATURE:
<223> OTHER INFORMATION: CDRH2 of 1H10

<400> SEQUENCE: 219

Asp Pro Ser Gly Gly Ser
1 5

<210> SEQ ID NO 220
<211> LENGTH: 7
<212> TYPE: PRT
<213> ORGANISM: Artificial Sequence
<220> FEATURE:
<223> OTHER INFORMATION: CDRH1 of 1A9 and/or 2D3

<400> SEQUENCE: 220

Gly Phe Thr Phe Ser Ile Tyr
1 5

<210> SEQ ID NO 221
<211> LENGTH: 5
<212> TYPE: PRT
<213> ORGANISM: Artificial Sequence
<220> FEATURE:
<223> OTHER INFORMATION: CDRH2 of 1A9

<400> SEQUENCE: 221

Gly Thr Ala Gly Asp
1 5

<210> SEQ ID NO 222
<211> LENGTH: 7
<212> TYPE: PRT
<213> ORGANISM: Artificial Sequence
<220> FEATURE:
<223> OTHER INFORMATION: CDRH1 of 1E6, 1D2, and/or 2E3

<400> SEQUENCE: 222

Gly Phe Thr Phe Ser Ser Tyr
1 5

<210> SEQ ID NO 223
<211> LENGTH: 6
<212> TYPE: PRT
<213> ORGANISM: Artificial Sequence
<220> FEATURE:
<223> OTHER INFORMATION: CDRH2 of 1E6 and/or 1B9

<400> SEQUENCE: 223

Trp Tyr Asp Gly Ser His
1 5

<210> SEQ ID NO 224
<211> LENGTH: 6
<212> TYPE: PRT
<213> ORGANISM: Artificial Sequence
<220> FEATURE:
<223> OTHER INFORMATION: CDRH2 of 1D2

<400> SEQUENCE: 224

Trp Tyr Asp Gly Ser Gln
1 5

<210> SEQ ID NO 225
<211> LENGTH: 7
<212> TYPE: PRT
<213> ORGANISM: Artificial Sequence
<220> FEATURE:
<223> OTHER INFORMATION: CDRH1 of 1B9

<400> SEQUENCE: 225

Gly Phe Ile Phe Ser Ser Tyr
1 5

<210> SEQ ID NO 226
<211> LENGTH: 7
<212> TYPE: PRT
<213> ORGANISM: Artificial Sequence
<220> FEATURE:
<223> OTHER INFORMATION: CDRH1 of 1H8

<400> SEQUENCE: 226

Gly Phe Thr Phe Gly Ser Tyr
1 5

<210> SEQ ID NO 227
<211> LENGTH: 6
<212> TYPE: PRT
<213> ORGANISM: Artificial Sequence
<220> FEATURE:
<223> OTHER INFORMATION: CDRH2 of 1H8

<400> SEQUENCE: 227

Trp Tyr Asp Gly Ser Asn
1 5

<210> SEQ ID NO 228
<211> LENGTH: 6
<212> TYPE: PRT
<213> ORGANISM: Artificial Sequence
<220> FEATURE:
<223> OTHER INFORMATION: CDRH2 of 2D3

<400> SEQUENCE: 228

Ser Asp Ser Gly Gly Thr
1 5

<210> SEQ ID NO 229
<211> LENGTH: 6
<212> TYPE: PRT
<213> ORGANISM: Artificial Sequence
<220> FEATURE:
<223> OTHER INFORMATION: CDRH2 of 2E3

<400> SEQUENCE: 229

Trp Tyr Gly Gly Ser Asn
1 5

<210> SEQ ID NO 230

<211> LENGTH: 260
<212> TYPE: PRT
<213> ORGANISM: Artificial Sequence
<220> FEATURE:
<223> OTHER INFORMATION: 1H10 scFv VH-VL orientation

<400> SEQUENCE: 230

Met Glu Thr Asp Thr Leu Leu Leu Trp Val Leu Leu Leu Trp Val Pro
1 5 10 15

Gly Ser Thr Gly Gln Val Gln Leu Val Gln Ser Gly Ala Glu Val Lys
20 25 30

Lys Pro Gly Ala Ser Val Lys Val Ser Cys Lys Gly Ser Gly Tyr Ile
35 40 45

Phe Thr Ser Tyr Asp Met His Trp Val Arg Gln Ala Pro Gly Gln Gly
50 55 60

Leu Glu Trp Met Gly Ile Ile Asp Pro Ser Gly Gly Ser Thr Ser Tyr
65 70 75 80

Ala Gln Lys Phe Gln Gly Arg Val Thr Met Thr Arg Asp Thr Ser Met
85 90 95

Ser Thr Val Tyr Met Glu Leu Ser Ser Leu Arg Ser Glu Asp Thr Ala
100 105 110

Val Tyr Tyr Cys Thr Arg Asp Tyr Ser Trp Ser Tyr Phe Asp Tyr Trp
115 120 125

Gly Gln Gly Thr Leu Val Thr Val Ser Ser Gly Gly Gly Gly Ser Gly
130 135 140

Gly Gly Gly Ser Gly Gly Gly Gly Ser Ala Ile Gln Met Thr Gln Ser
145 150 155 160

Pro Ser Ser Leu Ser Ala Ser Val Gly Asp Arg Val Thr Ile Thr Cys
165 170 175

Arg Ala Ser Gln Gly Ile Arg Ile Tyr Leu Gly Trp Tyr Gln Gln Lys
180 185 190

Pro Gly Lys Ala Pro Lys Leu Leu Ile Tyr Ala Thr Ser Ser Leu Gln
195 200 205

Ser Gly Val Pro Ser Arg Phe Ser Gly Ser Gly Ser Gly Thr Asp Phe
210 215 220

Thr Leu Thr Ile Ser Ser Leu Gln Pro Glu Asp Phe Ala Thr Tyr Tyr
225 230 235 240

Cys Leu Gln Asp Tyr Asn Tyr Pro Trp Thr Phe Gly Gln Gly Thr Lys
245 250 255

Val Glu Ile Lys
260

<210> SEQ ID NO 231
<211> LENGTH: 260
<212> TYPE: PRT
<213> ORGANISM: Artificial Sequence
<220> FEATURE:
<223> OTHER INFORMATION: 1H10 scFv VL-VH orientation

<400> SEQUENCE: 231

Met Glu Thr Asp Thr Leu Leu Leu Trp Val Leu Leu Leu Trp Val Pro
1 5 10 15

Gly Ser Thr Gly Ala Ile Gln Met Thr Gln Ser Pro Ser Ser Leu Ser
20 25 30

Ala Ser Val Gly Asp Arg Val Thr Ile Thr Cys Arg Ala Ser Gln Gly
35 40 45

Ile Arg Ile Tyr Leu Gly Trp Tyr Gln Gln Lys Pro Gly Lys Ala Pro 50 55 60

Lys Leu Leu Ile Tyr Ala Thr Ser Ser Leu Gln Ser Gly Val Pro Ser
65 70 75 80

Arg Phe Ser Gly Ser Gly Ser Gly Thr Asp Phe Thr Leu Thr Ile Ser
85 90 95

Ser Leu Gln Pro Glu Asp Phe Ala Thr Tyr Tyr Cys Leu Gln Asp Tyr
100 105 110

Asn Tyr Pro Trp Thr Phe Gly Gln Gly Thr Lys Val Glu Ile Lys Gly
115 120 125

Gly Gly Gly Ser Gly Gly Gly Gly Ser Gly Gly Gly Gly Ser Gln Val
130 135 140

Gln Leu Val Gln Ser Gly Ala Glu Val Lys Lys Pro Gly Ala Ser Val
145 150 155 160

Lys Val Ser Cys Lys Gly Ser Gly Tyr Ile Phe Thr Ser Tyr Asp Met
165 170 175

His Trp Val Arg Gln Ala Pro Gly Gln Gly Leu Glu Trp Met Gly Ile
180 185 190

Ile Asp Pro Ser Gly Gly Ser Thr Ser Tyr Ala Gln Lys Phe Gln Gly
195 200 205

Arg Val Thr Met Thr Arg Asp Thr Ser Met Ser Thr Val Tyr Met Glu
210 215 220

Leu Ser Ser Leu Arg Ser Glu Asp Thr Ala Val Tyr Tyr Cys Thr Arg
225 230 235 240

Asp Tyr Ser Trp Ser Tyr Phe Asp Tyr Trp Gly Gln Gly Thr Leu Val
245 250 255

Thr Val Ser Ser
260

<210> SEQ ID NO 232
<211> LENGTH: 259
<212> TYPE: PRT
<213> ORGANISM: Artificial Sequence
<220> FEATURE:
<223> OTHER INFORMATION: 1A9 scFv VH-VL orientation

<400> SEQUENCE: 232

Met Glu Thr Asp Thr Leu Leu Leu Trp Val Leu Leu Leu Trp Val Pro
1 5 10 15

Gly Ser Thr Gly Glu Val Gln Leu Val Glu Ser Gly Gly Gly Leu Val
20 25 30

Gln Pro Gly Gly Ser Leu Arg Leu Ser Cys Ala Ala Ser Gly Phe Thr
35 40 45

Phe Ser Ile Tyr Asp Met His Trp Val Arg Gln Ala Thr Gly Lys Gly
50 55 60

Leu Glu Trp Val Ser Ala Ile Gly Thr Ala Gly Asp Thr Tyr Tyr Ala
65 70 75 80

Gly Ser Val Lys Gly Arg Phe Thr Ile Ser Arg Glu Asn Ala Lys Asn
85 90 95

Ser Leu Tyr Leu Gln Met Asn Ser Leu Arg Ala Gly Asp Thr Ala Val
100 105 110

Tyr Tyr Cys Ala Arg Glu Tyr Ser Gly Tyr Tyr Phe Asp Tyr Trp Gly
115 120 125

Gln Gly Thr Leu Val Thr Val Ser Ser Gly Gly Gly Gly Ser Gly Gly
130 135 140

Gly Gly Ser Gly Gly Gly Gly Ser Ala Ile Gln Met Thr Gln Ser Pro

-continued

```
145                 150                 155                 160

Ser Ser Leu Ser Ala Ser Val Gly Asp Arg Val Thr Ile Thr Cys Arg
                165                 170                 175

Ala Ser Gln Asp Ile Arg Asn Asp Leu Gly Trp Tyr Gln Gln Lys Pro
            180                 185                 190

Gly Lys Ala Pro Lys Ile Leu Ile Tyr Gly Ala Ser Ser Leu Gln Ser
        195                 200                 205

Gly Val Pro Ser Arg Phe Ser Gly Ser Gly Ser Gly Thr Asp Phe Thr
    210                 215                 220

Phe Thr Ile Ser Ser Leu Gln Pro Glu Asp Phe Ala Thr Tyr Tyr Cys
225                 230                 235                 240

Leu Gln Glu Tyr Asn Tyr Pro Cys Thr Phe Gly Gln Gly Thr Lys Leu
                245                 250                 255

Glu Ile Lys


<210> SEQ ID NO 233
<211> LENGTH: 259
<212> TYPE: PRT
<213> ORGANISM: Artificial Sequence
<220> FEATURE:
<223> OTHER INFORMATION: 1A9 scFv VL-VH orientation

<400> SEQUENCE: 233

Met Glu Thr Asp Thr Leu Leu Leu Trp Val Leu Leu Leu Trp Val Pro
1               5                   10                  15

Gly Ser Thr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Arg Asn Asp Leu Gly Trp Tyr Gln Gln Lys Pro Gly Lys Ala Pro
    50                  55                  60

Lys Ile Leu Ile Tyr Gly Ala Ser Ser Leu Gln Ser Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Phe Ala Thr Tyr Tyr Cys Leu Gln Glu Tyr
            100                 105                 110

Asn Tyr Pro Cys Thr Phe Gly Gln Gly Thr Lys Leu Glu Ile Lys Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Phe Thr Phe Ser Ile Tyr Asp Met
                165                 170                 175

His Trp Val Arg Gln Ala Thr Gly Lys Gly Leu Glu Trp Val Ser Ala
            180                 185                 190

Ile Gly Thr Ala Gly Asp Thr Tyr Tyr Ala Gly Ser Val Lys Gly Arg
        195                 200                 205

Phe Thr Ile Ser Arg Glu Asn Ala Lys Asn Ser Leu Tyr Leu Gln Met
    210                 215                 220

Asn Ser Leu Arg Ala Gly Asp Thr Ala Val Tyr Tyr Cys Ala Arg Glu
225                 230                 235                 240

Tyr Ser Gly Tyr Tyr Phe Asp Tyr Trp Gly Gln Gly Thr Leu Val Thr
                245                 250                 255
```

Val Ser Ser

<210> SEQ ID NO 234
<211> LENGTH: 260
<212> TYPE: PRT
<213> ORGANISM: Artificial Sequence
<220> FEATURE:
<223> OTHER INFORMATION: 1E6 scFv VH-VL orientation

<400> SEQUENCE: 234

Met Glu Thr Asp Thr Leu Leu Leu Trp Val Leu Leu Leu Trp Val Pro
1 5 10 15

Gly Ser Thr Gly Gln Val Gln Leu Val Glu Ser Gly Gly Gly Val Val
20 25 30

Gln Pro Gly Arg Ser Leu Arg Leu Ser Cys Ala Ala Ser Gly Phe Thr
35 40 45

Phe Ser Ser Tyr Asp Ile His Trp Val Arg Gln Ala Pro Gly Lys Gly
50 55 60

Leu Glu Trp Val Ala Val Ile Trp Tyr Asp Gly Ser His Asn Tyr Tyr
65 70 75 80

Ser Asp Ser Val Lys Gly Arg Phe Thr Ile Ser Arg Asp Asn Ser Lys
85 90 95

Asn Thr Leu Tyr Leu Gln Met Asn Ser Leu Arg Ala Glu Asp Thr Ala
100 105 110

Val Tyr Tyr Cys Ala Arg Asp Tyr Ser Gly Ser Tyr Tyr Asp Tyr Trp
115 120 125

Gly Gln Gly Thr Leu Val Thr Val Ser Ser Gly Gly Gly Gly Ser Gly
130 135 140

Gly Gly Gly Ser Gly Gly Gly Gly Ser Ala Ile Gln Met Thr Gln Ser
145 150 155 160

Pro Ser Ser Leu Ser Ala Ser Val Gly Asp Arg Val Thr Ile Thr Cys
165 170 175

Arg Ala Ser Gln Gly Ile Arg Asn Asp Leu Gly Trp Tyr Gln Gln Lys
180 185 190

Pro Gly Lys Ala Pro Lys Leu Leu Ile Tyr Ala Ala Ser Asn Leu Gln
195 200 205

Ser Gly Val Pro Ser Arg Phe Ser Gly Ser Gly Ser Gly Thr Asp Phe
210 215 220

Thr Leu Thr Ile Ser Ser Leu Gln Pro Glu Asp Phe Ala Thr Tyr Tyr
225 230 235 240

Cys Leu Gln Asp Tyr Ser Tyr Pro Arg Thr Phe Gly Gln Gly Thr Lys
245 250 255

Val Glu Ile Lys
260

<210> SEQ ID NO 235
<211> LENGTH: 260
<212> TYPE: PRT
<213> ORGANISM: Artificial Sequence
<220> FEATURE:
<223> OTHER INFORMATION: 1E6 scFv VL-VH orientation

<400> SEQUENCE: 235

Met Glu Thr Asp Thr Leu Leu Leu Trp Val Leu Leu Leu Trp Val Pro
1 5 10 15

Gly Ser Thr Gly Ala Ile Gln Met Thr Gln Ser Pro Ser Ser Leu Ser
20 25 30

-continued

```
Ala Ser Val Gly Asp Arg Val Thr Ile Thr Cys Arg Ala Ser Gln Gly
        35                  40                  45

Ile Arg Asn Asp Leu Gly Trp Tyr Gln Gln Lys Pro Gly Lys Ala Pro
    50                  55                  60

Lys Leu Leu Ile Tyr Ala Ala Ser Asn Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Asp Tyr
            100                 105                 110

Ser Tyr Pro Arg Thr Phe Gly Gln Gly Thr Lys Val Glu Ile Lys Gly
        115                 120                 125

Gly Gly Gly Ser Gly Gly Gly Gly Ser Gly Gly Gly Gly Ser Gln Val
    130                 135                 140

Gln Leu Val Glu Ser Gly Gly Gly Val Val Gln Pro Gly Arg Ser Leu
145                 150                 155                 160

Arg Leu Ser Cys Ala Ala Ser Gly Phe Thr Phe Ser Ser Tyr Asp Ile
                165                 170                 175

His Trp Val Arg Gln Ala Pro Gly Lys Gly Leu Glu Trp Val Ala Val
            180                 185                 190

Ile Trp Tyr Asp Gly Ser His Asn Tyr Tyr Ser Asp Ser Val Lys Gly
        195                 200                 205

Arg Phe Thr Ile Ser Arg Asp Asn Ser Lys Asn Thr Leu Tyr Leu Gln
    210                 215                 220

Met Asn Ser Leu Arg Ala Glu Asp Thr Ala Val Tyr Tyr Cys Ala Arg
225                 230                 235                 240

Asp Tyr Ser Gly Ser Tyr Tyr Asp Tyr Trp Gly Gln Gly Thr Leu Val
                245                 250                 255

Thr Val Ser Ser
            260


<210> SEQ ID NO 236
<211> LENGTH: 262
<212> TYPE: PRT
<213> ORGANISM: Artificial Sequence
<220> FEATURE:
<223> OTHER INFORMATION: 2D3 scFv VH-VL orientation

<400> SEQUENCE: 236

Met Glu Thr Asp Thr Leu Leu Leu Trp Val Leu Leu Leu Trp Val Pro
1               5                   10                  15

Gly Ser Thr Gly Glu Val Gln Leu Leu Glu Ser Gly Gly Gly Leu Val
            20                  25                  30

Gln Pro Gly Gly Ser Leu Ser Leu Ser Cys Ala Ala Ser Gly Phe Thr
        35                  40                  45

Phe Ser Ile Tyr Ala Met Ser Trp Val Arg Gln Ala Pro Gly Lys Gly
    50                  55                  60

Leu Glu Trp Val Ser Ala Ile Ser Asp Ser Gly Gly Thr Thr Tyr Tyr
65                  70                  75                  80

Ala Asp Ser Val Lys Gly Arg Phe Thr Ile Ser Arg Asp Asn Ser Lys
                85                  90                  95

Asn Met Leu Tyr Leu Glu Met Asn Ser Leu Arg Ala Glu Asp Thr Ala
            100                 105                 110

Ile Tyr Tyr Cys Ala Lys Arg Thr Arg Tyr Phe Asn Gly Met Asp Val
        115                 120                 125
```

```
Trp Gly Gln Gly Thr Thr Val Thr Val Ser Ser Gly Gly Gly Gly Ser
    130                 135                 140

Gly Gly Gly Gly Ser Gly Gly Gly Gly Ser Glu Ile Val Met Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Gly Ser Ser Ser Phe Leu Ser Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Ala Arg Phe Ser Gly Ser Gly Ser Gly Thr
    210                 215                 220

Asp Phe Thr Leu Thr Ile Ser Ser Leu Gln Pro Glu Asp Phe Ala Val
225                 230                 235                 240

Tyr Tyr Cys Gln Gln Asp Tyr Asn Leu Pro Phe Thr Phe Gly Pro Gly
                245                 250                 255

Thr Lys Val Asp Ile Lys
            260
```

<210> SEQ ID NO 237
<211> LENGTH: 262
<212> TYPE: PRT
<213> ORGANISM: Artificial Sequence
<220> FEATURE:
<223> OTHER INFORMATION: 2D3 scFv VL-VH orientation

<400> SEQUENCE: 237

```
Met Glu Thr Asp Thr Leu Leu Leu Trp Val Leu Leu Leu Trp Val Pro
1               5                   10                  15

Gly Ser Thr Gly Glu Ile Val Met Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Gly Ser Ser Ser Phe Leu Ser Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Gln Pro Glu Asp Phe Ala Val Tyr Tyr Cys Gln Gln Asp
            100                 105                 110

Tyr Asn Leu Pro Phe Thr Phe Gly Pro Gly Thr Lys Val Asp Ile Lys
        115                 120                 125

Gly Gly Gly Gly Ser Gly Gly Gly Gly Ser Gly Gly Gly Gly Ser Glu
    130                 135                 140

Val Gln Leu Leu Glu Ser Gly Gly Gly Leu Val Gln Pro Gly Gly Ser
145                 150                 155                 160

Leu Ser Leu Ser Cys Ala Ala Ser Gly Phe Thr Phe Ser Ile Tyr Ala
                165                 170                 175

Met Ser Trp Val Arg Gln Ala Pro Gly Lys Gly Leu Glu Trp Val Ser
            180                 185                 190

Ala Ile Ser Asp Ser Gly Gly Thr Thr Tyr Tyr Ala Asp Ser Val Lys
        195                 200                 205

Gly Arg Phe Thr Ile Ser Arg Asp Asn Ser Lys Asn Met Leu Tyr Leu
    210                 215                 220
```

Glu Met Asn Ser Leu Arg Ala Glu Asp Thr Ala Ile Tyr Tyr Cys Ala
225 230 235 240

Lys Arg Thr Arg Tyr Phe Asn Gly Met Asp Val Trp Gly Gln Gly Thr
245 250 255

Thr Val Thr Val Ser Ser
260

<210> SEQ ID NO 238
<211> LENGTH: 520
<212> TYPE: PRT
<213> ORGANISM: Artificial Sequence
<220> FEATURE:
<223> OTHER INFORMATION: 1H10 scFv /CD3 bispecific antibody

<400> SEQUENCE: 238

Met Glu Thr Asp Thr Leu Leu Leu Trp Val Leu Leu Leu Trp Val Pro
1 5 10 15

Gly Ser Thr Gly Gln Val Gln Leu Val Gln Ser Gly Ala Glu Val Lys
20 25 30

Lys Pro Gly Ala Ser Val Lys Val Ser Cys Lys Gly Ser Gly Tyr Ile
35 40 45

Phe Thr Ser Tyr Asp Met His Trp Val Arg Gln Ala Pro Gly Gln Gly
50 55 60

Leu Glu Trp Met Gly Ile Ile Asp Pro Ser Gly Gly Ser Thr Ser Tyr
65 70 75 80

Ala Gln Lys Phe Gln Gly Arg Val Thr Met Thr Arg Asp Thr Ser Met
85 90 95

Ser Thr Val Tyr Met Glu Leu Ser Ser Leu Arg Ser Glu Asp Thr Ala
100 105 110

Val Tyr Tyr Cys Thr Arg Asp Tyr Ser Trp Ser Tyr Phe Asp Tyr Trp
115 120 125

Gly Gln Gly Thr Leu Val Thr Val Ser Ser Gly Gly Gly Gly Ser Gly
130 135 140

Gly Gly Gly Ser Gly Gly Gly Gly Ser Ala Ile Gln Met Thr Gln Ser
145 150 155 160

Pro Ser Ser Leu Ser Ala Ser Val Gly Asp Arg Val Thr Ile Thr Cys
165 170 175

Arg Ala Ser Gln Gly Ile Arg Ile Tyr Leu Gly Trp Tyr Gln Gln Lys
180 185 190

Pro Gly Lys Ala Pro Lys Leu Leu Ile Tyr Ala Thr Ser Ser Leu Gln
195 200 205

Ser Gly Val Pro Ser Arg Phe Ser Gly Ser Gly Ser Gly Thr Asp Phe
210 215 220

Thr Leu Thr Ile Ser Ser Leu Gln Pro Glu Asp Phe Ala Thr Tyr Tyr
225 230 235 240

Cys Leu Gln Asp Tyr Asn Tyr Pro Trp Thr Phe Gly Gln Gly Thr Lys
245 250 255

Val Glu Ile Lys Gly Gly Gly Gly Ser Glu Val Gln Leu Val Glu Ser
260 265 270

Gly Gly Gly Leu Val Gln Pro Gly Gly Ser Leu Lys Leu Ser Cys Ala
275 280 285

Ala Ser Gly Phe Thr Phe Asn Lys Tyr Ala Met Asn Trp Val Arg Gln
290 295 300

Ala Pro Gly Lys Gly Leu Glu Trp Val Ala Arg Ile Arg Ser Lys Tyr
305 310 315 320

```
Asn Asn Tyr Ala Thr Tyr Tyr Ala Asp Ser Val Lys Asp Arg Phe Thr
                325                 330                 335

Ile Ser Arg Asp Asp Ser Lys Asn Thr Ala Tyr Leu Gln Met Asn Asn
            340                 345                 350

Leu Lys Thr Glu Asp Thr Ala Val Tyr Tyr Cys Val Arg His Gly Asn
        355                 360                 365

Phe Gly Asn Ser Tyr Ile Ser Tyr Trp Ala Tyr Trp Gly Gln Gly Thr
    370                 375                 380

Leu Val Thr Val Ser Ser Gly Gly Gly Gly Ser Gly Gly Gly Gly Ser
385                 390                 395                 400

Gly Gly Gly Gly Ser Gln Thr Val Val Thr Gln Glu Pro Ser Leu Thr
                405                 410                 415

Val Ser Pro Gly Gly Thr Val Thr Leu Thr Cys Gly Ser Ser Thr Gly
            420                 425                 430

Ala Val Thr Ser Gly Asn Tyr Pro Asn Trp Val Gln Gln Lys Pro Gly
        435                 440                 445

Gln Ala Pro Arg Gly Leu Ile Gly Gly Thr Lys Phe Leu Ala Pro Gly
    450                 455                 460

Thr Pro Ala Arg Phe Ser Gly Ser Leu Leu Gly Gly Lys Ala Ala Leu
465                 470                 475                 480

Thr Leu Ser Gly Val Gln Pro Glu Asp Glu Ala Glu Tyr Tyr Cys Val
                485                 490                 495

Leu Trp Tyr Ser Asn Arg Trp Val Phe Gly Gly Gly Thr Lys Leu Thr
            500                 505                 510

Val Leu His His His His His His
        515                 520
```

<210> SEQ ID NO 239
<211> LENGTH: 520
<212> TYPE: PRT
<213> ORGANISM: Artificial Sequence
<220> FEATURE:
<223> OTHER INFORMATION: 1H10 scFv /CD3 bispecific antibody

<400> SEQUENCE: 239

```
Met Glu Thr Asp Thr Leu Leu Leu Trp Val Leu Leu Leu Trp Val Pro
1               5                   10                  15

Gly Ser Thr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Arg Ile Tyr Leu Gly Trp Tyr Gln Gln Lys Pro Gly Lys Ala Pro
    50                  55                  60

Lys Leu Leu Ile Tyr Ala Thr Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Asp Tyr
            100                 105                 110

Asn Tyr Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ser Gln Val
    130                 135                 140

Gln Leu Val Gln Ser Gly Ala Glu Val Lys Lys Pro Gly Ala Ser Val
145                 150                 155                 160
```

-continued

```
Lys Val Ser Cys Lys Gly Ser Gly Tyr Ile Phe Thr Ser Tyr Asp Met
                165                 170                 175

His Trp Val Arg Gln Ala Pro Gly Gln Gly Leu Glu Trp Met Gly Ile
            180                 185                 190

Ile Asp Pro Ser Gly Gly Ser Thr Ser Tyr Ala Gln Lys Phe Gln Gly
        195                 200                 205

Arg Val Thr Met Thr Arg Asp Thr Ser Met Ser Thr Val Tyr Met Glu
    210                 215                 220

Leu Ser Ser Leu Arg Ser Glu Asp Thr Ala Val Tyr Tyr Cys Thr Arg
225                 230                 235                 240

Asp Tyr Ser Trp Ser Tyr Phe Asp Tyr Trp Gly Gln Gly Thr Leu Val
                245                 250                 255

Thr Val Ser Ser Gly Gly Gly Gly Ser Glu Val Gln Leu Val Glu Ser
            260                 265                 270

Gly Gly Gly Leu Val Gln Pro Gly Gly Ser Leu Lys Leu Ser Cys Ala
        275                 280                 285

Ala Ser Gly Phe Thr Phe Asn Lys Tyr Ala Met Asn Trp Val Arg Gln
    290                 295                 300

Ala Pro Gly Lys Gly Leu Glu Trp Val Ala Arg Ile Arg Ser Lys Tyr
305                 310                 315                 320

Asn Asn Tyr Ala Thr Tyr Tyr Ala Asp Ser Val Lys Asp Arg Phe Thr
                325                 330                 335

Ile Ser Arg Asp Asp Ser Lys Asn Thr Ala Tyr Leu Gln Met Asn Asn
            340                 345                 350

Leu Lys Thr Glu Asp Thr Ala Val Tyr Tyr Cys Val Arg His Gly Asn
        355                 360                 365

Phe Gly Asn Ser Tyr Ile Ser Tyr Trp Ala Tyr Trp Gly Gln Gly Thr
    370                 375                 380

Leu Val Thr Val Ser Ser Gly Gly Gly Gly Ser Gly Gly Gly Gly Ser
385                 390                 395                 400

Gly Gly Gly Gly Ser Gln Thr Val Val Thr Gln Glu Pro Ser Leu Thr
                405                 410                 415

Val Ser Pro Gly Gly Thr Val Thr Leu Thr Cys Gly Ser Ser Thr Gly
            420                 425                 430

Ala Val Thr Ser Gly Asn Tyr Pro Asn Trp Val Gln Gln Lys Pro Gly
        435                 440                 445

Gln Ala Pro Arg Gly Leu Ile Gly Gly Thr Lys Phe Leu Ala Pro Gly
    450                 455                 460

Thr Pro Ala Arg Phe Ser Gly Ser Leu Leu Gly Gly Lys Ala Ala Leu
465                 470                 475                 480

Thr Leu Ser Gly Val Gln Pro Glu Asp Glu Ala Glu Tyr Tyr Cys Val
                485                 490                 495

Leu Trp Tyr Ser Asn Arg Trp Val Phe Gly Gly Gly Thr Lys Leu Thr
            500                 505                 510

Val Leu His His His His His His
        515                 520
```

<210> SEQ ID NO 240
<211> LENGTH: 519
<212> TYPE: PRT
<213> ORGANISM: Artificial Sequence
<220> FEATURE:
<223> OTHER INFORMATION: 1A9 scFv/CD3 bispecific antibody

<400> SEQUENCE: 240

-continued

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ile Tyr Asp Met His Trp Val Arg Gln Ala Thr Gly Lys Gly
    50                  55                  60

Leu Glu Trp Val Ser Ala Ile Gly Thr Ala Gly Asp Thr Tyr Tyr Ala
65                  70                  75                  80

Gly Ser Val Lys Gly Arg Phe Thr Ile Ser Arg Glu Asn Ala Lys Asn
                85                  90                  95

Ser Leu Tyr Leu Gln Met Asn Ser Leu Arg Ala Gly Asp Thr Ala Val
            100                 105                 110

Tyr Tyr Cys Ala Arg Glu Tyr Ser Gly Tyr Tyr Phe Asp Tyr Trp Gly
        115                 120                 125

Gln Gly Thr Leu Val Thr Val Ser Ser Gly Gly Gly Gly Ser Gly Gly
    130                 135                 140

Gly Gly Ser Gly Gly Gly Gly Ser Ala Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Asp Ile Arg Asn Asp Leu Gly Trp Tyr Gln Gln Lys Pro
            180                 185                 190

Gly Lys Ala Pro Lys Ile Leu Ile Tyr Gly Ala Ser Ser Leu Gln Ser
        195                 200                 205

Gly Val Pro Ser Arg Phe Ser Gly Ser Gly Ser Gly Thr Asp Phe Thr
    210                 215                 220

Phe Thr Ile Ser Ser Leu Gln Pro Glu Asp Phe Ala Thr Tyr Tyr Cys
225                 230                 235                 240

Leu Gln Glu Tyr Asn Tyr Pro Cys Thr Phe Gly Gln Gly Thr Lys Leu
                245                 250                 255

Glu Ile Lys Gly Gly Gly Gly Ser Glu Val Gln Leu Val Glu Ser Gly
            260                 265                 270

Gly Gly Leu Val Gln Pro Gly Gly Ser Leu Lys Leu Ser Cys Ala Ala
        275                 280                 285

Ser Gly Phe Thr Phe Asn Lys Tyr Ala Met Asn Trp Val Arg Gln Ala
    290                 295                 300

Pro Gly Lys Gly Leu Glu Trp Val Ala Arg Ile Arg Ser Lys Tyr Asn
305                 310                 315                 320

Asn Tyr Ala Thr Tyr Tyr Ala Asp Ser Val Lys Asp Arg Phe Thr Ile
                325                 330                 335

Ser Arg Asp Asp Ser Lys Asn Thr Ala Tyr Leu Gln Met Asn Asn Leu
            340                 345                 350

Lys Thr Glu Asp Thr Ala Val Tyr Tyr Cys Val Arg His Gly Asn Phe
        355                 360                 365

Gly Asn Ser Tyr Ile Ser Tyr Trp Ala Tyr Trp Gly Gln Gly Thr Leu
    370                 375                 380

Val Thr Val Ser Ser Gly Gly Gly Gly Ser Gly Gly Gly Gly Ser Gly
385                 390                 395                 400

Gly Gly Gly Ser Gln Thr Val Val Thr Gln Glu Pro Ser Leu Thr Val
                405                 410                 415
```

```
Ser Pro Gly Gly Thr Val Thr Leu Thr Cys Gly Ser Ser Thr Gly Ala
            420                 425                 430

Val Thr Ser Gly Asn Tyr Pro Asn Trp Val Gln Gln Lys Pro Gly Gln
        435                 440                 445

Ala Pro Arg Gly Leu Ile Gly Gly Thr Lys Phe Leu Ala Pro Gly Thr
    450                 455                 460

Pro Ala Arg Phe Ser Gly Ser Leu Leu Gly Gly Lys Ala Ala Leu Thr
465                 470                 475                 480

Leu Ser Gly Val Gln Pro Glu Asp Glu Ala Glu Tyr Tyr Cys Val Leu
                485                 490                 495

Trp Tyr Ser Asn Arg Trp Val Phe Gly Gly Gly Thr Lys Leu Thr Val
            500                 505                 510

Leu His His His His His His
        515


<210> SEQ ID NO 241
<211> LENGTH: 519
<212> TYPE: PRT
<213> ORGANISM: Artificial Sequence
<220> FEATURE:
<223> OTHER INFORMATION: 1A9 scFv/CD3 bispecific antibody

<400> SEQUENCE: 241

Met Glu Thr Asp Thr Leu Leu Leu Trp Val Leu Leu Leu Trp Val Pro
1               5                   10                  15

Gly Ser Thr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Arg Asn Asp Leu Gly Trp Tyr Gln Gln Lys Pro Gly Lys Ala Pro
    50                  55                  60

Lys Ile Leu Ile Tyr Gly Ala Ser Ser Leu Gln Ser Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Phe Ala Thr Tyr Tyr Cys Leu Gln Glu Tyr
            100                 105                 110

Asn Tyr Pro Cys Thr Phe Gly Gln Gly Thr Lys Leu Glu Ile Lys Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Phe Thr Phe Ser Ile Tyr Asp Met
                165                 170                 175

His Trp Val Arg Gln Ala Thr Gly Lys Gly Leu Glu Trp Val Ser Ala
            180                 185                 190

Ile Gly Thr Ala Gly Asp Thr Tyr Tyr Ala Gly Ser Val Lys Gly Arg
        195                 200                 205

Phe Thr Ile Ser Arg Glu Asn Ala Lys Asn Ser Leu Tyr Leu Gln Met
    210                 215                 220

Asn Ser Leu Arg Ala Gly Asp Thr Ala Val Tyr Tyr Cys Ala Arg Glu
225                 230                 235                 240

Tyr Ser Gly Tyr Tyr Phe Asp Tyr Trp Gly Gln Gly Thr Leu Val Thr
                245                 250                 255
```

```
Val Ser Ser Gly Gly Gly Gly Ser Glu Val Gln Leu Val Glu Ser Gly
            260                 265                 270

Gly Gly Leu Val Gln Pro Gly Gly Ser Leu Lys Leu Ser Cys Ala Ala
        275                 280                 285

Ser Gly Phe Thr Phe Asn Lys Tyr Ala Met Asn Trp Val Arg Gln Ala
    290                 295                 300

Pro Gly Lys Gly Leu Glu Trp Val Ala Arg Ile Arg Ser Lys Tyr Asn
305                 310                 315                 320

Asn Tyr Ala Thr Tyr Tyr Ala Asp Ser Val Lys Asp Arg Phe Thr Ile
                325                 330                 335

Ser Arg Asp Asp Ser Lys Asn Thr Ala Tyr Leu Gln Met Asn Asn Leu
            340                 345                 350

Lys Thr Glu Asp Thr Ala Val Tyr Tyr Cys Val Arg His Gly Asn Phe
        355                 360                 365

Gly Asn Ser Tyr Ile Ser Tyr Trp Ala Tyr Trp Gly Gln Gly Thr Leu
    370                 375                 380

Val Thr Val Ser Ser Gly Gly Gly Gly Ser Gly Gly Gly Gly Ser Gly
385                 390                 395                 400

Gly Gly Gly Ser Gln Thr Val Val Thr Gln Glu Pro Ser Leu Thr Val
                405                 410                 415

Ser Pro Gly Gly Thr Val Thr Leu Thr Cys Gly Ser Ser Thr Gly Ala
            420                 425                 430

Val Thr Ser Gly Asn Tyr Pro Asn Trp Val Gln Gln Lys Pro Gly Gln
        435                 440                 445

Ala Pro Arg Gly Leu Ile Gly Gly Thr Lys Phe Leu Ala Pro Gly Thr
    450                 455                 460

Pro Ala Arg Phe Ser Gly Ser Leu Leu Gly Gly Lys Ala Ala Leu Thr
465                 470                 475                 480

Leu Ser Gly Val Gln Pro Glu Asp Glu Ala Glu Tyr Tyr Cys Val Leu
                485                 490                 495

Trp Tyr Ser Asn Arg Trp Val Phe Gly Gly Gly Thr Lys Leu Thr Val
            500                 505                 510

Leu His His His His His His
        515


<210> SEQ ID NO 242
<211> LENGTH: 520
<212> TYPE: PRT
<213> ORGANISM: Artificial Sequence
<220> FEATURE:
<223> OTHER INFORMATION: 1E6 scFv/CD3 bispecific antibody

<400> SEQUENCE: 242

Met Glu Thr Asp Thr Leu Leu Leu Trp Val Leu Leu Leu Trp Val Pro
1               5                   10                  15

Gly Ser Thr Gly Gln Val Gln Leu Val Glu Ser Gly Gly Gly Val Val
            20                  25                  30

Gln Pro Gly Arg Ser Leu Arg Leu Ser Cys Ala Ala Ser Gly Phe Thr
        35                  40                  45

Phe Ser Ser Tyr Asp Ile His Trp Val Arg Gln Ala Pro Gly Lys Gly
    50                  55                  60

Leu Glu Trp Val Ala Val Ile Trp Tyr Asp Gly Ser His Asn Tyr Tyr
65                  70                  75                  80

Ser Asp Ser Val Lys Gly Arg Phe Thr Ile Ser Arg Asp Asn Ser Lys
                85                  90                  95
```

-continued

```
Asn Thr Leu Tyr Leu Gln Met Asn Ser Leu Arg Ala Glu Asp Thr Ala
            100                 105                 110

Val Tyr Tyr Cys Ala Arg Asp Tyr Ser Gly Ser Tyr Tyr Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Ala Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Gly Ile Arg Asn Asp Leu Gly Trp Tyr Gln Gln Lys
            180                 185                 190

Pro Gly Lys Ala Pro Lys Leu Leu Ile Tyr Ala Ala Ser Asn Leu Gln
        195                 200                 205

Ser Gly Val Pro Ser Arg Phe Ser Gly Ser Gly Ser Gly Thr Asp Phe
    210                 215                 220

Thr Leu Thr Ile Ser Ser Leu Gln Pro Glu Asp Phe Ala Thr Tyr Tyr
225                 230                 235                 240

Cys Leu Gln Asp Tyr Ser Tyr Pro Arg Thr Phe Gly Gln Gly Thr Lys
                245                 250                 255

Val Glu Ile Lys Gly Gly Gly Gly Ser Glu Val Gln Leu Val Glu Ser
            260                 265                 270

Gly Gly Gly Leu Val Gln Pro Gly Gly Ser Leu Lys Leu Ser Cys Ala
        275                 280                 285

Ala Ser Gly Phe Thr Phe Asn Lys Tyr Ala Met Asn Trp Val Arg Gln
    290                 295                 300

Ala Pro Gly Lys Gly Leu Glu Trp Val Ala Arg Ile Arg Ser Lys Tyr
305                 310                 315                 320

Asn Asn Tyr Ala Thr Tyr Tyr Ala Asp Ser Val Lys Asp Arg Phe Thr
                325                 330                 335

Ile Ser Arg Asp Asp Ser Lys Asn Thr Ala Tyr Leu Gln Met Asn Asn
            340                 345                 350

Leu Lys Thr Glu Asp Thr Ala Val Tyr Tyr Cys Val Arg His Gly Asn
        355                 360                 365

Phe Gly Asn Ser Tyr Ile Ser Tyr Trp Ala Tyr Trp Gly Gln Gly Thr
    370                 375                 380

Leu Val Thr Val Ser Ser Gly Gly Gly Gly Ser Gly Gly Gly Gly Ser
385                 390                 395                 400

Gly Gly Gly Gly Ser Gln Thr Val Val Thr Gln Glu Pro Ser Leu Thr
                405                 410                 415

Val Ser Pro Gly Gly Thr Val Thr Leu Thr Cys Gly Ser Ser Thr Gly
            420                 425                 430

Ala Val Thr Ser Gly Asn Tyr Pro Asn Trp Val Gln Gln Lys Pro Gly
        435                 440                 445

Gln Ala Pro Arg Gly Leu Ile Gly Gly Thr Lys Phe Leu Ala Pro Gly
    450                 455                 460

Thr Pro Ala Arg Phe Ser Gly Ser Leu Leu Gly Gly Lys Ala Ala Leu
465                 470                 475                 480

Thr Leu Ser Gly Val Gln Pro Glu Asp Glu Ala Glu Tyr Tyr Cys Val
                485                 490                 495

Leu Trp Tyr Ser Asn Arg Trp Val Phe Gly Gly Gly Thr Lys Leu Thr
            500                 505                 510

Val Leu His His His His His His
```

515 520

<210> SEQ ID NO 243
<211> LENGTH: 520
<212> TYPE: PRT
<213> ORGANISM: Artificial Sequence
<220> FEATURE:
<223> OTHER INFORMATION: 1E6 scFv/CD3 bispecific antibody

<400> SEQUENCE: 243

Met Glu Thr Asp Thr Leu Leu Leu Trp Val Leu Leu Leu Trp Val Pro
1 5 10 15

Gly Ser Thr Gly Ala Ile Gln Met Thr Gln Ser Pro Ser Ser Leu Ser
20 25 30

Ala Ser Val Gly Asp Arg Val Thr Ile Thr Cys Arg Ala Ser Gln Gly
35 40 45

Ile Arg Asn Asp Leu Gly Trp Tyr Gln Gln Lys Pro Gly Lys Ala Pro
50 55 60

Lys Leu Leu Ile Tyr Ala Ala Ser Asn Leu Gln Ser Gly Val Pro Ser
65 70 75 80

Arg Phe Ser Gly Ser Gly Ser Gly Thr Asp Phe Thr Leu Thr Ile Ser
85 90 95

Ser Leu Gln Pro Glu Asp Phe Ala Thr Tyr Tyr Cys Leu Gln Asp Tyr
100 105 110

Ser Tyr Pro Arg Thr Phe Gly Gln Gly Thr Lys Val Glu Ile Lys Gly
115 120 125

Gly Gly Gly Ser Gly Gly Gly Gly Ser Gly Gly Gly Gly Ser Gln Val
130 135 140

Gln Leu Val Glu Ser Gly Gly Gly Val Val Gln Pro Gly Arg Ser Leu
145 150 155 160

Arg Leu Ser Cys Ala Ala Ser Gly Phe Thr Phe Ser Ser Tyr Asp Ile
165 170 175

His Trp Val Arg Gln Ala Pro Gly Lys Gly Leu Glu Trp Val Ala Val
180 185 190

Ile Trp Tyr Asp Gly Ser His Asn Tyr Tyr Ser Asp Ser Val Lys Gly
195 200 205

Arg Phe Thr Ile Ser Arg Asp Asn Ser Lys Asn Thr Leu Tyr Leu Gln
210 215 220

Met Asn Ser Leu Arg Ala Glu Asp Thr Ala Val Tyr Tyr Cys Ala Arg
225 230 235 240

Asp Tyr Ser Gly Ser Tyr Tyr Asp Tyr Trp Gly Gln Gly Thr Leu Val
245 250 255

Thr Val Ser Ser Gly Gly Gly Gly Ser Glu Val Gln Leu Val Glu Ser
260 265 270

Gly Gly Gly Leu Val Gln Pro Gly Gly Ser Leu Lys Leu Ser Cys Ala
275 280 285

Ala Ser Gly Phe Thr Phe Asn Lys Tyr Ala Met Asn Trp Val Arg Gln
290 295 300

Ala Pro Gly Lys Gly Leu Glu Trp Val Ala Arg Ile Arg Ser Lys Tyr
305 310 315 320

Asn Asn Tyr Ala Thr Tyr Tyr Ala Asp Ser Val Lys Asp Arg Phe Thr
325 330 335

Ile Ser Arg Asp Asp Ser Lys Asn Thr Ala Tyr Leu Gln Met Asn Asn
340 345 350

Leu Lys Thr Glu Asp Thr Ala Val Tyr Tyr Cys Val Arg His Gly Asn 355 360 365

Phe Gly Asn Ser Tyr Ile Ser Tyr Trp Ala Tyr Trp Gly Gln Gly Thr
370 375 380

Leu Val Thr Val Ser Ser Gly Gly Gly Gly Ser Gly Gly Gly Gly Ser
385 390 395 400

Gly Gly Gly Gly Ser Gln Thr Val Val Thr Gln Glu Pro Ser Leu Thr
405 410 415

Val Ser Pro Gly Gly Thr Val Thr Leu Thr Cys Gly Ser Ser Thr Gly
420 425 430

Ala Val Thr Ser Gly Asn Tyr Pro Asn Trp Val Gln Gln Lys Pro Gly
435 440 445

Gln Ala Pro Arg Gly Leu Ile Gly Gly Thr Lys Phe Leu Ala Pro Gly
450 455 460

Thr Pro Ala Arg Phe Ser Gly Ser Leu Leu Gly Gly Lys Ala Ala Leu
465 470 475 480

Thr Leu Ser Gly Val Gln Pro Glu Asp Glu Ala Glu Tyr Tyr Cys Val
485 490 495

Leu Trp Tyr Ser Asn Arg Trp Val Phe Gly Gly Gly Thr Lys Leu Thr
500 505 510

Val Leu His His His His His His
515 520

<210> SEQ ID NO 244
<211> LENGTH: 522
<212> TYPE: PRT
<213> ORGANISM: Artificial Sequence
<220> FEATURE:
<223> OTHER INFORMATION: 2D3 scFv/CD3 bispecific antibody

<400> SEQUENCE: 244

Met Glu Thr Asp Thr Leu Leu Leu Trp Val Leu Leu Leu Trp Val Pro
1 5 10 15

Gly Ser Thr Gly Glu Val Gln Leu Leu Glu Ser Gly Gly Gly Leu Val
20 25 30

Gln Pro Gly Gly Ser Leu Ser Leu Ser Cys Ala Ala Ser Gly Phe Thr
35 40 45

Phe Ser Ile Tyr Ala Met Ser Trp Val Arg Gln Ala Pro Gly Lys Gly
50 55 60

Leu Glu Trp Val Ser Ala Ile Ser Asp Ser Gly Gly Thr Thr Tyr Tyr
65 70 75 80

Ala Asp Ser Val Lys Gly Arg Phe Thr Ile Ser Arg Asp Asn Ser Lys
85 90 95

Asn Met Leu Tyr Leu Glu Met Asn Ser Leu Arg Ala Glu Asp Thr Ala
100 105 110

Ile Tyr Tyr Cys Ala Lys Arg Thr Arg Tyr Phe Asn Gly Met Asp Val
115 120 125

Trp Gly Gln Gly Thr Thr Val Thr Val Ser Ser Gly Gly Gly Gly Ser
130 135 140

Gly Gly Gly Gly Ser Gly Gly Gly Gly Ser Glu Ile Val Met Thr Gln
145 150 155 160

Ser Pro Ala Thr Leu Ser Leu Ser Pro Gly Glu Arg Ala Thr Leu Ser
165 170 175

Cys Arg Ala Ser Gln Ser Gly Ser Ser Ser Phe Leu Ser Trp Tyr Gln
180 185 190

Gln Lys Pro Gly Gln Ala Pro Arg Leu Leu Ile Tyr Gly Ala Ser Thr

```
        195                 200                 205

Arg Ala Thr Gly Ile Pro Ala Arg Phe Ser Gly Ser Gly Ser Gly Thr
    210                 215                 220

Asp Phe Thr Leu Thr Ile Ser Ser Leu Gln Pro Glu Asp Phe Ala Val
225                 230                 235                 240

Tyr Tyr Cys Gln Gln Asp Tyr Asn Leu Pro Phe Thr Phe Gly Pro Gly
                245                 250                 255

Thr Lys Val Asp Ile Lys Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Met Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Ser Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Gly Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Gly Ser Gly Gly Gly Gly Ser Gln Thr Val Val Thr Gln Glu Pro Ser
                405                 410                 415

Leu Thr Val Ser Pro Gly Gly Thr Val Thr Leu Thr Cys Gly Ser Ser
            420                 425                 430

Thr Gly Ala Val Thr Ser Gly Asn Tyr Pro Asn Trp Val Gln Gln Lys
        435                 440                 445

Pro Gly Gln Ala Pro Arg Gly Leu Ile Gly Gly Thr Lys Phe Leu Ala
    450                 455                 460

Pro Gly Thr Pro Ala Arg Phe Ser Gly Ser Leu Leu Gly Gly Lys Ala
465                 470                 475                 480

Ala Leu Thr Leu Ser Gly Val Gln Pro Glu Asp Glu Ala Glu Tyr Tyr
                485                 490                 495

Cys Val Leu Trp Tyr Ser Asn Arg Trp Val Phe Gly Gly Gly Thr Lys
            500                 505                 510

Leu Thr Val Leu His His His His His His
        515                 520


<210> SEQ ID NO 245
<211> LENGTH: 522
<212> TYPE: PRT
<213> ORGANISM: Artificial Sequence
<220> FEATURE:
<223> OTHER INFORMATION: 2D3 scFv/CD3 bispecific antibody

<400> SEQUENCE: 245

Met Glu Thr Asp Thr Leu Leu Leu Trp Val Leu Leu Leu Trp Val Pro
1               5                   10                  15

Gly Ser Thr Gly Glu Ile Val Met Thr Gln Ser Pro Ala Thr Leu Ser
            20                  25                  30

Leu Ser Pro Gly Glu Arg Ala Thr Leu Ser Cys Arg Ala Ser Gln Ser
```

-continued

```
        35                  40                  45

Gly Ser Ser Ser Phe Leu Ser Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Gln Pro Glu Asp Phe Ala Val Tyr Tyr Cys Gln Gln Asp
            100                 105                 110

Tyr Asn Leu Pro Phe Thr Phe Gly Pro Gly Thr Lys Val Asp Ile Lys
        115                 120                 125

Gly Gly Gly Gly Ser Gly Gly Gly Gly Ser Gly Gly Gly Gly Ser Glu
    130                 135                 140

Val Gln Leu Leu Glu Ser Gly Gly Gly Leu Val Gln Pro Gly Gly Ser
145                 150                 155                 160

Leu Ser Leu Ser Cys Ala Ala Ser Gly Phe Thr Phe Ser Ile Tyr Ala
                165                 170                 175

Met Ser Trp Val Arg Gln Ala Pro Gly Lys Gly Leu Glu Trp Val Ser
            180                 185                 190

Ala Ile Ser Asp Ser Gly Gly Thr Thr Tyr Tyr Ala Asp Ser Val Lys
        195                 200                 205

Gly Arg Phe Thr Ile Ser Arg Asp Asn Ser Lys Asn Met Leu Tyr Leu
    210                 215                 220

Glu Met Asn Ser Leu Arg Ala Glu Asp Thr Ala Ile Tyr Tyr Cys Ala
225                 230                 235                 240

Lys Arg Thr Arg Tyr Phe Asn Gly Met Asp Val Trp Gly Gln Gly Thr
                245                 250                 255

Thr Val Thr Val Ser Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Met Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Ser Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Gly Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Gly Ser Gly Gly Gly Gly Ser Gln Thr Val Val Thr Gln Glu Pro Ser
                405                 410                 415

Leu Thr Val Ser Pro Gly Gly Thr Val Thr Leu Thr Cys Gly Ser Ser
            420                 425                 430

Thr Gly Ala Val Thr Ser Gly Asn Tyr Pro Asn Trp Val Gln Gln Lys
        435                 440                 445

Pro Gly Gln Ala Pro Arg Gly Leu Ile Gly Gly Thr Lys Phe Leu Ala
    450                 455                 460
```

```
Pro Gly Thr Pro Ala Arg Phe Ser Gly Ser Leu Leu Gly Gly Lys Ala
465                 470                 475                 480

Ala Leu Thr Leu Ser Gly Val Gln Pro Glu Asp Glu Ala Glu Tyr Tyr
                485                 490                 495

Cys Val Leu Trp Tyr Ser Asn Arg Trp Val Phe Gly Gly Gly Thr Lys
            500                 505                 510

Leu Thr Val Leu His His His His His His
        515                 520


<210> SEQ ID NO 246
<211> LENGTH: 1092
<212> TYPE: DNA
<213> ORGANISM: Homo sapiens

<400> SEQUENCE: 246

atgccgctgc tgctactgct gcccctgctg tgggcagggg ccctggctat ggatccaaat      60

ttctggctgc aagtgcagga gtcagtgacg gtacaggagg gtttgtgcgt cctcgtgccc     120

tgcactttct tccatcccat accctactac gacaagaact ccccagttca tggttactgg     180

ttccgggaag gagccattat atccagggac tctccagtgg ccacaaacaa gctagatcaa     240

gaagtacagg aggagactca gggcagattc cgcctccttg gggatcccag taggaacaac     300

tgctccctga gcatcgtaga cgccaggagg agggataatg gttcatactt ctttcggatg     360

gagagaggaa gtaccaaata cagttacaaa tctccccagc tctctgtgca tgtgacagac     420

ttgacccaca ggcccaaaat cctcatccct ggcactctag aacccggcca ctccaaaaac     480

ctgacctgct ctgtgtcctg ggcctgtgag cagggaacac cccgatctt ctcctggttg      540

tcagctgccc ccacctccct gggccccagg actactcact cctcggtgct cataatcacc     600

ccacggcccc aggaccacgg caccaacctg acctgtcagg tgaagttcgc tggagctggt     660

gtgactacgg agagaaccat ccagctcaac gtcacctatg ttccacagaa cccaacaact     720

ggtatctttc caggagatgg ctcagggaaa caagagacca gagcaggagt ggttcatggg     780

gccattggag gagctggtgt tacagccctg ctcgctcttt gtctctgcct catcttcttc     840

atagtgaaga cccacaggag gaaagcagcc aggacagcag tgggcaggaa tgacacccac     900

cctaccacag ggtcagcctc cccgaaacac cagaagaagt ccaagttaca tggccccact     960

gaaacctcaa gctgttcagg tgccgcccct actgtggaga tggatgagga gctgcattat    1020

gcttccctca actttcatgg gatgaatcct tccaaggaca cctccaccga atactcagag    1080

gtcaggaccc ag                                                        1092


<210> SEQ ID NO 247
<211> LENGTH: 364
<212> TYPE: PRT
<213> ORGANISM: Homo sapiens

<400> SEQUENCE: 247

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60
```

-continued

```
Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360


<210> SEQ ID NO 248
<211> LENGTH: 22
<212> TYPE: PRT
<213> ORGANISM: Artificial Sequence
<220> FEATURE:
<223> OTHER INFORMATION: 1H10, 1A9, 1E6, and/or 1B9 light chain signal
      peptide

<400> SEQUENCE: 248

Met Asp Met Arg Val Pro Ala Gln Leu Leu Gly Leu Leu Leu Leu Trp
1               5                   10                  15

Leu Pro Gly Ala Arg Cys
            20


<210> SEQ ID NO 249
<211> LENGTH: 20
<212> TYPE: PRT
<213> ORGANISM: Artificial Sequence
```

<220> FEATURE:
<223> OTHER INFORMATION: 1D2 light chain signal peptide

<400> SEQUENCE: 249

Met Arg Val Pro Ala Gln Leu Leu Gly Leu Leu Leu Leu Trp Leu Pro
1 5 10 15

Gly Ala Arg Cys
20

<210> SEQ ID NO 250
<211> LENGTH: 22
<212> TYPE: PRT
<213> ORGANISM: Artificial Sequence
<220> FEATURE:
<223> OTHER INFORMATION: 1H8 light chain signal peptide

<400> SEQUENCE: 250

Met Asp Met Arg Leu Pro Ala Gln Leu Leu Gly Leu Leu Met Leu Trp
1 5 10 15

Val Pro Ala Ser Arg Gly
20

<210> SEQ ID NO 251
<211> LENGTH: 22
<212> TYPE: PRT
<213> ORGANISM: Artificial Sequence
<220> FEATURE:
<223> OTHER INFORMATION: 2D3 light chain signal peptide

<400> SEQUENCE: 251

Met Glu Pro Trp Lys Pro Gln His Ser Phe Phe Phe Leu Leu Leu Trp
1 5 10 15

Leu Pro Asp Ser Thr Gly
20

<210> SEQ ID NO 252
<211> LENGTH: 19
<212> TYPE: PRT
<213> ORGANISM: Artificial Sequence
<220> FEATURE:
<223> OTHER INFORMATION: 1H10 heavy chain signal peptide

<400> SEQUENCE: 252

Met Asp Trp Thr Trp Arg Val Phe Cys Leu Leu Ala Val Ala Pro Gly
1 5 10 15

Val His Ser

<210> SEQ ID NO 253
<211> LENGTH: 19
<212> TYPE: PRT
<213> ORGANISM: Artificial Sequence
<220> FEATURE:
<223> OTHER INFORMATION: 1A9 heavy chain signal peptide

<400> SEQUENCE: 253

Met Glu Leu Gly Leu Ser Trp Val Phe Leu Val Ala Ile Leu Glu Gly
1 5 10 15

Val Gln Cys

<210> SEQ ID NO 254
<211> LENGTH: 19
<212> TYPE: PRT
<213> ORGANISM: Artificial Sequence
<220> FEATURE:

-continued

<223> OTHER INFORMATION: 1E6 and/or 2E3 heavy chain signal peptide

<400> SEQUENCE: 254

Met Glu Phe Gly Leu Ser Trp Val Phe Leu Val Ala Leu Leu Arg Gly
1 5 10 15

Val Gln Cys

<210> SEQ ID NO 255
<211> LENGTH: 19
<212> TYPE: PRT
<213> ORGANISM: Artificial Sequence
<220> FEATURE:
<223> OTHER INFORMATION: 1D2 heavy chain signal peptide

<400> SEQUENCE: 255

Met Glu Ser Gly Leu Ser Trp Val Phe Leu Val Ala Leu Leu Arg Gly
1 5 10 15

Val Gln Cys

<210> SEQ ID NO 256
<211> LENGTH: 19
<212> TYPE: PRT
<213> ORGANISM: Artificial Sequence
<220> FEATURE:
<223> OTHER INFORMATION: 1B9 heavy chain signal peptide

<400> SEQUENCE: 256

Met Glu Phe Gly Leu Ser Trp Val Phe Leu Ile Ala Leu Leu Arg Gly
1 5 10 15

Val Gln Cys

<210> SEQ ID NO 257
<211> LENGTH: 22
<212> TYPE: PRT
<213> ORGANISM: Artificial Sequence
<220> FEATURE:
<223> OTHER INFORMATION: 1H8 heavy chain signal peptide

<400> SEQUENCE: 257

Met Leu Leu Leu Val Thr Ser Leu Leu Leu Cys Glu Leu Pro His Pro
1 5 10 15

Ala Phe Leu Leu Ile Pro
20

<210> SEQ ID NO 258
<211> LENGTH: 19
<212> TYPE: PRT
<213> ORGANISM: Artificial Sequence
<220> FEATURE:
<223> OTHER INFORMATION: 2D3 heavy chain signal peptide

<400> SEQUENCE: 258

Met Glu Phe Gly Leu Ser Trp Leu Phe Leu Val Ala Ile Leu Lys Gly
1 5 10 15

Val Gln Cys

<210> SEQ ID NO 259
<211> LENGTH: 531
<212> TYPE: PRT
<213> ORGANISM: Artificial Sequence
<220> FEATURE:
<223> OTHER INFORMATION: V-set directed CD33/CD3 BsAb (RC1)

<400> SEQUENCE: 259

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Glu Ser Val Lys Val Ser Cys Lys Ala Ser Gly Tyr Thr
        35                  40                  45

Phe Thr Asn Tyr Gly Met Asn Trp Val Lys Gln Ala Pro Gly Gln Gly
    50                  55                  60

Leu Glu Trp Met Gly Trp Ile Asn Thr Tyr Thr Gly Glu Pro Thr Tyr
65                  70                  75                  80

Ala Asp Lys Phe Gln Gly Arg Val Thr Met Thr Thr Asp Thr Ser Thr
                85                  90                  95

Ser Thr Ala Tyr Met Glu Ile Arg Asn Leu Gly Gly Asp Asp Thr Ala
            100                 105                 110

Val Tyr Tyr Cys Ala Arg Trp Ser Trp Ser Asp Gly Tyr Tyr Val Tyr
        115                 120                 125

Phe Asp Tyr Trp Gly Gln Gly Thr Ser Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Asp Ser Leu Thr Val Ser Leu Gly Glu Arg Thr
                165                 170                 175

Thr Ile Asn Cys Lys Ser Ser Gln Ser Val Leu Asp Ser Ser Thr Asn
            180                 185                 190

Lys Asn Ser Leu Ala Trp Tyr Gln Gln Lys Pro Gly Gln Pro Pro Lys
        195                 200                 205

Leu Leu Leu Ser Trp Ala Ser Thr Arg Glu Ser Gly Ile Pro Asp Arg
    210                 215                 220

Phe Ser Gly Ser Gly Ser Gly Thr Asp Phe Thr Leu Thr Ile Asp Ser
225                 230                 235                 240

Pro Gln Pro Glu Asp Ser Ala Thr Tyr Tyr Cys Gln Gln Ser Ala His
                245                 250                 255

Phe Pro Ile Thr Phe Gly Gln Gly Thr Arg Leu Glu Ile Lys Ser Gly
            260                 265                 270

Gly Gly Gly Ser Glu Val Gln Leu Val Glu Ser Gly Gly Gly Leu Val
        275                 280                 285

Gln Pro Gly Gly Ser Leu Lys Leu Ser Cys Ala Ala Ser Gly Phe Thr
    290                 295                 300

Phe Asn Lys Tyr Ala Met Asn Trp Val Arg Gln Ala Pro Gly Lys Gly
305                 310                 315                 320

Leu Glu Trp Val Ala Arg Ile Arg Ser Lys Tyr Asn Asn Tyr Ala Thr
                325                 330                 335

Tyr Tyr Ala Asp Ser Val Lys Asp Arg Phe Thr Ile Ser Arg Asp Asp
            340                 345                 350

Ser Lys Asn Thr Ala Tyr Leu Gln Met Asn Asn Leu Lys Thr Glu Asp
        355                 360                 365

Thr Ala Val Tyr Tyr Cys Val Arg His Gly Asn Phe Gly Asn Ser Tyr
    370                 375                 380

Ile Ser Tyr Trp Ala Tyr Trp Gly Gln Gly Thr Leu Val Thr Val Ser
385                 390                 395                 400

Ser Gly Gly Gly Gly Ser Gly Gly Gly Gly Ser Gly Gly Gly Gly Ser
                405                 410                 415
```

Gln Thr Val Val Thr Gln Glu Pro Ser Leu Thr Val Ser Pro Gly Gly
420 425 430

Thr Val Thr Leu Thr Cys Gly Ser Ser Thr Gly Ala Val Thr Ser Gly
435 440 445

Asn Tyr Pro Asn Trp Val Gln Gln Lys Pro Gly Gln Ala Pro Arg Gly
450 455 460

Leu Ile Gly Gly Thr Lys Phe Leu Ala Pro Gly Thr Pro Ala Arg Phe
465 470 475 480

Ser Gly Ser Leu Leu Gly Gly Lys Ala Ala Leu Thr Leu Ser Gly Val
485 490 495

Gln Pro Glu Asp Glu Ala Glu Tyr Tyr Cys Val Leu Trp Tyr Ser Asn
500 505 510

Arg Trp Val Phe Gly Gly Gly Thr Lys Leu Thr Val Leu His His His
515 520 525

His His His
530

<210> SEQ ID NO 260
<211> LENGTH: 505
<212> TYPE: PRT
<213> ORGANISM: Artificial Sequence
<220> FEATURE:
<223> OTHER INFORMATION: V-set directed CD33/CD3 BsAb (RC1) without leader sequence or His tag

<400> SEQUENCE: 260

Gln Val Gln Leu Val Gln Ser Gly Ala Glu Val Lys Lys Pro Gly Glu
1 5 10 15

Ser Val Lys Val Ser Cys Lys Ala Ser Gly Tyr Thr Phe Thr Asn Tyr
20 25 30

Gly Met Asn Trp Val Lys Gln Ala Pro Gly Gln Gly Leu Glu Trp Met
35 40 45

Gly Trp Ile Asn Thr Tyr Thr Gly Glu Pro Thr Tyr Ala Asp Lys Phe
50 55 60

Gln Gly Arg Val Thr Met Thr Thr Asp Thr Ser Thr Ser Thr Ala Tyr
65 70 75 80

Met Glu Ile Arg Asn Leu Gly Gly Asp Asp Thr Ala Val Tyr Tyr Cys
85 90 95

Ala Arg Trp Ser Trp Ser Asp Gly Tyr Tyr Val Tyr Phe Asp Tyr Trp
100 105 110

Gly Gln Gly Thr Ser Val Thr Val Ser Ser Gly Gly Gly Gly Ser Gly
115 120 125

Gly Gly Gly Ser Gly Gly Gly Gly Ser Asp Ile Val Met Thr Gln Ser
130 135 140

Pro Asp Ser Leu Thr Val Ser Leu Gly Glu Arg Thr Thr Ile Asn Cys
145 150 155 160

Lys Ser Ser Gln Ser Val Leu Asp Ser Ser Thr Asn Lys Asn Ser Leu
165 170 175

Ala Trp Tyr Gln Gln Lys Pro Gly Gln Pro Pro Lys Leu Leu Leu Ser
180 185 190

Trp Ala Ser Thr Arg Glu Ser Gly Ile Pro Asp Arg Phe Ser Gly Ser
195 200 205

Gly Ser Gly Thr Asp Phe Thr Leu Thr Ile Asp Ser Pro Gln Pro Glu
210 215 220

Asp Ser Ala Thr Tyr Tyr Cys Gln Gln Ser Ala His Phe Pro Ile Thr
225 230 235 240

-continued

```
Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505
```

HUMAN ANTI-CD33 ANTIBODIES AND USES THEREOF

CROSS-REFERENCE TO RELATED APPLICATION

This application is a U.S. National Phase based on International Patent Application No. PCT/US2021/025220, filed on Mar. 31, 2021, which claims priority to U.S. Provisional Patent Application No. 63/003,203 filed on Mar. 31, 2020, each of which is incorporated herein by reference in its entirety as if fully set forth herein.

STATEMENT REGARDING FEDERALLY SPONSORED RESEARCH OR DEVELOPMENT

This invention was made with government support under CA234203 and CA223409 awarded by the National Institutes of Health. The government has certain rights in the invention.

REFERENCE TO SEQUENCE LISTING

The Sequence Listing associated with this application is provided in text format in lieu of a paper copy and is hereby incorporated by reference into the specification. The name of the text file containing the Sequence Listing is 2RS4156_ST25.txt. The text file is 196 KB, was created on Sep. 27, 2022, and is being submitted electronically via Patent Center.

FIELD OF THE DISCLOSURE

A suite of novel anti-CD33 antibodies is described. The provided antibodies are pan-binders, binding the C2-set Ig-like domain in the presence or absence of the V-set Ig-like domain of CD33 or are V-set binders, binding the V-set Ig-like domain of CD33. The antibodies provide novel therapeutic and diagnostic tools against CD33-related disorders such as acute myeloid leukemia (AML).

BACKGROUND OF THE DISCLOSURE

According to the World Health Organization, cancer is the second leading cause of death globally, and was responsible for an estimated 9.6 million deaths in 2018. Acute myeloid leukemia (AML) is a type of cancer resulting from a malignancy of clonal, proliferative myeloid blast cells. There are 20,000 new cases of AML per year in the United States and 11,000 deaths from AML each year (Siegel, et al., 2021, CA Cancer J Clin. 71(1): 7-33). Although high complete remission rates can be achieved in younger patients with AML with conventional chemotherapy at rates of 60% to 80% (Döhner, et al., 2017. Blood. 129(4): 424-447), treatment outcomes for older patients, at the age of 65 or older, remains unsatisfactory with as many as 70% of patients dying of their disease within a year of diagnosis (Meyers, et al., Appl Health Econ Health Policy, 11:275-286, 2013). Unfortunately, because of the chemo-refractoriness of leukemic stem cells, relapse after conventional therapy is common (Eppert, et al., 2011. Nat. Med. 17(9): 1086-1093) and current treatment options for relapsed/refractory (R/R) AML are dismal, resulting in less than 30% overall survival at 12 months.

CD33 is a member of the sialic acid binding, immunoglobulin-like lectin (SIGLEC) protein family. It is a 67-kDa glycosylated transmembrane protein. CD33 (also known as SIGLEC-3) is a myeloid differentiation antigen that is found at least on some leukemic cells in almost all patients with AML and, perhaps, on AML stem cells in some cases. Based on this broad expression pattern, CD33 has been widely pursued as a therapeutic target in AML. Recent data from several randomized studies have demonstrated that the CD33 antibody-drug conjugate, gemtuzumab ozogamicin (GO), improves survival when added to chemotherapy in defined subsets of patients with newly diagnosed AML. This data has validated CD33 as the first (and so far, only) target for immunotherapy in AML. In parallel to the development of new, more effective CD33-directed therapeutics (e.g. antibody-drug conjugates, radioimmunoconjugates, bispecific antibodies, chimeric antigen receptor [CAR]-modified T cells) to overcome the limitations noted with GO, interest has grown in CD33 as a drug target for other malignant and non-malignant disorders. These efforts include the targeting of CD33 splice variants not recognized by GO as well as the targeting of CD33+ tumor cells in other hematologic malignancies, CD33+ myeloid-derived suppressor cells (MDSCs) in a variety of diseases, and normal CD33+ microglial cells in Alzheimer disease (Walter, Expert Opin Biol Ther. 2020, 20(9):955-958).

The full length CD33 protein ($CD33^{FL}$) is characterized by an amino-terminal, membrane-distant V-set immunoglobulin (Ig)-like domain and a membrane-proximal C2-set Ig-like domain in its extracellular portion (FIG. 1). Shorter isoforms of CD33 exist. A shorter isoform of CD33 includes one variant that lacks exon 2, which encodes the V-set domain ($CD33^{\Delta E2}$). At least at the mRNA level, $CD33^{\Delta E2}$ is broadly expressed in myeloid cells in the bone marrow and peripheral blood of patients with AML. Currently, however, almost all commercially and clinically available CD33 antibodies recognize the immune-dominant V-set Ig-like domain. This means that these antibodies would not recognize shorter forms of CD33 that lack the V-set domain such as $CD33^{\Delta E2}$. This may explain the observation made in one clinical trial in pediatric AML that patients with a single nucleotide polymorphism in the CD33 gene that leads to preferential transcription of $CD33^{\Delta E2}$ and reduced translation of $CD33^{FL}$ did not benefit from the addition of GO (which also binds to the V-set domain of CD33) to intensive chemotherapy.

SUMMARY OF THE DISCLOSURE

The current disclosure provides antibodies that bind/recognize the C2-set Ig-like domain in CD33 proteins regardless of whether the V-set Ig-like domain is present (FIG. 1). These antibodies are referred to as pan-binders ($CD33^{PAN}$ antibodies). Pan binders can target a higher percentage of CD33-expressing cells because they can bind target cells expressing $CD33^{FL}$ as well as shorter isoforms such as the $CD33^{\Delta E2}$ variant. The $CD33^{PAN}$ antibodies disclosed herein include: 1H10, 1A9, 1E6, 1D2, and 1B9.

The current disclosure also provides newly developed anti-CD33 antibodies that bind the V-set Ig-like domain of CD33. These V-set binders include 1H8, 2D3, and 2E3 and provide additional diagnostic and therapeutic options for patients expressing $CD33^{FL}$.

The antibodies disclosed herein can be engineered into numerous formats, such as anti-CD33 antibody conjugates. Anti-CD33 antibody conjugates are artificial molecules that include a molecule conjugated to a CD33 antibody-based binding domain. Anti-CD33 antibody conjugates include anti-CD33 immunotoxins, antibody-drug conjugates (ADCs), and radioisotope conjugates. The antibodies disclosed herein can also be engineered into anti-CD33 multi-specific antibodies (e.g. anti-CD33 bispecific antibodies, anti-CD33 trispecific antibodies, anti-CD33 tetraspecific antibodies, etc.). When in a multispecific format, the engineered molecules can bind CD33 and, for example, an immune activating epitope on an immune cell, such as CD3, CD16, CD28, CD64, and/or 4-1BB. These embodiments serve to bring activated immune cells to CD33-expressing cells to destroy the CD33-expressing cells.

BRIEF DESCRIPTION OF THE SEVERAL VIEWS OF THE DRAWINGS

Some of the drawings submitted herein are better understood in color. Applicant considers the color versions of the drawings as part of the original submission and reserves the right to present color images of the drawings in later proceedings.

FIGS. 7A, 7B. (7A) A kinetic profile was established from purified anti-CD33 antibodies by use of surface plasmon resonance technology (SPR) from the Carterra instrument. SPR is a great way to estimate the kinetic rate constants of binding interactions, of which can fit to a 1:1 Langmuir binding model to determine the on-rate (ka) and off-rate (kd). Both of these rate parameters allow for the calculation of the dissociation rate constant (kD), referred to as binding affinity. The antibody clones were captured as an array on a protein A/G lawn, which was immobilized to a HC30M chip. The first kinetic experiment used a full-length CD33 ($CD33^{FL}$) antigen which started at a concentration of 2 μM preceding a 4-fold titration to 2 nM. Following 10 HBSTE buffer blanks, 6 injections from low to high concentrations were subsequently flowed over the array to assess kinetics of each clone printed to the array, 1-min baseline, 5-min association, 10-min dissociation. The chip was then regenerated with 0.85% phosphoric acid pH 1.7 for a fresh reprint of the same array of clones to the protein A/G lawn, in case any lingering antigen stayed bound to the array preventing an interaction with the 2nd antigen of interest, of which CD33$^{\Delta E2}$ flowed over the array of antibodies. Carterra kinetic software was used to process the data to fit the raw data to kinetic curves for each concentration of antigen injected over the array. (7B) SPR assessment of purified ECD from CD33$^{FL}$ or CD33$^{\Delta E2}$ binding to captured 1H10 and 2D3. Experiments were performed at 25° C. on a Biacore T100 instrument with a Series S CM4 chip. Protein A/G at 60 μg/mL in 10 mM sodium acetate, pH 4.0 was immobilized on 2 flow cells (1000 RUs) using standard amine-coupling chemistry. Capture kinetic experiments were run in 10 mM HEPES, pH 7.4, 150 mM NaCl, 3 mM EDTA, 0.05% surfactant P20 and 0.1 mg/mL IgG free bovine serum albumin buffer. Anti-human CD33 antibodies at 0.5 μg/mL were injected at 10 μL/min over the second flow cell of immobilized Protein A/G for 30-40 s to capture 40 to 58 RUs of antibody for the CD33$^{FL}$ binding experiments, or 45-80 s to capture 75 to 95 RUs of antibody for the CD33$^{\Delta E2}$ binding experiments. Purified ectodomains for CD33$^{FL}$ and CD33$^{\Delta E2}$ were run as concentration series at 50 μL/min over both the captured antibody and Protein A/G alone (reference) surfaces. CD33$^{FL}$ series started at a high concentration of 160 nM for 2D3 and 1H10; CD33$^{\Delta E2}$ series started at 40 nM for 1H10 and 300 nM for 2D3. CD33 was injected for 7 minutes and allowed to dissociate for 20 or 30 minutes for most pairs. Serial 2-fold dilutions of ectodomain concentrations were run in duplicate, randomized, and included a buffer blank every 4th injection. The CM4 chip was regenerated with 2 30 s injections of 0.85% $H_3PO_4$ at 50 4/min and antibody recaptured prior to each CD33 injection. Data was double referenced and analyzed in BiaEval 2.0.4 software with a 1:1 binding model using local Rmax.

FIG. 14. Sequences supporting the disclosure: human full-length (FL) CD33 with a mouse Fc domain, used as an immunogen for human FL CD33 (hsCD33-mmFc; SEQ ID NO: 2); human ΔE2 version of CD33 (CD33$^{\Delta E2}$) with a mouse Fc domain, used as immunogen for human CD33$^{\Delta E2}$ (hsCD33_ΔE2-mmFc, SEQ ID NO: 3); ECD of mouse protein (SEQ ID NO: 4) and coding (SEQ ID NO: 5) CD33 where the C2-set Ig-like domain from mouse is replaced with the C2-set Ig-like domain from human CD33, combined with a Fc region from human IgG1, used as immunogen to generate antibodies against human C2-set domain of CD33 (mmCD33_Vset-mmCD33_C2set-hsCD33_Fc_hsIgG1); ECD of mouse protein (SEQ ID NO: 6) and coding (SEQ ID NO: 7) CD33 where the C2-set Ig-like domain from mouse has been replaced with the C2-set Ig-like domain from human CD33 combined with the transmembrane domain and a truncated intracellular domain both derived from human CD33, used as immunogen to generate antibodies against human C2-set domain of CD33; and full length human protein (SEQ ID NO: 8) and coding (SEQ ID NO:9 CD33 immunogen for human CD33; human ΔE2 protein (SEQ ID NO: 10) and coding (SEQ ID NO: 11) CD33 (CD33$^{\Delta E2}$), immunogen for human CD33$^{\Delta E2}$); CD33: CD22 4D protein (SEQ ID NO: 1) and coding sequence (SEQ ID NO: 135); CD33:CD22 2D protein (SEQ ID NO: 136) and coding sequence (SEQ ID NO: 137); CD33 V-set construct (exon 3 and 4 deleted) protein (SEQ ID NO: 138) and coding sequence (SEQ ID NO: 139); CD33 signal peptide (SEQ ID NO: 140) and coding sequence (SEQ ID NO: 141); 6-histidine tag (SEQ ID NO: 142) and coding sequence (SEQ ID NO: 143); 3× glycine linker and coding sequence; CD33 ECD (SEQ ID NO: 145) and coding sequence (SEQ ID NO: 146); CD33 ECD lacking CD33 amino acids 140-232 (SEQ ID NO: 147) and coding sequence (SEQ ID NO: 148); CD33 transmembrane domain (SEQ ID NO: 149) and coding sequence (SEQ ID NO: 150); CD33 intracellular domain (SEQ ID NO: 151) and coding sequence (SEQ ID NO: 152); Portion of CD22 ECD that contains CD22 domains defined as Ig-like C2-type 3, Ig-like C2-type 4, Ig-like C2-type 5, Ig-like C2-type 6 (SEQ ID NO: 153) and coding sequence (SEQ ID NO: 154); Portion of CD22 ECD that contains CD22 domains defined as Ig-like C2-type 5, Ig-like C2-type 6 (SEQ ID NO: 155) and coding sequence (SEQ ID NO: 156); 1E6/CD3 bispecific molecule (SEQ ID NO: 157); IgK signal peptide (SEQ ID NO: 158); 1H10 scFv VH-VL orientation (SEQ ID NO: 230); 1H10 scFv VL-VH orientation (SEQ ID NO: 231); 1A9 scFv VH-VL orientation (SEQ ID NO: 232); 1A9 scFv VL-VH orientation (SEQ ID NO: 233); 1E6 scFv VH-VL orientation (SEQ ID NO: 234); 1E6 scFv VL-VH orientation (SEQ ID NO: 235); 2D3 scFv VH-VL orientation (SEQ ID NO: 236); 2D3 scFv VL-VH orientation (SEQ ID NO: 237); 1H10 scFv VH-VL orientation, bispecific antibody CD33/CD3 engager (SEQ ID NO: 238); 1H10 scFv VL-VH orientation, bispecific antibody CD33/CD3 (SEQ ID NO: 239); 1A9 scFv VH-VL orientation, bispecific antibody CD33/CD3 engager (SEQ ID NO: 240); 1A9 scFv VL-VH orientation, bispecific antibody CD33/CD3 engager (SEQ ID NO: 241); 1E6 scFv VH-VL orientation, bispecific antibody CD33/CD3 engager (SEQ ID NO: 242); 1E6 scFv VL-VH orientation, bispecific antibody CD33/CD3 engager (SEQ ID NO: 243); 2D3 scFv VH-VL orientation, bispecific antibody CD33/CD3 engager (SEQ ID NO: 244); 2D3 scFv VL-VH orientation, bispecific antibody CD33/CD3 engager (SEQ ID NO: 245); human CD33 full length DNA coding (used for cell based immunogen; CD33 signal peptide coding sequence in bold) (SEQ ID NO: 246); human CD33 full length protein (SEQ ID NO: 247); and 1H10, 1A9, 1E6, and/or 1B9 light chain signal peptide (SEQ ID NO: 248); 1D2 light chain signal peptide (SEQ ID NO: 249); 1H8 light chain signal peptide (SEQ ID NO: 250); 2D3 light chain signal peptide (SEQ ID NO: 251); 1H10 heavy chain signal peptide (SEQ ID NO: 252); 1A9 heavy chain signal peptide (SEQ ID NO: 253); 1E6 and/or 2E3 heavy chain signal peptide (SEQ ID NO: 254); 1D2 heavy chain signal peptide (SEQ ID NO: 255); 1B9 heavy chain signal peptide (SEQ ID NO: 256); 1H8 heavy chain signal peptide (SEQ ID NO: 257); 2D3 heavy chain signal peptide (SEQ ID NO: 258); V-set directed CD33/CD3 BsAb (RC1) (SEQ ID NO: 259); and V-set directed CD33/CD3 BsAb (RC1) without leader sequence or His tag (SEQ ID NO: 260).

DETAILED DESCRIPTION

According to the World Health Organization, cancer is the second leading cause of death globally, and was responsible for an estimated 9.6 million deaths in 2018. Acute myeloid leukemia (AML) is a malignancy of clonal, proliferative myeloid blast cells. AML is also known as acute myelocytic leukemia, acute myelogenous leukemia, acute granulocytic leukemia, and acute nonlymphocytic leukemia.

High complete remission rates for patients with AML can be achieved with conventional chemotherapy at rates of 60% to 80% for younger adults and 40% to 60% for adults greater than age 60 (Döhner, et al., 2017. Blood. 129(4): 424-447). Unfortunately, because of the chemo-refractoriness of leukemic stem cells, relapse after conventional therapy is common (Eppert, et al., 2011. Nat. Med. 17(9): 1086-1093) and current treatment options for relapsed/refractory (R/R) AML are dismal, resulting in less than 30% overall survival at 12 months.

Figure 1:
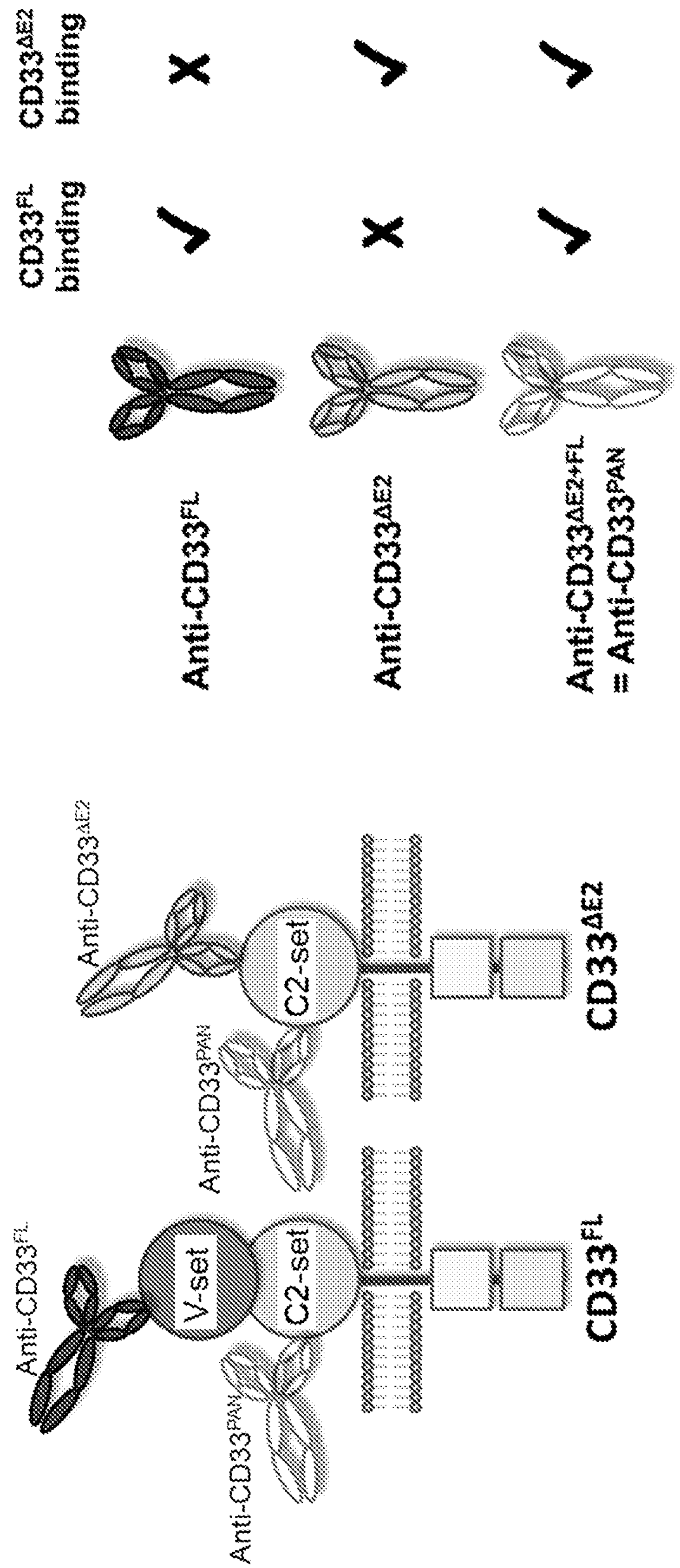
FIG. 1. Diagram of full-length CD33 ($CD33^{FL}$) and CD33 with deletion of exon 2, resulting deletion of V-set domain ($CD33^{\Delta E2}$). Depicted are an antibody that binds $CD33^{FL}$ only (anti-$CD33^{FL}$), $CD33^{\Delta E2}$ only (anti-$CD33^{\Delta E2}$), or $CD33^{FL}$ and $CD33^{\Delta E2}$ (anti-$CD33^{FL+\Delta E2}$ or anti-$CD33^{PAN}$).

The full length CD33 protein ($CD33^{FL}$) is a transmembrane glycoprotein that is characterized by an amino-terminal, membrane-distant V-set immunoglobulin (Ig)-like domain and a membrane-proximal C2-set Ig-like domain in its extracellular portion (FIG. 1).

$CD33^{FL}$ is primarily displayed on maturing and mature cells of the myeloid lineage, with initial expression on multipotent myeloid precursors. It is not found outside the hematopoietic system and is not thought to be expressed on pluripotent hematopoietic stem cells. Consistent with its role as a myeloid differentiation antigen, $CD33^{FL}$ is widely expressed on malignant cells in patients with myeloid neoplasms; e.g., in AML, it is found on at least a subset of the AML blast cells in almost all cases and possibly leukemic stem cells in some. Because of this expression pattern, $CD33^{FL}$ has been widely exploited as an antigen for targeted therapy of AML. (Walter et al., Blood 119(26):6198-6208, 2012; Cowan et al., Front. Biosci. (Landmark Ed) 18:1311-1334, 2013; Laszlo et al., Blood Ref. 28(4):143-153, 2014; and Walter, Expert Opin Investig Drugs 27(4):339-348, 2018) While unconjugated monoclonal CD33 antibodies have proved ineffective in the clinic, several recent randomized trials with the CD33 antibody-drug conjugate (ADC) gemtuzumab ozogamicin (GO) have demonstrated improved survival in subsets of patients with AML, establishing the value of antibodies in this disease and validating $CD33^{FL}$ as the first, and so far only, therapeutic target for immunotherapy of AML (Laszlo et al., Blood Rev. 28(4): 143-153, 2014; Godwin et al., Leukemia 31(9) 31(9):1855-1868, 2017). In parallel to the development of new, more effective CD33-directed therapeutics (e.g. antibody-drug conjugates, radioimmunoconjugates, bispecific antibodies, chimeric antigen receptor [CAR]-modified T cells) to overcome the limitations noted with GO, interest has grown in CD33 as a drug target for other malignant and non-malignant disorders. These efforts include the targeting of CD33 splice variants not recognized by GO as well as the targeting of CD33+ tumor cells in other hematologic malignancies, CD33+ myeloid-derived suppressor cells (MDSCs) in a variety of diseases, and normal CD33+ microglial cells in Alzheimer disease (Walter, Expert Opin Biol Ther. 2020, 20(9):955-958).

However, some patients express a truncated splice variant form of CD33 that is missing exon 2 and is referred to as $CD33^{\Delta E2}$. $CD33^{\Delta E2}$ has been identified at the mRNA level in normal hematopoietic cells as well as leukemia cells. Regarding the latter, $CD33^{\Delta E2}$ mRNA was identified in 29 of 29 tested AML patient specimens, indicating universal expression in human AML. $CD33^{\Delta E2}$ contains the C2-set Ig-like domain but not the V-set Ig-like domain of CD33 (FIG. 1). Additional splice variants, identified at the mRNA level, include $CD33^{E7a}$ and $CD33^{\Delta E2/E7a}$. $CD33^{E7a}$ uses an alternate exon 7 (E7a) which results in a truncation of the intracellular domain of CD33. $CD33^{\Delta E2/E7a}$ lacks exon 2 and also has the truncation of the intracellular domain of CD33.

Currently, however, almost all commercial diagnostic CD33 antibodies and currently clinically available CD33 antibody-based therapeutics recognize the immune-dominant V-set Ig-like domain that is encoded by exon 2 (FIG. 1). That is, $CD33^{\Delta E2}$ and other CD33 proteins that lack the V-set Ig-like domain are not recognized by almost any commercially and clinically available CD33 antibody. This means that these antibodies would not recognize shorter forms of CD33 that lack the V-set domain such as $CD33^{\Delta E2}$. This may explain the observation made in one clinical trial in pediatric AML that patients with a single nucleotide polymorphism in the CD33 gene that leads to preferential transcription of $CD33^{\Delta E2}$ and reduced translation of $CD33^{FL}$ did not benefit from the addition of GO (which also binds to the V-set domain of CD33) to intensive chemotherapy.

Antibodies that recognize and bind the C2-set Ig-like domain of CD33 proteins regardless of the presence/absence of the V-set Ig-like domain (e.g. antibodies that bind the $CD33^{\Delta E2}$ and $CD33^{FL}$ isoforms, referred to as $CD33^{PAN}$ antibodies) would provide a great advance in the targeting of all CD33 isoforms, providing for broader therapeutic efficacy. These pan-binding antibodies would also provide an advance because they bind closer to the cell membrane (FIG. 1). For several therapeutic targets, the specifics of the targeted epitope have been shown to be critically important for antibody-based therapy, with membrane-proximal epitopes resulting in more potent anti-tumor effects than membrane-distal ones, as shown for CD20, CD22, CD25, and EpCAM. See, for instance, Cleary et al., J Immunol. 2017; 198(10):3999-4011; Lin, Pharmgenomics Pers Med. 2010; 3:51-59; Haso et al., Blood. 2013; 121(7):1165-1174; and Bluemel et al., Cancer Immunol Immunother. 2010; 59(8):1197-1209.

The current disclosure provides novel pan-binding antibodies that bind the C2-set Ig-like domain of CD33 regardless of whether the V-set Ig-like domain is present. These $CD33^{PAN}$ binding antibodies include: 1H10, 1A9, 1E6, 1D2, and 1B9.

The current disclosure also provides newly developed anti-CD33 antibodies that bind the V-set Ig-like domain of CD33. These V-set binders include 1H8, 2D3, and 2E3 and provide additional diagnostic and therapeutic options for patients expressing $CD33^{FL}$.

In particular embodiments, antibodies disclosed herein bind to CD33 and have one or more of the following characteristics: (a) bind to recombinant human CD33; (b) bind to endogenous CD33 on the surface of human peripheral blood mononuclear cells (PBMCs) or other myeloid or non-myeloid human cells; (c) bind to endogenous CD33 on the surface of a cancer cell; (d) bind to endogenous CD33 on the surface of an AML cancer cell; (e) bind to an epitope within the CD33 C2-set Ig-like domain in the presence of a V-set Ig-like domain (e.g., in $CD33^{FL}$); (f) bind to an epitope within the CD33 C2-set Ig-like domain in the absence of a V-set Ig-like domain (e.g., in $CD33^{\Delta E2}$); (g) bind to a membrane proximal epitope of CD33; (h) include a $V_L$ chain and a $V_H$ chain of 1H10; (i) include a $V_L$ chain and a $V_H$ chain of 1A9; (j) include a $V_L$ chain and a $V_H$ chain of 1E6; (k) include a $V_L$ chain and a $V_H$ chain of 1D2; (I) include a $V_L$ chain and a $V_H$ chain of 1B9; (m) include a $V_L$ chain and a $V_H$ chain of 1H8; (n) include a $V_L$ chain and a $V_H$ chain of 2D3; (o) include a $V_L$ chain and a $V_H$ chain of 2E3; (p) include a CDR set of 1H10; (q) include a CDR set of 1A9; (r) include a CDR set of 1E6; s) include a CDR set of 1D2; (t) include a CDR set of 1B9; (u) include a CDR set of 1H8; (v) include a CDR set of 2D3; and/or (w) include a CDR set of 2E3. CDR sets can be as predicted by IGMT, Kabat, North, Chothia, or "Set 5".

Various forms of antibodies and binding fragments thereof described herein can be referred to herein as CD33-targeting agents.

Having highlighted key aspects of the current disclosure, the following additional details and options to practice the disclosure are provided as follows: (i) CD33 Antibodies; (ii) Anti-CD33 Antibody Conjugates; (iii) Anti-CD33 Multi-specific Antibodies; (iv) Formulations; (v) Immune Cell Sample Collection and Cell Enrichment; (vi) Genetically Modifying Cell Populations to Express Recombinant Proteins; (vii) Cell Activating Culture Conditions; (viii) Ex Vivo Manufactured Cell Formulations; (ix) Methods of Use; (x) Reference Levels Derived from Control Populations; (xi) Exemplary Embodiments; (xii) Experimental Examples; and (xiii) Closing Paragraphs. These headings are provided for organizational purposes only and do not limit the scope or interpretation of the disclosure.

(i) CD33 Antibodies

CD33 refers to any native, mature CD33 which results from processing of a CD33 precursor protein in a cell. A CD33-positive cell refers to any cell that expresses CD33 on its surface. A CD33-positive cancer refers to a cancer including one or more cells that express CD33 on their surface. Examples of CD33-positive cancers include leukemia, myeloid sarcoma, and lymphoma. More particular examples of such cancers include acute myeloid leukemia (AML), myelodysplastic syndrome (MDS), chronic myelogenous leukemia (CML), chronic myelomonocytic leukemia (CMML), acute promyelocytic leukemia (APL), myeloproliferative neoplasms, megakaryocytic leukemia, B-cell acute lymphoblastic leukemia (B-ALL), T-cell acute lymphoblastic leukemia (T-ALL), multiple myeloma (MM) and other plasma cell dyscrasias, mast cell disease, mast cell leukemia, mast cell sarcoma, and myeloid sarcomas.

The current disclosure provides antibodies that target the C2-set Ig-like domain of CD33 regardless of the presence/absence of the V-set Ig-like domain and antibodies that target the V-set Ig-like domain of CD33. In particular embodiments, combinations of antibodies can be selected. For example, if a subject expresses the V-set domain, a combination therapy including one or more of 1A9, 1H10, 1B9, 1E6, and 1D2 could be selected in combination with one or more of 2E3, 2D3, and 1H8. If a subject does not express the V-set domain, 2E3, 2D3, and 1H8 would not be administered.

Naturally occurring antibody structural units include a tetramer. Each tetramer includes two pairs of polypeptide chains, each pair having one light chain and one heavy chain. The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md., 1987 and 1991), or Chothia & Lesk, J. Mol. Biol., 196:901-917, 1987; Chothia et al., Nature, 342:878-883, 1989.

Definitive delineation of a CDR and identification of residues including the binding site of an antibody can be accomplished by solving the structure of the antibody and/or solving the structure of the antibody-epitope complex. In particular embodiments, this can be accomplished by methods such as X-ray crystallography. Alternatively, CDRs are determined by comparison to known antibodies (linear sequence) and without resorting to solving a crystal structure. To determine residues involved in binding, a co-crystal structure of the Fab (antibody fragment) bound to the target can optionally be determined. Software programs, such as ABodyBuilder can also be used.

The carboxy-terminal portion of each chain defines a constant region, which can be responsible for effector function particularly in the heavy chain (the Fc). Examples of effector functions include: C1q binding and complement dependent cytotoxicity (CDC); antibody-dependent cell-mediated cytotoxicity (ADCC); phagocytosis; down regulation of cell surface receptors (e.g. B-cell receptors); and B-cell activation.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989)). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgM has subclasses including IgM1 and IgM2. IgA is similarly subdivided into subclasses including IgA1 and IgA2.

As indicated, antibodies bind epitopes on antigens. The term antigen refers to a molecule or a portion of a molecule capable of being bound by an antibody. An epitope is a region of an antigen that is bound by the variable region of an antibody. Epitope determinants can include chemically active surface groupings of molecules such as amino acids, sugar side chains, phosphoryl or sulfonyl groups, and can have specific three-dimensional structural characteristics, and/or specific charge characteristics. When the antigen is a protein or peptide, the epitope includes specific amino acids within that protein or peptide that contact the variable region of an antibody.

In particular embodiments, an epitope denotes the binding site on CD33 bound by a corresponding variable region of an antibody. The variable region either binds to a linear epitope, (e.g., an epitope including a stretch of 5 to 12 consecutive amino acids), or the variable region binds to a three-dimensional structure formed by the spatial arrangement of several short stretches of the protein target. Three-dimensional epitopes recognized by a variable region, e.g. by the epitope recognition site or paratope of an antibody or antibody fragment, can be thought of as three-dimensional surface features of an epitope molecule. These features fit precisely (in)to the corresponding binding site of the variable region and thereby binding between the variable region and its target protein (more generally, antigen) is facilitated. In particular embodiments, an epitope can be considered to have two levels: (i) the "covered patch" which can be thought of as the shadow an antibody variable region would cast on the antigen to which it binds; and (ii) the individual participating side chains and backbone residues that facilitate binding. Binding is then due to the aggregate of ionic interactions, hydrogen bonds, and hydrophobic interactions.

In particular embodiments, epitopes of the currently disclosed antibodies (that is, epitopes to which the antibodies bind) are found within the C2-set Ig-like domain of CD33. The epitope provides a "pan binding" site, meaning that the antibody will bind regardless of whether the CD33 molecule also contains the V-set Ig-like domain (as in, for example, is $CD33^{FL}$) or not (as in, for example, $CD33^{\Delta E2}$) (FIG. 1). In particular embodiments, epitopes on the C2-set Ig-like domain are membrane-proximal epitopes. In particular embodiments, membrane-proximal epitopes are within 115 residues of the transmembrane region; within 100 residues of the transmembrane region; within 75 residues of the transmembrane region; within 50 residues of the transmembrane region; within 25 residues of the transmembrane region or within 15 residues of the transmembrane region. In particular embodiments, epitopes of the currently disclosed antibodies are found within the V-set Ig-like domain of CD33.

In particular embodiments, "bind" means that the variable region associates with its target epitope with a dissociation constant (Kd or KD) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$M, in particular embodiments of from $10^{-8}$ M to $10^{-13}$ M, or in particular embodiments of from $10^{-9}$ M to $10^{-13}$ M. The term can be further used to indicate that the variable region does not bind to other biomolecules present (e.g., it binds to other biomolecules with a dissociation constant (Kd) of $10^{-4}$ M or more, in particular embodiments of from $10^{-4}$ M to 1 M).

In particular embodiments, Kd can be characterized using BIAcore. For example, in particular embodiments, Kd can be measured using surface plasmon resonance assays using a BIACORE®-2000 or a BIACORE®-3000 (BIAcore, Inc., Piscataway, N.J.) at 25° C. with immobilized antigen CM5 chips at 10 response units (RU). Briefly, carboxymethylated dextran biosensor chips (CM5, BIACORE, Inc.) can be activated with N-ethyl-N'-(3-dimethylaminopropyl)-carbodiimide hydrochloride (EDC) and N-hydroxysuccinimide (NHS) according to the supplier's instructions. Antigen can be diluted with 10 mM sodium acetate, pH 4.8, to 5 μg/ml (0.2 μM) before injection at a flow rate of 5 μl/minute to achieve y 10 response units (RU) of coupled protein. Following the injection of antigen, 1 M ethanolamine can be injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of 25 μl/min. Association rates ($k_{on}$) and dissociation rates ($k_{off}$) can be calculated using a simple one-to-one Langmuir binding model (BIACORE® Evaluation Software version 3.2) by simultaneously fitting the association and dissociation sensorgrams. The equilibrium dissociation constant (Kd) can be calculated as the ratio $k_{off}/k_{on}$. See, e.g., Chen et al., J. Mol. Biol. 293:865-881, 1999. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

Unless otherwise indicated, the term "antibody" includes (in addition to antibodies having two full-length heavy chains and two full-length light chains as described above) variants, derivatives, and fragments thereof, examples of which are described below. Furthermore, unless explicitly excluded, antibodies can include monoclonal antibodies, human antibodies, bispecific antibodies, trispecific antibodies, tetraspecific antibodies, multi-specific antibodies, polyclonal antibodies, linear antibodies, minibodies, domain antibodies, synthetic antibodies, chimeric antibodies, antibody fusions, and fragments thereof, respectively. In particular embodiments, antibodies can include oligomers or multiplexed versions of antibodies.

A monoclonal antibody refers to an antibody obtained from a population of substantially homogeneous antibodies, i.e., the individual antibodies including the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, monoclonal antibodies can be made by a variety of techniques, including the hybridoma method, recombinant DNA methods, phage-display methods, and methods utilizing transgenic animals containing all or part of the human immunoglobulin loci.

A "human antibody" is one which includes an amino acid sequence which corresponds to that of an antibody produced by a human or a human cell or derived from a non-human source that utilizes human antibody repertoires or other human antibody-encoding sequences.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al. (supra). In particular embodiments, for the $V_H$, the subgroup is subgroup III as in Kabat et al. (supra).

Referring to the antibodies provided herein, the following CDR sets are provided. A CDR set refers to 3 light chain CDRs and 3 heavy chain CDRs that together result in binding to CD33.

TABLE 1

Antibody CDR Sequences using North

| Antibody | CDR | SEQUENCE | SEQ ID NO: |
|---|---|---|---|
| 1H10 | CDRL1 | RASQGIRIYLG | 12 |
| | CDRL2 | YATSSLQS | 13 |
| | CDRL3 | LQDYNYPWT | 14 |
| | CDRH1 | KGSGYIFTSYDMH | 15 |
| | CDRH2 | IIDPSGGSTS | 16 |
| | CDRH3 | TRDYSWSYFDY | 17 |
| 1A9 | CDRL1 | RASQDIRNDLG | 18 |
| | CDRL2 | YGASSLQS | 19 |
| | CDRL3 | LQEYNYPCT | 20 |
| | CDRH1 | AASGFTFSIYDMH | 21 |
| | CDRH2 | AIGTAGDTY | 22 |
| | CDRH3 | AREYSGYYFDY | 23 |
| 1E6 | CDRL1 | RASQGIRNDLG | 24 |
| | CDRL2 | YAASNLQS | 25 |
| | CDRL3 | LQDYSYPRT | 26 |
| | CDRH1 | AASGFTFSSYDIH | 27 |
| | CDRH2 | VIWYDGSHNY | 28 |
| | CDRH3 | ARDYSGSYYDY | 29 |
| 1D2 | CDRL1 | RASQGIRNDLG | 24 |
| | CDRL2 | YATSSLQS | 13 |
| | CDRL3 | LQDYSYPRT | 26 |
| | CDRH1 | AASGFTFSSYDIH | 27 |
| | CDRH2 | VIWYDGSQKY | 30 |

TABLE 1-continued

Antibody CDR Sequences using North

| Antibody | CDR | SEQUENCE | SEQ ID NO: |
|---|---|---|---|
| | CDRH3 | ARDYSGSYYDY | 29 |
| 1B9 | CDRL1 | RASQDIRNDLG | 18 |
| | CDRL2 | YAASSLQS | 31 |
| | CDRL3 | LQDYSYPRT | 26 |
| | CDRH1 | AASGFIFSSYDIH | 32 |
| | CDRH2 | VIWYDGSHNY | 28 |
| | CDRH3 | ARDYSGSYFDY | 33 |
| 1H8 | CDRL1 | RASQNIGGNLH | 34 |
| | CDRL2 | RYATQPFS | 163 |
| | CDRL3 | HQSSSLPLT | 36 |
| | CDRH1 | AASGFTFGSYGMH | 164 |
| | CDRH2 | VIWYDGSNEY | 165 |
| | CDRH3 | ARDLDYDSSGGDY | 166 |
| 2D3 | CDRL1 | RASQSGSSSFLS | 167 |
| | CDRL2 | YGASTRAT | 168 |
| | CDRL3 | QQDYNLPFT | 42 |
| | CDRH1 | AASGFTFSIYAMS | 169 |
| | CDRH2 | AISDSGGTTY | 170 |
| | CDRH3 | AKRTRYFNGMDV | 171 |
| 2E3 | CDRL1 | RASQSVSSSYLA | 172 |
| | CDRL2 | YGTSSRAT | 173 |
| | CDRL3 | QQYGSSPT | 48 |
| | CDRH1 | AASGFTFSSYGMH | 174 |
| | CDRH2 | VIWYGGSNKY | 175 |
| | CDRH3 | ARDGTGENYYYYVMDV | 176 |

TABLE 2

Antibody CDR Sequences using IMGT.

| Antibody | CDR | SEQUENCE | SEQ ID NO: |
|---|---|---|---|
| 1H10 | CDRL1 | QGIRIY | 177 |
| | CDRL2 | ATS | N/A |
| | CDRL3 | LQDYNYPWT | 14 |
| | CDRH1 | GYIFTSYD | 178 |
| | CDRH2 | IDPSGGST | 179 |
| | CDRH3 | TRDYSWSYFDY | 17 |

TABLE 2-continued

| Antibody CDR Sequences using IMGT. | | | |
|---|---|---|---|
| Antibody | CDR | SEQUENCE | SEQ ID NO: |
| 1A9 | CDRL1 | QDIRND | 180 |
| | CDRL2 | GAS | N/A |
| | CDRL3 | LQEYNYPCT | 20 |
| | CDRH1 | GFTFSIYD | 181 |
| | CDRH2 | IGTAGDT | 182 |
| | CDRH3 | AREYSGYYFDY | 23 |
| 1E6 | CDRL1 | QGIRND | 183 |
| | CDRL2 | AAS | N/A |
| | CDRL3 | LQDYSYPRT | 26 |
| | CDRH1 | GFTFSSYD | 184 |
| | CDRH2 | IWYDGSHN | 185 |
| | CDRH3 | ARDYSGSYYDY | 29 |
| 1D2 | CDRL1 | QGIRND | 183 |
| | CDRL2 | ATS | N/A |
| | CDRL3 | LQDYSYPRT | 26 |
| | CDRH1 | GFTFSSYD | 184 |
| | CDRH2 | IWYDGSQK | 186 |
| | CDRH3 | ARDYSGSYYDY | 29 |
| 1B9 | CDRL1 | QDIRND | 180 |
| | CDRL2 | AAS | N/A |
| | CDRL3 | LQDYSYPRT | 26 |
| | CDRH1 | GFIFSSYD | 187 |
| | CDRH2 | IWYDGSHN | 185 |
| | CDRH3 | ARDYSGSYFDY | 33 |
| 1H8 | CDRL1 | QNIGGN | 188 |
| | CDRL2 | YAT | N/A |
| | CDRL3 | HQSSSLPLT | 36 |
| | CDRH1 | GFTFGSYG | 189 |
| | CDRH2 | IWYDGSNE | 190 |
| | CDRH3 | ARDLDYDSSGGDY | 166 |
| 2D3 | CDRL1 | QSGSSSF | 191 |
| | CDRL2 | GAS | N/A |
| | CDRL3 | QQDYNLPFT | 42 |
| | CDRH1 | GFTFSIYA | 192 |
| | CDRH2 | ISDSGGTT | 193 |
| | CDRH3 | AKRTRYFNGMDV | 171 |
| 2E3 | CDRL1 | QSVSSSY | 194 |
| | CDRL2 | GTS | N/A |
| | CDRL3 | QQYGSSPT | 48 |
| | CDRH1 | GFTFSSYG | 195 |
| | CDRH2 | IWYGGSNK | 196 |
| | CDRH3 | ARDGTGENYYYYVMDV | 176 |

TABLE 3

| Antibody CDR Sequences using Kabat. | | | |
|---|---|---|---|
| Antibody | CDR | SEQUENCE | SEQ ID NO: |
| 1H10 | CDRL1 | RASQGIRIYLG | 12 |
| | CDRL2 | ATSSLQS | 208 |
| | CDRL3 | LQDYNYPWT | 14 |
| | CDRH1 | SYDMH | 197 |
| | CDRH2 | 11DPSGGSTSYAQKFQG | 198 |
| | CDRH3 | DYSWSYFDY | 199 |
| 1A9 | CDRL1 | RASQDIRNDLG | 18 |
| | CDRL2 | GASSLQS | 200 |
| | CDRL3 | LQEYNYPCT | 20 |
| | CDRH1 | IYDMH | 201 |
| | CDRH2 | AIGTAGDTYYAGSVKG | 202 |
| | CDRH3 | EYSGYYFDY | 203 |
| 1E6 | CDRL1 | RASQGIRNDLG | 24 |
| | CDRL2 | AASNLQS | 204 |
| | CDRL3 | LQDYSYPRT | 26 |
| | CDRH1 | SYDIH | 205 |
| | CDRH2 | VIWYDGSHNYYSDSVKG | 206 |
| | CDRH3 | DYSGSYYDY | 207 |
| 1D2 | CDRL1 | RASQGIRNDLG | 24 |
| | CDRL2 | ATSSLQS | 208 |
| | CDRL3 | LQDYSYPRT | 26 |
| | CDRH1 | SYDIH | 205 |
| | CDRH2 | VIWYDGSQKYYADSVKG | 209 |
| | CDRH3 | DYSGSYYDY | 207 |
| 1B9 | CDRL1 | RASQDIRNDLG | 18 |
| | CDRL2 | AASSLQS | 210 |
| | CDRL3 | LQDYSYPRT | 26 |
| | CDRH1 | SYDIH | 205 |

TABLE 3-continued

Antibody CDR Sequences using Kabat.

| Antibody | CDR | SEQUENCE | SEQ ID NO: |
|---|---|---|---|
| | CDRH2 | VIWYDGSH NYYSDSVKG | 206 |
| | CDRH3 | DYSGSYFDY | 211 |
| 1H8 | CDRL1 | RASQNIGGNLH | 34 |
| | CDRL2 | YATQPFS | 35 |
| | CDRL3 | HQSSSLPLT | 36 |
| | CDRH1 | SYGMH | 37 |
| | CDRH2 | VIWYDGSNEYYADSVKG | 212 |
| | CDRH3 | DLDYDSSGGDY | 213 |
| 2D3 | CDRL1 | RASQSGSSSFLS | 167 |
| | CDRL2 | GASTRAT | 41 |
| | CDRL3 | QQDYNLPFT | 42 |
| | CDRH1 | IYAMS | 43 |
| | CDRH2 | AISDSGGTTYYADSVKG | 214 |
| | CDRH3 | RTRYFNGMDV | 215 |
| 2E3 | CDRL1 | RASQSVSSSYLA | 172 |
| | CDRL2 | GTSSRAT | 47 |
| | CDRL3 | QQYGSSPT | 48 |
| | CDRH1 | SYGMH | 37 |
| | CDRH2 | VIWYGGSNKYYADSVKG | 216 |
| | CDRH3 | DGTGENYYYYVMDV | 217 |

TABLE 4

Antibody CDR Sequences using Chothia.

| Antibody | CDR | SEQUENCE | SEQ ID NO: |
|---|---|---|---|
| 1H10 | CDRL1 | RASQGIRIYLG | 12 |
| | CDRL2 | ATSSLQS | 208 |
| | CDRL3 | LQDYNYPWT | 14 |
| | CDRH1 | GYIFTSY | 218 |
| | CDRH2 | DPSGGS | 219 |
| | CDRH3 | DYSWSYFDY | 199 |
| 1A9 | CDRL1 | RASQDIRNDLG | 18 |
| | CDRL2 | GASSLQS | 200 |
| | CDRL3 | LQEYNYPCT | 20 |
| | CDRH1 | GFTFSIY | 220 |
| | CDRH2 | GTAGD | 221 |
| | CDRH3 | EYSGYYFDY | 203 |

TABLE 4-continued

Antibody CDR Sequences using Chothia.

| Antibody | CDR | SEQUENCE | SEQ ID NO: |
|---|---|---|---|
| 1E6 | CDRL1 | RASQGIRNDLG | 24 |
| | CDRL2 | AASNLQS | 204 |
| | CDRL3 | LQDYSYPRT | 26 |
| | CDRH1 | GFTFSSY | 222 |
| | CDRH2 | WYDGSH | 223 |
| | CDRH3 | DYSGSYYDY | 207 |
| 1D2 | CDRL1 | RASQGIRNDLG | 24 |
| | CDRL2 | ATSSLQS | 208 |
| | CDRL3 | LQDYSYPRT | 26 |
| | CDRH1 | GFTFSSY | 222 |
| | CDRH2 | WYDGSQ | 224 |
| | CDRH3 | DYSGSYYDY | 207 |
| 1B9 | CDRL1 | RASQDIRNDLG | 18 |
| | CDRL2 | AASSLQS | 210 |
| | CDRL3 | LQDYSYPRT | 26 |
| | CDRH1 | GFIFSSY | 225 |
| | CDRH2 | WYDGSH | 223 |
| | CDRH3 | DYSGSYFDY | 211 |
| 1H8 | CDRL1 | RASQNIGGNLH | 34 |
| | CDRL2 | YATQPFS | 35 |
| | CDRL3 | HQSSSLPLT | 36 |
| | CDRH1 | GFTFGSY | 226 |
| | CDRH2 | WYDGSN | 227 |
| | CDRH3 | DLDYDSSGGDY | 213 |
| 2D3 | CDRL1 | RASQSGSSSFLS | 167 |
| | CDRL2 | GASTRAT | 41 |
| | CDRL3 | QQDYNLPFT | 42 |
| | CDRH1 | GFTFSIY | 220 |
| | CDRH2 | SDSGGT | 228 |
| | CDRH3 | RTRYFNGMDV | 215 |
| 2E3 | CDRL1 | RASQSVSSSYLA | 172 |
| | CDRL2 | GTSSRAT | 47 |
| | CDRL3 | QQYGSSPT | 48 |
| | CDRH1 | GFTFSSY | 222 |
| | CDRH2 | WYGGSN | 229 |
| | CDRH3 | DGTGENYYYYVMDV | 217 |

TABLE 5

| Antibody CDR Sequences-Set 5. | | | |
|---|---|---|---|
| Antibody | CDR | SEQUENCE | SEQ ID NO: |
| 1H10 | CDRL1 | RASQGIRIYLG | 12 |
| | CDRL2 | YATSSLQS | 13 |
| | CDRL3 | LQDYNYPWT | 14 |
| | CDRH1 | KGSGYIFTSYDMH | 15 |
| | CDRH2 | IIDPSGGSTS | 16 |
| | CDRH3 | TRDYSWSYFDY | 17 |
| 1A9 | CDRL1 | RASQDIRNDLG | 18 |
| | CDRL2 | YGASSLQS | 19 |
| | CDRL3 | LQEYNYPCT | 20 |
| | CDRH1 | AASGFTFSIYDMH | 21 |
| | CDRH2 | AIGTAGDTY | 22 |
| | CDRH3 | AREYSGYYFDY | 23 |
| 1E6 | CDRL1 | RASQGIRNDLG | 24 |
| | CDRL2 | YAASNLQS | 25 |
| | CDRL3 | LQDYSYPRT | 26 |
| | CDRH1 | AASGFTFSSYDIH | 27 |
| | CDRH2 | VIWYDGSHNY | 28 |
| | CDRH3 | ARDYSGSYYDY | 29 |
| 1D2 | CDRL1 | RASQGIRNDLG | 24 |
| | CDRL2 | YATSSLQS | 13 |
| | CDRL3 | LQDYSYPRT | 26 |
| | CDRH1 | AASGFTFSSYDIH | 27 |
| | CDRH2 | VIWYDGSQKY | 30 |
| | CDRH3 | ARDYSGSYYDY | 29 |
| 1B9 | CDRL1 | RASQDIRNDLG | 18 |
| | CDRL2 | YAASSLQS | 31 |
| | CDRL3 | LQDYSYPRT | 26 |
| | CDRH1 | AASGFIFSSYDIH | 32 |
| | CDRH2 | VIWYDGSHNY | 28 |
| | CDRH3 | ARDYSGSYFDY | 33 |
| 1H8 | CDRL1 | RASQNIGGNLH | 34 |
| | CDRL2 | YATQPFS | 35 |
| | CDRL3 | HQSSSLPLT | 36 |
| | CDRH1 | SYGMH | 37 |
| | CDRH2 | IWYDGSNEYYADSVKG | 38 |
| | CDRH3 | DLDYDSSG | 39 |
| 2D3 | CDRL1 | QSGSSSFLS | 40 |
| | CDRL2 | GASTRAT | 41 |

TABLE 5-continued

| Antibody CDR Sequences-Set 5. | | | |
|---|---|---|---|
| Antibody | CDR | SEQUENCE | SEQ ID NO: |
| | CDRL3 | QQDYNLPFT | 42 |
| | CDRH1 | IYAMS | 43 |
| | CDRH2 | ISDSGGTTYYADSVKG | 44 |
| | CDRH3 | RTRYFNG | 45 |
| 2E3 | CDRL1 | QSVSSSYLA | 46 |
| | CDRL2 | GTSSRAT | 47 |
| | CDRL3 | QQYGSSPT | 48 |
| | CDRH1 | SYGMH | 37 |
| | CDRH2 | IWYGGSNKYYADSVKG | 49 |
| | CDRH3 | DGTGENYYYYV | 50 |

In particular embodiments, the 1H10 antibody includes a variable light chain including the sequence: AIQMTQSPSSLSASVGDRVTITCRASQ-GIRIYLGWYQQKPGKAPKLLIYATSSLQSGVPSRFSG SGSGTDFTLTISSLQPEDFATYYCLQ-DYNYPWTFGQGTKVEIK (SEQ ID NO: 51) and a variable heavy chain including the sequence:

(SEQ ID NO: 52)
QVQLVQSGAEVKKPGASVKVSCKGSGYIFTSYDMH
WRQAPGQGLEWMGIIDPSGGSTSYAQKFQGRVTMT
RDTSMSTVYMELSSLRSEDTAVYYCTRDYSWSYFD
YWGQGTLVTVSS.

In particular embodiments, the 1A9 antibody includes a variable light chain including the sequence: AIQMTQSPSSLSASVGDRVTIT-CRASQDIRNDLGWYQQKPGKAPKILIY-GASSLQSGVPSRFSG SGSGTDFTFTISSLQPEDFATYY-CLQEYNYPCTFGQGTKLEIK (SEQ ID NO: 53) and a variable heavy chain including the sequence:

(SEQ ID NO: 54)
EVQLVESGGGLVQPGGSLRLSCAASGFTFSIYDMH
WRQATGKGLEVSAIGTAGDTYYAGSVKGRFTISRE
NAKNSLYLQMNSLRAGDTAVYYCAREYSGYYFDYW
GQGTLVTVSS.

In particular embodiments, the 1E6 antibody includes a variable light chain including the sequence: AIQMTQSPSSLSASVGDRVTITCRASQ-GIRNDLGWYQQKPGKAPKLLIYAASNLQSGVPSRFS GSGSGTDFTLTISSLQPEDFATYYCLQDYSY-PRTFGQGTKVEIK (SEQ ID NO: 55) and a variable heavy chain including the sequence:

(SEQ ID NO: 56)
QVQLVESGGGVVQPGRSLRLSCAASGFTFSSYDIH

VRQAPGKGLEVAVIWYDGSHNYYSDSVKGRFTISR

DNSKNTLYLQMNSLRAEDTAVYYCARDYSGSYYDY

WGQGTLVTVSS.

In particular embodiments, the 1D2 antibody includes a variable light chain including the sequence: AIQMTQSPSSLSASVGDRVTITCRASQ-GIRNDLGWYQQKPGKAPELLIYATSSLQSGVPSRFSG SGSGTDFTLIISSLQPEDFATYYCLQDYSY-PRTFGQGTKVEIK (SEQ ID NO: 57) and a variable heavy chain including the sequence:

(SEQ ID NO: 58)
QVQLVESGGGVVQPGRSLRLSCAASGFTFSSYDIH

WRQAPGKGLEVAVIWYDGSQKYYADSVKGRFTISR

DNSKNTLYLQMNSLRAEDTAVYYCARDYSGSYYDY

WGQGTLVTVSS.

In particular embodiments, the 1B9 antibody includes a variable light chain including the sequence: AIQMTQSPSSLSASVGDRVTIT-CRASQDIRNDLGWYLQRPGKAPKLLI-YAASSLQSGVPSRFSG SGSGTDFTLTISSLQPEDFA-TYYCLQDYSYPRTFGQGTTVEIK (SEQ ID NO: 59) and a variable heavy chain including the sequence:

(SEQ ID NO: 60)
QVQLVESGGGVVQPGRSLRLSCAASGFIFSSYDIH

WRQAPGKGLEWAVIWYDGSHNYYSDSVKGRFTISR

DNSKNTLYLQMNSLRAEDTAVYYCARDYSGSYFDY

WGQGTLVTVSS.

In particular embodiments, the CD33$^{V\text{-}set}$ antibody includes 1H8. In particular embodiments, the 1H8 antibody includes a variable light chain including the sequence: EIVLTQSPDFQSVTPKEKVTITCRASQNIGG-NLHWYQQKPDQSPKLLIRYATQPFSGVPSRFGG SGSGTDFTLTINSLEAEDAATYY-CHQSSSLPLTFGGGTKVEIK (SEQ ID NO: 61) and a variable heavy chain including the sequence:

(SEQ ID NO: 62)
QVQLVESGGGVVQPGGSLRLSCAASGFTFGSYGMH

WRQAPGKGLEVAVIWYDGSNEYYADSVKGRFTVSR

DNSKHTLYLQMNRLRAEDTAVYYCARDLDYDSSGG

DYWGQGILVLVSS.

In particular embodiments, the CD33$^{V\text{-}set}$ antibody includes 2D3. In particular embodiments, the 2D3 antibody includes a variable light chain including the sequence: EIVMTQSPATLSLSPGER-ATLSCRASQSGSSSFLSWYQQKPGQAPRLLIYGAS-TRATGIPARFS GSGSGTDFTLTISSLQPEDFAVYYCQQ-DYNLPFTFGPGTKVDIK (SEQ ID NO: 63) and a variable heavy chain including the sequence:

(SEQ ID NO: 64)
EVQLLESGGGLVQPGGSLSLSCAASGFTFSIYAMS

WRQAPGKGLEWSAISDSGGTTYYADSVKGRFTISR

DNSKNMLYLEMNSLRAEDTAIYYCAKRTRYFNGMD

VWGQGTTVTVSS.

In particular embodiments, the CD33$^{V\text{-}set}$ antibody includes 2E3. In particular embodiments, the 2E3 antibody includes a variable light chain including the sequence: EIVLTQSPGTLSLSPGERATLSCRASQSVSSSY-LAWYQQKPGQAPRLLIYGTSSRATGIPDRFS GSGSGTDFTLTISRLEPED-FAVYYCQQYGSSPTFGGGTKVEIK (SEQ ID NO: 65) and a variable heavy chain including the sequence:

(SEQ ID NO: 66)
QVCLVESGGGVVQPGKSLRLSCAASGFTFSSYGMH

VRQAPGKGLEVAVIWYGGSNKYYADSVKGRFTISR

DNSKNTLYLQMNSLRAEDTAVYYCARDGTGENYYY

YVMDVWGQGTTVTVS.

Antibodies disclosed herein can be utilized to prepare various forms of relevant binding domain molecules. For example, particular embodiments can include binding fragments of an antibody, e.g., Fv, Fab, Fab', F(ab')$_2$, and single chain Fv fragments (scFvs) or any biologically effective fragments of an immunoglobulin that bind specifically to an epitope described herein.

In particular embodiments, an antibody fragment is used. An "antibody fragment" denotes a portion of a complete or full-length antibody that retains the ability to bind to an epitope. Antibody fragments can be made by various techniques, including proteolytic digestion of an intact antibody as well as production by recombinant host-cells (e.g., mammalian suspension cell lines, *E. coli* or phage), as described herein. Antibody fragments can be screened for their binding properties in the same manner as intact antibodies. Examples of antibody fragments include Fv, scFv, Fab, Fab', Fab'-SH, F(ab')$_2$; diabodies; and linear antibodies.

A single chain variable fragment (scFv) is a fusion protein of the variable regions of the heavy and light chains of immunoglobulins connected with a short linker peptide. Fv fragments include the $V_L$ and $V_H$ domains of a single arm of an antibody but lack the constant regions. Although the two domains of the Fv fragment, $V_L$ and $V_H$, are coded by separate genes, they can be joined, using, for example, recombinant methods, by a synthetic linker that enables them to be made as a single protein chain in which the $V_L$ and $V_H$ regions pair to form monovalent molecules (single chain Fv (scFv)). For additional information regarding Fv and scFv, see e.g., Bird, et al., Science 242:423-426, 1988; Huston, et al., Proc. Natl. Acad. Sci. USA 85:5879-5883, 1988; Plueckthun, in The Pharmacology of Monoclonal Antibodies, vol. 113, Rosenburg and Moore (eds.), Springer-Verlag, New York), (1994) 269-315; WO 1993/16185; U.S. Pat. Nos. 5,571,894; and 5,587,458.

Linker sequences that are used to connect the VL and VH of an scFv are generally five to 35 amino acids in length. In particular embodiments, a VL-VH linker includes from five to 35, ten to 30 amino acids or from 15 to 25 amino acids. Variation in the linker length may retain or enhance activity, giving rise to superior efficacy in activity studies. Linker sequences of scFv are commonly Gly-Ser linkers, described in more detail elsewhere herein.

Additional examples of antibody-based binding domain formats include scFv-based grababodies and soluble VH domain antibodies. These antibodies form binding regions using only heavy chain variable regions. See, for example, Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008.

A Fab fragment is a monovalent antibody fragment including $V_L$, $V_H$, CL and CH1 domains. A $F(ab')_2$ fragment is a bivalent fragment including two Fab fragments linked by a disulfide bridge at the hinge region. For discussion of Fab and $F(ab')_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90:6444-6448, 1993. Dual affinity retargeting antibodies (DART™; based on the diabody format but featuring a C-terminal disulfide bridge for additional stabilization (Moore et al., Blood 117:4542-51, 2011)) can also be used. Antibody fragments can also include isolated CDRs. For a review of antibody fragments, see Hudson, et al., Nat. Med. 9:129-134, 2003.

In particular embodiments, one or more amino acid modifications may be introduced into the Fc region of an antibody, thereby generating an Fc region variant. The Fc region variant may include a human Fc region sequence (e.g., a human IgG1, IgG2, IgG3 or IgG4 Fc region) including an amino acid modification (e.g., a substitution) at one or more amino acid positions. Numerous Fc modifications are known in the art, and a representative sampling of such possible modifications are described herein.

In particular embodiments, variants (including Fc variants) have been modified from a reference sequence to produce an administration benefit. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-live. While the disclosure below describes these modifications in terms of their application to antibodies, when applicable to another particular anti-CD33 binding domain format (e.g., an scFv, bispecific antibodies), the modifications can also be applied to these other formats.

In particular embodiments the antibodies can be mutated to increase their affinity for Fc receptors. Exemplary mutations that increase the affinity for Fc receptors include: G236A/S239D/A330L/I332E (GASDALIE). Smith et al., Proceedings of the National Academy of Sciences of the United States of America, 109(16), 6181-6186, 2012. In particular embodiments, an antibody variant includes an Fc region with one or more amino acid substitutions which improve ADCC, e.g., substitutions at positions 298, 333, and/or 334 of the Fc region (EU numbering of residues). In particular embodiments, alterations are made in the Fc region that result in altered C1q binding and/or Complement Dependent Cytotoxicity (CDC), e.g., as described in U.S. Pat. No. 6,194,551, WO 99/51642, and Idusogie et al., J. Immunol. 164: 4178-4184, 2000.

In particular embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further below. In particular embodiments, residue 5400 (EU numbering) of the heavy chain Fc region is selected. Cysteine engineered antibodies may be generated as described, e.g., in U.S. Pat. No. 7,521,541.

Antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at position 297 in the Fc region (Eu numbering of Fc region residues); however, Asn297 may also be located ±3 amino acids upstream or downstream of position 297, i.e., between positions 294 and 300, due to minor sequence variations in antibodies. Such fucosylation variants may have improved ADCC function. See, e.g., WO2000/61739; WO 2001/29246; WO2002/031140; US2002/0164328; WO2003/085119; WO2003/084570; US2003/0115614; US2003/0157108; US2004/0093621; US2004/0110704; US2004/0132140; US2004/0110282; US2004/0109865; WO2005/035586; WO2005/035778; WO2005/053742; Okazaki et al. J. Mol. Biol. 336:1239-1249 (2004); and Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545, 1986, and knockout cell lines, such as alpha-1,6-fucosyltransferase gene, FUT8, knockout CHO cells (see, e.g., Yamane-Ohnuki et al., Biotech. Bioeng. 87: 614, 2004; Kanda et al., Biotechnol. Bioeng., 94(4):680-688, 2006; and WO2003/085107).

In particular embodiments, modified antibodies include those wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. Amino acid(s) can be modified, for example, co-translationally or post-translationally during recombinant production (e.g., N-linked glycosylation at N—X-S/T motifs during expression in mammalian cells) or modified by synthetic means. The modified amino acid can be within the sequence or at the terminal end of a sequence. Modifications also include nitrited constructs.

In particular embodiments, variants include glycosylation variants wherein the number and/or type of glycosylation site has been altered compared to the amino acid sequences of a reference sequence. In particular embodiments, glycosylation variants include a greater or a lesser number of N-linked glycosylation sites than the reference sequence. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (e.g., those that are naturally occurring) are eliminated and one or more new N-linked sites are created. Additional antibody variants include cysteine variants wherein one or more cysteine residues are deleted from or substituted for another amino acid (e.g., serine) as compared to the reference sequence. These cysteine variants can be useful when antibodies must be refolded into a biologically active conformation such as after the isolation of insoluble inclusion bodies. These cysteine variants generally have fewer cysteine residues than the reference sequence, and typically have an even number to minimize interactions resulting from unpaired cysteines.

PEGylation particularly is a process by which polyethylene glycol (PEG) polymer chains are covalently conjugated to other molecules such as proteins. Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

Covalent attachment of proteins to PEG has proven to be a useful method to increase the half-lives of proteins in the body (Abuchowski, A. et al., Cancer Biochem. Biophys., 1984, 7:175-186; Hershfield, M. S. et al., N. Engl. J. Medicine, 1987, 316:589-596; and Meyers, F. J. et al., Clin. Pharmacol. Ther., 49:307-313, 1991). The attachment of PEG to proteins not only protects the molecules against enzymatic degradation, but also reduces their clearance rate from the body. The size of PEG attached to a protein has significant impact on the half-life of the protein. The ability of PEGylation to decrease clearance is generally not a function of how many PEG groups are attached to the protein, but the overall molecular weight of the altered protein. Usually the larger the PEG is, the longer the in vivo half-life of the attached protein. In addition, PEGylation can also decrease protein aggregation (Suzuki et al., Biochem. Bioph. Acta 788:248, 1984), alter protein immunogenicity (Abuchowski et al., J. Biol. Chem. 252: 3582, 1977), and increase protein solubility as described, for example, in PCT Publication No. WO 92/16221).

Several sizes of PEGs are commercially available (Nektar Advanced PEGylation Catalog 2005-2006; and NOF DDS Catalogue Ver 7.1), which are suitable for producing proteins with targeted circulating half-lives. A variety of active PEGs have been used including mPEG succinimidyl succinate, mPEG succinimidyl carbonate, and PEG aldehydes, such as mPEG-propionaldehyde.

In particular embodiments, the antibody can be fused or coupled to an Fc polypeptide that includes amino acid alterations that extend the in vivo half-life of an antibody that contains the altered Fc polypeptide as compared to the half-life of a similar antibody containing the same Fc polypeptide without the amino acid alterations. In particular embodiments, Fc polypeptide amino acid alterations can include M252Y, S254T, T256E, M428L, and/or N434S and can be used together, separately or in any combination. For example, M428L/N434S is a pair of mutations that increase the half-life of antibodies in serum, as described in Zalevsky et al., Nature Biotechnology 28, 157-159, 2010. Other alterations that can be helpful are described in U.S. Pat. Nos. 7,083,784, 7,670,600, US Publication No. 2010/0234575, PCT/US2012/070146, and Zwolak, Scientific Reports 7: 15521, 2017. In particular embodiments, any substitution at one of the following amino acid positions in an Fc polypeptide can be considered an Fc alteration that extends half-life: 250, 251, 252, 259, 307, 308, 332, 378, 380, 428, 430, 434, 436. Each of these alterations or combinations of these alterations can be used to extend the half-life of a bispecific antibody as described herein.

In particular embodiments, Fc modifications include huIgG4 ProAlaAla, huIgG2m4, and/or huIgG2sigma mutations.

In particular embodiments, antibodies disclosed herein are formed using the Daedalus expression system as described in Pechman et al. (Am J Physiol 294: R1234-R1239, 2008). The Daedalus system utilizes inclusion of minimized ubiquitous chromatin opening elements in transduction vectors to reduce or prevent genomic silencing and to help maintain the stability of decigram levels of expression. This system can bypass tedious and time-consuming steps of other protein production methods by employing the secretion pathway of serum-free adapted human suspension cell lines, such as 293 Freestyle. Using optimized lentiviral vectors, yields of 20-100 mg/l of correctly folded and post-translationally modified, endotoxin-free protein of up to 70 kDa in size, can be achieved in conventional, small-scale (100 ml) culture. At these yields, most proteins can be purified using a single size-exclusion chromatography step, immediately appropriate for use in structural, biophysical or therapeutic applications. Bandaranayake et al., Nucleic Acids Res., 39(21) 2011. In some instances, purification by chromatography may not be needed due to the purity of manufacture according to the methods described herein.

(ii) Anti-CD33 Antibody Conjugates

Anti-CD33 antibody conjugates include anti-CD33 immunotoxins, antibody-drug conjugates (ADCs), fluorescent conjugates, and radioisotope conjugates.

Anti-CD33 Immunotoxins. In particular embodiments, the antibodies can also be formed as immunotoxins. Anti-CD33 immunotoxins include an anti-CD33 antibody disclosed herein conjugated to one or more cytotoxins (e.g., protein toxins, enzymatically active toxins of bacterial, fungal, plant, or animal origin, or fragments thereof). A toxin can be any agent that is detrimental to cells. Frequently used plant toxins are divided into two classes: (1) holotoxins (or class II ribosome inactivating proteins), such as ricin, abrin, mistletoe lectin, and modeccin, and (2) hemitoxins (class I ribosome inactivating proteins), such as pokeweed antiviral protein (PAP), saporin, Bryodin 1, bouganin, and gelonin. Commonly used bacterial toxins include diphtheria toxin (DT) and *Pseudomonas* exotoxin (PE). Kreitman, Current Pharmaceutical Biotechnology 2:313-325 (2001). The toxin may be obtained from essentially any source and can be a synthetic or a natural product.

Immunotoxins with multiple (e.g., four) cytotoxins per binding domain can be prepared by partial reduction of the binding domain with an excess of a reducing reagent such as dithiothreitol (DTT) or tris(2-carboxyethyl)phosphine (TCEP) at 37° C. for 30 min, then the buffer can be exchanged by elution through SEPHADEX G-25 resin with 1 mM DTPA (diethylene triamine penta-acetic acid) in Dulbecco's phosphate-buffered saline (DPBS). The eluent can be diluted with further DPBS, and the thiol concentration of the binding domain can be measured using 5,5'- dithiobis(2-nitrobenzoic acid) [Ellman's reagent]. An excess, for example 5-fold, of the linker-cytotoxin conjugate can be added at 4° C. for 1 hr, and the conjugation reaction can be quenched by addition of a substantial excess, for example 20-fold, of cysteine. The resulting immunotoxin mixture can be purified on SEPHADEX G-25 equilibrated in PBS to remove unreacted linker-cytotoxin conjugate, desalted if desired, and purified by size-exclusion chromatography. The resulting immunotoxin can then be sterile filtered, for example, through a 0.2 μm filter, and can be lyophilized if desired for storage.

Antibody-drug conjugates (ADC) allow for the targeted delivery of a drug moiety to a CD33-expressing cell, and, in particular embodiments intracellular accumulation therein, where systemic administration of unconjugated drugs may result in unacceptable levels of toxicity to normal cells (Polakis P. (2005) Current Opinion in Pharmacology 5:382-387).

In particular embodiments, ADC refer to targeted chemotherapeutic molecules which combine properties of both antibodies and cytotoxic drugs by targeting potent cytotoxic drugs to antigen-expressing cancer cells (Teicher, B. A. (2009) Current Cancer Drug Targets 9:982-1004), thereby enhancing the therapeutic index by maximizing efficacy and minimizing off-target toxicity (Carter, P. J. and Senter P. D. (2008) The Cancer Jour. 14(3):154-169; Chari, R. V. (2008) Acc. Chem. Res. 41:98-107). See also Kamath & Iyer (Pharm Res. 32(11): 3470-3479, 2015), which describes considerations for the development of ADCs.

The drug moiety (D) of the ADC may include any compound, moiety or group that has a cytotoxic or cytostatic effect. Drug moieties may impart their cytotoxic and cytostatic effects by mechanisms including tubulin binding, DNA binding or intercalation, and inhibition of RNA polymerase, protein synthesis, and/or topoisomerase. Exemplary drugs include actinomycin D, anthracycline, auristatin, calicheamicin, camptothecin, CC1065, colchicin, cytochalasin B, daunorubicin, 1-dehydrotestosterone, dihydroxy anthracinedione, dolastatin, doxorubicin, duocarmycin, elinafide, emetine, ethidium bromide, etoposide, gramicidin D, glucocorticoids, lidocaine, maytansinoid (including monomethyl auristatin E [MMAE]; vedotin), mithramycin, mitomycin, mitoxantrone, nemorubicin, PNU-159682, procaine, propranolol, puromycin, pyrrolobenzodiazepine (PBD), taxane, taxol, tenoposide, tetracaine, trichothecene, vinblastine, vinca alkaloid, vincristine, and stereoisomers, isosteres, analogs, and derivatives thereof that have cytotoxic activity.

The drug may be obtained from essentially any source; it may be synthetic or a natural product isolated from a selected source, e.g., a plant, bacterial, insect, mammalian or fungal source. The drug may also be a synthetically modified natural product or an analogue of a natural product.

ADC compounds of the disclosure include those with anti-CD33 activity. In particular embodiments, the ADC compounds include an antibody conjugated, i.e. covalently attached, to the drug moiety. In particular embodiments, the antibody is covalently attached to the drug moiety through a linker. A linker can include any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid-based linker. The ADCs selectively deliver an effective dose of a drug to cancer cells whereby greater selectivity, i.e. a lower efficacious dose, may be achieved while increasing the therapeutic index ("therapeutic window").

To prepare ADCs, linker-cytotoxin conjugates can be made by conventional methods analogous to those described by Doronina et al. (Bioconjugate Chem. 17: 114-124, 2006). Antibody-drug conjugates with multiple (e.g., four) drugs per antibody can be prepared by partial reduction of the antibody with an excess of a reducing reagent such as dithiothreitol (DTT) or tris(2-carboxyethyl)phosphine (TCEP) at 37° C. for 30 min, then the buffer can be exchanged by elution through SEPHADEX G-25 resin with 1 mM DTPA in Dulbecco's phosphate-buffered saline (DPBS). The eluent can be diluted with further DPBS, and the thiol concentration of the antibody can be measured using 5,5'-dithiobis(2-nitrobenzoic acid) [Ellman's reagent]. An excess, for example 5-fold, of the linker-cytotoxin conjugate can be added at 4° C. for 1 hr, and the conjugation reaction can be quenched by addition of a substantial excess, for example 20-fold, of cysteine. The resulting ADC mixture can be purified on SEPHADEX G-25 equilibrated in PBS to remove unreacted linker-cytotoxin conjugate, desalted if desired, and purified by size-exclusion chromatography. The resulting ADC can then be sterile filtered, for example, through a 0.2 μm filter, and can be lyophilized if desired for storage.

Anti-CD33 fluorescent conjugates include a CD33 binding domain linked to a fluorescent label. Fluorescent labels can include any suitable label or detectable group detectable by, for example, optical, spectroscopic, photochemical, biochemical, immunochemical, electrical, optical or chemical means.

Fluorescent labels can be particularly useful in cell staining, identification, and isolation uses. Exemplary fluorescent labels include blue fluorescent proteins (e.g. eBFP, eBFP2, Azurite, mKalama1, GFPuv, Sapphire, T-sapphire); cyan fluorescent proteins (e.g. eCFP, Cerulean, CyPet, AmCyanl, Midoriishi-Cyan, mTurquoise); green fluorescent proteins (e.g. GFP, GFP-2, tagGFP, turboGFP, EGFP, Emerald, Azami Green, Monomeric Azami Green (mAzamigreen)), CopGFP, AceGFP, avGFP, ZsGreenI, Oregon Green™ (Thermo Fisher Scientific)); Luciferase; orange fluorescent proteins (mOrange, mKO, Kusabira-Orange, Monomeric Kusabira-Orange, mTangerine, tdTomato); red fluorescent proteins (mKate, mKate2, mPlum, DsRed monomer, mCherry, mRuby, mRFP1, DsRed-Express, DsRed2, DsRed-Monomer, HcRed-Tandem, HcRedl, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellowI); and tandem conjugates.

Anti-CD33-radioisotope conjugates include a CD33 binding domain linked to a radioisotope for use in nuclear medicine. Nuclear medicine refers to the diagnosis and/or treatment of conditions by administering radioactive isotopes (radioisotopes or radionuclides) to a subject. Therapeutic nuclear medicine is often referred to as radiation therapy or radioimmunotherapy (RIT).

Examples of radioactive isotopes that can be conjugated to antibodies of the present disclosure include iodine-131, arsenic-72, arsenic-74, iodine-131, indium-111, yttrium-90, and lutetium-177, as well as alpha-emitting radionuclides such as astatine-211, actinium-225, bismuth-212 or bismuth- 213. Methods for preparing radioimmunoconjugates are established in the art. Examples of radioimmunoconjugates are commercially available, including Zevalin™ (DEC Pharmaceuticals), and similar methods can be used to prepare radioimmunoconjugates using the antibodies of the disclosure.

Examples of radionuclides that are useful for radiation therapy include $^{225}$Ac and $^{227}$Th. $^{225}$Ac is a radionuclide with the half-life of ten days. As $^{225}$Ac decays the daughter isotopes $^{221}$Fr, $^{213}$Bi, and $^{209}$Pb are formed. $^{227}$Th has a half-life of 19 days and forms the daughter isotope $^{223}$Ra.

Additional examples of useful radioisotopes include $^{228}$Ac, $^{111}$Ag, $^{124}$Am, $^{74}$As, $^{211}$At, $^{209}$At, $^{194}$Au, $^{128}$Ba, $^{7}$Be, $^{206}$Bi, $^{245}$Bk, $^{246}$Bk, $^{76}$Br, $^{11}$C, $^{47}$Ca, $^{254}$Cf, $^{242}$Cm, $^{51}$Cr, $^{67}$Cu, $^{153}$Dy, $^{157}$Dy, $^{159}$Dy, $^{165}$Dy, $^{166}$Dy, $^{171}$Er, $^{250}$Es, $^{254}$Es, $^{147}$Eu, $^{157}$Eu, $^{52}$Fe, $^{59}$Fe, $^{251}$Fm, $^{252}$Fm, $^{253}$Fm, $^{66}$Ga, $^{72}$Ga, $^{146}$Gd, $^{153}$Gd, $^{68}$Ge, $^{170}$Hf, $^{171}$Hf, $^{193}$Hg, $^{193}$mHg, $^{160}$mHo, $^{130}$I, $^{131}$I, $^{135}$I, $^{114}$mIn, $^{185}$Ir, $^{42}$K, $^{43}$K, $^{76}$Kr, $^{79}$Kr, $^{81}$mKr, $^{132}$La, $^{262}$Lr, $^{169}$Lu, $^{174}$mLu, $^{176}$mLu, $^{257}$Md, $^{260}$Md, $^{28}$Mg, $^{52}$Mn, $^{90}$Mo, $^{24}$Na, $^{95}$Nb, $^{138}$Nd, $^{57}$Ni, $^{66}$Ni, $^{234}$Np, $^{15}$O, $^{182}$Os, $^{189}$mOs, $^{191}$Os, $^{32}$P, $^{201}$Pb, $^{101}$Pd, $^{143}$Pr, $^{191}$Pt, $^{243}$Pu, $^{225}$Ra, $^{81}$Rb, $^{188}$Re, $^{105}$Rh, $^{211}$Rn, $^{103}$Ru, $^{35}$S, $^{44}$Sc, $^{72}$Se, $^{153}$Sm, $^{125}$Sn, $^{91}$Sr, $^{173}$Ta, $^{154}$Tb, $^{127}$Te, $^{234}$Th, $^{45}$Ti, $^{166}$Tm, $^{230}$U, $^{237}$U, $^{240}$U, $^{48}$V, $^{178}$W, $^{181}$W, $^{188}$W, $^{125}$Xe, $^{127}$Xe, $^{133}$Xe, $^{133}$mXe, $^{135}$Xe, $^{85}$mY, $^{86}$Y, $^{90}$Y, $^{93}$Y, $^{169}$Yb, $^{175}$Yb, $^{65}$Zn, $^{71}$mZn, $^{86}$Zr, $^{95}$Zr, and/or $^{97}$Zr.

(iii) Anti-CD33 Multi-Specific Antibodies

Anti-CD33 bispecific antibodies bind at least two epitopes wherein at least one of the epitopes is located on CD33. Anti-CD33 trispecific antibodies bind at least 3 epitopes, wherein at least one of the epitopes is located on CD33, and so on.

Bispecific antibodies can be prepared as full-length antibodies or antibody fragments (for example, $F(ab')_2$ bispecific antibodies). For example, WO 1996/016673 describes a bispecific anti-ErbB2/anti-Fc gamma RIII antibody; U.S. Pat. No. 5,837,234 describes a bispecific anti-ErbB2/anti-Fc gamma RI antibody; WO 1998/002463 describes a bispecific anti-ErbB2/Fc alpha antibody; and U.S. Pat. No. 5,821,337 describes a bispecific anti-ErbB2/anti-CD3 antibody. In particular embodiments, a bispecific antibody can be in the form of a Bispecific T-cell Engaging (BITE®) antibody.

Some additional exemplary bispecific antibodies have two heavy chains (each having three heavy chain CDRs, followed by (N-terminal to C-terminal) a CH1 domain, a hinge, a CH2 domain, and a CH3 domain), and two immunoglobulin light chains that confer antigen-binding specificity through association with each heavy chain. However, as indicated, additional architectures are envisioned, including bi-specific antibodies in which the light chain(s) associate with each heavy chain but do not (or minimally) contribute to antigen-binding specificity, or that can bind one or more of the epitopes bound by the heavy chain antigen-binding regions, or that can associate with each heavy chain and enable binding of one or both of the heavy chains to one or both epitopes.

scFv dimers or diabodies may be used, rather than whole antibodies. Diabodies and scFv can be constructed without an Fc region, using only variable domains (usually including the variable domain components from both light and heavy chains of the source antibody), potentially reducing the effects of anti-idiotypic reaction. Other forms of bispecific antibodies include the single chain "Janusins" described in Traunecker et al. (Embo Journal, 10, 3655-3659, 1991).

Bispecific antibodies with extended half-lives are described in, for example, U.S. Pat. No. 8,921,528 and US Patent Publication No. 2014/0308285.

Methods for making bispecific antibodies are known in the art. For example, traditional production of full-length bispecific antibodies is based on the co-expression of two immunoglobulin heavy chain-light chain pairs, where the two chains have different specificities (see, for example, Millstein et al. Nature 305:37-39, 1983). Similar procedures are disclosed in, for example, WO 1993/008829, Traunecker et al., EMBO J. 10:3655-3659, 1991 and Holliger & Winter, Current Opinion Biotechnol. 4, 446-449 (1993).

In particular embodiments, bispecific antibodies can be prepared using chemical linkage. For example, Brennan et al. (Science 229: 81, 1985) describes a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody.

In particular embodiments, binding domains disclosed herein can be used to create bi- tri, (or more) specific immune cell engaging antibody constructs.

In particular embodiments, binding domains disclosed herein can be used to create bi- tri, (or more) specific immune cell engaging antibody constructs. The immune cell engaging antibody constructs can engage, for example, T-cells, B cells, natural killer (NK) cells, NK-T cells, monocytes/macrophages, lymphocytes, hematopoietic stem cells (HSCs), hematopoietic progenitor cells (HPC), and/or a mixture of HSC and HPC (i.e., HSPC). In particular embodiments, the immune cell engaging antibody constructs engage T-cells.

Several different subsets of T-cells have been discovered, each with a distinct function. For example, a majority of T-cells have a T-cell receptor (TCR) existing as a complex of several proteins. The actual T-cell receptor is composed of two separate peptide chains, which are produced from the independent T-cell receptor alpha and beta (TCR$\alpha$ and TCR$\beta$) genes and are called $\alpha$- and $\beta$-TCR chains.

$\gamma\delta$ T-cells represent a small subset of T-cells that possess a distinct T-cell receptor (TCR) on their surface. In $\gamma\delta$ T-cells, the TCR is made up of one $\gamma$-chain and one $\delta$-chain. This group of T-cells is much less common (2% of total T-cells) than the $\alpha\beta$ T-cells.

CD3 is expressed on all mature T cells. Activated T-cells express 4-1BB (CD137), CD69, and CD25. CD5 and transferrin receptor are also expressed on T-cells.

T-cells can further be classified into helper cells (CD4+ T-cells) and cytotoxic T-cells (CTLs, CD8+ T-cells), which include cytolytic T-cells. T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T-cells destroy virally infected cells and tumor cells and are also implicated in transplant rejection. These cells are also known as CD8+ T-cells because they express the CD8 glycoprotein on their surface. These cells recognize their targets by binding to antigen associated with MHC class I, which is present on the surface of nearly every cell of the body.

"Central memory" T-cells (or "TCM") as used herein refers to an antigen experienced CTL that expresses CD62L or CCR7 and CD45RO on the surface thereof and does not express or has decreased expression of CD45RA as compared to naive cells. In particular embodiments, central memory cells are positive for expression of CD62L, CCR7, CD25, CD127, CD45RO, and CD95, and have decreased expression of CD45RA as compared to naive cells.

"Effector memory" T-cell (or "TEM") as used herein refers to an antigen experienced T-cell that does not express or has decreased expression of CD62L on the surface thereof as compared to central memory cells and does not express or has decreased expression of CD45RA as compared to a naive cell. In particular embodiments, effector memory cells are negative for expression of CD62L and CCR7, compared to naive cells or central memory cells, and have variable expression of CD28 and CD45RA. Effector T-cells are positive for granzyme B and perforin as compared to memory or naive T-cells.

"Naive" T-cells as used herein refers to a non-antigen experienced T cell that expresses CD62L and CD45RA and does not express CD45RO as compared to central or effector memory cells. In particular embodiments, naive CD8+ T lymphocytes are characterized by the expression of phenotypic markers of naive T-cells including CD62L, CCR7, CD28, CD127, and CD45RA.

Natural killer cells (also known as NK cells, K cells, and killer cells) are activated in response to interferons or macrophage-derived cytokines. They serve to contain viral infections while the adaptive immune response is generating antigen-specific cytotoxic T cells that can clear the infection. NK cells express CD8, CD16 and CD56 but do not express CD3.

NK cells include NK-T cells. NK-T cells are a specialized population of T cells that express a semi invariant T cell receptor (TCR ab) and surface antigens typically associated with natural killer cells. NK-T cells contribute to antibacterial and antiviral immune responses and promote tumor-related immunosurveillance or immunosuppression. Like natural killer cells, NK-T cells can also induce perforin-, Fas-, and TNF-related cytotoxicity. Activated NK-T cells are capable of producing IFN-$\gamma$ and IL-4. In particular embodiments, NK-T cells are CD3+/CD56+.

Macrophages (and their precursors, monocytes) reside in every tissue of the body (in certain instances as microglia, Kupffer cells and osteoclasts) where they engulf apoptotic cells, pathogens and other non-self-components. Monocytes/macrophages express CD11b, F4/80; CD68; CD11c; IL-4R$\alpha$; and/or CD163.

Immature dendritic cells (i.e., pre-activation) engulf antigens and other non-self-components in the periphery and subsequently, in activated form, migrate to T-cell areas of lymphoid tissues where they provide antigen presentation to T cells. Dendritic cells express CD1a, CD1b, CD1c, CD1d, CD21, CD35, CD39, CD40, CD86, CD101, CD148, CD209, and DEC-205.

Hematopoietic Stem/Progenitor Cells or HSPC refer to a combination of hematopoietic stem cells and hematopoietic progenitor cells.

Hematopoietic stem cells refer to undifferentiated hematopoietic cells that are capable of self-renewal either in vivo, essentially unlimited propagation in vitro, and capable of differentiation to all other hematopoietic cell types.

A hematopoietic progenitor cell is a cell derived from hematopoietic stem cells or fetal tissue that is capable of further differentiation into mature cell types. In certain embodiments, hematopoietic progenitor cells are $CD24^{lo}$ $Lin^-$ $CD117^+$ hematopoietic progenitor cells. HPC can differentiate into (i) myeloid progenitor cells which ultimately give rise to monocytes and macrophages, neutrophils, basophils, eosinophils, erythrocytes, megakaryocytes/platelets, or dendritic cells; or (ii) lymphoid progenitor cells which ultimately give rise to T-cells, B-cells, and N K-cells.

HSPC can be positive for a specific marker expressed in increased levels on HSPC relative to other types of hematopoietic cells. For example, such markers include CD34, CD43, CD45RO, CD45RA, CD59, CD90, CD109, CD117, CD133, CD166, HLA DR, or a combination thereof. Also, the HSPC can be negative for an expressed marker relative to other types of hematopoietic cells. For example, such markers include Lin, CD38, or a combination thereof. Preferably, the HSPC are $CD34^+$ cells.

A statement that a cell or population of cells is "positive" for or expressing a particular marker refers to the detectable presence on or in the cell of the particular marker. When referring to a surface marker, the term can refer to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

A statement that a cell or population of cells is "negative" for a particular marker or lacks expression of a marker refers to the absence of substantial detectable presence on or in the cell of a particular marker. When referring to a surface marker, the term can refer to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

An example of a multi-specific immune cell engaging antibody construct includes those which bind both CD33 and an immune cell (e.g., T-cell or NK-cells) activating epitope, with the goal of bringing immune cells to CD33-expressing cells to destroy the CD33-expressing cells. See, for example, US 2008/0145362. Such constructs are referred to herein as immune-activating multi-specifics or I-AMS). BiTEs® (Amgen, Thousand Oaks, CA) are one form of I-AMS. Immune cells that can be targeted for localized activation by I-AMS within the current disclosure include, for example, T-cells, natural killer (NK) cells, and macrophages which are discussed in more detail herein.

T-cell activation can be mediated by two distinct signals: those that initiate antigen-dependent primary activation and provide a T-cell receptor like signal (primary cytoplasmic signaling sequences) and those that act in an antigen independent manner to provide a secondary or co-stimulatory signal (secondary cytoplasmic signaling sequences). I-AMS disclosed herein can target any T-cell activating epitope that upon binding induces T-cell activation. Examples of such T-cell activating epitopes are on T-cell markers including CD2, CD3, CD7, CD27, CD28, CD30, CD40, CD83, 4-1BB (CD 137), OX40, lymphocyte function-associated antigen-1 (LFA-1), LIGHT, NKG2C, and B7-H3.

In particular embodiments the CD3 binding domain includes a variable light chain (LcFv) including the sequence: QTVVTQEPSLTVSPGGTVTLTCGSST-GAVTSGNYPNWVQQKPGQAPRGLIGGTKFLAPGTPA RFSGSLLGGKAALTLSGVQPEDE-AEYYCVLWYSNRWVFGGGTKLTVL (SEQ ID NO: 162) and a variable heavy chain (HcFv) including the sequence:

```
                                    (SEQ ID NO: 161)
EVQLVESGGGLVQPGGSLKLSCAASGFTFNKYAMN

WRQAPGKGLEWARIRSKYNNYATYYADSVKDRFTI

SRDDSKNTAYLQMNNLKTEDTAVYYCVRHGNFGNS

YISYWAYWGQGTLVTVSS.
```

In particular embodiments, the CD3 binding domain (e.g., scFv) is derived from the OKT3 antibody (the same as the one utilized in blinatumomab). The OKT3 antibody is described in detail in U.S. Pat. No. 5,929,212. It includes a variable light chain including a CDRL1 sequence including SASSSVSYMN (SEQ ID NO: 67), a CDRL2 sequence including RWIYDTSKLAS (SEQ ID NO: 68), and a CDRL3 sequence including QQWSSNPFT (SEQ ID NO: 69). In particular embodiments, the CD3 T-cell activating epitope binding domain is a human or humanized binding domain (e.g., scFv) including a variable heavy chain including a CDRH1 sequence including KASGYTFTRYTMH (SEQ ID NO: 70), a CDRH2 sequence including INPSR-GYTNYNQKFKD (SEQ ID NO: 71), and a CDRH3 sequence including YYDDHYCLDY (SEQ ID NO: 72).

The following sequence is an scFv derived from OKT3 which retains the capacity to bind CD3: QVQLQQSGAELARPGASVKMSCK-ASGYTFTRYTMHWVKQRPGQGLEWIGYINPSR-GYTNYN QKFKDKATLTTDKSSSTAYMQLSSLTSED-SAVYYCARYYDDHYCLDYWGQGTTLTVSSSGGG GSGGGGSGGGGSQIVLTQSPAIM-SASPGEKVTMTCSASSSVSYMNWYQQKSGTSPKR-WIYD TSKLASGVPAHFRGSGSGTSYSLTISGMEAE-DAATYYCQQWSSNPFTFGSGTKLEINR (SEQ ID NO: 73). It may also be used as a CD3 binding domain.

In particular embodiments, the CD3 T-cell activating epitope binding domain is a human or humanized binding domain (e.g., scFv) including a variable light chain including a CDRL1 sequence including QSLVHNNGNTY (SEQ ID NO: 74), a CDRL2 sequence including KVS, and a CDRL3 sequence including GQGTQYPFT (SEQ ID NO: 75). In particular embodiments, the CD3 T-cell activating epitope binding domain is a human or humanized binding domain (e.g., scFv) including a variable heavy chain including a CDRH1 sequence including GFTFTKAW (SEQ ID NO: 76), a CDRH2 sequence including IKDKSNSYAT (SEQ ID NO: 77), and a CDRH3 sequence including RGVYYALSPFDY (SEQ ID NO: 78). These reflect CDR sequences of the 20G6-F3 antibody.

In particular embodiments, the CD3 T-cell activating epitope binding domain is a human or humanized binding domain (e.g., scFv) including a variable light chain including a CDRL1 sequence including QSLVHDNGNTY (SEQ ID NO: 79), a CDRL2 sequence including KVS, and a CDRL3 sequence including GQGTQYPFT (SEQ ID NO: 75). In particular embodiments, the CD3 T-cell activating epitope binding domain is a human or humanized binding domain (e.g., scFv) including a variable heavy chain including a CDRH1 sequence including GFTFSNAW (SEQ ID NO: 80), a CDRH2 sequence including IKARSNNYAT (SEQ ID NO: 81), and a CDRH3 sequence including RGTYYASKPFDY (SEQ ID NO: 82). These reflect CDR sequences of the 4B4-D7 antibody.

In particular embodiments, the CD3 T-cell activating epitope binding domain is a human or humanized binding domain (e.g., scFv) including a variable light chain including a CDRL1 sequence including QSLEHNNGNTY (SEQ ID NO: 83), a CDRL2 sequence including KVS; not included in Sequence Listing), and a CDRL3 sequence including GQGTQYPFT (SEQ ID NO: 75). In particular embodiments, the CD3 T-cell activating epitope binding domain is a human or humanized binding domain (e.g., scFv) including a variable heavy chain including a CDRH1 sequence including GFTFSNAW (SEQ ID NO: 80), a CDRH2 sequence including IKDKSNNYAT (SEQ ID NO: 84), and a CDRH3 sequence including RYVHYGIG-YAMDA (SEQ ID NO: 85). These reflect CDR sequences of the 4E7-C9 antibody.

In particular embodiments, the CD3 T-cell activating epitope binding domain is a human or humanized binding domain (e.g., scFv) including a variable light chain including a CDRL1 sequence including QSLVHTNGNTY (SEQ ID NO: 86), a CDRL2 sequence including KVS, and a CDRL3 sequence including GQGTHYPFT (SEQ ID NO: 87). In particular embodiments, the CD3 T-cell activating epitope binding domain is a human or humanized binding domain (e.g., scFv) including a variable heavy chain including a CDRH1 sequence including GFTFTNAW (SEQ ID NO: 88), a CDRH2 sequence including KDKSNNYAT (SEQ ID NO: 89), and a CDRH3 sequence including RYVHYRFAYALDA (SEQ ID NO: 90). These reflect CDR sequences of the 18F5-H10 antibody.

Additional examples of anti-CD3 antibodies, binding domains, and CDRs can be found in WO2016/116626. TR66 may also be used.

CD28 is a surface glycoprotein present on 80% of peripheral T-cells in humans and is present on both resting and activated T-cells. CD28 binds to B7-1 (CD80) and B7-2 (CD86) and is the most potent of the known co-stimulatory molecules (June et al., Immunol. Today 15:321, 1994; Linsley et al., Ann. Rev. Immunol. 11:191, 1993). In particular embodiments, the CD28 binding domain (e.g., scFv) is derived from CD80, CD86 or the 9D7 antibody. Additional antibodies that bind CD28 include 9.3, KOLT-2, 15E8, 248.23.2, and EX5.3D10. Further, 1YJD provides a crystal structure of human CD28 in complex with the Fab fragment of a mitogenic antibody (5.11A1).

In particular embodiments, a CD28 binding domain is derived from TGN1412. In particular embodiments, the variable heavy chain of TGN1412 includes: QVQLVQS-GAEVKKPGASVKVSCKASGYTFT-SYYIHWVRQAPGQGLEWIGCIYPGNVNTNYNE KFKDRATLTVDTSISTAYMELSRLRSDDTAVYFCTR-SHYGLDWNFDVWGQGTTVTVSS (SEQ ID NO: 91) and the variable light chain of TGN1412 includes:

(SEQ ID NO: 92)

```
DIQMTQSPSSLSASVGDRVTITCHASQNIYVWLNW

YQQKPGKAPKLLIYKASNLHTGVPSRFSGSGSGTD

FTLTISSLQPEDFATYYCQQGQTYPYTFGGGTKVE

IK.
```

In particular embodiments, the CD28 binding domain includes a variable light chain including a CDRL1 sequence including HASQNIYVWLN (SEQ ID NO: 93), CDRL2 sequence including KASNLHT (SEQ ID NO: 94), and CDRL3 sequence including QQGQTYPYT (SEQ ID NO: 95), a variable heavy chain including a CDRH1 sequence including GYTFTSYYIH (SEQ ID NO: 96), a CDRH2 sequence including CIYPGNVNTNYNEK (SEQ ID NO: 97), and a CDRH3 sequence including SHYGLDWNFDV (SEQ ID NO: 98).

In particular embodiments, the CD28 binding domain including a variable light chain including a CDRL1 sequence including HASQNIYVWLN (SEQ ID NO: 93), a CDRL2 sequence including KASNLHT (SEQ ID NO: 94), and a CDRL3 sequence including QQGQTYPYT (SEQ ID NO: 95) and a variable heavy chain including a CDRH1 sequence including SYYIH (SEQ ID NO: 99), a CDRH2 sequence including CIYPGNVNTNYNEKFKD (SEQ ID NO: 100), and a CDRH3 sequence including SHYGLDWNFDV (SEQ ID NO: 98).

Activated T-cells express 4-1BB (CD137). In particular embodiments, the 4-1BB binding domain includes a variable light chain including a CDRL1 sequence including RASQSVS (SEQ ID NO: 101), a CDRL2 sequence including ASNRAT (SEQ ID NO: 102), and a CDRL3 sequence including QRSNWPPALT (SEQ ID NO: 103) and a variable heavy chain including a CDRH1 sequence including YYWS (SEQ ID NO: 104), a CDRH2 sequence including INH, and a CDRH3 sequence including YGPGNYDWYFDL (SEQ ID NO: 105).

In particular embodiments, the 4-1BB binding domain includes a variable light chain including a CDRL1 sequence including SGDNIGDQYAH (SEQ ID NO: 106), a CDRL2 sequence including QDKNRPS (SEQ ID NO: 107), and a CDRL3 sequence including ATYTGFGSLAV (SEQ ID NO: 108) and a variable heavy chain including a CDRH1 sequence including GYSFSTYWIS (SEQ ID NO: 109), a CDRH2 sequence including KIYPGDSYTNYSPS (SEQ ID NO: 110) and a CDRH3 sequence including GYGIFDY (SEQ ID NO: 111).

Particular embodiments disclosed herein including binding domains that bind epitopes on CD8. In particular embodiments, the CD8 binding domain (e.g., scFv) is derived from the OKT8 antibody. For example, in particular embodiments, the CD8 T-cell activating epitope binding domain is a human or humanized binding domain (e.g., scFv) including a variable light chain including a CDRL1 sequence including RTSRSISQYLA (SEQ ID NO: 112), a CDRL2 sequence including SGSTLQS (SEQ ID NO: 113), and a CDRL3 sequence including QQHNENPLT (SEQ ID NO: 114). In particular embodiments, the CD8 T-cell activating epitope binding domain is a human or humanized binding domain (e.g., scFv) including a variable heavy chain including a CDRH1 sequence including GFNIKD (SEQ ID NO: 115), a CDRH2 sequence including RIDPANDNT (SEQ ID NO: 116), and a CDRH3 sequence including GYGYYVFDH (SEQ ID NO: 117). These reflect CDR sequences of the OKT8 antibody.

In particular embodiments natural killer cells (also known as NK-cells, K-cells, and killer cells) are targeted for localized activation by I-AMS. NK cells can induce apoptosis or cell lysis by releasing granules that disrupt cellular membranes and can secrete cytokines to recruit other immune cells.

Examples of activating proteins expressed on the surface of NK cells include NKG2D, CD8, CD16, KIR2DL4, KIR2DS1, KIR2DS2, KIR3DS1, NKG2C, NKG2E, NKG2D, and several members of the natural cytotoxicity receptor (NCR) family. Examples of NCRs that activate NK cells upon ligand binding include NKp30, NKp44, NKp46, NKp80, and DNAM-1.

Examples of commercially available antibodies that bind to an NK cell receptor and induce and/or enhance activation of NK cells include: 5C6 and 1D11, which bind and activate NKG2D (available from BioLegend® San Diego, CA); mAb 33, which binds and activates KIR2DL4 (available from BioLegend®); P44-8, which binds and activates NKp44 (available from BioLegend®); SK1, which binds and activates CD8; and 3G8 which binds and activates CD16.

In particular embodiments, the I-AMS can bind to and block an NK cell inhibitory receptor to enhance NK cell activation. Examples of NK cell inhibitory receptors that can be bound and blocked include KIR2DL1, KIR2DL2/3, KIR3DL1, NKG2A, and KLRG1. In particular embodiments, a binding domain that binds and blocks the NK cell inhibitory receptors KIR2DL1 and KIR2DL2/3 includes a variable light chain region of the sequence EIVLTQSPVTLSLSPGERATLSCRASQSVSSY-LAWYQQKPGQAPRLLIYDASNRATGIPARFSG SGSGTDFTLTISSLEPED-FAVYYCQQRSNWMYTFGQGTKLEIKRT (SEQ ID NO: 118) and a variable heavy chain region of the sequence QVQLVQSGAEVKKPGSSVKVS CKASGGTFSFYAISWVRQAPGQGLEWMGGFIP-IFGAANYAQKFQGRVTITADESTSTAYMELS SLRSDDTAVYYCAR-IPSGSYYYDYDMDVWGQGTTVTVSS (SEQ ID NO: 119). Additional NK cell activating antibodies are described in WO/2005/0003172 and U.S. Pat. No. 9,415,104.

In particular embodiments macrophages are targeted for localized activation by I-AMS. Macrophages are a type of leukocyte (or white blood cell) that can engulf and digest cells, cellular debris, and/or foreign substances in a process known as phagocytosis.

The I-AMS can be designed to bind to a protein expressed on the surface of macrophages. Examples of activating proteins expressed on the surface of macrophages (and their precursors, monocytes) include CD11b, CD11c, CD64, CD68, CD119, CD163, CD206, CD209, F4/80, IFGR2 Toll-like receptors (TLRs) 1-9, IL-4Rα, and MARCO. Commercially available antibodies that bind to proteins expressed on the surface of macrophages include M1/70, which binds and activates CD11b (available from BioLegend®); KP1, which binds and activates CD68 (available from ABCAM®, Cambridge, United Kingdom); and ab87099, which binds and activates CD163 (available from ABCAM®).

In particular embodiments, I-AMS can target a pathogen recognition receptor (PRR). PRRs are proteins or protein complexes that recognize a danger signal and activate and/or enhance the innate immune response. Examples of PRRs include the TLR4/MD-2 complex, which recognizes gram negative bacteria; Dectin-1 and Dectin-2, which recognize mannose moieties on fungus and other pathogens; TLR2/

TLR6 or TLR2/TLR1 heterodimers, which recognize gram positive bacteria; TLR5, which recognizes flagellin; and TLR9 (CD289), which recognizes CpG motifs in DNA. In particular embodiments, I-AMS can bind and activate TLR4/MD-2, Dectin-1, Dectin-2, TRL2/TLR6, TLR2/TLR1, TLR5, and/or TLR9.

In particular embodiments, I-AMS can target the complement system. The complement system refers to an immune pathway that is induced by antigen-bound antibodies and involves signaling of complement proteins, resulting in immune recognition and clearance of the antibody-coated antigens.

Binding domains of I-AMS and other engineered formats described herein may be joined through a linker. A linker is an amino acid sequence which can provide flexibility and room for conformational movement between the binding domains of a I-AM. Any appropriate linker may be used.

Examples of linkers can be found in Chen et al., Adv Drug Deliv Rev. 2013 Oct. 15; 65(10): 1357-1369. Linkers can be flexible, rigid, or semi-rigid, depending on the desired functional domain presentation to a target.

Commonly used flexible linkers include linker sequence with the amino acids glycine and serine (Gly-Ser linkers). In particular embodiments, the linker sequence includes sets of glycine and serine repeats such as from one to ten repeats of $(Gly_xSer_y)_n$ (SEQ ID NO: 120), wherein x and y are independently an integer from 0 to 10 provided that x and y are not both 0 and wherein n is an integer of 1, 2, 3, 4, 5, 6, 7, 8, 9 or 10). Particular examples include $(Gly_4Ser)_n$ (SEQ ID NO: 121), $(Gly_3Ser)_n(Gly_4Ser)_n$ (SEQ ID NO: 122), $(Gly_3Ser)_n(Gly_2Ser)_n$ (SEQ ID NO: 123), and $(Gly_3Ser)_n(Gly_4Ser)_1$ (SEQ ID NO: 124). In particular embodiments, the linker is $(Gly_4Ser)_4$ (SEQ ID NO: 125), $(Gly_4Ser)_3$ (SEQ ID NO: 126), $(Gly_4Ser)_2$ (SEQ ID NO: 127), $(Gly_4Ser)_1$ (SEQ ID NO: 128), $(Gly_3Ser)_2$ (SEQ ID NO: 129), $(Gly_3Ser)_1$ (SEQ ID NO: 130), $(Gly_2Ser)_2$ (SEQ ID NO: 131) or $(Gly_2Ser)_1$, GGSGGGSGGSG (SEQ ID NO: 132), GGSGGGSGSG (SEQ ID NO: 133), or GGSGGGSG (SEQ ID NO: 134).

Linkers that include one or more antibody hinge regions and/or immunoglobulin heavy chain constant regions, such as CH3 alone or a CH2CH3 sequence can also be used.

In some situations, flexible linkers may be incapable of maintaining a distance or positioning of binding domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

Cytolytic properties of I-AMS molecules can be confirmed in comparative in vitro assays. Briefly, for cell line experiments, target cancer cells can be incubated in 96-well round bottom plates at 5-10,000 cells/well containing increasing concentrations of the various I-AMS antibodies (e.g., CD33/CD3 I-AMS including a CD33-CD3 bispecific antibody (BsAb)) with/without healthy donor T-cells (used at an E:T cell ratio of 1:1 and 3:1). After 48 hours, cell numbers and drug-induced cytotoxicity, using 4',6-diamidino-2-phenylindole (DAPI) to detect non-viable cells, can be determined by flow cytometry. In experiments where healthy donor T-cells are added, cancer cells can be identified by forward/side scatter properties and negativity for CellVue Burgundy dye. Experiments can include technical duplicates.

In particular embodiments including I-AMS constructs, T-cell activating epitope binding domains include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a $V_\alpha$, $V_\beta$, $C_\alpha$, or $C_\beta$ region, including at the amino- or carboxy-terminus or both ends of these regions, provided that each CDR includes zero changes or at most one, two, or three changes and provided a binding domain including a modified $V_\alpha$, $V_\beta$, $C_\alpha$, or $C_\beta$ region can still specifically bind its target with an affinity similar to wild type.

In particular embodiments, using variable region CD33 antibody sequences derived from 5' RACE (rapid cloning of cDNA ends) cloning and the CD3 sequence from CD33-CD3 BsAb, bispecific molecules can be assembled by synthesizing each scFv as a DNA fragment with overlapping Gibson assembly-compatible ends in the canonical BiTE® antibody format. Prototypical intervening regions such as $(Gly_4Ser)_3$ (SEQ ID NO: 126) linkers can be used between paired variable domains and a short $Gly_4Ser$ (SEQ ID NO: 128) linker between the two scFvs.

Anti-CD33 tri-specific antibodies are artificial proteins that simultaneously bind to three different types of antigens, wherein at least one of the antigens is CD33. Tri-specific antibodies are described in, for example, WO2016/105450, WO 2010/028796; WO 2009/007124; WO 2002/083738; US 2002/0051780; and WO 2000/018806.

(iv) Formulations

Any of the antibodies described herein in any exemplary format can be formulated alone or in combination into compositions for administration to subjects. Salts and/or pro-drugs of the antibodies can also be used.

A pharmaceutically acceptable salt includes any salt that retains the activity of the antibody and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes an active ingredient which is converted to a therapeutically active compound after administration, such as by cleavage or by hydrolysis of a biologically labile group.

In particular embodiments, the compositions include antibodies of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA (ethylene-diamine-tetra-acetic acid).

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the antibodies or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, α-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on therapeutic weight.

The compositions disclosed herein can be formulated for administration by, for example, injection, inhalation, infusion, perfusion, lavage, or ingestion. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral, sublingual, and/or subcutaneous administration.

For injection, compositions can be formulated as aqueous solutions, such as in buffers including Hanks' solution, Ringer's solution, or physiological saline. The aqueous solutions can include formulatory agents such as suspending, stabilizing, and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g., lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated as an aerosol. In particular embodiments, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated including a powder mix of the composition and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salt.

Additionally, compositions can be formulated as sustained-release systems utilizing semipermeable matrices of solid polymers including at least one type of antibody. Various sustained-release materials have been established and are well known by those of ordinary skill in the art. Sustained-release systems may, depending on their chemical nature, release one or more antibodies following administration for a few weeks up to over 100 days. Depot preparations can be administered by injection; parenteral injection; instillation; or implantation into soft tissues, a body cavity, or occasionally into a blood vessel with injection through fine needles.

Depot formulations can include a variety of bioerodible polymers including poly(lactide), poly(glycolide), poly(caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Delaware), poly(vinyl alcohol) (PVA), Brij® (Croda Americas, Wilmington, Delaware), sucrose acetate isobutyrate (SAIB), salts, and buffers.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

(v) Immune Cell Sample Collection and Cell Enrichment

Types of immune cells are described above. The present disclosure describes cells genetically modified to express a recombinant protein, such as a bi-specific antibody. Cells to be genetically modified according to the teachings of the current disclosure can be patient-derived cells (autologous) or, when appropriate can be allogeneic.

Methods of sample collection and enrichment are known by those skilled in the art. In some embodiments, cells are derived from cell lines. The cells in some embodiments are obtained from a xenogeneic source, for example, from mouse, rat, non-human primate, or pig. In particular embodiments, cells are derived from humans.

In some embodiments, T cells are derived or isolated from samples such as whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. In particular embodiments, cells from the circulating blood of a subject are obtained, e.g., by apheresis or leukapheresis. The samples, in particular embodiments, contain lymphocytes, including T cells, monocytes, granulocytes, B cells, other nucleated white blood cells, HSC, HPC, HSPC, red blood cells, and/or platelets, and in some aspects contains cells other than red blood cells and platelets and further processing is necessary.

In some embodiments, blood cells collected from a subject are washed, e.g., to remove the plasma fraction and to place the cells in an appropriate buffer or media for subsequent processing steps. In particular embodiments, the cells are washed with phosphate buffered saline (PBS). In some embodiments, the wash solution lacks calcium and/or magnesium and/or many or all divalent cations. Washing can be accomplished using a semi-automated "flow-through" centrifuge (for example, the Cobe 2991 cell processor, Baxter) according to the manufacturer's instructions. Tangential flow filtration (TFF) can also be performed. In particular embodiments, cells can be re-suspended in a variety of biocompatible buffers after washing, such as, Ca++/Mg++ free PBS.

The isolation can include one or more of various cell preparation and separation steps, including separation based on one or more properties, such as size, density, sensitivity or resistance to particular reagents, and/or affinity, e.g., immunoaffinity, to antibodies or other binding partners. In particular embodiments, the isolation is carried out using the same apparatus or equipment sequentially in a single process stream and/or simultaneously. In particular embodiments, the isolation, culture, and/or engineering of the different populations is carried out from the same starting composition or material, such as from the same sample.

In particular embodiments, a sample can be enriched for T cells by using density-based cell separation methods and related methods. For example, white blood cells can be separated from other cell types in the peripheral blood by lysing red blood cells and centrifuging the sample through a Percoll or Ficoll gradient.

In particular embodiments, a bulk T cell population can be used that has not been enriched for a particular T cell type. In particular embodiments, a selected T cell type can be enriched for and/or isolated based on cell-marker based positive and/or negative selection. In positive selection, cells having bound cellular markers are retained for further use. In negative selection, cells not bound by a capture agent, such as an antibody to a cellular marker are retained for further use. In some examples, both fractions can be retained for a further use.

The separation need not result in 100% enrichment or removal of a particular cell population or cells expressing a particular marker. For example, positive selection of or enrichment for cells of a particular type refers to increasing the number or percentage of such cells but need not result in a complete absence of cells not expressing the marker. Likewise, negative selection, removal, or depletion of cells of a particular type refers to decreasing the number or percentage of such cells but need not result in a complete removal of all such cells.

In some examples, multiple rounds of separation steps are carried out, where the positively or negatively selected fraction from one step is subjected to another separation step, such as a subsequent positive or negative selection.

In some embodiments, an antibody or binding domain for a cellular marker is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ); see also U.S. Pat. Nos. 4,452,773; 4,795,698; 5,200,084; and EP 452342.

In some embodiments, affinity-based selection is via magnetic-activated cell sorting (MACS) (Miltenyi Biotec, Auburn, CA). MACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376). In both cases, cells can be labeled with multiple markers, allowing for the isolation of well-defined cell subsets at high purity.

Cell-markers for different T cell subpopulations are described above. In particular embodiments, specific sub-populations of T cells, such as cells positive or expressing high levels of one or more surface markers, e.g., CCR7, CD45RO, CD8, CD27, CD28, CD62L, CD127, CD4, and/or CD45RA T cells, are isolated by positive or negative selection techniques.

CD3+, CD28+ T cells can be positively selected for and expanded using anti-CD3/anti-CD28 conjugated magnetic beads (e.g., DYNABEADS® M-450 CD3/CD28 T Cell Expander).

In particular embodiments, a CD8+ or CD4+ selection step is used to separate CD4+ helper and CD8+ cytotoxic T cells. Such CD8+ and CD4+ populations can be further sorted into sub-populations by positive or negative selection for markers expressed or expressed to a relatively higher degree on one or more naive, memory, and/or effector T cell subpopulations.

In some embodiments, enrichment for central memory T (TCM) cells is carried out. In particular embodiments, memory T cells are present in both CD62L subsets of CD8+ peripheral blood lymphocytes. PBMC can be enriched for or depleted of CD62L, CD8 and/or CD62L+CD8+ fractions, such as by using anti-CD8 and anti-CD62L antibodies.

In some embodiments, the enrichment for central memory T (TCM) cells is based on positive or high surface expression of CCR7, CD45RO, CD27, CD62L, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CCR7, CD45RO, and/or CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or RORI, and positive selection based on a marker characteristic of central memory T cells, such as CCR7, CD45RO, and/or CD62L, where the positive and negative selections are carried out in either order.

In particular embodiments, cell enrichment results in a bulk CD8+ FACs-sorted cell population.

Other cell types can be enriched based on known marker profiles and techniques. For example, CD34+ HSC, HSP, and HSPC can be enriched using anti-CD34 antibodies directly or indirectly conjugated to magnetic particles in connection with a magnetic cell separator, for example, the CliniMACS® Cell Separation System (Miltenyi Biotec, Bergisch Gladbach, Germany).

(vi) Genetically Modifying Cell Populations to Express Recombinant Proteins

Desired genes encoding a recombinant protein disclosed herein can be introduced into cells by any method known in the art, including transfection, electroporation, microinjection, lipofection, calcium phosphate mediated transfection, infection with a viral or bacteriophage vector including the gene sequences, cell fusion, chromosome-mediated gene transfer, microcell-mediated gene transfer, spheroplast fusion, in vivo nanoparticle-mediated delivery, etc. Numerous techniques are known in the art for the introduction of foreign genes into cells (see e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92) and may be used, provided that the necessary developmental and physiological functions of the recipient cells are not unduly disrupted. The technique can provide for the stable transfer of the gene to the cell, so that the gene is expressible by the cell and, in certain instances, preferably heritable and expressible by its cell progeny.

The term "gene" refers to a nucleic acid sequence (used interchangeably with polynucleotide or nucleotide sequence) that encodes a recombinant protein disclosed herein. This definition includes various sequence polymorphisms, mutations, and/or sequence variants wherein such alterations do not substantially affect the function of the encoded CAR. The term "gene" may include not only coding sequences but also regulatory regions such as promoters, enhancers, and termination regions. The term further can include all introns and other DNA sequences spliced from an mRNA transcript, along with variants resulting from alternative splice sites. Gene sequences encoding the molecule can be DNA or RNA that directs the expression of the chimeric molecule. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Portions of complete gene sequences are referenced throughout the disclosure as is understood by one of ordinary skill in the art.

Gene sequences encoding recombinant proteins are provided herein and can also be readily prepared by synthetic or recombinant methods from the relevant amino acid sequences and other description provided herein. In embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In embodiments, the gene sequence encoding the sequences can be codon optimized for expression in mammalian cells.

"Encoding" refers to the property of specific sequences of nucleotides in a gene, such as a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "gene sequence encoding a protein" includes all nucleotide sequences that are degenerate versions of each other and that code for the same amino acid sequence or amino acid sequences of substantially similar form and function.

A "vector" is a nucleic acid molecule that is capable of transporting another nucleic acid. Vectors may be, e.g., plasmids, cosmids, viruses, or phage. An "expression vector" is a vector that is capable of directing the expression of a protein encoded by one or more genes carried by the vector when it is present in the appropriate environment.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

Retroviral vectors (see Miller, et al., 1993, *Meth. Enzymol.* 217:581-599) can be used. In such embodiments, the gene to be expressed is cloned into the retroviral vector for its delivery into cells. In particular embodiments, a retroviral vector includes all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, *Biotherapy* 6:291-302; Clowes, et al., 1994, *J. Clin. Invest.* 93:644-651; Kiem, et al., 1994, *Blood* 83:1467-1473; Salmons and Gunzberg, 1993, *Human Gene Therapy* 4:129-141; and Grossman and Wilson, 1993, *Curr. Opin. in Genetics and Devel.* 3:110-114. Adenoviruses, adeno-associated viruses (AAV) and alphaviruses can also be used. See Kozarsky and Wilson, 1993, *Current Opinion in Genetics and Development* 3:499-503, Rosenfeld, et al., 1991, *Science* 252:431-434; Rosenfeld, et al., 1992, *Cell* 68:143-155; Mastrangeli, et al., 1993, *J. Clin. Invest.* 91:225-234; Walsh, et al., 1993, *Proc. Soc. Exp. Bioi. Med.* 204:289-300; and Lundstrom, 1999, *J. Recept. Signal Transduct. Res.* 19: 673-686. Other methods of gene delivery include use of mammalian artificial chromosomes (Vos, 1998, *Curr. Op. Genet. Dev.* 8:351-359); liposomes (Tarahovsky and Ivanitsky, 1998, Biochemistry (Mosc) 63:607-618); ribozymes (Branch and Klotman, 1998, *Exp. Nephrol.* 6:78-83); and triplex DNA (Chan and Glazer, 1997, *J. Mol. Med.* 75:267-282).

There are a large number of available viral vectors suitable within the current disclosure, including those identified for human gene therapy applications (see Pfeifer and Verma, 2001, *Ann. Rev. Genomics Hum. Genet.* 2:177). Methods of using retroviral and lentiviral viral vectors and packaging cells for transducing mammalian host cells with viral particles including transgenes are described in, e.g., U.S. Pat. No. 8,119,772; Walchli, et al., 2011, *PLoS One* 6:327930; Zhao, et al., 2005, *J. Immunol.* 174:4415; Engels, et al., 2003, *Hum. Gene Ther.* 14:1155; Frecha, et al., 2010, *Mol. Ther.* 18:1748; and Verhoeyen, et al., 2009, *Methods Mol. Biol.* 506:97. Retroviral and lentiviral vector constructs and expression systems are also commercially available.

Targeted genetic engineering approaches may also be utilized. The CRISPR (Clustered Regularly Interspaced Short Palindromic Repeats)/Cas (CRISPR-associated protein) nuclease system is an engineered nuclease system used for genetic engineering that is based on a bacterial system. Information regarding CRISPR-Cas systems and components thereof are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments utilize zinc finger nucleases (ZFNs) as gene editing agents. ZFNs are a class of site-specific nucleases engineered to bind and cleave DNA at specific positions. ZFNs are used to introduce double stranded breaks (DSBs) at a specific site in a DNA sequence which enables the ZFNs to target unique sequences within a genome in a variety of different cells. For additional information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; US 2003/0232410 and US 2009/0203140 as well as Gaj et al., Nat Methods, 2012, 9(8):805-7; Ramirez et al., Nucl Acids Res, 2012, 40(12):5560-8; Kim et al., Genome Res, 2012, 22(7): 1327-33; Urnov et al., Nature Reviews Genetics, 2010, 11:636-646; Miller, et al.

Nature biotechnology 25, 778-785 (2007); Bibikova, et al. Science 300, 764 (2003); Bibikova, et al. Genetics 161, 1169-1175 (2002); Wolfe, et al. Annual review of biophysics and biomolecular structure 29, 183-212 (2000); Kim, et al. Proceedings of the National Academy of Sciences of the United States of America 93, 1156-1160 (1996); and Miller, et al. The EMBO journal 4, 1609-1614 (1985).

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing double DSBs in the DNA, which induce repair mechanisms in cells. Generally, two TALENs must bind and flank each side of the target DNA site for the DNA cleavage domain to dimerize and induce a DSB. For additional information regarding TALENs, see U.S. Pat. Nos. 8,440,431; 8,440,432; 8,450,471; 8,586,363; and 8,697,853; as well as Joung and Sander, Nat Rev Mol Cell Biol, 2013, 14(I):49-55; Beurdeley et al., Nat Commun, 2013, 4: 1762; Scharenberg et al., Curr Gene Ther, 2013, 13(4):291-303; Gaj et al., Nat Methods, 2012, 9(8):805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

Particular embodiments can utilize MegaTALs as gene editing agents. MegaTALs have a sc rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Nanoparticles that result in selective in vivo genetic modification of targeted cell types have been described and can be used within the teachings of the current disclosure. In particular embodiments, the nanoparticles can be those described in WO2014153114, WO2017181110, and WO201822672.

(vii) Cell Activating Culture Conditions

Cell populations can be incubated in a culture-initiating composition to expand genetically modified cell populations. The incubation can be carried out in a culture vessel, such as a bag, cell culture plate, flask, chamber, chromatography column, cross-linked gel, cross-linked polymer, column, culture dish, hollow fiber, microtiter plate, silica-coated glass plate, tube, tubing set, well, vial, or other container for culture or cultivating cells.

Culture conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in US 6,040,177, Klebanoff et al. (2012) J Immunother. 35(9): 651-660, Terakura et al. (2012) Blood. 1:72-82, and/or Wang et al. (2012) J Immunother. 35(9):689-701.

Exemplary culture media for culturing T cells include (i) RPMI supplemented with non-essential amino acids, sodium pyruvate, and penicillin/streptomycin; (ii) RPMI with HEPES, 5-15% human serum, 1-3% L-Glutamine, 0.5-1.5% penicillin/streptomycin, and 0.25×10-4–0.75×10-4 M ß-MercaptoEthanol; (iii) RPMI-1640 supplemented with 10% fetal bovine serum (FBS), 2 mM L-glutamine, 10 mM HEPES, 100 U/ml penicillin and 100 m/mL streptomycin; (iv) DMEM medium supplemented with 10% FBS, 2 mM L-glutamine, 10 mM HEPES, 100 U/ml penicillin and 100 m/mL streptomycin; and (v) X-Vivo 15 medium (Lonza, Walkersville, MD) supplemented with 5% human AB serum (Gemcell, West Sacramento, CA), 1% HEPES (Gibco, Grand Island, NY), 1% Pen-Strep (Gibco), 1% GlutaMax (Gibco), and 2% N-acetyl cysteine (Sigma-Aldrich, St. Louis, MO). T cell culture media are also commercially available from Hyclone (Logan, UT). Additional T cell activating components that can be added to such culture media are described in more detail below.

In some embodiments, the T cells are expanded by adding to the culture-initiating composition feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can include gamma-irradiated PBMC feeder cells. In some embodiments, the PBMC are irradiated with gamma rays in the range of 3000 to 3600 rads to prevent cell division. In some aspects, the feeder cells are added to culture medium prior to the addition of the populations of T cells.

Optionally, the incubation may further include adding non-dividing EBV-transformed lymphoblastoid cells (LCL) as feeder cells. LCL can be irradiated with gamma rays in the range of 6000 to 10,000 rads. The LCL feeder cells in some aspects is provided in any suitable amount, such as a ratio of LCL feeder cells to initial T lymphocytes of at least 10:1.

In some embodiments, the stimulating conditions include temperature suitable for the growth of human T lymphocytes, for example, at least 25° C., at least 30° C., or 37° C.

In particular embodiments, T cell activating culture condition conditions can include T cell stimulating epitopes. T cell stimulating epitopes include CD3, CD27, CD2, CD4, CD5, CD7, CD8, CD28, CD30, CD40, CD56, CD83, CD90, CD95, 4-1BB (CD 137), B7-H3, CTLA-4, Frizzled-1 (FZD1), FZD2, FZD3, FZD4, FZD5, FZD6, FZD7, FZD8, FZD9, FZD10, HVEM, ICOS, IL-1R, LAT, LFA-1, LIGHT, MHCI, MHCII, NKG2D, OX40, ROR2 and RTK.

CD3 is a primary signal transduction element of T cell receptors. As indicated previously, CD3 is expressed on all mature T cells. In particular embodiments, the CD3 stimulating molecule (i.e., CD3 binding domain) can be derived from the OKT3 antibody (see U.S. Pat. Nos. 5,929,212; 4,361,549; ATCC® CRL-8001™; and Arakawa et al., J. Biochem. 120, 657-662 (1996)), the 20G6-F3 antibody, the 4B4-D7 antibody, the 4E7-C9, or the 18F5-H10 antibody.

In particular embodiments, CD3 stimulating molecules can be included within culture media at a concentration of at least 0.25 or 0.5 ng/ml or at a concentration of 2.5-10 μg/ml. Particular embodiments utilize a CD3 stimulating molecule (e.g., OKT3) at 5 μg/ml.

In particular embodiments, activating molecules associated with avi-tags can be biotinylated and bound to streptavidin beads. This approach can be used to create, for example, a removable T cell epitope stimulating activation system.

An exemplary binding domain for CD28 can include or be derived from TGN1412, CD80, CD86 or the 9D7 antibody. Additional antibodies that bind CD28 include 9.3, KOLT-2, 15E8, 248.23.2, EX5.3D10, and CD28.3 (deposited as a synthetic single chain Fv construct under GenBank Accession No. AF451974.1; see also Vanhove et al., BLOOD, 15 Jul. 2003, Vol. 102, No. 2, pages 564-570). Further, 1YJD provides a crystal structure of human CD28 in complex with the Fab fragment of a mitogenic antibody (5.11A1). In particular embodiments, antibodies that do not compete with 9D7 are selected.

4-1BB binding domains can be derived from LOB12, IgG2a, LOB12.3, or IgG1 as described in Taraban et al. Eur J Immunol. 2002 December; 32(12):3617-27. In particular embodiments a 4-1BB binding domain is derived from a monoclonal antibody described in U.S. Pat. No. 9,382,328. Additional 4-1BB binding domains are described in U.S. Pat. Nos. 6,569,997, 6,303,121, and Mittler et al. Immunol Res. 2004; 29(1-3):197-208.

OX40 (CD134) and/or ICOS activation may also be used. OX40 binding domains are described in US20100196359, US 20150307617, WO 2015/153513, WO2013/038191 and Melero et al. Clin Cancer Res. 2013 Mar. 1; 19(5):1044-53. Exemplary binding domains that can bind and activate ICOS are described in e.g., US20080279851 and Deng et al. Hybrid Hybridomics. 2004 June; 23(3):176-82.

When in soluble form, T-cell activating agents can be coupled with another molecule, such as polyethylene glycol (PEG) molecule. Any suitable PEG molecule can be used. Typically, PEG molecules up to a molecular weight of 1000 Da are soluble in water or culture media. In some cases, such PEG based reagent can be prepared using commercially available activated PEG molecules (for example, PEG-NHS derivatives available from NOF North America Corporation, Irvine, Calif., USA, or activated PEG derivatives available from Creative PEGWorks, Chapel Hills, NC, USA).

In particular embodiments, cell stimulating agents are immobilized on a solid phase within the culture media. In particular embodiments, the solid phase is a surface of the culture vessel (e.g., bag, cell culture plate, chamber, chromatography column, cross-linked gel, cross-linked polymer, column, culture dish, hollow fiber, microtiter plate, silica-coated glass plate, tube, tubing set, well, vial, other structure or container for culture or cultivation of cells).

In particular embodiments, a solid phase can be added to a culture media. Such solid phases can include, for example, beads, hollow fibers, resins, membranes, and polymers.

Exemplary beads include magnetic beads, polymeric beads, and resin beads (e.g., Strep-Tactin® Sepharose, Strep-Tactin® Superflow, and Strep-Tactin® MacroPrep IBA GmbH, Gottingen)). Anti-CD3/anti-CD28 beads are commercially available reagents for T cell expansion (Invitrogen). These beads are uniform, 4.5 μm superparamagnetic, sterile, non-pyrogenic polystyrene beads coated with a mixture of affinity purified monoclonal antibodies against the CD3 and CD28 cell surface molecules on human T cells. Hollow fibers are available from TerumoBCT Inc. (Lakewood, Colo., USA). Resins include metal affinity chromatography (IMAC) resins (e.g., TALON® resins (Westburg, Leusden)). Membranes include paper as well as the membrane substrate of a chromatography matrix (e.g., a nitrocellulose membrane or a polyvinylidene difluoride (PVDF) membrane).

Exemplary polymers include polysaccharides, such as polysaccharide matrices. Such matrices include agarose gels (e.g., Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare.

Synthetic polymers that may be used include polyacrylamide, polymethacrylate, a co-polymer of polysaccharide and agarose (e.g. a polyacrylamide/agarose composite) or a polysaccharide and N,N'-methylenebisacrylamide. An example of a copolymer of a dextran and N,N'-methylenebisacrylamide is the Sephacryl® (Pharmacia Fine Chemicals, Inc., Piscataway, NJ) series of materials.

Particular embodiments may utilize silica particles coupled to a synthetic or to a natural polymer, such as polysaccharide grafted silica, polyvinylpyrrolidone grafted silica, polyethylene oxide grafted silica, poly(2-hydroxyethylaspartamide) silica and poly(N-isopropylacrylamide) grafted silica.

Cell activating agents can be immobilized to solid phases through covalent bonds or can be reversibly immobilized through non-covalent attachments.

In particular embodiments, a T-cell activating culture media includes a FACS-sorted T cell population cultured within RPMI with HEPES, 5-15% human serum, 1-3% L-Glutamine, 0.5-1.5% Pen/strep, 0.25×10-4-0.75×$10^{-4}$ M β-MercaptoEthanol, with IL-7, IL-15 and IL-21 individually included at 5-15 (e.g., 10) ng/μl. The culture is carried out on a flat-bottom well plate with 0.1-0.5×10e6 plated cells/well. On Day 3 post activation cells are transferred to a TC-treated plate.

In particular embodiments, a T-cell activating culture media includes a FACS-sorted CD8+ T population cultured within RPMI with HEPES, 10% human serum, 2% L-Glutamine, 1% Pen/strep, 0.5×$10^{-4}$ M β-MercaptoEthanol, with IL-7, IL-15 and IL-21 individually included at 5-15 (e.g., 10) ng/μl. The culture is carried out on a flat-bottom non-tissue culture (TC)-treated 96/48-well plate with 0.1-0.5×10e6 plated cells/well. On Day 3 post activation cells are transferred to TC-treated plate.

Culture conditions for HSC/HSP can include expansion with a Notch agonist (see, e.g., U.S. Pat. Nos. 7,399,633; 5,780,300; 5,648,464; 5,849,869; and 5,856,441 and growth factors present in the culture condition as follows: 25-300 ng/ml SCF, 25-300 ng/ml Flt-3L, 25-100 ng/ml TPO, 25-100 ng/ml IL-6 and 10 ng/ml IL-3. In more specific embodiments, 50, 100, or 200 ng/ml SCF; 50, 100, or 200 ng/ml of Flt-3L; 50 or 100 ng/ml TPO; 50 or 100 ng/ml IL-6; and 10 ng/ml IL-3 can be used.

(viii) Ex Vivo Manufactured Cell Formulations

In particular embodiments, genetically modified cells can be harvested from a culture medium and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE A® (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions or formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions or formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In compositions and formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml.

As indicated, compositions include at least one genetically modified cell type (e.g., modified T cells, NK cells, or stem cells). Formulations can include different types of genetically-modified cells (e.g., T cells, NK cells, and/or stem cells in combination).

Different types of genetically-modified cells or cell subsets (e.g., modified T cells, NK cells, and/or stem cells) can be provided in different ratios e.g., a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc. These ratios can also apply to numbers of cells expressing the same or different recombinant proteins. If only two of the cell types are combined or only 2 combinations of recombinant proteins are included within a formulation, the ratio can include any 2-number combination that can be created from the 3 number combinations provided above. In embodiments, the combined cell populations are tested for efficacy and/or cell proliferation in vitro, in vivo and/or ex vivo, and the ratio of cells that provides for efficacy and/or proliferation of cells is selected. Particular embodiments include a 1:1 ratio of CD4 T cells and CD8 T cells.

The cell-based compositions disclosed herein can be prepared for administration by, e.g., injection, infusion, perfusion, or lavage. The compositions and formulations can further be formulated for bone marrow, intravenous, intradermal, intraarterial, intranodal, intralymphatic, intraperitoneal, intralesional, intratumoral, intravesicular, and/or subcutaneous injection.

(ix) Methods of Use

Methods disclosed herein include treating subjects (humans, veterinary animals (dogs, cats, reptiles, birds, etc.) livestock (horses, cattle, goats, pigs, sheep, chickens, etc.) and research animals (monkeys, rats, mice, fish, etc.) with compositions disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. Effective amounts are often administered for research purposes. Effective amounts disclosed herein can cause a statistically significant effect in an animal model or in vitro assay relevant to the assessment of a CD33-related disorder's development or progression.

A "prophylactic treatment" includes a treatment administered to a subject who does not display signs or symptoms of a CD33-related (for instance, CD33-expressing) disorder or displays only early signs or symptoms of a CD33-related disorder such that treatment is administered for the purpose of diminishing or decreasing the risk of developing the CD33-related disorder further. Thus, a prophylactic treatment functions as a preventative treatment against a CD33-related disorder.

A "therapeutic treatment" can include a treatment administered to a subject who displays symptoms or signs of a CD33-related disorder and is administered to the subject for the purpose of diminishing or eliminating those signs or symptoms of the CD33-related disorder. The therapeutic treatment can reduce, control, or eliminate the presence or activity of the CD33-related disorder and/or reduce control or eliminate side effects of the CD33-related disorder.

A "therapeutic treatment" can also include a treatment administered to a subject in need of imaging. The subject can be in need of imaging to aid in diagnosis; to locate a position for a therapeutic intervention; to assess the functioning of a body part; and/or to assess the presence or absence of a condition. The effectiveness of a therapeutic imaging treatment can be confirmed based on the capture of an image sufficient for its intended purpose. Exemplary types of imaging include: positron emission tomography (PET), single photon emission computed tomography, radioisotope renography, and scintigraphy.

Function as an effective amount, prophylactic treatment or therapeutic treatment are not mutually exclusive, and in particular embodiments, administered dosages may accomplish more than one treatment type.

In particular embodiments, therapeutically effective amounts provide anti-cancer effects. Anti-cancer effects include a decrease in the number of cancer cells, decrease in the number of metastases, prevented or reduced metastases, a decrease in tumor volume, inhibited tumor growth, an increase in life expectancy, prolonged subject life, induced chemo- or radiosensitivity in cancer cells, inhibited cancer cell proliferation, reduced cancer-associated pain, and/or reduced relapse or re-occurrence of cancer following treatment.

A "tumor" is a swelling or lesion formed by an abnormal growth of cells (called neoplastic cells or tumor cells). A "tumor cell" is an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be benign, pre-malignant or malignant.

In particular embodiments, therapeutically effects amounts induce an immune response. The immune response can be against a cancer cell.

Examples of CD33-related disorders include hematological cancers such as leukemias and lymphomas and other myelo- or lymphoproliferative disorders.

Exemplary leukemias include acute lymphoblastic leukemia (ALL), acute myeloid leukemia (AML), chronic myelogenous leukemia (CML), chronic myelomonocytic leukemia (CML), mast cell leukemia, myelodysplastic syndrome (MDS), B-cell acute lymphoblastic leukemia (B-ALL), T-cell acute lymphoblastic leukemia (T-ALL), and megakaryocytic leukemia.

Exemplary sub-types of AML include: acute basophilic leukemia, acute erythroid leukemia (AML-M6), acute megakaryoblastic leukemia (AML-M7), acute monoblastic leukemia (AML-M5a), acute monocytic leukemia (AML-M5b), acute myeloblasts leukemia with granulocytic maturation, acute myeloblasts leukemia without maturation, acute myelomonocytic leukemia (AML-M4), acute panmyelosis with myelofibrosis, acute promyelocytic leukemia (APL), erythroleukemia (AML-M6a), minimally differentiated acute myeloblasts leukemia, myelomonocytic leukemia with bone marrow eosinophilia, and pure erythroid leukemia (AML-M6b).

An exemplary lymphoma includes multiple myeloma.

Compositions disclosed herein can also be used to treat a complication or disease related to the above-noted lymphoproliferative disorders and hematological cancers. For example, complications relating to AML may include a preceding myelodysplastic syndrome (MDS, formerly known as "preleukemia"), secondary leukemia, in particular secondary AML, high white blood cell count, and absence of Auer rods. Among others, leukostasis and involvement of the central nervous system (CNS), hyperleukocytosis, residual disease, are also considered complications or diseases related to AML.

Compositions disclosed herein can be used to target myeloid-derived suppressor cells (MDSCs). MDSCs are a major player in the immunosuppressive tumor microenvironment and have been found to inhibit the antitumor reactivity of T cells and NK cells. Particular MDSCs have high CD33 expression and can be targeted with anti-CD33 treatments, including monocytic MDSCs and immature MDSCs.

Compositions disclosed herein may also find use in the treatment of other pathological conditions or genetic syndromes associated with the risk of AML such as Down syndrome, trisomy, Fanconi anemia, Bloom syndrome, Ataxia-telangiectasia, Diamond-Blackfan anemia, Schwachman-Diamond syndrome, Li-Fraumeni syndrome, Neurofibromatosis type 1, Severe congenital neutropenia (also called Kostmann syndrome).

Compositions disclosed herein may also find use in the treatment of Alzheimer's disease.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of CD33-related disorder, stage of CD33-related disorder, previous or concurrent therapeutic interventions, idiopathy of the subject and route of administration.

Useful doses can range from 0.1 to 5 μg/kg or from 0.5 to 1 μg/kg. In other examples, a dose can include 1 μg/kg, 15 μg/kg, 30 μg/kg, 50 μg/kg, 55 μg/kg, 70 μg/kg, 90 μg/kg, 150 μg/kg, 350 μg/kg, 500 μg/kg, 750 μg/kg, 1000 μg/kg, 0.1 to 5 mg/kg or from 0.5 to 1 mg/kg. In other examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically effective amounts of cell-based compositions can include $10^4$ to $10^9$ cells/kg body weight, or $10^3$ to $10^{11}$ cells/kg body weight. Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly). In particular embodiments, the treatment protocol may be dictated by a clinical trial protocol or an FDA-approved treatment protocol.

The pharmaceutical compositions described herein can be administered by injection, inhalation, infusion, perfusion, lavage or ingestion. Routes of administration can include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

Methods of use also include use of antibodies described herein in image-based diagnostics, for example, when the antibody is formatted as a radioisotope conjugate.

(x) Reference Levels Derived from Control Populations

Obtained values for parameters associated with a therapy described herein can be compared to a reference level derived from a control population, and this comparison can indicate whether a therapy described herein is effective for a subject in need thereof. Reference levels can be obtained from one or more relevant datasets from a control population. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual data points; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a control population. A "control population" is any grouping of subjects or samples of like specified characteristics. The grouping could be according to, for example, clinical parameters, clinical assessments, therapeutic regimens, disease status, severity of condition, etc. In particular embodiments, the grouping is based on age range (e.g., 60-65 years) and non-immuno-compromised status. In particular embodiments, a normal control population includes individuals that are age-matched to a test subject and non-immune compromised. In particular embodiments, age-matched includes, e.g., 0-10 years old; 30-40 years old, 60-65 years old, 70-85 years old, etc., as is clinically relevant under the circumstances. In particular embodiments, a control population can include those that have a CD33-related disorder and have not been administered a therapeutically effective amount of a composition or formulation.

In particular embodiments, the relevant reference level for values of a particular parameter associated with a therapy described herein is obtained based on the value of a particular corresponding parameter associated with a therapy in a control population to determine whether a therapy disclosed herein has been therapeutically effective for a subject in need thereof.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular data point, where the data point is the result of random chance alone. A result is often considered significant (not random chance) at a p-value less than or equal to 0.05. In particular embodiments, a sample value is "comparable to" a reference level derived from a normal control population if the sample value and the reference level are not statistically significantly different.

The Exemplary Embodiments and Examples below are included to demonstrate particular, non-limiting embodiments of the disclosure. Those of ordinary skill in the art will recognize in light of the present disclosure that many changes can be made to the specific embodiments disclosed herein and still obtain a like or similar result without departing from the spirit and scope of the disclosure.

(xi) Exemplary Embodiments

1. An antibody or antigen binding fragment thereof including a complementarity determining region (CDR) set of 1H10, 1A9, 1E6, 1D2, 1B9, 1H8, 2D3, or 2E3, according to North, IMGT, Kabat, Chothia, or Set 5.

2. An antibody or antigen binding fragment thereof including the variable light chain and the variable heavy chain of 1H10, 1A9, 1E6, 1D2, 1B9, 1H8, 2D3, or 2E3 or a variable light chain having at least 90% sequence identity to the variable light chain of 1H10, 1A9, 1E6, 1D2, 1B9, 1H8, 2D3, or 2E3 and a variable heavy chain having at least 90% sequence identity to the corresponding variable heavy chain of 1H10, 1A9, 1E6, 1D2, 1B9, 1H8, 2D3, or 2E3.

3. An antibody or antigen binding fragment of embodiments 1 or 2, wherein the antigen binding fragment includes an Fv, Fab, Fab', $F(ab')_2$, or single chain Fv fragment (scFv) in a VH-VL or a VL-VH orientation (see, e.g., SEQ ID NOs: 230-237 in FIG. 14).

4. An antibody or antigen binding fragment thereof of any of embodiments 1-3, wherein the antibody or antigen binding fragment thereof is PEGylated.

5. An antibody or antigen binding fragment thereof of any of embodiments 1-4, wherein the antibody includes an Fc modification.

6. An antibody or antigen binding fragment thereof of embodiment 5, wherein the Fc modification includes M428L/N434S, G236A/S239D/A330L/I332E (GASDALIE), huIgG4 ProAlaAla, huIgG2m4, and/or huIgG2sigma mutations.

7. An antibody or antigen binding fragment thereof of any of embodiments 1-6 that binds the C2-set Ig-like domain of CD33 within 115 residues of the transmembrane region regardless of the presence of the V-set domain or that binds the C2-set Ig-like domain but only in the absence of the V-set domain.

8. A CD33-targeting agent including a binding domain including the complementarity determining region (CDR) set of 1H10, 1A9, 1E6, 1D2, 1B9, 1H8, 2D3, or 2E3 according to North, IMGT, Kabat, Chothia, or Set 5 as part of an anti-CD33 immunotoxin, an anti-CD33 antibody-drug conjugate, an anti-CD33 antibody-fluorophore conjugate, an anti-CD33 antibody-radioisotope conjugate, an anti-CD33 bispecific antibody, an anti-CD33 bispecific immune cell engaging antibody, an anti-CD33 trispecific antibody, and/or an anti-CD33 tetraspecific antibody.

9. A CD33-targeting agent including a binding domain including the variable heavy and variable light chain of 1H10, 1A9, 1E6, 1D2, 1B9, 1H8, 2D3, or 2E3 as part of an anti-CD33 immunotoxin, an anti-CD33 antibody-drug conjugate, an anti-CD33 antibody-fluorophore conjugate, an anti-CD33 anti-CD33 antibody-radioisotope conjugate, an anti-CD33 bispecific antibody, an anti-CD33 bispecific immune cell engaging antibody, an anti-CD33 trispecific antibody, and/or an anti-CD33 tetraspecific antibody; or a variable heavy and light chain having at least 90% sequence identity to the corresponding variable heavy and light chain of 1H10, 1A9, 1E6, 1D2, 1B9, 1H8, 2D3, or 2E3 as part of an anti-CD33 immunotoxin, an anti-CD33 antibody-drug conjugate, an anti-CD33 anti-CD33 antibody-radioisotope conjugate, an anti-CD33 bispecific antibody, an anti-CD33 bispecific immune cell engaging antibody, an anti-CD33 trispecific antibody, and/or an anti-CD33 tetraspecific antibody.

10. A CD33-targeting agent of embodiments 8 or 9, wherein the CD33-targeting agent includes an anti-CD33 immunotoxin wherein the toxin includes a holotoxin or a hemitoxin.

11. A CD33-targeting agent of any of embodiments 8-10, wherein the CD33-targeting agent includes an anti-CD33 immunotoxin wherein the toxin includes abrin, bouganin, Bryodin 1, diphtheria toxin (DT), gelonin, mistletoe lectin, modeccin, pokeweed antiviral protein (PAP), *Pseudomonas* exotoxin (PE), ricin, and/or saporin.

12. A CD33-targeting agent of any of embodiments 8-11, wherein the CD33-targeting agent includes an anti-CD33 antibody-drug conjugate wherein the drug includes monomethyl auristatin E [MMAE], vedotin, dolastatin, auristatin, calicheamicin, pyrrolobenzodiazepine (PBD), nemorubicin, PNU-159682, anthracycline, duocarmycin, vinca alkaloid, taxane, trichothecene, CC1065, camptothecin, elinafide, taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, and/or propranolol.

13. A CD33-targeting agent of any of embodiments 8-12, wherein the CD33-targeting agent includes an anti-CD33 antibody-radioisotope conjugate wherein the radioisotope includes arsenic-72, arsenic-74, iodine-131, indium-111, yttrium-90, lutetium-177, astatine-211, actinium-225, or bismuth-212 and/or bismuth-213.

14. A CD33-targeting agent of any of embodiments 8-13, wherein the CD33-targeting agent includes an anti-CD33 antibody-radioisotope conjugate wherein the radioisotope includes $^{225}$Ac, $^{228}$Ac, $^{111}$Ag, $^{124}$Am, $^{74}$As, $^{211}$At, $^{209}$At, $^{194}$Au, $^{128}$Ba, $^{7}$Be, $^{206}$Bi, $^{245}$Bk, $^{246}$Bk, $^{76}$Br, $^{11}$C, $^{47}$Ca, $^{254}$Cf, $^{242}$Cm, $^{51}$Cr, $^{67}$Cu, $^{153}$Dy, $^{157}$Dy, $^{159}$Dy, $^{165}$Dy, $^{166}$Dy, $^{171}$Er, $^{250}$Es, $^{254}$Es, $^{147}$Eu, $^{157}$Eu, $^{52}$Fe, $^{59}$Fe, $^{251}$Fm, $^{252}$Fm, $^{253}$Fm, $^{66}$Ga, $^{72}$Ga, $^{146}$Gd, $^{153}$Gd, $^{66}$Ge, $^{170}$Hf, $^{171}$Hf, $^{193}$Hg, $^{193}$mHg, $^{160}$mHo, $^{130}$I, $^{131}$I, $^{135}$I, $^{114}$mIn, $^{185}$Ir, $^{42}$K, $^{43}$K, $^{78}$Kr, $^{79}$Kr, $^{81}$mKr, $^{132}$La, $^{262}$Lr, $^{169}$Lu, $^{174}$mLu, $^{176}$mLu, $^{257}$Md, $^{260}$Md, $^{28}$Mg, $^{52}$Mn, $^{90}$Mo, $^{24}$Na, $^{95}$Nb, $^{138}$Nd, $^{57}$Ni, $^{66}$Ni, $^{234}$Np, $^{15}$O, $^{182}$Os, $^{189}$mOs, $^{191}$Os, $^{32}$Pb, $^{201}$Pb, $^{101}$Pd, $^{143}$Pr, $^{191}$Pt, $^{243}$Pu, $^{225}$Ra, $^{81}$Rb, $^{188}$Re, $^{105}$Rh, $^{211}$Rn, $^{103}$Ru, $^{35}$S, $^{44}$Sc, $^{72}$Se, $^{153}$Sm, $^{125}$Sn, $^{91}$Sr, $^{173}$Ta, $^{154}$Tb, $^{127}$Te, $^{234}$Th, $^{45}$Ti, $^{166}$Tm, $^{230}$U, $^{237}$U, $^{240}$U, $^{48}$V, $^{178}$W, $^{181}$W, $^{188}$W, $^{125}$Xe, $^{127}$Xe, $^{133}$Xe, $^{133}$mXe, $^{135}$Xe, $^{85}$mY, $^{86}$Y, $^{90}$Y, $^{93}$Y, $^{169}$Yb, $^{175}$Yb, $^{65}$Zn, $^{71}$mZn, $^{86}$Zr, $^{95}$Zr, and/or $^{97}$Zr.

15. A CD33-targeting agent of any of embodiments 8-14, wherein the CD33-targeting agent includes a multispecific antibody.

16. A CD33-targeting agent of embodiment 15, wherein the multispecific antibody includes a bispecific antibody, a trispecific antibody, or a tetraspecific antibody.

17. A CD33-targeting agent of embodiments 15 or 16, wherein the multispecific antibody includes a binding domain that activates an immune cell (see, e.g., SEQ ID NOs: 157 and 238-245 in FIG. 14).

18. A CD33-targeting agent of embodiment 17, wherein the immune cell is a T-cell, natural killer (NK) cell, NK-T cell, or a macrophage.

19. A CD33-targeting agent of embodiment 18, wherein the T cell is a CD3 T cell, a CD4 T cell, a CD8 T cell, a central memory T cell, an effector memory T cell, and/or a naïve T cell 20. A CD33-targeting agent of any of embodiments 17-19, wherein the binding domain that activates an immune cell binds CD3, CD28, CD8, NKG2D, CD8, CD16, KIR2DL4, KIR2DS1, KIR2DS2, KIR3DS1, NKG2C, NKG2E, NKG2D, NKp30, NKp44, NKp46, NKp80, DNAM-1, CD11b, CD11c, CD64, CD68, CD119, CD163, CD206, CD209, F4/80, IFGR2, Toll-like receptors 1-9, IL-4Rα, or MARCO.

21. A CD33-targeting agent of any of embodiments 17-20, wherein the binding domain activates a T cell and includes CDRs of the OKT3 antibody, the 4B4-D7 antibody, the 4E7-C9 antibody, the 18F5-H10 antibody, or includes the CD3 HcFv and CD3 LcFv as set forth in SEQ ID Nos. 161 and 162.

22. A CD33-targeting agent of any of embodiments 17-21, wherein the binding domain activates a T cell and includes CDRs of the TGN1412 antibody.

23. A CD33-targeting agent of any of embodiments 17-22, wherein the binding domain activates a T cell and includes CDRs of the OKT8 antibody.

24. A CD33-targeting agent of any of embodiments 17-23, wherein the binding domain activates a T cell and includes a TCR.

25. A CD33-targeting agent of any of embodiments 17-24, wherein the CD33-targeting agent has a CDR set of 1H10 and the CD3 HcFv having the sequence as set forth in SEQ ID NO: 161 and the CD3 LcFv having the sequence as set forth in SEQ ID NO: 162;

a CDR set of 1A9 and the CD3 HcFv having the sequence as set forth in SEQ ID NO: 161 and the CD3 LcFv having the sequence as set forth in SEQ ID NO: 162;

a CDR set of 1E6 and the CD3 HcFv having the sequence as set forth in SEQ ID NO: 161 and the CD3 LcFv having the sequence as set forth in SEQ ID NO: 162;

a CDR set of 1D2 and the CD3 HcFv having the sequence as set forth in SEQ ID NO: 161 and the CD3 LcFv having the sequence as set forth in SEQ ID NO: 162;

a CDR set of 1B9 and the CD3 HcFv having the sequence as set forth in SEQ ID NO: 161 and the CD3 LcFv having the sequence as set forth in SEQ ID NO: 162;

a CDR set of 1H8 and the CD3 HcFv having the sequence as set forth in SEQ ID NO: 161 and the CD3 LcFv having the sequence as set forth in SEQ ID NO: 162;

a CDR set of 2D3 and the CD3 HcFv having the sequence as set forth in SEQ ID NO: 161 and the CD3 LcFv having the sequence as set forth in SEQ ID NO: 162; or a CDR set of 2E3 and the CD3 HcFv having the sequence as set forth in SEQ ID NO: 161 and the CD3 LcFv having the sequence as set forth in SEQ ID NO: 162;

26. A CD33-targeting agent of any of embodiments 17-25, wherein the CD33-targeting agent has the sequence as set forth in SEQ ID NOs: 234 or 235.

27. A CD33-targeting agent of any of embodiments 8-26, including an Fv, Fab, Fab', F(ab')$_2$, or single chain Fv fragment (scFv) of 1H10, 1A9, 1E6, 1D2, 1B9, 1H8, 2D3, or 2E3, wherein the scFv can be in the VH-VL orientation or the VL-VH orientation (see, e.g., SEQ ID NOs: 230-237 in FIG. 14).

28. An antibody or antigen binding fragment thereof of any of embodiments 1-7 or the CD33-targeting agent of any of embodiments 8-27, further including a linker.

29. A CD33-targeting agent of embodiment 28, wherein the linker is a Gly-Ser linker.

30. A CD33-targeting agent of embodiment 29, wherein the Gly-Ser linker includes $(Gly_xSer_y)_n$, wherein x and y are independently an integer from 0 to 10 provided that x and y are not both 0 and wherein n is an integer of 1, 2, 3, 4, 5, 6, 7, 8, 9 or 10).

31. A CD33-targeting agent of embodiment 30, wherein the Gly-Ser linker includes $(Gly_4Ser)_4$ (SEQ ID NO: 125), $(Gly_4Ser)_3$ (SEQ ID NO: 126), $(Gly_4Ser)_2$ (SEQ ID NO: 127), $(Gly_4Ser)_1$ (SEQ ID NO: 128), $(Gly_3Ser)_2$ (SEQ ID NO: 129), $(Gly_3Ser)_1$ (SEQ ID NO: 130), $(Gly_2Ser)_2$ (SEQ ID NO: 131), $(Gly_2Ser)_1$, GGSGGGSGGSG (SEQ ID NO: 132), GGSGGGSGSG (SEQ ID NO: 133), or GGSGGGSG (SEQ ID NO: 134).

32. A composition including an antibody or antigen binding fragment thereof of any of embodiments 1-7 or 28 and/or a CD33-targeting agent of any of embodiments 8-31 formulated for administration to a subject.

33. A cell genetically modified to express an antibody or antigen binding fragment thereof of any of embodiments 1-7 and/or the CD33-targeting agent of any of embodiments 8, 9, or 15-31 formulated for administration to a subject.

34. A cell of embodiment 33, wherein the cell is in vivo or ex vivo.

35. A cell of embodiments 33 or 34, wherein the cell is a T cell, B cell, natural killer (NK) cell, NK-T cell, monocyte/macrophage, hematopoietic stem cells (HSC), or a hematopoietic progenitor cell (HPC).

36. A cell of any of embodiment 33-35, wherein the cell is a T cell selected from a CD3+ T cell, a CD4+ T cell, a CD8+ T cell, a central memory T cell, an effector memory T cell, and/or a naïve T cell, 37. A cell of any of embodiments 33-36, wherein the cell is a CD8+ T cell.

38. A formulation including a population of cells of any of embodiments 33-37 and a pharmaceutically acceptable carrier, 39. A method of treating a CD33-related disorder in a subject in need thereof including administering a therapeutically effective amount of the composition of embodiment 32 and/or a formulation of embodiment 38 to the subject thereby treating the CD33-related disorder in a subject in need thereof.

40. A method of embodiment 39, wherein the CD33-related disorder includes acute myeloid leukemia (AML).

41. A method of embodiment 39, wherein the CD33-related disorder includes acute lymphoblastic leukemia (ALL), chronic myelogenous leukemia (CML), chronic myelomonocytic leukemia (CML), mast cell leukemia, myelodysplastic syndrome (MDS), B-cell acute lymphoblastic leukemia (B-ALL), T-cell acute lymphoblastic leukemia (T-ALL), or megakaryocytic leukemia.

42. A method of any of embodiments 39-41, wherein the population of cells in the formulation is autologous or allogeneic to the subject.

43. A method of any of embodiments 39-42, further including determining whether the subject expresses or lacks the V-set domain of CD33, and if the subject expresses the V-set domain of CD33, selecting a combination therapy including a composition including a binding domain of one or more of 1H10, 1A9, 1E6, 1D2, and 1B9 and a binding domain of one or more of one or more of 1H8, 2D3, and 2E3.

44. A method of any of embodiments 39-42, further including determining whether the subject expresses or lacks the V-set domain of CD33, and if the subject does not express the V-set domain of CD33, selecting a therapy including a composition including a binding domain of one or more of 6H9, 9G2, 3A5, 7D5, 1H7, and 2D5.

45. A method of activating an immune response against CD33-expressing cells in a subject in need thereof including administering a therapeutically effective amount of the composition of embodiment 32 and/or a formulation of embodiment 38 to the subject activating an immune response against CD33-expressing cells in the subject in need.

46. A method of embodiment 45, wherein the CD33-expressing cells include acute myeloid leukemia (AML) cells.

47. A method of embodiment 45, wherein the CD33-expressing cells include acute lymphoblastic leukemia (ALL), chronic myelogenous leukemia (CML), chronic myelomonocytic leukemia (CML), mast cell leukemia, myelodysplastic syndrome (MDS), B-cell acute lymphoblastic leukemia (B-ALL), T-cell acute lymphoblastic leukemia (T-ALL), or megakaryocytic leukemia cells.

48. A method of any of embodiments 45-47, wherein the population of cells in the formulation is autologous or allogeneic to the subject.

49. A method of any of embodiments 45-48, further including determining whether the subject expresses or lacks the V-set domain of CD33, and if the subject expresses the V-set domain of CD33, selecting a combination therapy including a composition including a binding domain of one or more of 1H10, 1A9, 1E6, 1D2, and 1B9 and a binding domain of one or more of one or more of 1H8, 2D3, and 2E3.

50. A method of any of embodiments 45-48, further including determining whether the subject expresses or lacks the V-set domain of CD33, and if the subject does not express the V-set domain of CD33, selecting a therapy including a composition including a binding domain of one or more of 6H9, 9G2, 3A5, 7D5, 1H7, and 2D5.

51. A kit including a composition including a binding domain of one or more of 1H10, 1A9, 1E6, 1 D2, and 1B9 and a binding domain of one or more of one or more of 1H8, 2D3, and 2E3.

52. A kit including a composition including a binding domain of one or more of 1H10, 1A9, 1E6, 1 D2, and 1B9 and a composition including a binding domain of one or more of one or more of 1H8, 2D3, and 2E3.

53. Use of an antibody or antigen binding fragment thereof of any of the preceding embodiments or a CD33-targeting agent of any of the preceding embodiments in in vivo imaging and/or to enrich for, isolate, and/or detect a CD33-expressing cell in vitro or in vivo.

(xii) Experimental Examples

Abstract. There is increasing interest in targeting CD33 in malignant and non-malignant disorders. In acute myeloid leukemia, longer survival with the CD33 antibody-drug conjugate gemtuzumab ozogamicin (GO) validates this strategy. Still, GO benefits only some patients, prompting efforts to develop more potent CD33-directed therapeutics. As one limitation, CD33 antibodies typically recognize the membrane-distal V-set domain. Using various artificial CD33 proteins, in which this domain was differentially positioned within the extracellular portion of the molecule, it was tested whether targeting membrane-proximal targeting epitopes enhances the effector functions of CD33 antibody-based therapeutics. Consistent with this idea, a $CD33^{V\text{-}set}$/CD3 bispecific antibody (BsAb) elicited substantially greater cytotoxicity against cells expressing a CD33 variant lacking the entire C2-set domain than cells expressing full-length CD33, whereas cytotoxic effects induced by GO were independent of the position of the V-set domain. Therefore, murine and human antibodies were raised against the C2-set domain of human CD33 and antibodies that bound CD33 regardless of the presence/absence of the V-set domain ("$CD33^{PAN}$ antibodies") were identified. These antibodies internalized when bound to CD33 and, as $CD33^{PAN}$/CD3 BsAb, had potent cytolytic effects against CD33+ cells. The data provide rationale for further development of $CD33^{PAN}$ antibody-based therapeutics.

Introduction. CD33 (Siglec-3) is a differentiation antigen that is primarily displayed on maturing and mature myeloid cells and their neoplastic cell counterparts (Walter et al., *Blood.* 119(26): 6198-6208, 2012; and Duan et al., *Annu Rev Immunol.* 38: 365-395, 2020). With this expression pattern, there have been long-standing efforts in therapeutically targeting CD33+ cells, first and foremost in acute myeloid leukemia (AML) (Walter et al., *Blood.* 119(26): 6198-6208, 2012; Grossbard et al., *Blood.* 80(4): 863-878, 1992; and Laszlo et al., *Blood Rev.* 28(4): 143-153, 2014) but also CD33+ tumor cells in other malignancies, CD33+ myeloid-derived suppressor cells, and normal CD33+ microglial cells (Walter, *Expert Opin Biol Ther.* 20(9): 955-958, 2020). In AML, longer survival of some patients treated with the antibody-drug conjugate GO validates CD33 as drug target (Godwin et al., *Leukemia.* 31(9): 1855-1868, 2017).

The success and limitations of GO have fueled ongoing work to develop more effective CD33-directed therapeutics. However, targeting CD33 has proven difficult, and several drugs failed clinically because of lack of efficacy. Efforts have therefore centered around developing more potent anti-CD33 treatment modalities, including T cell engaging bispecific antibodies (BsAbs). As one important limitation of these efforts, existing and investigational therapeutics, including GO, almost exclusively recognize immune-dominant epitope(s) within the exon 2-encoded membrane-distal V-set domain of CD33 (FIG. 1) (Walter, *Expert Opin Investig Drugs.* 27(4): 339-348, 2018). Since membrane-proximal binding of antibodies can increase their effector functions (Bluemel et al., *Cancer Immunol Immunother.* 59(8): 1197-1209, 2010; Lin, *Pharmgenomics Pers Med.* 3: 51-59, 2010; Haso et al., *Blood.* 121(7): 1165-1174, 2013; Cleary et al., *J Immunol.* 198(10): 3999-4011, 2017), targeting CD33 with antibodies against the membrane-proximal C2-set domain should optimize CD33-directed therapy that engage immune effector cells. Here, this concept was tested experimentally and the generation of a series of C2-set domain-directed CD33 antibodies and derived therapeutics is described.

Figure 2:
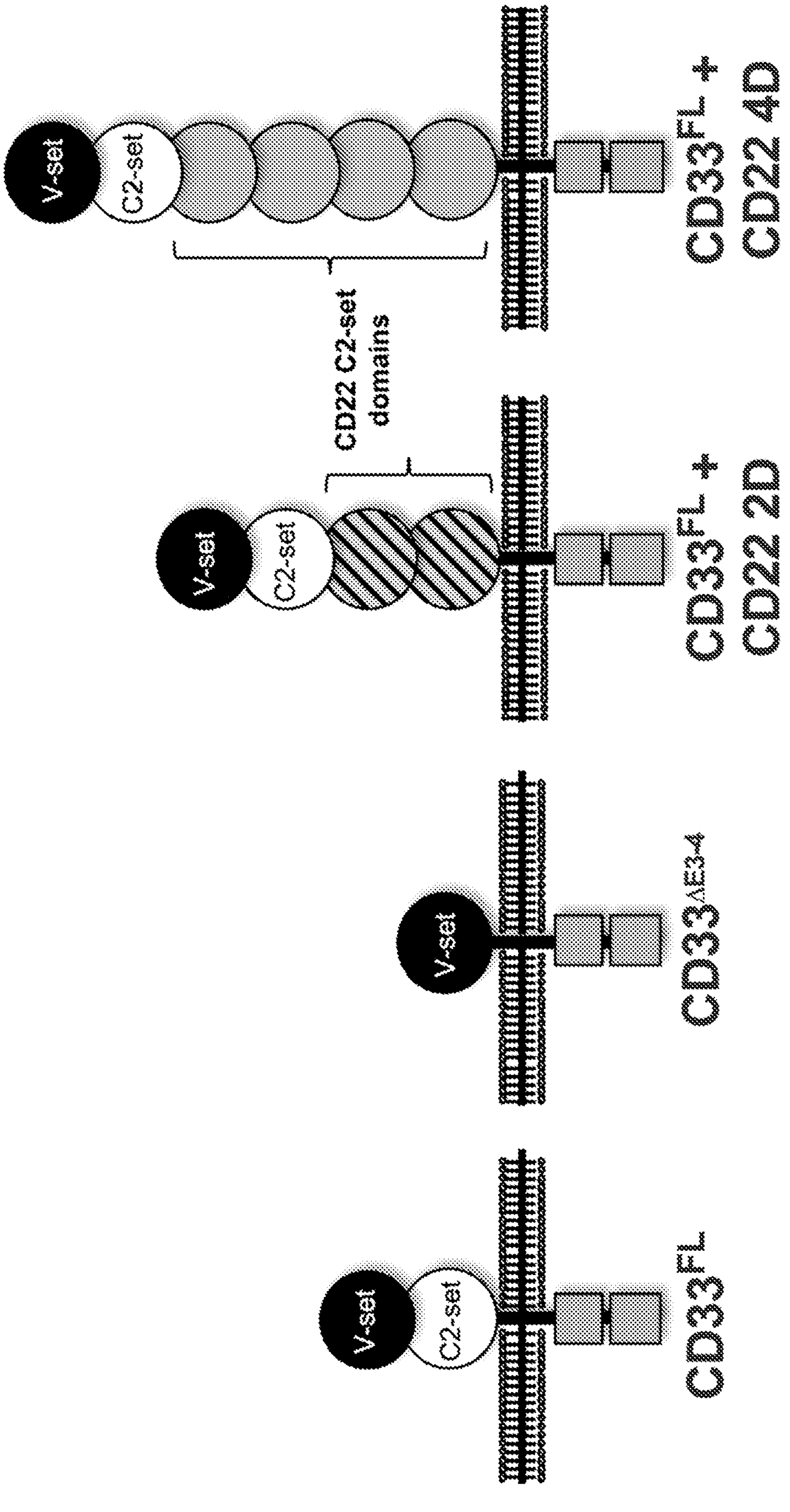
FIG. 2. Schematic of $CD33^{FL}$ and artificial CD33 molecules with deletion of exons 3 and 4, resulting in membrane proximal relocation of the V-set domain ($CD33^{\Delta E3-4}$), or insertion of either 2 C2-set domains of CD22 ("$CD33^{FL}$+CD22 2D") or 4 C2-set domains of CD22 ("$CD33^{FL}$+CD22 4D"). $CD33^{\Delta E3-4}$ was engineered using site-directed mutagenesis to splice out CD33 amino acids (aa) 140-232 of the human $CD33^{FL}$ extracellular domain (ECD). $CD33^{FL}$+CD22 4D was generated using the endogenous CD33 signal peptide (aa 1-17), a 6-histidine tag, 3× glycine linker, the human CD33 ECD (aa 18-259), a portion of the human CD22 ECD including C2-type domains 3-6 (aa 331-683), the CD33 transmembrane domain, and the CD33 intracellular domain (aa 260-364). CD22 aa 331-504 (C2-type domains 3 and 4) were removed from $CD33^{FL}$+CD22 24 to generate $CD33^{FL}$+CD22 2D.
Figure 3A:
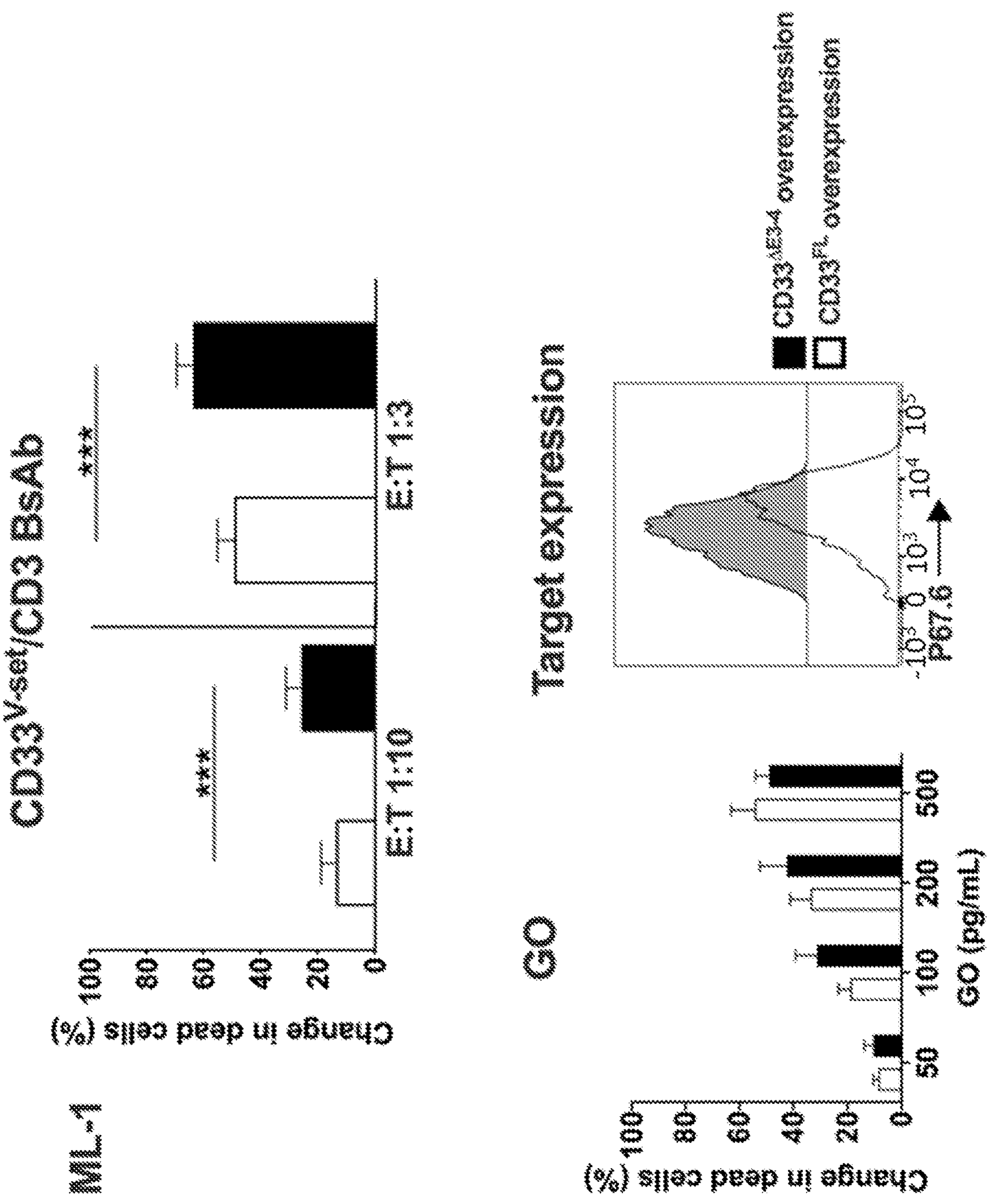
FIGS. 3A-3C. Reducing the binding distance from cell membrane enhances the anti-tumor efficacy of CD33/CD3 BsAbs against human myeloid leukemia cells. Human CD33+ myeloid leukemia cell lines ((3A) ML-1, (3B) HL-60, (3C) K562) with CRISPR/Cas9-mediated deletion of the endogenous CD33 locus were engineered to overexpress either $CD33^{FL}$ or $CD33^{\Delta E3-4}$ via lentiviral gene transfer. Relative expression of the target proteins was flow cytometrically assessed via V-set domain CD33 antibody, P67.6, with representative histograms shown in the bottom right panel. Cells were then treated with a V-set domain-targeting CD33/CD3 BsAb at a concentration of 1000 pg/mL and healthy donor T cells enriched from unstimulated peripheral blood mononuclear cells collected from healthy adult volunteers at the effector:target (E:T) cell ratios shown (top panel). Myeloid cells were also treated with gemtuzumab ozogamicin (GO) at the concentrations shown (bottom left panel). Cytotoxicity was quantified flow cytometrically after 2 days (for BsAbs) or 3 days (for GO) as a change in the percentage of dead cells as measured by 4',6-diamidino-2-phenylindole (DAPI) staining. The anti-V-set domain-directed CD33/CD3 BsAb was constructed in the scFv-scFv format using a construct referred to herein as RC1 or A3 that utilizes the sequence as set forth in SEQ ID NO: 259 and described in United States patent application publication US 2016/0317657 A1. *$p<0.05$; $p<0.01$; *$p<0.001$.
Figure 3B:
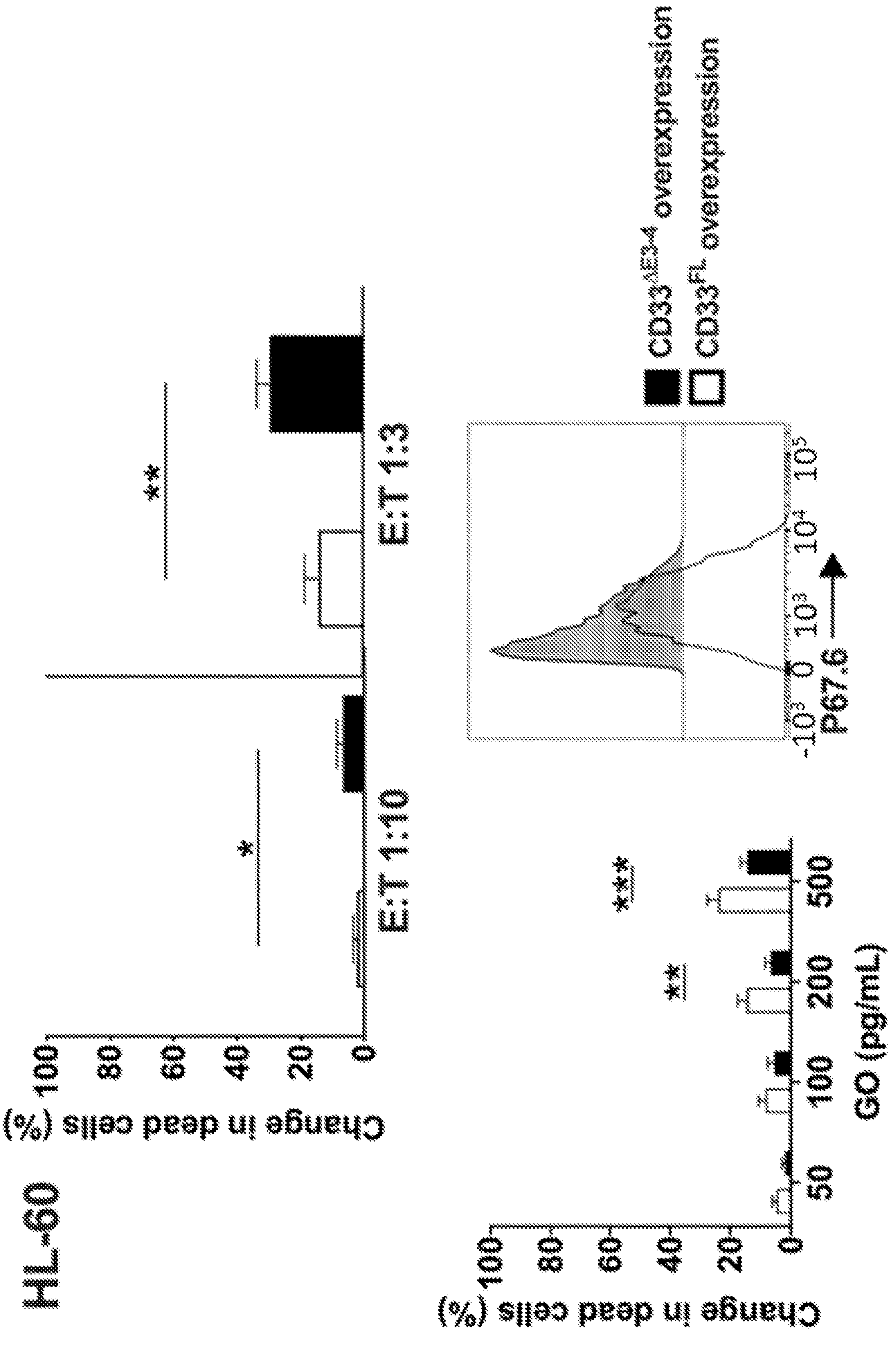
Figure 3C:
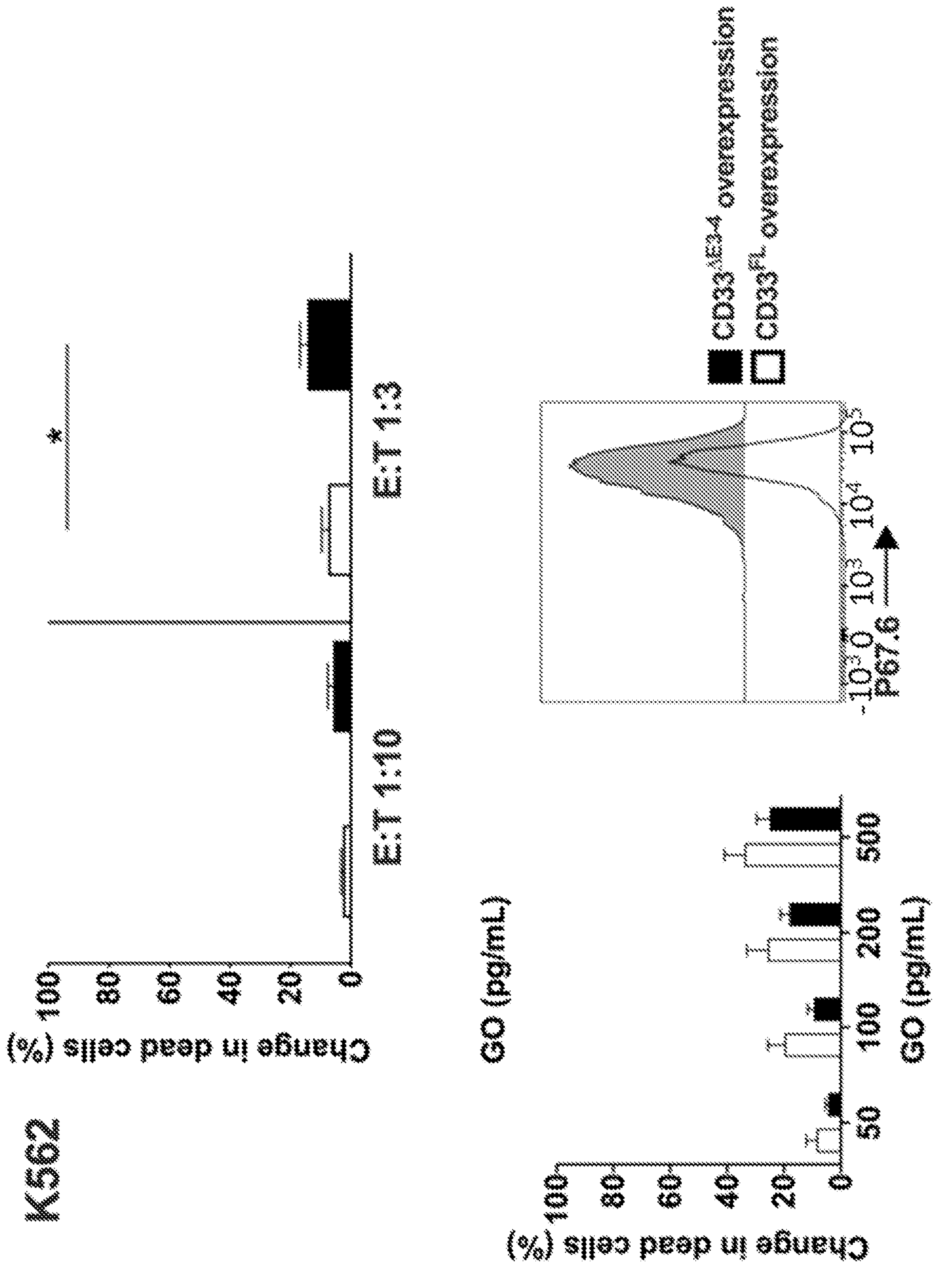
Figure 4:
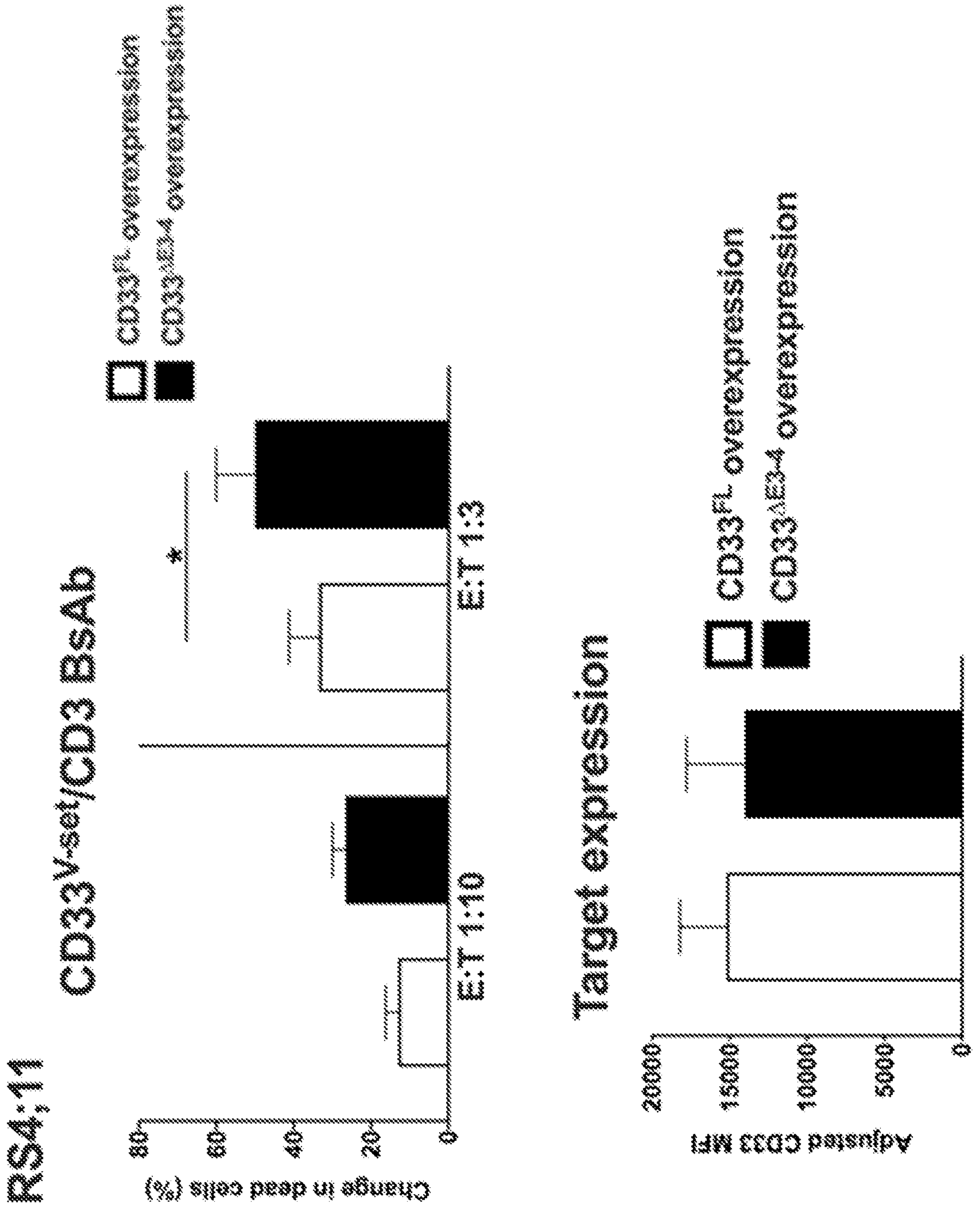
FIG. 4. Reducing the binding distance from cell membrane enhances the anti-tumor efficacy of CD33/CD3 BsAbs against human acute lymphoblastic leukemia cells engineered to express CD33 proteins. The human $CD33^{neg}$ acute lymphoblastic leukemia (ALL) cell line RS4; 11 was engineered to overexpress either $CD33^{FL}$ or $CD33^{\Delta E3-4}$ via lentiviral gene transfer. Relative expression of the target proteins was flow cytometrically assessed via V-set domain CD33 antibody, P67.6, with representative histograms shown in the bottom panel. Cells were then treated with a V-set domain-targeting CD33/CD3 BsAb at a concentration of 1000 pg/mL and healthy donor T cells enriched from unstimulated peripheral blood mononuclear cells collected from healthy adult volunteers at the effector:target (E:T) cell ratios shown (top panel). Cytotoxicity was quantified flow cytometrically after 2 days as a change in the percentage of dead cells as measured by DAPI staining. The anti-V-set domain-directed CD33/CD3 BsAb was constructed in the scFv-scFv format using a construct referred to herein as RC1 or A3 that utilizes the sequence as set forth in SEQ ID NO: 259 and described in United States patent application publication US 2016/0317657 A1. *$p<0.05$; $p<0.01$; *$p<0.001$.
Figure 5:
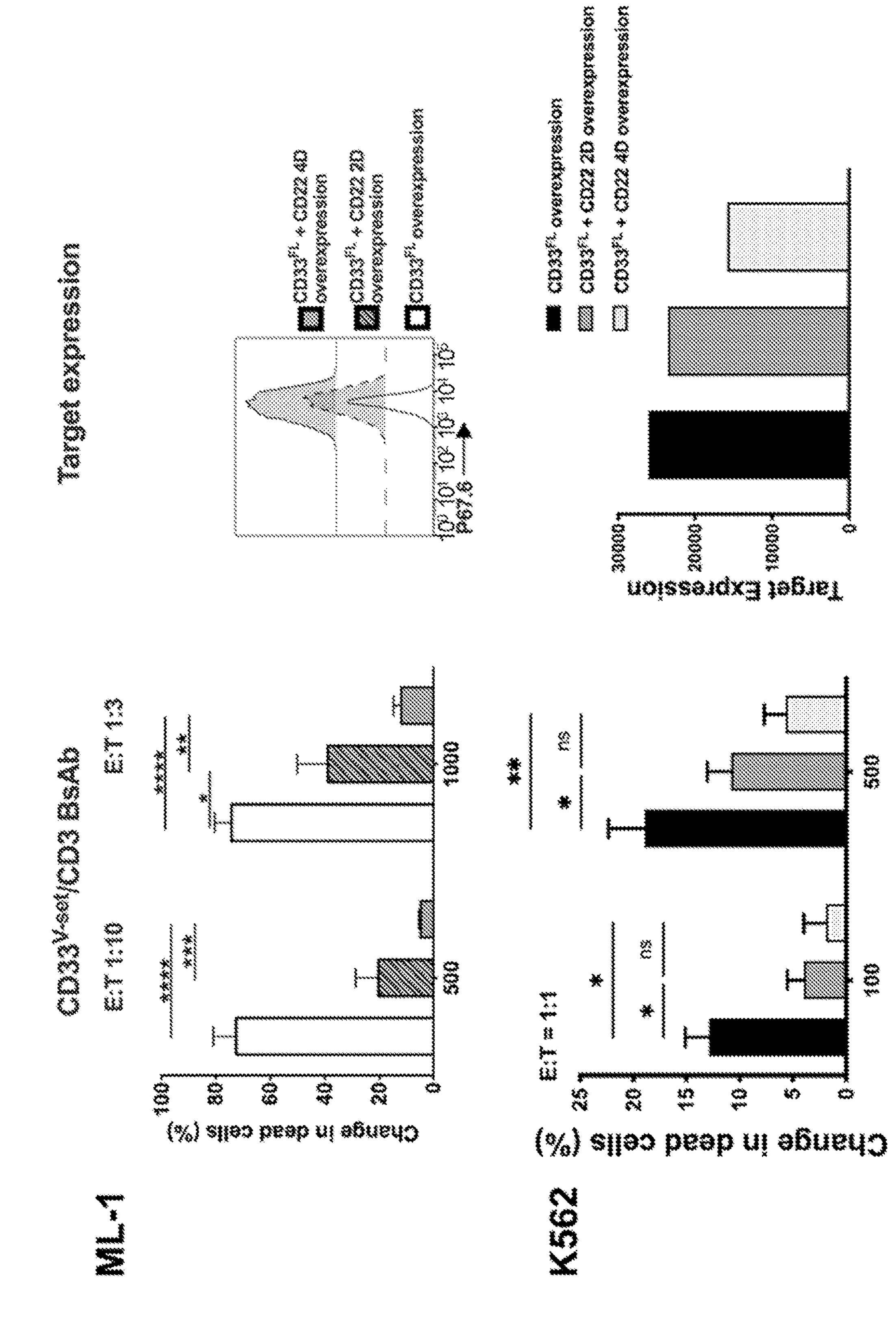
FIG. 5. Increasing the binding distance from cell membrane reduces the anti-tumor efficacy of CD33/CD3 BsAbs. Human myeloid leukemia cell lines (ML-1 [upper panel], K562 [lower panel]) with CRISPR/Cas9-mediated deletion of the endogenous CD33 locus were engineered to overexpress CD33FL, CD33FL+CD22 2D or CD33FL+CD22 4D via lentiviral gene transfer. Relative expression of the CD33 constructs was flow cytometrically assessed using the V-set domain CD33 antibody, P67.6 (right panel). Cells were then treated with a V-set domain-targeting CD33/CD3 BsAb at the concentrations shown (in pg/mL) and healthy donor T cells enriched from unstimulated peripheral healthy donor blood mononuclear cells at an E:T cell ratio of 1:1. Cytotoxicity was quantified flow cytometrically after 2 days as a change in the percentage of dead cells as measured by DAPI staining. The anti-V-set domain-directed CD33/CD3 BsAb was constructed in the scFv-scFv format using a construct referred to herein as RC1 or A3 that utilizes the sequence as set forth in SEQ ID NO: 259 and described in United States patent application publication US 2016/0317657 A1. *$p<0.05$; $p<0.01$; *$p<0.001$.

Results. Binding distance from cell membrane correlates with immune effector functions of CD33 antibodies. To examine whether the distance between target epitope and the cell membrane influences the efficacy of T cell-engaging immunotherapies, a series of artificial proteins were generated in which the V-set domain of human CD33 was held at different distances from the cell membrane to allow targeting with a V-set domain-directed CD33 antibody-based therapeutic such as a $CD33^{V\text{-}set}$/CD3 BsAb (FIG. 2). Specifically, to bring the CD33 target epitope closer to the cell membrane, an artificial CD33 protein that lacked the entire C2-set domain by removing exons 3 and 4 ($CD33^{\Delta E3\text{-}4}$) was generated. Engineered human $CD33^{+}$ AML cell lines in which endogenous CD33 was deleted via CRISPR/Cas9 (Humbert et al., *Leukemia.* 33(3): 762-808, 2019) were used to express either $CD33^{FL}$ or $CD33^{\Delta E3\text{-}4}$. In a first series of experiments, sublines expressing relatively similar levels of target molecules were subjected to short-term in vitro cytotoxicity assays with various doses of a $CD33^{V\text{-}set}$/CD3 BsAb and healthy donor T cells as immune effector cells. As comparator, GO was used, which entirely depends on the toxic effects induced by the calicheamicin-$\gamma_1$ payload for anti-tumor effects (Walter et al., *Blood.* 119(26): 6198-6208, 2012; Laszlo et al., *Blood Rev.* 28(4): 143-153, 2014; and Godwin et al., *Leukemia.* 31(9): 1855-1868, 2017). As shown in FIGS. 3A-3C, $CD33^{V\text{-}set}$/CD3 BsAbs exerted greater cytotoxicity against AML and ALL cells expressing $CD33^{\Delta E3\text{-}4}$ than cells expressing $CD33^{FL}$, whereas cytotoxic effects induced by GO were similar. Similar effects were seen in REH and RS4; 11 cells (human $CD33^{-}$ B-acute lymphoblastic leukemia [B-ALL] cell lines) expressing these same CD33 constructs when treated with $CD33^{V\text{-}set}$/CD3 BsAbs (data for RS4; 11 shown in FIG. 4). To further demonstrate the importance of target epitope membrane distance for efficacy of CD33-directed therapies engaging T cells, chimeric proteins were generated using various portions of human CD22 to extend the distance between CD33 target epitope and the cell membrane (FIG. 2). As summarized in FIG. 5, the cytotoxic effects of $CD33^{V\text{-}set}$/CD3 BsAbs were lower against AML cells expressing CD22/$CD33^{FL}$ chimeric proteins than paired cells expressing $CD33^{FL}$. Together, these data demonstrated that altering the position of the CD33 antibody binding epitope changes the effector functions of the CD33 antibody-derived therapies and suggested that membrane-proximal targeting of CD33 via C2-set domain-specific therapeutics could improve the efficacy of CD33-targeted T cell immunotherapy.

Figure 6A:
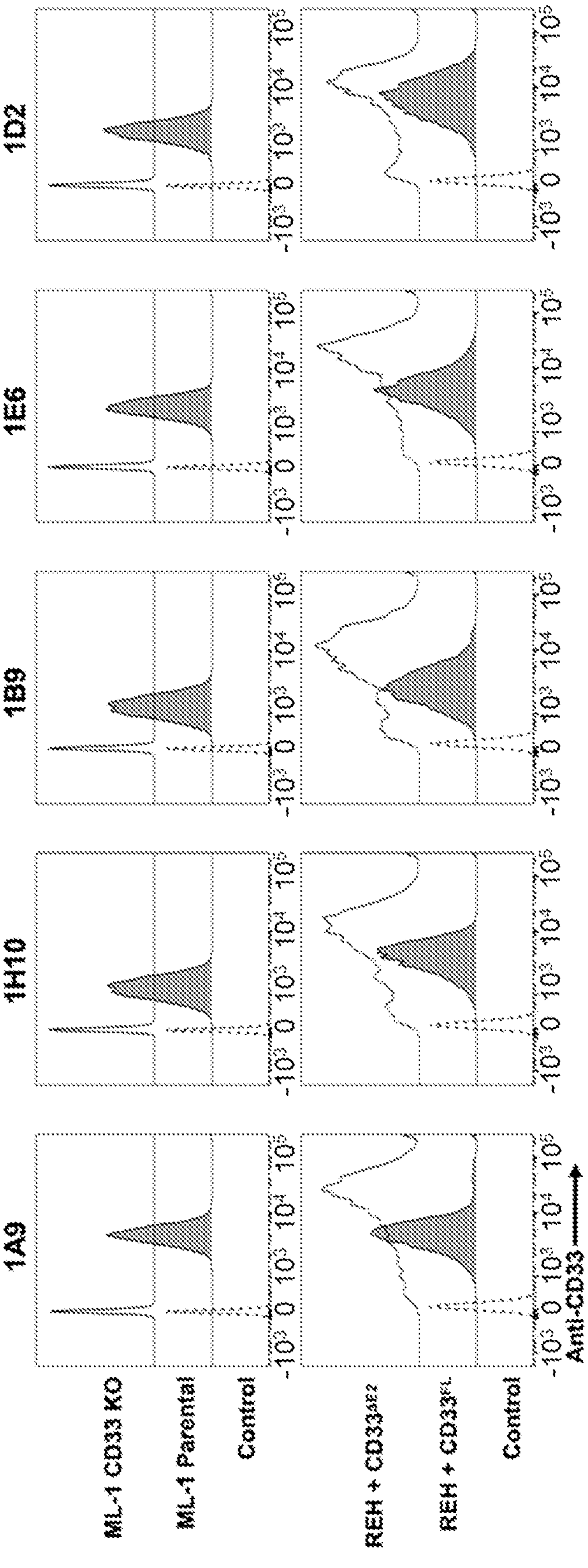
FIGS. 6A, 6B. (6A) Human $CD33^{PAN}$ antibody clones (clones 1A9, 1H10, 1B9, 1E6, and 1D2) and (6B) human $CD33^{V\text{-}set}$ antibody clones (clones 2E3, 2D3, and 1H8) were tested flow cytometrically against CD33+ parental ML-1 cells and ML-1 cells with CRISPR/Cas9-mediated deletion of CD33 ("CD33 KO") as well as against REH sublines engineered to express $CD33^{FL}$ or $CD33^{\Delta E2}$, as indicated. A control without primary antibody was included.
Figure 6B:
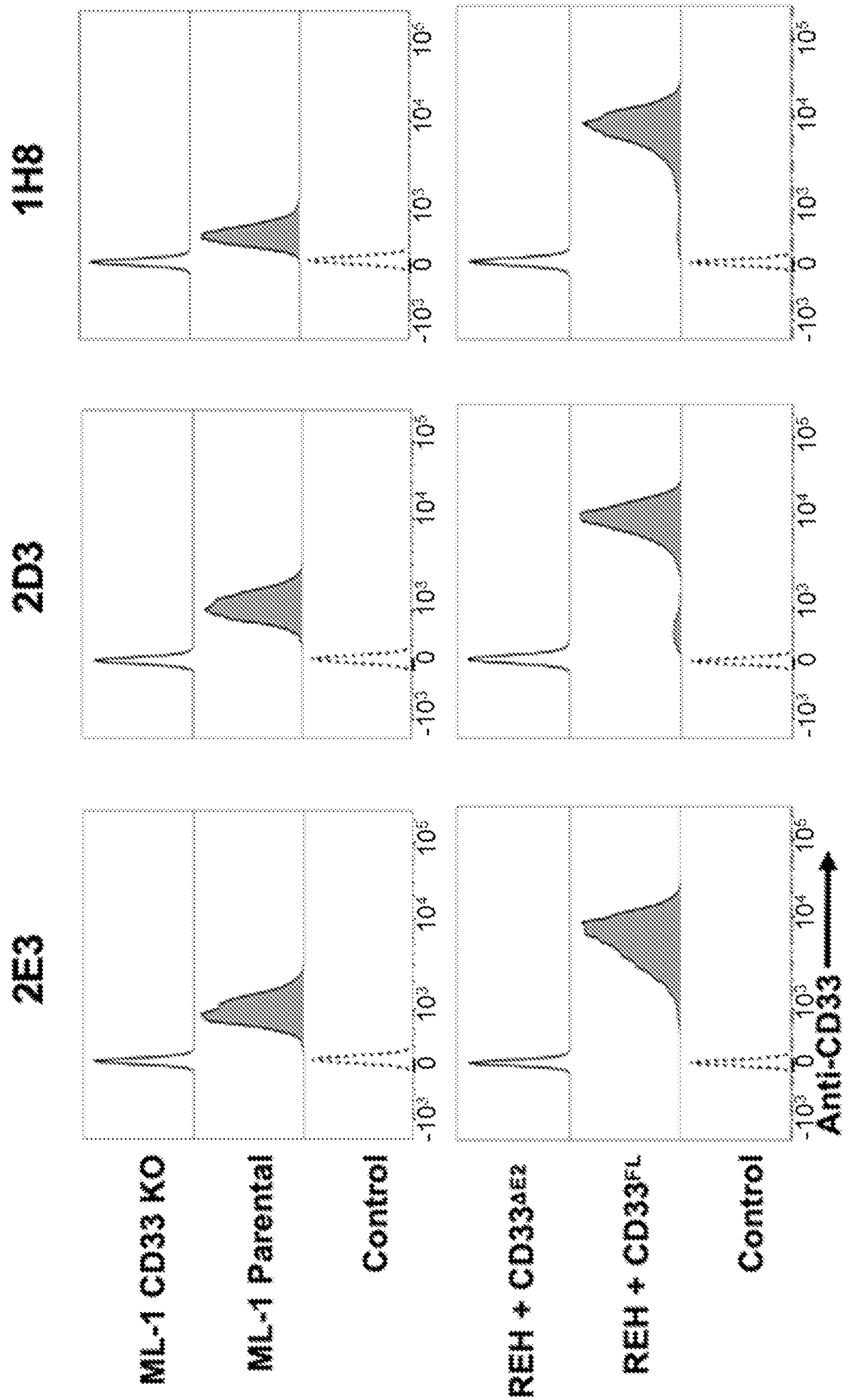
Figure 7B:
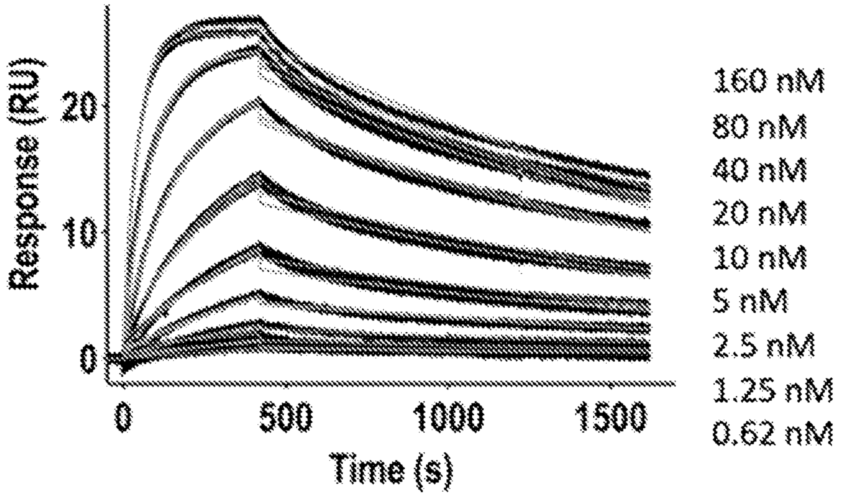
Figure 7B:
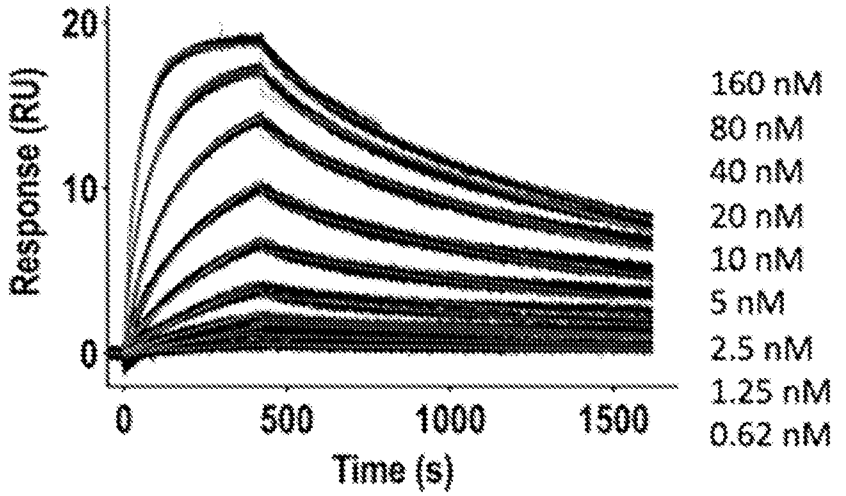
Figure 7B:
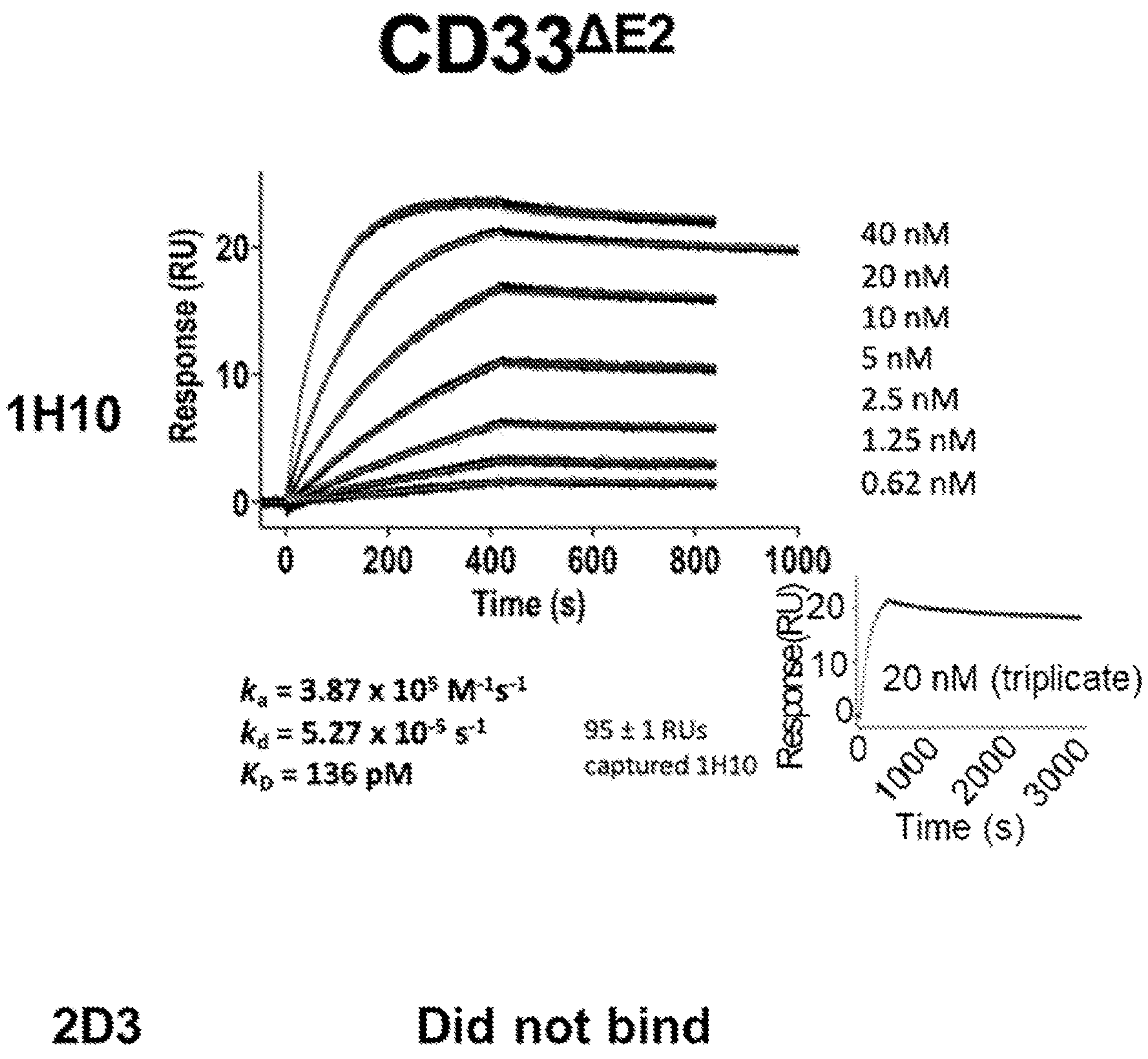
Figure 8:
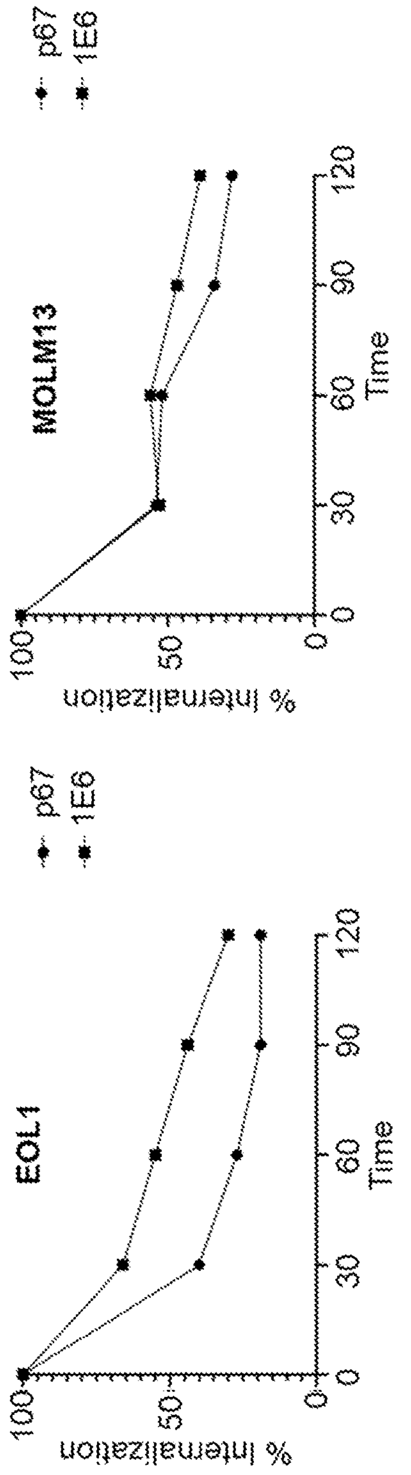
FIG. 8. Internalization of 1E6 and P67.6. AML cell lines were incubated with CD33 antibody at 37° C. for the time indicated. Fluorescently labeled secondary antibody was then added to quantify remaining CD33 antibody on the cell surface. Results are presented as a percentage of the fluorescence signal present at time 0.
Figure 9:
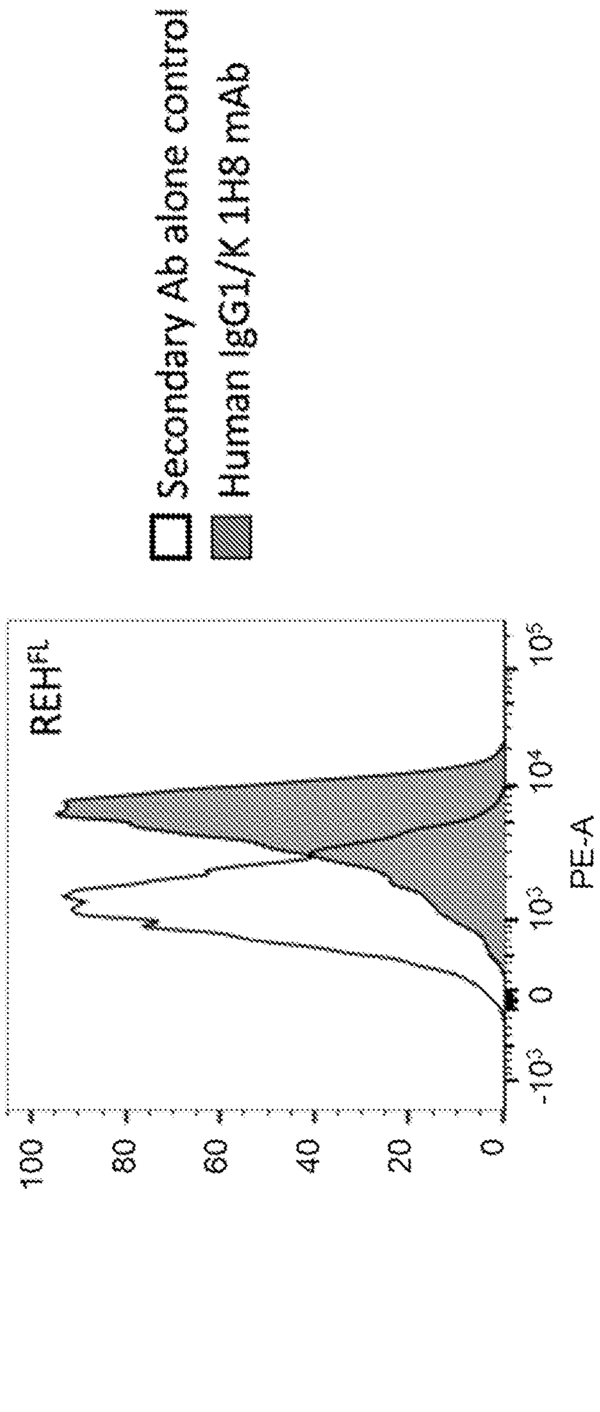
FIG. 9. Binding of recombinant fully human CD33$^{V\text{-}set}$ antibody 1H8 with human IgG1 framework to REH cells (human acute lymphoblastic leukemia cell line, endogenously CD33$^{neg}$) engineered to express human CD33$^{FL}$.

Second-generation $CD33^{PAN}$ antibodies with fully human variable domain sequences and derived therapeutics. Since well-characterized antibodies recognizing the C2-set domain of human CD33 currently do not exist, antibodies were raised with this specificity in BALB/c, CD1, and F1 mice injected with immunogens including of the murine IgG1 Fc domain linked to the entire ECD of human $CD33^{FL}$ or the entire ECD of human $CD33^{\Delta E2}$. Data was recently reported on a series of murine anti-human $CD33^{PAN}$ antibodies (Godwin et al., *Leukemia.* 2021, DOI: 10.1038/s41375-021-01160-1). Because the immunogenicity of murine amino acid sequences is a potential clinical concern, a second immunization campaign was conducted in which the same CD33 immunogens were used in humanized mice to yield antibodies with fully human variable domain sequences. As shown in FIGS. 6A and 6B, hybridomas recognizing only $CD33^{FL}$ were identified along with several hybridomas with binding to both $CD33^{\Delta E2}$ and $CD33^{FL}$ (i.e. $CD33^{PAN}$ antibody specificity). Experiments with CD33+ ML-1 cells and an ML-1 subline in which CD33 was removed via CRISPR/Cas9-mediated gene editing confirmed binding specificity of these antibodies to human CD33. A summary of biophysical characterization studies via Carterra is depicted in FIG. 7A, 7B. For further characterization, 1E6 was subjected to antibody internalization experiments. As shown in FIG. 8, 1E6 was indeed internalized in human AML cells with similar kinetics as P67.6, the parent murine $CD33^{V\text{-}set}$ antibody used in GO. Since hybridomas derived from Trianni mice secrete chimeric antibodies (human variable binding sequences, murine constant regions), species switching methodologies were used to generate recombinant fully human $CD33^{PAN}$ antibodies. FIG. 9 shows one example (1E6 antibody with human IgG1 framework).

Figure 10:
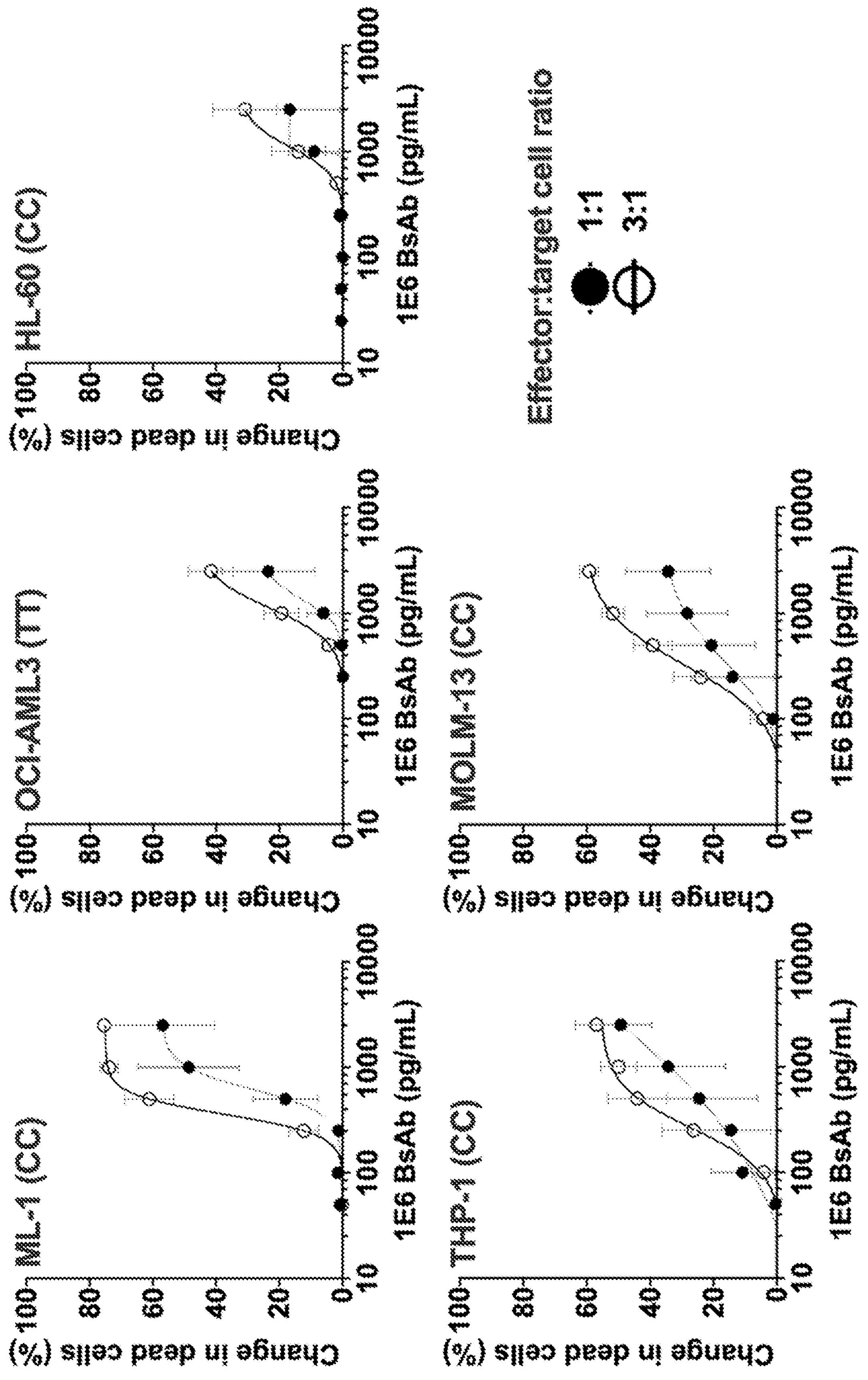
FIG. 10. A human CD33$^{PAN}$/CD3 BsAb redirects T cell-mediated cytotoxicity against human CD33+ AML cells. Parental AML cell lines were treated with healthy donor T cells at the effector:target (E:T) cell ratios shown and various doses of 1E6/CD3 BsAb. Cytotoxicity was quantified flow cytometrically after 2 days as a change in the percentage of dead cells as measured by DAPI staining. The CD33 rs12459419 genotype is indicated in parentheses.
Figure 11:
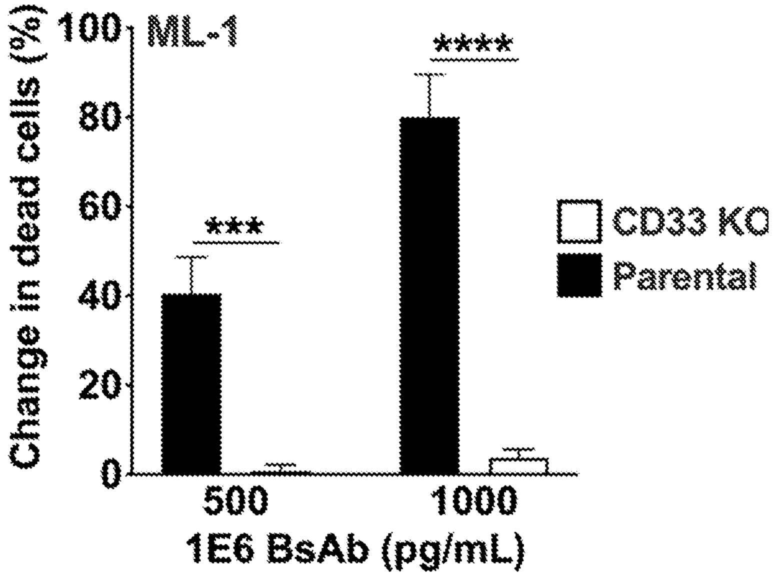
FIG. 11. A human CD33$^{PAN}$/CD3 BsAb redirects T cell-mediated cytotoxicity against human AML cells in a CD33-specific manner. Parental ML-1 cells and a subline with CRISPR/Cas9-mediated knockout (KO) of CD33 were treated with 1E6 BsAb at the indicated concentrations and healthy donor T cells at an E:T of 1:1. Dead leukemic cells were enumerated after 48 hours via flow cytometry, and change in dead cells compared to no BsAb treatment is shown. Mean values±SEM of 3 separate experiments are shown. *p<0.001; **p<0.0001.
Figure 12:
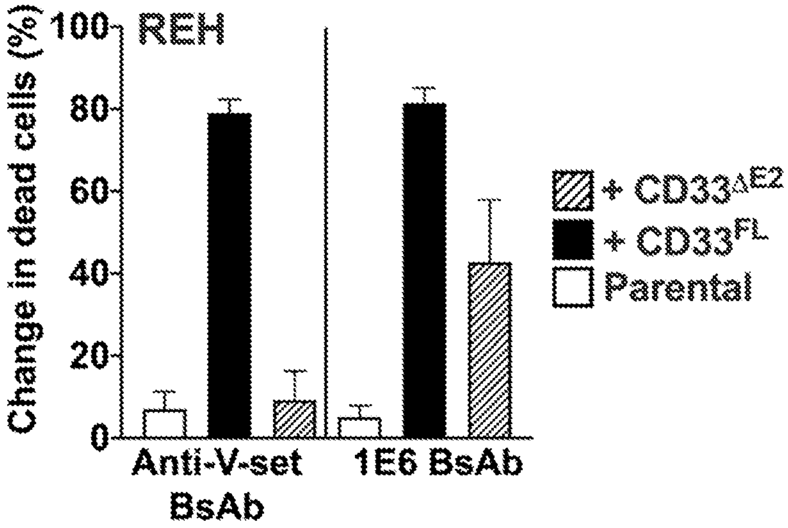
FIG. 12. A human CD33$^{PAN}$/CD3 BsAb redirects T cell-mediated cytotoxicity against human acute leukemia cells in a CD33– and epitope-specific manner. Parental CD33$^{neg}$ REH cells or sublines engineered to overexpress CD33$^{FL}$ or CD33$^{\Delta E2}$ were treated with anti-V-set CD33/CD3 BsAb or 1E6 BsAb at a dose of 1000 pg/mL and an E:T of 3:1. Dead leukemic cells were enumerated after 48 hours via flow cytometry, and change in dead cells compared to no BsAb treatment is shown. Mean values±SEM of three separate experiments are shown.
Figure 13:
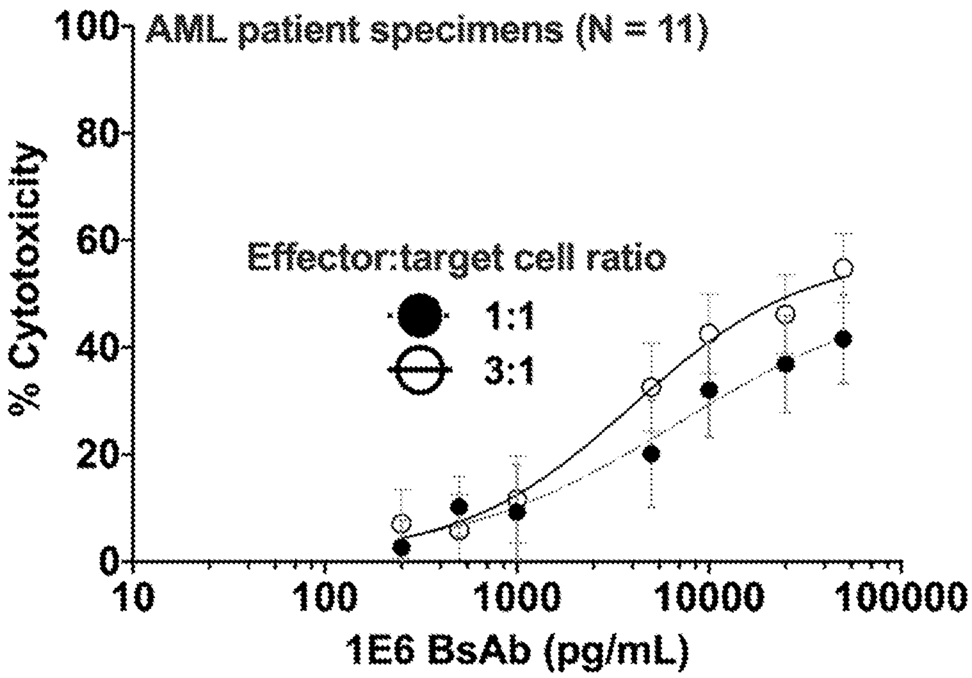
FIG. 13. A human CD33$^{PAN}$/CD3 BsAb redirects T cell-mediated cytotoxicity against primary human AML cells. A panel of 11 primary AML patient samples was treated with the 1E6/CD3 BsAb and healthy donor T-cells at the E:T ratios shown. Cytotoxicity was determined after 2 days by flow cytometry enumerating both dead cells (using 4',6-diamidino-2-phenylindole [DAPI] staining) and total cell number. Mean cytotoxicity±SEM across the 11 patient samples is shown.

For proof-of-principle studies on the therapeutic value of human $CD33^{PAN}$ antibodies, a 1E6/CD3 BsAb was built in the scFv-scFv format. Similar to what was found for a murine $CD33^{PAN}$/CD3 BsAb, Godwin et al., *Leukemia.* 2021, DOI: 10.1038/s41375-021-01160-1) the 1E6/CD3 BsAb was highly potent against CD33+ human acute leukemia cells (FIG. 10) but lacked activity against CD33 knockout cells (FIG. 11). The 1E6/CD3 BsAb also potently killed REH cells overexpressing both $CD33^{FL}$ and $CD33^{\Delta E2}$, whereas the $CD33^{V\text{-}set}$/CD3 BsAb had activity only against $CD33^{FL}$-expressing cells (FIG. 12). Finally, it was determined that the 1E6/CD3 BsAb also had robust activity against a variety of primary AML patient specimens in vitro (FIG. 13).

(xiii) Closing Paragraphs

The nucleic acid and amino acid sequences provided herein are shown using letter abbreviations for nucleotide bases and amino acid residues, as defined in 37 C.F.R. § 1.822 and set forth in the tables in WIPO Standard ST.25 (1998), Appendix 2, Tables 1 and 3. Only one strand of each nucleic acid sequence is shown, but the complementary strand is understood as included in embodiments where it would be appropriate.

To the extent not explicitly provided herein, coding sequences for proteins disclosed herein and protein sequences for coding sequences disclosed herein can be readily derived from one of ordinary skill in the art.

The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, Md. (Kabat numbering scheme); A1-Lazikani et al. (1997) J Mol Biol 273: 927-948 (Chothia numbering scheme); Maccallum et al. (1996) J Mol Biol 262: 732-745 (Contact numbering scheme); Martin et al. (1989) Proc. Natl. Acad. Sci., 86: 9268-9272 (AbM numbering scheme); Lefranc M P et al. (2003) Dev Comp Immunol 27(1): 55-77 (IMGT numbering scheme); and Honegger and Pluckthun (2001) J Mol Biol 309(3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wis.) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

Variants of antibodies can include those having one or more conservative amino acid substitutions or one or more non-conservative substitutions that do not adversely affect the binding of the protein.

In particular embodiments, a $V_L$ region can be derived from or based on a disclosed $V_L$ and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the disclosed $V_L$. An insertion, deletion or substitution may be anywhere in the $V_L$ region, including at the amino- or carboxy-terminus or both ends of this region, provided that each CDR includes zero changes or at most one, two, or three changes and provided an antibody including the modified $V_L$ region can still specifically bind its target epitope with an affinity similar to the wild type binding domain.

In particular embodiments, a $V_H$ region can be derived from or based on a disclosed $V_H$ and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_H$ disclosed herein. An insertion, deletion or substitution may be anywhere in the $V_H$ region, including at the amino- or carboxy-terminus or both ends of this region, provided that each CDR includes zero changes or at most one, two, or three changes and provided an antibody including the modified $V_H$ region can still specifically bind its target epitope with an affinity similar to the wild type binding domain.

In particular embodiments, a conservative amino acid substitution may not substantially change the structural characteristics of the reference sequence (e.g., a replacement amino acid should not tend to break a helix that occurs in the reference sequence or disrupt other types of secondary structure that characterizes the reference sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden & J. Tooze, eds., Garland Publishing, New York, NY (1991)); and Thornton et al., Nature, 354:105 (1991).

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gin), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

In particular embodiments, a variant includes or is a sequence that has at least 90%, at least 91%, at least 92%, at least 93%, at least 94%, at least 95%, at least 96%, at least 97%, at least 98%, at least 99%, at least 99.5% sequence identity to an antibody sequence disclosed herein. In particular embodiments, a variant includes or is a sequence that has at least 90%, at least 91%, at least 92%, at least 93%, at least 94%, at least 95%, at least 96%, at least 97%, at least 98%, at least 99%, at least 99.5% sequence identity to a light chain variable region ($V_L$) and/or to a heavy chain variable region ($V_H$), or both, wherein each CDR includes zero changes or at most one, two, or three changes, from the reference antibody disclosed herein or fragment or derivative thereof that specifically binds to the C2-set Ig-like CD33 epitope regardless of the presence or absence of the V-set Ig-like domain or binds the V-set Ig-like domain according to an antibody's epitope specificity as described herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, NY Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, SXSSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. SXSSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

"Specifically binds" refers to an association of a binding domain (of, for example, a bispecific antibody binding domain or a nanoparticle selected cell targeting ligand) to its cognate binding molecule with an affinity or $K_a$ (i.e., an equilibrium association constant of a particular binding interaction with units of 1/M) equal to or greater than $10^5$ $M^{-1}$, while not significantly associating with any other molecules or components in a relevant environment sample. Binding domains may be classified as "high affinity" or "low affinity". In particular embodiments, "high affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. In particular embodiments, "low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domains with stronger binding to a cognate binding molecule than a wild type (or parent) binding domain. For example, enhanced affinity may be due to a $K_a$ (equilibrium association constant) for the cognate binding molecule that is higher than the reference binding domain or due to a Kd (dissociation constant) for the cognate binding molecule that is less than that of the reference binding domain, or due to an off-rate ($K_{off}$) for the cognate binding molecule that is less than that of the reference binding domain. A variety of assays are known for detecting binding domains that specifically bind a particular cognate binding molecule as well as determining binding affinities, such as Western blot, ELISA, and BIACORE® analysis (see also, e.g., Scatchard, et al., 1949, *Ann. N.Y. Acad. Sci.* 51:660; and U.S. Pat. Nos. 5,283,173, 5,468,614, or the equivalent).

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in binding between an antibody and antigen.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A CD33-binding antibody or antigen binding fragment thereof comprising a six-member complementarity determining region (CDR) set, wherein the six-member CDR set comprises:

(i) a CDRL1 having the sequence as set forth in SEQ ID NO: 24,
a CDRL2 having the sequence as set forth in SEQ ID NO: 25,
a CDRL3 having the sequence as set forth in SEQ ID NO: 26,
a CDRH1 having the sequence as set forth in SEQ ID NO: 27,
a CDRH2 having the sequence as set forth in SEQ ID NO: 28, and
a CDRH3 having the sequence as set forth in SEQ ID NO: 29; according to North;

(ii) a CDR having the sequence as set forth in SEQ ID NO: 183,
a CDRL2 having the sequence AAS,
a CDRL3 having the sequence as set forth in SEQ ID NO: 26,
a CDRH1 having the sequence as set forth in SEQ ID NO: 184,
a CDRH2 having the sequence as set forth in SEQ ID NO: 185, and
a CDRH3 having the sequence as set forth in SEQ ID NO: 29; according toe IMGT;

(iii) a CDRL1 having the sequence as set forth in SEQ ID NO: 24,
a CDRL2 having the sequence as set forth in SEQ ID NO: 204,
a CDRL3 having the sequence as set forth in SEQ ID NO: 26,
a CDRH1 having the sequence as set forth in SEQ ID NO: 205,
a CDRH2 having the sequence as set forth in SEQ ID NO: 206, and
a CDRH3 having the sequence as set forth in SEQ ID NO: 207; according to Kabat; or (iv) a CDRL1 having the sequence as set forth in SEQ ID NO: 24,
a CDRL2 having the sequence as set forth in SEQ ID NO: 204, a CDRL3 having the sequence as set forth in SEQ ID NO: 26, a CDRH1 having the sequence as set forth in SEQ ID NO: 222, a CDRH2 having the sequence as set forth in SEQ ID NO: 223, and a CDRH3 having the sequence as set forth in SEQ ID NO: 207, according to Chothia.

2. The CD33-binding antibody or antigen binding fragment thereof of claim 1, comprising a variable light chain comprising at least 90% sequence identity to SEQ ID NO: 55 and a variable heavy chain comprising at least 90% sequence identity to SEQ ID NO: 56.

3. The CD33-binding antibody or antigen binding fragment thereof of claim 1, comprising a variable light chain comprising SEQ ID NO: 55 and a variable heavy chain comprising SEQ ID NO: 56.

4. The CD33-binding antibody or antigen binding fragment thereof of claim 1, further comprising an Fc region, wherein the Fc region comprises M428L/N434S, or G236A/S239D/A330L/I332E and wherein the numbering is according to the EU index.

5. The CD33-binding antibody or antigen binding fragment thereof of claim 1, wherein the antigen binding fragment is a single chain variable fragment (scFv).

6. The CD33-binding antibody or antigen binding fragment thereof of claim 5, wherein the scFv comprises a Gly-Ser linker comprising SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, or SEQ ID NO: 134.

7. The CD33-binding antibody or antigen binding fragment thereof of claim 5, wherein the scFv has the sequence of SEQ ID NO: 234 or SEQ ID NO:235.

8. A conjugate antibody comprising the CD33-binding antibody or antigen binding fragment thereof of claim 1, wherein the CD33-binding antibody or antigen binding fragment thereof is conjugated to an immunotoxin, a drug, or a radioisotope.

9. The conjugate antibody of claim 8, wherein, the immunotoxin is selected from the group consisting of holotoxin, hemitoxin, abrin, bouganin, Bryodin 1, diphtheria toxin (DT), gelonin, mistletoe lectin, modeccin, pokeweed antiviral protein (PAP), Pseudomonas exotoxin (PE), ricin, and saporin.

10. The conjugate antibody of claim 8, wherein the drug is selected from the group consisting of monomethyl auristatin E (MMAE), vedotin, dolastatin, auristatin, calicheamicin, pyrrolobenzodiazepine (PBD), nemorubicin, PNU-159682, anthracycline, duocarmycin, vinca alkaloid, taxane, trichothecene, CC1065, camptothecin, elinafide, taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, and propranolol.

11. The conjugate antibody of claim 8 wherein the radioisotope is selected from the group consisting of $^{72}$As, $^{74}$As, $^{131}$I, $^{49}$In, $^{90}$Y, $^{177}$Lu, $^{211}$At, $^{225}$Ac, $^{212}$Bi, $^{213}$Bi, $^{225}$Ac, $^{228}$Ac, $^{111}$Ag, $^{124}$Am, $^{74}$As, $^{211}$At, $^{209}$At, $^{194}$Au, $^{128}$Ba, $^{7}$Be, $^{206}$Bi, $^{245}$Bk, $^{246}$Bk, $^{76}$Br, $^{11}$C, $^{47}$Ca, $^{254}$Cf, $^{242}$Cm, $^{51}$Cr, $^{67}$Cu, $^{153}$Dy, $^{157}$Dy, $^{159}$Dy, $^{165}$Dy, $^{166}$Dy, $^{171}$Er, $^{250}$Es, $^{254}$Es, $^{147}$Eu, $^{157}$Eu, $^{52}$Fe, $^{59}$Fe, $^{251}$Fm, $^{252}$Fm, $^{253}$Fm, $^{66}$Ga, $^{72}$Ga, $^{146}$Gd, $^{153}$Gd, $^{68}$Ge, $^{170}$Hf, $^{171}$Hf, $^{193}$mHg, $^{193}$mHg, $^{160}$mHo, $^{130}$I, $^{131}$I, $^{135}$I, $^{114}$mIn, $^{185}$Ir, $^{42}$K, $^{43}$K, $^{76}$Kr, $^{79}$Kr, $^{81}$mKr, $^{132}$La, $^{262}$Lr, $^{169}$Lu, $^{174}$mLu, $^{176}$mLu, $^{257}$Md, $^{260}$Md, $^{28}$Mg, $^{52}$Mn, $^{90}$Mo, $^{24}$Na, $^{95}$Nb, $^{138}$Nd, $^{57}$Ni, $^{66}$Ni, $^{234}$Np, $^{15}$O, $^{182}$Os, $^{189}$mOs, $^{191}$Os, $^{32}$P, $^{201}$Pb, $^{101}$Pd, $^{143}$Pr, $^{191}$Pt, $^{243}$Pu, $^{225}$Ra, $^{81}$Rb, $^{188}$Re, $^{105}$Rh, $^{211}$Rn, $^{103}$Ru, $^{35}$S, $^{44}$Sc, $^{72}$Se, $^{153}$Sm, $^{125}$Sn, $^{91}$Sr, $^{173}$Ta, $^{154}$Tb, $^{127}$Te, $^{234}$Th, $^{45}$Ti, $^{166}$Tm, $^{230}$U, $^{237}$U, $^{240}$U, $^{48}$V, $^{178}$W, $^{181}$W, $^{188}$W, $^{125}$Xe, $^{127}$Xe, $^{133}$Xe, $^{133}$mXe, $^{135}$Xe, $^{85}$mY, $^{86}$Y, $^{90}$Y, $^{93}$Y, $^{169}$Yb, $^{175}$Yb, $^{65}$Zn, $^{71}$mZn, $^{86}$Zr, $^{95}$Zr, and $^{97}$Zr.

12. A multispecific antibody comprising the CD33-binding antibody or antigen binding fragment thereof of claim 1, and a second antibody or antigen binding fragment thereof that binds CD3.

13. A composition comprising one of the CD33-binding antibody or antigen binding fragments thereof of claim 1 and a pharmaceutically acceptable carrier.

* * * * *